US012416005B2

(12) United States Patent
Cigan et al.

(10) Patent No.: US 12,416,005 B2
(45) Date of Patent: *Sep. 16, 2025

(54) PIG WITH A GENETICALLY MODIFIED CD163 GENE RESISTANT TO PRRSv

(71) Applicant: Genus PLC, DeForest, WI (US)

(72) Inventors: Andrew Mark Cigan, Madison, WI (US); Jonathan Edward Lightner, Jefferson, WI (US); Matthew Scott Culbertson, Wilmington, NC (US); William Thomas Christianson, Hendersonville, TN (US); Benjamin Beaton, DeForest, WI (US); Brian Burger, Madison, WI (US); Dylan Barnes, Madison, WI (US); Matthew Campbell, Madison, WI (US)

(73) Assignee: Genus plc, DeForest, WI (US)

( * ) Notice: Subject to any disclaimer, the term of this patent is extended or adjusted under 35 U.S.C. 154(b) by 238 days.

This patent is subject to a terminal disclaimer.

(21) Appl. No.: 17/515,139

(22) Filed: Oct. 29, 2021

(65) Prior Publication Data

US 2022/0042017 A1 Feb. 10, 2022

Related U.S. Application Data

(63) Continuation of application No. 17/307,369, filed on May 4, 2021, now Pat. No. 11,208,659.

(60) Provisional application No. 63/021,370, filed on May 7, 2020, provisional application No. 63/020,128, filed on May 5, 2020.

(51) Int. Cl.
| | |
|---|---|
| *A01K 67/027* | (2024.01) |
| *A01K 67/0275* | (2024.01) |
| *C12N 9/22* | (2006.01) |
| *C12N 15/113* | (2010.01) |
| *C12N 15/877* | (2010.01) |

(52) U.S. Cl.
CPC ........ *C12N 15/113* (2013.01); *A01K 67/0275* (2013.01); *C12N 9/22* (2013.01); *C12N 15/8778* (2013.01); *A01K 2217/052* (2013.01); *A01K 2227/108* (2013.01); *C12N 2310/20* (2017.05); *C12N 2320/34* (2013.01)

(58) Field of Classification Search
USPC ......................................................... 800/17
See application file for complete search history.

(56) References Cited

U.S. PATENT DOCUMENTS

| | | | |
|---|---|---|---|
| 4,873,191 A | 10/1989 | Wagner et al. | |
| 9,820,475 B2 | 11/2017 | Prather et al. | |
| 10,091,975 B2 | 10/2018 | Prather et al. | |
| 10,827,730 B2 | 11/2020 | Prather et al. | |
| 11,208,659 B2 * | 12/2021 | Cigan | A01K 67/0276 |
| 11,535,850 B2 * | 12/2022 | Cigan | A01K 67/0275 |
| 2014/0068797 A1 | 3/2014 | Doudna et al. | |

FOREIGN PATENT DOCUMENTS

| | | | |
|---|---|---|---|
| WO | WO2017023337 | | 2/2017 |
| WO | WO 2018073237 | * | 4/2018 |
| WO | WO2019203807 | | 10/2019 |

OTHER PUBLICATIONS

Yang, Dongshan, et al., Generation of PPARγ mono-allelic knockout pigs via zinc-finger nucleases and nuclear transfer cloning, Cell Research, 2011, 21:979-982.
Yoon, In J., et al., Persistent and contact infection in nursery pigs experimentally infected with reproductive and respiratory syndrome (PPRS) virus, Swine Health and Production, 1993, 1(4):5-8.
Yoshioka, Kojn, et al., Birth of Piglets Derived from Porcine Zygotes Cultured in a Chemically Defined Medium, Biol of Reprod, 2002, 66:112-119.
Zhang, Qingzhan and Yoo, Dongwan, PRRS virus receptors and their role for pathogenesis, Veternary Microbiology, 2015, 177:229-241.
Zhao, Jianguo, et al., Histone Deacetylase Inhibitors Improve In Vitro and In Vivo Development Competence of Somatic Cell Nuclear Transfer Porcine Embryos, Cellular Reprogramming, 2010, 12(1):75-83.
Zhao, Jianguo, et al., Significant Improvement in Cloning Efficiency of an Inbred Miniature Pig by Histone Deacetylase Inhibitor Treatment after Somatic Cell Nuclear Transfer, Biology of Reproduction, 2009, 81:525-530.
Abeydeera, L.R. and Day, B.N., Fertilization and subsequent development in vitro of pig oocytes inseminated in a modified trisbuffered medium with frozen-thawed ejaculated spermatozoa, *Biol. Reprod.*, 1997, 57:729-734.
Agung et al., In vitro fertilization and development of porcine oocytes matured in follicular fluid, *J Reprod Dev.*, 2013, 59:103-106.
Alkan, F., et al., CRISPR-Cas9 off-targeting assessment with nucleic acid duplex energy parameters, Genome Biol., 2018, 19:177.
Altschul, S.P., et al., Basic local alignment search tool, *J. Mol. Biol.*, 1990, 215:403-410.
Appeltant et al., Porcine oocyte maturation in vitro: role of cAMP and oocyte-secreted factors—A practical approach, *J Reprod Dev.*, 2016, 62:439-449.

(Continued)

*Primary Examiner* — Michael C Wilson
(74) *Attorney, Agent, or Firm* — Daniel M. Lorentzen; Christopher J. Arnold

(57) ABSTRACT

The present disclosure relates to methods and compositions useful for prevention of porcine reproductive and respiratory syndrome virus (PRRSv) in animals, including animals of the species *Sus scrofa*. The present teachings relate to swine wherein at least one allele of a CD163 gene has been inactivated, and to specific methods and nucleic acid sequences used in gene editing to inactivate the CD163 gene. Swine wherein both alleles of the CD163 gene are inactivated are resistant to porcine reproductive and respiratory syndrome virus (PRRSv). Elite lines comprising homozygous CD163-edited genes retain their superior properties.

3 Claims, No Drawings
Specification includes a Sequence Listing.

(56) References Cited

OTHER PUBLICATIONS

Bae, S., et al., Cas-OFFinder: a fast and versatile algorithm that searches for potential off-target sites of Cas9 RNA-guided endonucleases, Bioinformatics, 2014, 30:1473-1475.
Cameron, P., et al., Mapping porcine landscape of CRISPR-Cas9 cleavage, Nat Methods 2017, 14:600-606.
Chenna, R., et al., Multiple sequence alignment with the Clustal series of programs, *Nucleic Acids Research,* 2003, 31:3497-3500.
Fowler et al., The production of pig preimplantation embryos in vitro: Current progress and future prospects, *Reprod Biol.,* 2018, 18:203-211.
Fonfara et al., Phylogeny of Cas9 determines functional exchangeability of dual-RNA and Cas9 among orthologous type II CRISPR-Cas systems, *Nucleic Acids Research,* 2014, 42:2577-2590.
Gnirke, A., et al., Solution hybrid selection with ultra-long oligonucleotides for massively parallel targeted sequencing, Nat. Biotechnol., 2009, 27:182-189.
Guo, Chunhe, et al., Highly Efficient Generation of Pigs Harboring a Partial Deletion of the CD163 SRCR5 Domain, Which are Fully Resistant to Porcine Reproductive and Respiratory Syndrome Virus 2 Infection, Frontiers in immunology, 2019, 10(1846):1-14.
Haft, Daniel H., et al., A guild of 45 CRISPR-associated (Cas) protein families and multiple CRISPR/Cas subtypes exist in prokaryotic genomes, *PLoS Comput. Bio.,* 2005, 1(6):474-483.
Jinek, M., et al., A programmable dual RNA-guided DNA endonuclease in adaptive bacterial immunity, *Science,* 2012, 337:816-821.
Joung et al., TALENs: a widely applicable technology for targeted genome editing, *Nat. Rev. Mol. Cell. Biol.,* 2013, 14:49-55.
Kang, Soo Ji, et al., Comparision of Seven Commercial TaqMan Master Mixes and Two Real-Time PCR Platforms Regarding the Rapid Detection of Porcine DNA, Food Sci Anim Resour, 2021, 41(1):85-94.
Karvelis et al., Rapid characterization of CRISPR-Cas9 protospacer adjacent motif sequence elements, *Genome Biology,* 2015, 16:253.
Larkin Ma et al., Clustal W and Clustal X version 2.0, *Bioinformatics,* 2007, 23:2947-2948.
Lavitrano et al., Efficient production by sperm-mechiated gene transfer of human decay accelerating factor (hDAF) transgenic pigs for xenotransplantation, *Proc. Natl. Acod. Sci. USA,* 2002, 99:14230-14236.
Lavitrano et al., Sperm-mediated gene transfer, *Reprod. Fert. Develop.,* 2006, 18:19-23.
Lo, Transformation by iontophoretic microinjection of DNA: multiple integrations without tandem insertions, *Mol. Cell. Biol.,* 1983, 3:1803-1814.
Onofre, Gabriela et al., Scavenger receptor CD163 and its biological functions, *Acta Medica,* 2009, 52:57-61.
Ran, F. A., et al., In vivo genome editing using *Staphylococcus aureus* Cas9, *Nature,* 2015, 520:186-191.
Sapranauskas et al., The *Streptococcus thermophilus* CRISPR/Cas system provides immunity in *Escherichia coli, Nucleic Acids Research,* 2011, 39:9275-9282.
Shah et al., Protospacer recognition motifs: mixed identities and functional diversity, *RNA Biol.,* 2013, 10:891-899.
Suzuki, C., et al., Effects of amino acid supplements and replacement of polyvinyl alcohol with bovine serum albumin in porcine zygote medium, Reprod. Fertil. Dev., 2006 18:789-795.
Svitashev et al., Genome editing in maize directed by CRISPR-Cas9 ribonucleoprotein complexes, Nature Communications, 2016, 7:113274.
Thompson et al., Germ line transmission and expression of a corrected HPRT gene produced by gene targeting in embryonic stem cells, *Cell,* 1989, 56:313-321.
Thompson, J.D. and Clustal, W: improving the sensitivity of progressive multiple sequence alignment through sequence weighting, position-specific gap penalties and weight matrix choice et al., *Nucleic Acids Research,* 1994, 22:4673-4680.
Tsai, S.Q., et al., GUIDE-seq enables genome-wide profiling of off-target cleavage by CRISPR-Cas nucleases, Nat. Biotechnol. 2015, 33;187-197.
Tsai, S.Q., et al., CIRCLE-seq: a highly sensitive in vitro screen for genome-wide CRISPR-Cas9 nuclease off-targets, Nat. Methods, 2017, 14;607-614.
Van Der Putten et al., Efficient insertion of genes into the mouse germ line via retroviral vectors, *Proc. Natl. Acad. Sci. USA,* 1985, 82:6148-1652.
Wakayama et al., Full-term development of mice from enucleated oocytes injected with cumulus cell nuclei, *Nature,* 1998, 394:369-374.
Wilmut et al., Viable offspring derived from fetal and adult mammalian cells, Nature, *1997,* 385:810-813.
Yoshioka, K., et al., Birth of piglets derived from porcine zygotes cultured in a chemically defined medium, Biol. Reprod., 2002, 60:112-119.
Yoshioka, K., Defined System for In Vitro Production of Porcine Embryos Using a Single Basic Mediom, J. Reprod. Dev. 2008, 54:208-213.
Yoshioka, K., J., Development and application of a chemically defined medium for the in vitro production of porcine embryos, *Reprod. Dev.,* 2011, 57:9-16.
Zetsche et al., Cpf1 is a single RNA-guided endonuclease of a class 2 CRISPR-Cas system, *Cell,* 2015, 163:759-771.
Zhang et al., Off-target Effects in CRISPR/Cas9-mediated Genome Engineering, *Mol Ther Nucleic Acids,* 2015, 4:e264.
Zhao, C., et al., CRISPR-offinder: a CRISPR guide RNA design and off-target searching tool for user-defined protospacer adjacent motif, Int. J. Biol. Sci., 2017, 13:1470-1478.
Merck Sharp and Dohme Corp., Normal Rectal Temperature Ranges, 2009, pp. I.
Miao, Yi-hang, et al., Centrosome Abnormalilties During Porcine Oocyte Aging, Environmental and Molecular Mutagenesis, 2009, 50:666-671.
Misinzo, Gerald, M., et al., Involvement of proteases in porcine reproductive and respiratory syndrome virus uncoating upon internalization in primary macrophages, Vet. Res., 2008, 39:55-69.
Molitor, T.W., et al., Immunity to PRRSV: Double-edged sword, Veterinary Microbiology, 1997, 55:265-276.
Morgan, S.B., et al., Pathology and Virus Distribution in the Lung and Lymphoid Tissues of Pigs Experimentally Inoculated with Three Distinct Type 1 PRRS Virus Isolates of Varying Pathogenicity, Transboundary and Emerging Diseases, 2014, 63(2016):285-295.
Murtaugh, M.P., et al., Comparison of the structural protein coding sequences of the VR-2332 and Lelystad virus strains of the PRRS virus, Arch Virol, 1995, 140:1451-1460.
Nath, Deepa, et al., The Amino-terminal Immunoglobulin-like Domain of Sialoadhesin Contains the Sialic Acid Binding Site, J Biol Chem, 1995, 270(44):26184-26191.
Nauwynck, H.J., et al, Entry of porcine reproductive and respiratory syndrome virus into porcine alveolar macrophages via receptor-medicated endocytosis, J General Virology, 1999, 80:297-305.
Nelson, Chris J., et al., Porcine Reproductive and Respiratory Syndrome Virus Comparison: Divergent Evolution on Two Continents, J Virology, 999, 73(1):270-280.
Neumann, Eric J., et al., Assessment of the economic impact of porcine reproductive and respiratory syndrome on swine production in the United States, JAVMA, 2005, 227(3):385-392.
Nielsen, H.S., et al., Generation of an Infectious Clone of VR-2332, a Highly Virulent North American-Type Isolate of Porcine Reproductive and Respiratory Syndrome Virus, J Virology, 2003, 77(6):3702-3711.
Nielsen, Marianne Jensby, et al., The macrophage scavenger receptor CD163: endocytic properties of cytoplasmic tail variants, J Leukocyte Biology, 2006, 79:837-845.
Niu, Yaya, et al., Generation of Gene-Modified Cynomolgus Monkeys via Cas9/RNA-Mediated Gene Targeting in One-Cell Embryos, Cell, 2014, 156:836-843.
Nussbaum, Diana J. and Prather, Randall S., Differential Effects of Protein Synthesis Inhibitors on Porcine Oocyte Activation, Mol Reprod and Develop, 1995, 41:70-75.
Oetke, Cornelia, et al., Sialoadhesin-Deficient Mice Exhibit Subtle Changes in B- and T-Cell Populations and Reduced Immunoglobulin M Levels, Mol and Cell Biol, 2006, 26(4):1549-1557.

(56) References Cited

OTHER PUBLICATIONS

Park, Kwang-Wook, et al., Developmental Potential of Porcine Nuclear Transfer Embryos Derived from Transgenic Fetal Fibroblasts Infected with the Gene for the Green Fluorescent Protein: Comparison of Different Pasion/Activation Conditions, Biol of Reprod, 2001, 65:1681-1685.

Park, Kwang-Wook, et al., Production fo Nuclear Transfer-Derived Swine That Express the Enhanced Green Fluorescent Protein, Animal Biotech, 2001, 12(2). 173-181.

Patience, John F. and Thacker, Phil A., Nutrition of the Breeding Herd, Prairie Swine Centre, 1989, pp. 149-171.

Patton, John B., et al., Modulation of CD163 receptor expression and replication of porcine reproductive and respiratory syndrome virus in porcine macrophages, Virus Research, 2009, 140:161-171.

Plagemann, Peter O.W., Lactage Dehydrogenase-Elevating Virus and Related Viruses, Fields Virology, $3^{rd}$ Ed., 1996, Ch. 36, pp. 1105-1120.

Popescu, Luca, et al., Genetically edited pigs lacking CD163 show no resistance following infection with the African swine fever virus isolate, Georgia Jan. 2007, Virology, 2017, 501:102-106.

Prather, Randall S., et al., Genetic engineering alveolar macrophages for host resistance to PRRSV, Veterinary Microbiology, 2017, 209:124-129.

Prather, Randall S., et al., Knockout of maternal CD163 protects fetuses from infection with porcine reproductive and respiratory syndrome virus (PRRSV), Nature Scientific Reports, 2017, 7(13371):1-5.

Prather, R.S., et al., Genetic Engineering of Pigs for PRRSV Resistance, Animal Sciences, Univ Missouri-Columbia, College of Ag Food and Natural Resources, Animal Reproductive Biology Group, Slides, pp. 1-43.

Prather, Randall S., et al., An Intact Staloadhesin (Sn/SIGLEC1/CD169) Is Not Required for Attachment/Internalization of the Porcine Reproductive and Respiratory Syndrome Virus, J Virology, 2013, 87(17):9538-9546.

Prather, R.S., Genetic Engineering of Pigs for PRRSV resistance, Animal Sciences, Univ Missouri-Columbia, College of Ag Food and Natural Resources, Animal Reproductive Biology Group, Slides, pp. 1-55.

Prather, R.S., et al., Genetic engineering the pig to better understand PRRSv infection, 2014 North American PRRS Symposium, 2014, p. 33.

Prather, R.S., Genetic Engineering for Profitable Port Production: Is Resistance to PRRSv Possible?, Animal Sciences, Univ Missouri-Columbia, College of Ag Food and Natural Resources, Animal Reproductive Biology Group, Slides, pp. 1-70.

Prather, Randall S., et al. CRISPR/Cas9-Mediated Genetic Engineering: Is CD163 an Entry Mediator for PRRSv Infection?, International Plant and Animal Genome Conference XXIII, Abstract, Jan. 9-15, 2015, 1 page.

Provost, Chantale, et al., Identification of a new cell line permissive to porcine reproductive and respiratory syndrome virus infection and replication which is phenotypically distinct from MARC-145 cell line, Virology Journal, 2012, 9(267):1-14.

Reed, L.J. and Muench, H., A Simple Method of Estimating Fifty Per Cent Endpoints, American Journal of Hygiene, 1938, 27(3):493-497.

Rezaee, Ramin and Abdollahi, Mohammad, The Importance of Transistability in Drug Discovery, Expert Opinion on Drug Discovery, 2017, 12(3):237-239.

Ritter, M., et al., The Scavenger Receptor CD163: Regulation, Promoter Structure and Genomic Organization, Pathobiology, 1999, 67:257-261.

Ritter, Mirko, et al., Genomic Organization and Chromosomal Localization of the Human CD163 (M130) Gene: A Member of the Scavenger Receptor Cysteine-Rich Superfamily, Biochem and Biophysical Research Communications, 1999, 260(2):466-474.

Robl, J.M., et al., Nuclear Transplantation in Bovine Embryos, J Anim Sci., 1987, 64:642-647.

Ropp, Susan L., et al., Characterization of Emerging European-Like Porcine Reproductive and Respiratory Syndrome Virus Isolates in the United States, J Virology, 2004, 78(7):3684-3703.

Ross, Jason W., et al., Optimization of square-wave electroporation for transfection of porcine fetal fibroblasts, Transgenic Res, 2010, 19(4):611-620.

Rowland, Raymond R.R., et al., Control of porcine reproductive and respiratory syndrome (PRRS) through genetic improvements in disease resistance and tolerance, Frontiers in Genetics, 2012, 3(260):1-6.

Rowland, Raymond R.R., et al., The Evolution of Porcine Reproductive and Respiratory Syndrome Virus: Quasispecies and Emergence of a Virus Subpopulation during Infection of Pigs with VR-2332, Virology, 1999, 259:262-266.

Saeidnia, Soodabeh, et al., From in vitro Experiments to in vivo and Clinical Studies; Pros and Cons, Current Drug Discovery Technologies, 2015, 12(4):218-224.

Sanchez, Carmen, et al., The Porcine 2A10 Antigen Is Homologous to Human CD163 and Related to Macrophage Differentiation, J Immunology, 19 162:5230-5237.

Sanchez-Torres, C., et al., Expression of porcine CD163 on monocytes/macrophages correlates with permissiveness to African swine fever infection, Arch Virol, 2003, 148:2307-2323.

Sangamo BioSciences, Efficient Generation of Transgenic Pigs Using Zinc Finger Nuclease (ZFN) Technology, Demonstration of ZEN Technology for Efficient Creation of Animals as a Source of Organs for Transplantation into Humans, Press Release, 2011, p. 1.

Schaer, Christian A., et al., Constitutive Endocytosis of CD163 Mediates Hemoglobin-Heme Uptake and Determines the Noninflammatory and Protective Transcriptional Response of Macrophages to Hemoglobin, Circ Res, 2006, 99:943-950.

Schaer, Dominik J., et al., CD163 is the macrophage scavenger receptor for native and chemically modified hemoglobins in the absence of haptoglobin, Blood, 2006, 107(1):373-380.

Schaer, DJ, et al., Hemophagocytic macrophages constitute a major compartment of hemne oxygenase expression in sepsis, Eur J Haematol, 2006, 77:432-436.

Schurgers, Evelien, et al., Discrepancy between the in vitro and in vivo effects of murine mesenchymal stem cells on T-cell proliferation and collagen-induced arthritis, Arthritis Research & Therapy, 2010, 12(R31):3-11.

Aigner, Bernhard, et al., Transgenic pigs as models for translational biomedical research, J Mol Med, 2010, 88:653-664.

Albina, E., et al., Immune response and persistence of the porcine reproductive and respiratory syndrome virus in infected pigs and far units, The Veterinary Record, May 28, 1994, 134.567-573.

Allende, R., et al., North American and European porcine reproductive and respiratory syndrome viruses differ in non-structural protein coding regions, J General Virology, 1999, 80:307-315.

Allende, R., et al., Porcine Reproductive and Respiratory Syndrome Virus: Deseption of Persistence in Individual Pigs upon Experimental Infection, J Virology, Nov. 2000, 74(22):10834-10837.

American Society for Cell Biology, "Small details between 'in vivo' and 'in vitro' studies make for big differences." ScienceDaily. ScienceDaily, Dec. 13, 2010.

Andreyev, V.G., et al., Genetic variation and phylogenetic relationships of 22 poreine reproductive and respiratory syndrome virus (PRRSV) field strains based on sequence analysis of open reading frame 5, Arch Virol 1997, 142:993-1001.

ATCC CRL-3216, 293T, Organism: *Homo sapiens*, human, Tissue: embryonic kidney.

Bauer, B.K., et al., 1 Arginine Supplementation in vitro Increases Porcine Embryo Development and Affects mRNA Transcript Expression, Reproduction, Fertility and Development, Dec. 7, 2010, 23(1):107.

Beaton, Benjamin P. and Wells, Kevin D., Compound Transgenics: Recombinase-Mediated Gene Stacking, Transgenic Animal Technology, pp. 565-678.

Benfield, David A., et al., Characterization of swine infertility and respiratory syndrome (SIRS) virus (isolate ATCC VR-2332), J Vet Diagn Invest, 1992 4:127-133.

Benfield, David A., et al., Pathogenesis and persistence of PRRS, Allen D. Leman Swine Conference, 1998, pp. 169-171.

(56) References Cited

OTHER PUBLICATIONS

Berg, H., 200-Biological Implications of Electric Field Effects Part V. Fusion of Blastomeres and Blastocysts of Mouns Embryos, Bioelectrochemistry and Bioenergetics, 1982, 9:223-228.

Boddicker, Nicholas J., et al., Genome-wide association and genomic prediction for host response to porcine reproductive and respiratory syndrome virus infection, Genetics Selection Evolution, 2014, 46(18):1-14.

Bookstein, Robert, et al., Promoter deletion and loss of retinoblastoma gene expression in human prostate carcinoma, Proc. Natl. Acad. Sci. USA, 1990, 87:7762-7766.

Borg, Natalie A., et al., CD1d-lipid-antigen recognition by the semi-invariant NKT T-cell receptor, Nature, Jul. 5, 2007, 448:44-49.

Brinster, Ralph L., et al., Factors affecting the efficiency of introducing foreign DNA into mice by microinjecting eggs, Proc. Natl. Acad. Sci., Jul. 1985, 82:4438-4442.

Burkard, Christine, et al., Pigs Lacking the Scavenger Receptor Cysteme-Rich Domain 5 of CD163 Are Resistant to Procine Reproductive and Respiratory Syndrome Virus 1 Infection, J. Virology, 2018, 92(16):1-17.

Burkard, Christine, et al., Precision engineering for PRRSV resistance in pigs: Macrophages from genome edited pigs lacking CD163 SRCR5 domain are fully resistant to both PRRSV genotypes while maintaining biological function, PLOS Pathogens, Feb. 23, 2017, 13(2):1-28.

Burlac, C., et al., Identification of human preformed antibody targets in GTKO pigs, Xenotransplantation 2012, 19:92-101

Calvert, Jay G., et al., CD163 Expression Confers Susceptibility to Porcine Reproductive and Respiratory Syndrome Viruses, J of Virology, Jul. 2007, 81(14):7371-7379.

Carter, D. Bart, et al., Phenotyping of Transgenic Cloned Piglets, Cloning and Stem Cells, 2002, 4(2):131-145.

Chin, Kun-Kuet and Shwu-Pen Chang, The −104G nucleotide of the human CYP21 gene is important for CYP21 transcription activity and protein interaction, Nucleic Acids Research, 1998, 26(8):1959-1964.

Christopher-Hennings, Jane, et al., Persistence of porcine reproductive and respiratory syndrome virus in serum and semen of adult boars, J Vet Diagn Invest, 1995, 7:456-464.

Christopher-Hennings, J, et al., Effects of a modified-live virus vaccine against porcine reproductive and respiratory syndrome in boars, AJVR, 1997, 58(1):40-45.

Ciotti, M., et al., Coding defect and a TATA box mutation at the bilirubin UDP-glucuronosyltransferase gene canse Crigler-Najjar type 1 disease, Biochimica et Biophysica Acta, 1998, 1407:40-S0.

Cong, Le, et al., Multiplex Genome Engineering Using CRISPR/Cas Systems, Science, Feb. 15, 2013, 339(6121):819-823.

Cooper, David K C. Modifying the sugar icing on the transplantation cake, Glycobiology, 2016, 26(6):571-581.

Crocker, Paul R. and Gordon, Siamon, Properties and Distribution of a Lectin-Like Hemagglutinin Differentially Expressed by Murine Stromal Tissue Macrophages, J Exp Med, The Rockefeller Univ. Press, Dec. 1986, 164:1862-1875.

Crocker, Pant R., et al., Molecular analysis of sialoside binding to sialoadhesin by NMR and site-directed mutagenesis, Biochem J, 1999, 341:355-361.

Dai, Yifan, et al., Targeted disruption of the α1, 3-galactosyltransferase gene in cloned pigs, Nature, Mar. 2002, 20:251-255.

Das, Phani B., et al., The Minor Envelope Glycoproteins GP2a and GP4 of Porcine Reproductive and Respiratory Syndrome Virus Interact with the Receptor CD163, J Virology, Feb. 2010, 84(4):1731-1740

Dee, S. A. and Molitor, T. W., Elimination of porcine reproductive and respiratory syndrome virus using a test and removal process, Veterinary Record, 1998, 143:474-476.

Delputte, P.L., et al., Effect of virus-specific antibodies on attachment, internalization and infection of porcine reproductive and respiratory syndrome virus in primary macrophages, Vet Immunology and Immunopathology, 2004, 102:179-188.

Delputte, P.L., et al., Involvement of the Matrix Protein in Attachment of Porcine Reproductive and Respiratory Syndrome Virus to a Heparinlike Receptor on Porcine Alveolar Macrophages, J Virology, May 2002, 76(9) 4312-4320.

Delputte, P.L., et al., Poreine Arterivirus Infection of Alveolar Macrophages Is Mediated by Sialic Acid on the Virus, J Virology, Aug. 2004, 78(15):8094-8101.

Delputte, P.L., et al., Porcine Arterivirus Attachment to the Macrophage-Specific Receptor Sialoadhesin Is Dependent on the Sialic Acid-Binding Activity of the N-Terminal Immunoglobulin Domain of Sialoadhesin, J Virology, Sep. 2007, 81(17):9546-9550.

Delputte, P.L., et al., Porcine Sialoadhesin (CD169/Siglec-1) Is an Endocytic Receptor that Allows Targeted Delivery of Toxins and Antigens to Macrophages, PLoS ONE, Feb. 2011, 6(2):1-12.

Etzerodt, Anders, et al., Plasma Clearance of Hemoglobin and Haptoglobin in Mice and Effect of CD163 Gene Targeting Disruption, Antioxidants & Redox Signaling, 2013, 18(17):2254-2263.

Etzerodt, Andres and Moestrup, Soren K., CD163 and Inflammation: Biological, Diagnostic, and Therapeutic Aspects, Antioxidants & Redox Signaling, 2013, 18(17):2352-2363.

Fabriek, Babs O., et al., The macrophage scavenger receptor CD163, Immunobiology, 2005, 210:153-160

Fabriek, Babs O., et al., The macrophage scavenger receptor CD163 functions as an innate immune sensor for bacteria, Blood Journal, Jan. 22, 2009, 113(4):887-892.

Fisher, D. and Goodall, A.H., Membrane fusion by viruses and chemical agents, Techniques in Cellular Physiology, 1981, P115:1-36.

Fridman, AL and Tainsky, MA, Critical pathways in cellular senescence and immortalization revealed by gene expression profiling, Oncogene, 2008, 27:5975-5987.

Gaj, Thomas, et al., ZEN, TALEN and CRISPR/Cas-based methods for genome engineering, Trends Biotechnol, 2013, 31(7):397-405.

Galili, Uri, Xenotransplantation and ABO incompatible transplantation: The similarities they share, Transfusion and Apheresis Science, 2006, 35:45-58.

Gaudreault, N., et al., Factors affecting the permissiveness of porcine alveolar macrophages for porcine reproductive and respiratory syndrome virus, Arch Virol, 2009, 154:133-136.

Gerrits, Roger J., et al., Perspectives for artificial insemination and genomics to improve global swine populations, Theriogenology, 2005. 63:283-299.

Goryenin, Igor, et al., Applications of Whole Cell and Large Pathway Mathematical Models in the Pharmaceutical Industry, Chapter 12, Metabolic Engineering in the Post Genomic Era, Horizon Bioscience, 2004, p. 344.

Graham, Christopher F., The Fusion of Cells with One- and Two-Cell Mouse Embryos, Wistar Inst Symp Monogr., 1969, 9:19-35.

Graversen, Jonas H., et al., Targeting the Hemoglobin Scavenger receptor CD163 in Macrophages Highly Increases the Anti-Inflammatory Potency of Dexamethasone, Molecular Therapy, Ang. 2012, 20(8):1550-1558.

Groenen, Martien A. M., et al., Analyses of pig genomes provide insight into porcine demography and evolution, Nature, Nov. 15, 2012, 491(7424):393-398.

Hai, Tang et al., One-step generation of knockout pigs by zygote injection of CRISPR/Cas System, Cell Research, 2014, 34:372-375.

Halbur, P.O., et al., Comparison of the Pathogenicity of Two US Porcine Reproductive and Respiratory Syndrome Virus Isolates with that of the Lelystad Virus, Vet Pathol, 1995, 32:648-660.

Hammer, Robert E., et al., Production of transgenic rabbits, sheep and pigs by microinjection, Nature, Jun. 1985, 315:680-683.

Hao, Y.H., et al., Production of endothelial nitric oxide synthase (eNOS) over-expressing piglets, Transgenic Res, 2006, 15:739-750.

Hauschild, Janet, et al., Efficient generation of a biallelic knockout in pigs using zinc-finger nucleases, PNAS, 2011, 108(36):1-6.

Holtkamp, Derald J., et al., Assessment of the economic impact of porcine reproductive and respiratory syndrome virus on United States port producers, J Swine Health and Production, 2013, 21(2):72-84.

Huang, Y.W., et al., Porcine DC-SIGN: Moleenlat cloning, gene structure, tissue distribution and binding characteristics, Dev and Comparative Immunology, 2009, 33:464-480.

(56) References Cited

OTHER PUBLICATIONS

Hwang, Woong Y, et al., Efficient genome editing in zebrafish using a CRISPR-Cas system, Nature Biotechnology, 2013, 31(3):227-229.
Hyder, Salvoan M., et al., Identification of an Estrogen Response Element in the 3'-Flanking Region of the Murine e-fos Protooncogene, J Biological Chemistry, 1992, 267(25):18047-18054.
Im, Gi-Sun, et al., In vitro development of preimplantation porcine nuclear transfer embryos cultured in different media and gas atmospheres, Theriogenology, 2004, 61:1125-1135.
Jeney, Viktona, et al., Pro-oxidant and cytotoxic effects of circulating heme, 2002, 100(3):879-887.
Kefpaber, Kerry K., Reproductive Failure of Unknown Etiology, 1989, 1(2):1-10.
Kim, Hyongbum and Kim, Jin-Soo, A guide to genome engineering with programmable nucleases, Nature Reviews Genetic, 2014, 15:321-334.
Kim, H.S., et al., Enhanced replication of poreme reproductive and respiratory syndrome (PRRS) virus in a homogeneous subpopulation of MA-104 cell line, Arch Vitol, 1993, 133:477-483.
Kim, Jeong-Ki, et al., Defining the Cellilat Target(s) of Porcine Reproductive and Respiratory Syndrome Virus Blocking Monoclonal Antibody 7G10, J Virology, 2006, 80(2):689-696.
Kleinjan, Dirk-Jan and Coutinho, Pedro, Cis-ruption mechanisms: disruption of cis-regulatory control as a cause of human genetic disease, Briefings Functional Genomics and Proteomics, 2009, 8(4):317-332.
Kolston, Paul J., Comparing in vitro, in situ, and in vivo experimental data in a three-dimensional model of mammalian cochlear mechanics, Proc Natl Acad Sci, 1999, 96:3676-3681.
Kristiansen, Mette, et al., Identification of the haemoglobin scavenger receptor, Nature, 2001, 409: 198-201.
Kwon, Deug-Nam, et al., Production of biallelic CMP-Neu5Ac hydroxylase knock-out pigs, Scientific Reports, 2013, 3(1981)1-10.
Ladinig, Andrea, et al., Pathogenicity of three type 2 porcine reproductive and respiratory syndrome virus strains in experimentally inoculated pregnant gilts, Virus Research, 2015, 203:34-35.
Lager, Kelly M., et al., Evaluation of protective immunity in gilts inoculated with the NADC-8 isolate of porcine reproductive and respiratory syndrome virus (PRRSV) and challenge-exposed with an antigenically distinct PRRSV isolate, AJVR, 1998, 60(8):1022-1027.
Lai, Liangxue, et al., Generation of cloned transgenic pigs rich in omega-3 fatty acids, Nature Biotechnology, 2006, 24(4):435-436.
Lai, Liangxue, et al., Production of α-1,3-Galactosyltransferase Knockout Pigs by Nuclear Transfer Cloning, Science, 2002, 295:1089-1092.
Lai, Liangxne, and Prather, Randall S., Creating genetically modified pigs by using nuclear transfer, Reprod Biol and Endocrinology, 2003, 1(82):1-6.
Lai, Liangxue and Prather, Randall S., Production of Cloned Pigs by Using Somatic Dells as Donors, Cloning and Stem Cells, 2003, 5(4):233-241.
Lai, Liangxue and Prather, Randall S., A method for Producing Cloned Pigs by Using Somatic Cells as Donors, Methods in Molecular Biology, Germ Cell Protocols, 2004, vol. 2, Ch. 9, pp. 149-163.
Lawson, Stevewn R., et al., Porcine reproductive and respiratory syndrome virus infection of gnotobiotic pigs: sites of virus replication and co-localization with MAC-387 staining at 21 days post-infection, Virus Research, 1997, 51:105-113.
Lee, Kiho, et al., Engraftment of human iPS cells and allogeneic porcine cells into pigs with inactivated RAG2 and accompanying severe combined immunodeficiency, PNAS, 2014, 111(20):7260-7265.
Lee, Kiho, et al., Piglets Produced From Cloned Blastocysts Cultured In Vitro With GM-CSF, Mol Reprod, Dev, 2013, 80(2):145-154.
Li, Dali, et al., Heritable gene targeting in the mouse and rat using a CRISPR-Cas system, Nature Biotechnology, 2013, 31(8):681-683.
Li, Rongfeng, et al., Cloned Transgenic Swine Via In Vitro Production and Cryopreservation, Biology of Reprod, 2006, 75:226-230.
Li, Ying and Jaiswal, Anil K., Regulation of Human NAD(P)H:Quinone Oxidereductase Gene, J Biol Chem, 1992, 267(21):15097-15104.
Lillico, Simon G., et al., Live pigs produced from genome edited zygotes, Scientific Reports, 2013, 3:2847-2850
Loudianos, O., et al., Molecular characterization of Wilson disease in the Sardinian population—evidence of a founder effect, Hum Matat, 1999, 14(4):294-303.
Lunney, Joan K. and Chen, Hongbo, Genetic control of host resistance to porcine reproductive and respiratory syndrome virus (PRRSV) infection, Virus Research, 2010, 154:161-169
MacHaty, Zoltan, et al., Complete Activation of Porcine Oocytes Induced by the Sulfhydryl Reagent, Thimerosal, Biol of Reprod, 1997, 57:1123-1127.
MacHaty, Zoltan, et al., Development of Early Porcine Embryos In Vitro and In Vivo, Biol of Reprod, 1998, 59:451-455.
Madsen, Mette, et al., Molecular Characterization of the Haptoglobin Hemoglobin Receptor CD163, J Biol Chem, 2004, 279(49):51561-51567.
Mansour, Suzanne L., et al., Disruption of the proto-oncogene int-2 in mouse embryo-derived stem cells. a general strategy for targeting mutations to non-selectable genes, Nature, 1988, 336:348-352.
Mayes, M.A., et al., Parthenogenic Activation of Pig Oocytes by Protein Kinase Inhibition, Biol of Reprod, 1995, 53:270-275.
McGrath, James and Solter, Davor, Nuclear Transplantation in the Mouse Embryo by Microsurgery and Cell Fusion, Science, 1983, 220(4603)1300-1302.
Meng, X.J., Heterogeneity of porcine reproductive and respiratory syndrome virus: implications for current vaccine efficacy and future vaccine development, Veterinary Microbiology, 2000, 74:309-329.
Meng, Xiang-Jin, et al., Sequence comparison of open reading frames 2 to 5 of low and high virulence United States isolates of porcine reproductive and respiratory syndrome virus, J Gen Virology, 1995, 76:3181-3188.
Mengeling, William L., et al., Identification and clinical assessment of suspected vaccine-related field strains of porcine reproductive and respiratory syndrome virus, AJVR, 1999, 60(3): 334-340.
Shanmukhappa, Kumar, et al., Role of CD151, A tetraspantin, in porcine reproductive and respiratory syndrome virus infection, Virology Journal, 2007, 4:62.
Shimozawa, Nobuhiro, et al., Abnormalities in Cloned Mice Are Not Transmitted to the Progeny, Genesis, 2002, 35:203-207.
Snuder, Eric J., and Meulenberg, Janneke J.M., The molecular biology of arerivimses, J Gen Virology, 1998, 79:961-979.
Soares, Mignel, P., Bach, Fritz H., Heme oxygenase-1: from biology to therapeutic potential, Trends in Molecular Medicine, 2009, 15(2):50-58.
Stein, Michael, et al., Interleukin 4 Potently Enhances Murine Macrophage Mannose Receptor Activity: A Marker of Alternative Immmmmologie Macrophage Activation, J Exp Med, 1992, 176:287-292.
Stephen, Sam L., et al., Scavenger Receptors and Their Potential as Therapeutic Targets in the Treatment of Cardiovascular Disease, International Journal of Hypertension, 2010, pp. 1-21.
Stephenson, Rachel J., et al., Multiplex Serology for Common Viral Infections in Feral Pigs (*Sus scrofa*) in Hawaii between 2007 and 2010, J. Wildlife Diseases, 2015, 51(1):239-243.
Suarez, Paloma, et al., Open Reading Frame 5 of Porcine Reproductive and Respiratory Syndrome Virus as a Cause of Virus-Induced Apoptosis, J Virology, 1996, 70(5):2876-2882.
Sulahian, Timothy H., et al., Human Monocytes Express CD163, Which is Unregulated by IL-10 and Identical to p155. Cytokine, 2000, 12(9):1312-1321.
Sur, Jung-Hyang, et al., In Vivo Detection of Poreme Reproductive and Respiratory Syndrome Virus RNA by In Situ Hybridization at Different Times Postinfection, J Clinical Microbiology, 1996, 34(9):2280-2286.

(56) References Cited

OTHER PUBLICATIONS

Sur, Jung-Hiyang, et al., Porcine Reproductive and Respiratory Syndrome Virus Replicates in Testienlat Germ Cells, Alters Spermatogenesis, and Induces Germ Cell Death by Apoptosis, J Virology, 1997, 71(12):9170-9179.

Tait-Burkard, Christine, et al., Livestock: 2.0—genome editing for fitter, healthier, and more productive farmed animals, Genome Biology, 2018, 19(204):1-11.

Terns, Michael P. and Terns, Rebecca M., CRISPR-Based Adaptive Imname Systems, Carr Opin Microbiol, 2011, 14(3):321-327.

Trible, Benjamin R., et al., Recognition of the Different Structural Forms of the Capsid Protein Determines the Outcome following Infection with Porcine Circovirus Type 2, J Virology, 2012, 86(24):13508-13514.

Vadori, M. and Cozzi, E., The immunological barriers to xenotransplantation, Tissue Antigens, 2015, 86:239-253.

Van Breedam, Wander, et al., Porcine reproductive and respiratory syndrome virus entry into the porcine macrophage, J General Virology, 2010, 91:1659-1667.

Van Breedam, Wander, et al., The M/GP5 Glycoprotein Complex of Porcine Reproductive and Respiratory Syndrome Virus Binds the Sialoadhesin Receptor in a Siabe Acid-Dependent Manner, PLoS Pathogens, 2010, 6(1):1-11.

Van Den Heuvel, Michel M., et al., Regulation of CD163 on human macrophages: cross-linking of CD163 induces signaling and activation, J Leukocyte Biology, 1999, 66(5):858-866.

Van Den Hoff, Maurice J.B., et al., Electroporation in 'intracellular' buffer increases cell survival, Nucleic Acids Research, 1992, 20(11):2902.

Vanderheiden, Nathalie, et al., Involvement of Sialoadhesin in Entry of Porcine Reproductive and Respiratory Syndrome Virus into Porcine Alveolar Macrophages, 2003, J Virology, 77(15):8207-8215.

Van Gorp, Hanne, et al., Scavenger receptor CD163, a Jack-of-all-trades and potential target for cell-directed therapy, 2010, 47:1650-1660.

Van Gorp, Hane, et al., Identification of the CD163 Protein Domains Involved in Infection of the Porcine Reproductive and Respiratory Syndrome Virus, 2010, J Virology, 84(6):3101-3105.

Van Gorp, Hanne, et al., Sialoadhesin and CD163 join forces during entry of the porcine reproductive and respiratory syndrome virus, J General Virology, 2008, 89:2943-2953.

Vinson, Mary, et al., Characterization of the Sialic Acid-binding Site in Sialoadhesin by Site-directed Mutagenesis, J Biological Chemistry, 1996, 271(16):9267-9272.

Walters, Eric M. and Prather, Randall S., Advancing Swine Models for Human Health and Diseases, Missouri Medicine, 2013, 110(3):212-215.

Wang, Haoyi, et al., One-Step Generation of Mice Carrying Mutations in Multiple Genes by CRISPR/Cas-Mediated Genome Engineering, Cell, 2013, 153(4):910-918.

Watanabe, Masahito, et al., Knockout of exogenous EGFP gene in porcine somatic cells using zine-finger nucleases, Biochem and Biophysical Research Communications, 2010, 402:14-18.

Welch, Siao-Kun and Calvert, Jay G., A brief review of CD163 and its role in PRRSV infection, Virus Research, 2010, 154:98-103.

Wells, Kevin D., et al., Replacement of Porcine CD163 Scavenger Receptor Cysteine-Rich Domain 5 with a CD163-Like Homolog Confers Resistance of Pigs to Genotype 1 but Not Genotype 2 Porcine Reproductive and Respiration Syndrome Virus, J Virology, 2017, 91(2):1-11.

Wensvoort, O., et al., Mystery swine disease in the Netherlands: The isolation of Lelystad virus, Veterinary Quarterly, 1991, 13(3):121-130.

Whitworth, Kristin M., et al., Gene-edited pigs are protected from porcine reproductive and respiratory syndrome virus, Nature Biotechnology, 2016, 34(1):20-22.

Whitworth, K. M., et al., "Disruption the Sialoadhesin and CD163 Genes to Create Pigs Resistant to PRRSV Infectivity," Abstract, Swine in Biomedical Research in Chicago, Illinois, Jul. 17-19, 2011, S1-25, pp. 39-40.

Whitworth, Kristin M., et al., Method of Oocyte Activation Affects Cloning Efficiency in Pigs, Mol Reprod Dev, 2002, 76:1.11.

Whitworth, Kristin M., et al., Activation Method Does Not Alter Abnormal Placental Gene Expression and Development in Cloned Pigs, Mol Reprod Dev, 2010, 77:1016-1030.

Whitworth, K. M., et al., "Pigs Resistant to PRRSV Infectivity. " Poster Presented at Swine in Biomedical Research in Chicago, Illinois, Jul. 18, 2011, 1 page.

Whitworth, Kristin M., et al., Scriptaid Corrects Gene Expression of a Few Aberrantly Reprogrammed Transcripts in Nuclear Transfer Pig Blastocyst Stage Embryos, Cellular Reprogramming, 2011, 13(3):191-204.

Whitworth, Kristin M. and Prather, Randall S., Gene editing as applied to prevention of reproductive porcine reproductive and respiratory syndrome, Mol Reprod Dev, 2017, 33.

Whitworth, Kristin M., et al., Use of the CRISPR/Cas9 System to Produce Genetically Engineered Pigs from In Vitro-Derived Oocytes and Embryos, Biol of Reproduction, 2014, 91(3):78, 1-13.

Whitworth, K. M., et al., "Use of the CRISPR/Cas9 System to Produce Pigs With a Genetically Modified CD163 Gene by Using Somatic Cell Nuclear Transfer of In Vitro Derived Oocytes," Abstract, Swine in Biomedical Research Conference, Raleigh, North Carolina, Jul. 20-22, 2014, p. 103.

Whitworth, Kristin M., et al., Use of the CRISPR/Cas9 system to produce pigs with a genetically modified CD163 gene by somatic cell unclear transfer of in vitro derived oocytes, Division of Animal Science, University of Missouri, Columbia, Poster, p. 1.

Whitworth, K.M., et al., Gene editing of CD163 protects pigs from PRRSV infectivity, Abstracts from the UC Davis Transgenic Animal Research Conference XI, Aug. 13-17, 2017, Transgenic Res, 2018, 27:473-474.

Whyte, Jeffrey J., et al., Gene Targeting With Zinc Finger Nucleases to Produce Cloned eGFP Kouckout Pigs, Mol Reprod Dev, 2011, 78(1):1-3.

Whyte, Jeffrey and Prather, Randall S., Genetic modifications of pigs for medicine and agriculture, Mol Reprod Dev, 2011, 78(10-11):879-891.

Wiedenheft, Blake, et al., RNA-guided genetic silencing systems in bacteria and archaea, Nature, 2012, 482:331-338.

Wills. R. W., et al., Porcine reproductive and respiratory syndrome virus: Persistent infection, Veterinary Microbiology 1997, 55:231-240.

Winckler, C. and Willen, S., The Reliability and Repeatability of a Lameness Scoring System for Use as an Indicator of Welfare in Dairy Cattle, Acta Agric Scand Sect A, Animal Sci Suppl, 2001, 30:103-107.

Wissink, E.H.J., et al., Identification of porcine alveolar macrophage glycoproteins involved in infection of porcine respiratory and reproductive syndrome virus, Arch Virol, 2003, 148:177-187.

\* cited by examiner

PIG WITH A GENETICALLY MODIFIED CD163 GENE RESISTANT TO PRRSv

CROSS REFERENCE TO RELATED APPLICATIONS

This application claims the benefit of and priority to U.S. Non-Provisional application Ser. No. 17/307,369, filed May 4, 2021. Ser. No. 17/307,369 claims priority to U.S. Provisional Application 63/020,128 filed on May 5, 2020 and to U.S. Provisional Application 63/021,370 filed on May 7, 2020. Each application is hereby incorporated by reference, each in their entirety.

REFERENCE TO SEQUENCE LISTING SUBMITTED ELECTRONICALLY

The official copy of the sequence listing is submitted electronically via EFS-Web as an ASCII-formatted sequence listing with a file named RD-12-2020-US2-SEQLST, created on Oct. 27, 2021, and having a size of 137,066 bytes is filed concurrently with the specification. The sequence listing contained in this ASCII-formatted document is part of the specification and is herein incorporated by reference in its entirety.

FIELD

The present disclosure relates to methods for improving the health of porcine species. In particular, the present disclosure relates to methods of protecting Sus scrofa animals and elite lines from infection by porcine reproductive and respiratory syndrome virus (PRRSv) through targeted polynucleotide edits of CD163 to prevent infection and generate resistant animals, herds, and cell lines.

BACKGROUND

Viral infections are a major source of morbidity and mortality in the livestock industry. In particular, Porcine Reproductive and Respiratory Syndrome (PRRS) is a panzootic infectious disease of pigs, causing major economic losses to the world-wide pig industry. PRRS manifests in pigs of all ages but primarily causes late-term abortions and stillbirths in sows and respiratory disease in piglets. The causative agent of the disease is the positive-strand RNA PRRS virus (PRRSv). PRRS is the most economically important disease of domestic swine in North America, Europe and Asia, costing producers in North America more than $600 million annually.

Currently, there are no effective treatment programs for acute PRRS. As a result, when incidence of PRRS is detected on a farm, depopulation, sufficient cleaning/disinfection, and proper disposal of the carcasses must be used to eliminate the virus. In more extreme cases, whole herd depopulation-repopulation has been documented as an effective method of eliminating the PRRSv from endemically infected herds; however, this method results in significant loss.

Vaccines for PRRSv do exist; however, these vaccines have been unable to control the disease largely due to the genetic diversity within the structural proteins of the virus. Consequently, prevention of infection is currently the best control measure. As a prophylactic measure, farms in a country or zone where PRRSv exists must use stringent control measures, involving an assessment of the health status of replacement gilts and boars, as well as 45-60 days of isolation and acclimatization for incoming stock.

In recent years, more attention has been given to the role CD163 may play in the occurrence of PRRS. Despite the significant heterogeneity in strains of PRRSv, strains of PRRSv all share a tropism for CD163-positive cells. Although CD163 is a virus receptor, the CD163 scavenger receptor is also involved in the adhesion of monocytes to endothelial cells. Functions and a detailed description of CD163 are provided in Onofre, Gabriela et al., *ACTA MEDICA*, 2009, 52, 57-61.

CD163 is a 130 kDa type 1 membrane protein considered to be a fusion receptor for the PRRS virus; it is mapped to chromosome 5 in pigs. The basic transcript encodes for a protein of 1076 amino acids. There are five reported isoforms of CD163; three of the isoforms display different splicing forms of their cytoplasmic domains. Generally, however, the genomic molecule sequence of CD163 comprises 17 exons coding for a peptide signal sequence, nine scavenger receptor cysteine-rich (SRCR) domains, two proline serine threonine (PST) linker domains, a cytoplasmic domain, and a short cytoplasmic tail. CD163 has been described as the receptor for PRRSv. Domain 5 (SRCR5) of the protein is the interaction site for the virus. Exon 7 of CD163 encodes the SRCR domain 5 (SRCR5) that serves as an interaction site for the PRRSv in vitro. Burkard (Burkard, C., PLoS Pathog. 2017, 23, 13, e1006206.) demonstrated that removal of CD163 exon 7 confers PRRSv resistance to porcine macrophages. The guides used in that work (set forth as targeting sequences including the PAM in SEQ ID NOs: 272 and 273), however, may lack sufficient activity and specificity for gene editing as part of a commercial breeding program. Further work by Whitworth and colleagues included creating a 123 bp deletion in Exon 7 using guides as set forth (including the PAM) in SEQ ID NO: 354 and SEQ ID NO: 211 (Whitworth, K. M., Biol. Reprod., 2014, 91, 1-13). Whitworth et al. (Whitworth, K. M., Nature Biotechnology, 2016, 34, 20-22) reported the preparation of PRRSv resistant pigs by knocking out the function of CD163.

Genome editing includes altering the genome by deleting, inserting, or substituting specific nucleic acid sequences. The alteration can be gene- or location-specific. Genome editing can use site-directed nucleases, such as Cas proteins and their cognate polynucleotides.

Clustered regularly interspaced short palindromic repeats (CRISPR) and CRISPR-associated proteins (Cas) constitute the CRISPR-Cas system.

Cas9 is an exemplary Type II CRISPR Cas protein. Cas9 is an endonuclease that can be programmed by the tracrRNA/crRNA to cleave, in a site-specific manner, a DNA target sequence using two distinct endonuclease domains (HNH and RuvC/RNase H-like domains) (see U.S. Patent Application Publication No. 2014-0068797, published 6 Mar. 2014; see also Jinek, M., et al., *Science*, 337:816-821 (2012) and Karvelis et al. *Genome Biology* (2015) 16:253.

The foregoing CD163 edits, while demonstrating some indication of efficacy against PRRSv, cannot be made as precisely and effectively as the edits disclosed herein. There is a need to improve the health of a porcine herd by editing the CD163 gene using guides for improved editing activity and reduced unintended edits, while conferring resistance to PRRSv.

SUMMARY

The present specification provides for and includes edited CD163 genes that confer PRRSv resistance on pigs comprising the edited gene.

In some embodiments, the present teachings provide for and include a CD163 gene edited to confer PRRSv resistance in *Sus scrofa* wherein the edit excises exon 7 and the edited gene can comprise a repaired genomic sequence as set forth in any one of SEQ ID NOs: 426-458 and 520-555. In some configurations, the edited gene can comprise a repaired genomic sequence selected from the group consisting of SEQ ID NOs: 426-458. In various configurations, the repaired gene sequence can comprise SEQ ID NO: 426, SEQ ID NO: 427, SEQ ID NO: 428, SEQ ID NO: 429, SEQ ID NO: 430, SEQ ID NO: 431, SEQ ID NO: 432, SEQ ID NO: 433, SEQ ID NO: 434, SEQ ID NO: 435, SEQ ID NO: 436, SEQ ID NO: 437, SEQ ID NO: 438, SEQ ID NO: 439, SEQ ID NO: 440, SEQ ID NO: 441, SEQ ID NO: 442, SEQ ID NO: 443, SEQ ID NO: 444, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 520, SEQ ID NO: 521, SEQ ID NO: 522, SEQ ID NO: 523, SEQ ID NO: 524, SEQ ID NO: 525, SEQ ID NO: 526, SEQ ID NO: 527, SEQ ID NO: 528, SEQ ID NO: 529, SEQ ID NO: 530, SEQ ID NO: 531, SEQ ID NO: 532, SEQ ID NO: 533, SEQ ID NO: 534, SEQ ID NO: 535, SEQ ID NO: 536, SEQ ID NO: 537, SEQ ID NO: 538, SEQ ID NO: 539, SEQ ID NO: 540, SEQ ID NO: 541, SEQ ID NO: 542, SEQ ID NO: 543, SEQ ID NO: 544, SEQ ID NO: 545, SEQ ID NO: 546, SEQ ID NO: 547, SEQ ID NO: 548, SEQ ID NO: 549, SEQ ID NO: 550, SEQ ID NO: 551, SEQ ID NO: 552, SEQ ID NO: 553, SEQ ID NO: 554, or SEQ ID NO: 555. In various configurations, the edit can be created using a pair of gRNAs, wherein the pair of gRNAs can be SEQ ID NOs: 229 and 256, SEQ ID NOs: 230 and 256, SEQ ID NOs: 231 and 256, SEQ ID NOs: 237 and 256, SEQ ID NOs: 241 and 256, SEQ ID NOs: 229 and 258, SEQ ID NOs: 230 and 258, SEQ ID NOs: 231 and 258, SEQ ID NOs: 237 and 258, SEQ ID NOs: 241 and 258, SEQ ID NOs: 229 and 261, SEQ ID NOs: 230 and 261, SEQ ID NOs: 231 and 261, SEQ ID NOs: 237 and 261, SEQ ID NOs: 241 and 261, SEQ ID NOs: 219 and 256, SEQ ID NOs: 221 and 256, SEQ ID NOs: 224 and 256, SEQ ID NOs: 227 and 256, SEQ ID NOs: 219 and 258, SEQ ID NOs: 221 and 258, SEQ ID NOs: 224 and 258, SEQ ID NOs: 227 and 258, SEQ ID NOs: 219 and 261, SEQ ID NOs: 221 and 261, SEQ ID NOs: 224 and 261, SEQ ID NOs: 227 and 261, SEQ ID NOs: 249 and 256, SEQ ID NOs: 250 and 256, SEQ ID NOs: 249 and 258, SEQ ID NOs: 250 and 258, SEQ ID NOs: 249 and 261, or SEQ ID NOs: 250 and 261. In various configurations, the edit can be created using a pair of gRNAs, wherein the pair of targeting regions can be SEQ ID NOs: 229 and 256, SEQ ID NOs: 230 and 256, SEQ ID NOs: 231 and 256, SEQ ID NOs: 241 and 256, SEQ ID NOs: 229 and 258, SEQ ID NOs: 231 and 258, SEQ ID NOs: 241 and 258, SEQ ID NOs: 219 and 256, SEQ ID NOs: 221 and 256, SEQ ID NOs: 224 and 256, SEQ ID NOs: 227 and 256, SEQ ID NOs: 227 and 258, SEQ ID NOs: 221 and 261, SEQ ID NOs: 249 and 256, SEQ ID NOs: 250 and 256, SEQ ID NOs: 249 and 258, or SEQ ID NOs: 249 and 261.

In various configurations, the edit can be created using a pair of gRNAs wherein the pair of gRNAs can be SEQ ID NOs: 229 and 256. In various configurations, the edit can be created using a pair of gRNAs wherein the pair of gRNAs can be SEQ ID NOs: 230 and 256. In various configurations, the edit can be created using a pair of gRNAs wherein the pair of gRNAs can be SEQ ID NOs: 231 and 256. In various configurations, the edit can be created using a pair of gRNAs wherein the pair of gRNAs can be SEQ ID NOs: 237 and 256. In various configurations, the edit can be created using a pair of gRNAs wherein the pair of gRNAs can be SEQ ID NOs: 241 and 256. In various configurations, the edit can be created using a pair of gRNAs wherein the pair of gRNAs can be SEQ ID NOs: 229 and 258. In various configurations, the edit can be created using a pair of gRNAs wherein the pair of gRNAs can be SEQ ID NOs: 230 and 258. In various configurations, the edit can be created using a pair of gRNAs wherein the pair of gRNAs wherein the pair of targeting regions can be SEQ ID NOs: 231 and 258. In various configurations, the edit can be created using a pair of gRNAs wherein the pair of gRNAs can be SEQ ID NOs: 237 and 258. In various configurations, the edit can be created using a pair of gRNAs wherein the pair of gRNAs can be SEQ ID NOs: 241 and 258. In various configurations, the edit can be created using a pair of gRNAs wherein the pair of gRNAs can be SEQ ID NOs: 229 and 261. In various configurations, the edit can be created using a pair of gRNAs wherein the pair of gRNAs can be SEQ ID NOs: 230 and 261. In various configurations, the edit can be a pair of gRNAs wherein the pair of gRNAs can be SEQ ID NOs: 231 and 261. In various configurations, the edit can be created using a pair of gRNAs wherein the pair of gRNAs can be SEQ ID NOs: 237 and 261. In various configurations, the edit can be created using a pair of gRNAs wherein the pair of gRNAs can be SEQ ID NOs: 241 and 261. In various configurations, the edit can be created using a pair of gRNAs wherein the pair of gRNAs can be SEQ ID NOs: 219 and 256. In various configurations, the edit can be created using a pair of gRNAs wherein the pair of gRNAs can be SEQ ID NOs: 221 and 256. In various configurations, the edit can be created using a pair of gRNAs wherein the pair of gRNAs can be SEQ ID NOs: 224 and 256. In various configurations, the edit can be created using a pair of gRNAs wherein the pair of gRNAs can be SEQ ID NOs: 227 and 256. In various configurations, the edit can be created using a pair of gRNAs wherein the pair of gRNAs can be SEQ ID NOs: 219 and 258. In various configurations, the edit can be created using a pair of gRNAs wherein the pair of gRNAs can be SEQ ID NOs: 221 and 258. In various configurations, the edit can be created using a pair of gRNAs wherein the pair of gRNAs can be SEQ ID NOs: 224 and 258. In various configurations, the edit can be created using a pair of gRNAs wherein the pair of gRNAs can be SEQ ID NOs: 227 and 258. In various configurations, the edit can be created using a pair of gRNAs wherein the pair of gRNAs can be SEQ ID NOs: 219 and 261. In various configurations, the edit can be created using a pair of gRNAs wherein the pair of gRNAs can be SEQ ID NOs: 221 and 261. In various configurations, the edit can be created using a pair of gRNAs wherein the pair of gRNAs can be SEQ ID NOs: 224 and 261. In various configurations, the edit can be created using a pair of gRNAs wherein the pair of gRNAs can be SEQ ID NOs: 227 and 261. In various configurations, the edit can be created using a pair of gRNAs wherein the pair of gRNAs can be SEQ ID NOs: 249 and 256. In various configurations, the edit can be created using a pair of gRNAs wherein the pair of gRNAs can be SEQ ID NOs: 250 and 256. In various configurations, the edit can be created using a pair of gRNAs wherein the pair of gRNAs can be SEQ ID NOs: 249 and 258. In various configurations, the edit can be created using a pair of gRNAs wherein the pair of gRNAs can be SEQ ID NOs: 250 and 258. In various configurations, the edit can be created a pair of gRNAs wherein the pair of gRNAs can be SEQ ID NOs: 249 and 261. In various configurations, the edit can be created using a pair of gRNAs wherein the pair of gRNAs can be SEQ ID NOs: 250 and 261. In various configurations, the repaired genomic sequence can comprise SEQ ID NO: 453 and the edit can be created using sequences set forth in SEQ ID NOs: 249 and 256.

In various configurations, the instant disclosure provides for and includes a *Sus scrofa* cell that can comprise the CD163 gene of the present teachings. In some configurations, the present teachings further provide for and include a cell line that can comprise a plurality of the *Sus scrofa* cell. In some configurations, the cell line can be a fibroblast cell line. In various configurations, the cell, plurality of cells, or cell line can be derived from PIC line 2, PIC line 3, PIC line 15, PIC line 19, PIC line 27, PIC line 62, or PIC line 65. The present teachings further provide for an embryo, piglet, or mature adult that can comprise a plurality of the cell.

The present disclosure also provides for a CD163 gene edited to confer PRRSv resistance in *Sus scrofa* wherein the edit creates a stop codon resulting in a predicted exon 7 amino acid sequence that can be selected from the group consisting of 506-517. In various configurations, the amino acid sequence can be set forth in SEQ ID NO: 506, SEQ ID NO: 507, SEQ ID NO: 508, SEQ ID NO: 509, SEQ ID NO: 510, SEQ ID NO: 511, SEQ ID NO: 512, SEQ ID NO: 513, SEQ ID NO: 514, SEQ ID NO: 515, SEQ ID NO: 516, or SEQ ID NO: 517. In various configurations, the predicted amino acid sequence of exon 7 can be set forth in SEQ ID NO: 513. In some configurations, the edit can be created using gRNAs selected from the group consisting of SEQ ID NOs: 351 and 365, SEQ ID NOs: 351 and 387, SEQ NOs.: 348 and 390, SEQ ID NOs: 348 and 388, SEQ ID NOs: 348 and 395, SEQ ID NOs: 352 and 365, SEQ ID NOs: 352 and 387, SEQ ID NOs: 352 and 399, SEQ ID NOs: 353 and 365, SEQ ID NOs: 353 and 387, SEQ ID NOs: 353 and 399, SEQ ID NOs:354 and 390, SEQ ID NOs: 354 and 388, SEQ ID NOs: 354 and 395, SEQ ID NOs: 358 and 361, SEQ ID NOs: 358 and 362, SEQ ID NOs: 358 and 368, SEQ ID NOs: 358 and 384, SEQ ID NOs: 358 and 394, SEQ ID NOs: 358 and 399, SEQ ID NOs: 359 and 390, SEQ ID NOs: 359 and 388, SEQ ID NOs: 359 and 395, SEQ ID NOs: 360 and 368, SEQ ID NOs: 360 and 384, SEQ ID NOs: 360 and 389, SEQ ID NOs: 360 and 394, SEQ ID NOs: 360 and 397, SEQ ID NOs: 361 and 365, SEQ ID NOs: 361 and 387, SEQ ID NOs: 362 and 390, SEQ ID NOs: 362 and 388, SEQ ID NOs: 362 and 395, SEQ ID NOs. 364 and 365, SEQ ID NOs: 364 and 387, SEQ ID NOs: 364 and 399, SEQ ID NOs: 365 and 368, SEQ ID NOs: 365 and 384, SEQ ID NOs: 365 and 389, SEQ ID NOs: 365 and 394, SEQ ID NOs: 365 and 397, SEQ ID NOs: 366 and 368, SEQ ID NOs: 366 and 384, SEQ ID NOs: 366 and 389, SEQ ID NOs: 366 and 394, and SEQ ID NOs: 366 and 397. In various configurations, the edit can be created using gRNAs selected from the group consisting of SEQ ID NOs: 351 and 365, SEQ ID NOs: 348 and 390, SEQ ID NOs: 348 and 388, SEQ ID NOs: 354 and 390, SEQ ID NOs: 358 and 394, SEQ ID NOs: 362 and 390, and SEQ ID NOs: 366 and 394. In various configurations, the gRNAs used to create the edit can be SEQ ID NOs: 351 and 365. In various configurations, the gRNAs used to create the edit can be SEQ ID NOs: 351 and 387. In various configurations, the gRNAs used to create the edit can be SEQ ID NOs: 348 and 390. In various configurations, the gRNAs used to create the edit can be SEQ ID NOs: 348 and 388. In various configurations, the gRNAs used to create the edit can be SEQ ID NOs: 348 and 395. In various configurations, the gRNAs used to create the edit can be SEQ ID NOs: 352 and 365. In various configurations, the gRNAs used to create the edit can be SEQ ID NOs: 352 and 387. In various configurations, the gRNAs used to create the edit can be SEQ ID NOs: 352 and 399. In various configurations, the gRNAs used to create the edit can be SEQ ID NOs: 353 and 365. In various configurations, the gRNAs used to create the edit can be SEQ ID NOs: 353 and 387. In various configurations, the gRNAs used to create the edit can be SEQ ID NOs: 353 and 399. In various configurations, the gRNAs used to create the edit can be SEQ ID NOs: 354 and 390. In various configurations, the gRNAs used to create the edit can be SEQ ID NOs: 354 and 388. In various configurations, the gRNAs used to create the edit can be SEQ ID NOs: 354 and 395. In various configurations, the gRNAs used to create the edit can be SEQ ID NOs: 358 and 361. In various configurations, the gRNAs used to create the edit can be SEQ ID NOs: 358 and 362. In various configurations, the gRNAs used to create the edit can be SEQ ID NOs: 358 and 368. In various configurations, the gRNAs used to create the edit can be SEQ ID NOs: 358 and 384. In various configurations, the gRNAs used to create the edit can be SEQ ID NOs: 358 and 394. In various configurations, the gRNAs used to create the edit can be SEQ ID NOs: 358 and 399. In various configurations, the gRNAs used to create the edit can be SEQ ID NOs: 359 and 390. In various configurations, the gRNAs used to create the edit can be SEQ ID NOs: 359 and 388. In various configurations, the gRNAs used to create the edit can be SEQ ID NOs: 359 and 395. In various configurations, the gRNAs used to create the edit can be SEQ ID NOs: 360 and 368. In various configurations, the gRNAs used to create the edit can be SEQ ID NOs: 360 and 384. In various configurations, the gRNAs used to create the edit can be SEQ ID NOs: 360 and 389. In various configurations, the gRNAs used to create the edit can be SEQ ID NOs: 360 and 394. In various configurations, the gRNAs used to create the edit can be SEQ ID NOs: 360 and 397. In various configurations, the gRNAs used to create the edit can be SEQ ID NOs: 361 and 365. In various configurations, the gRNAs used to create the edit can be SEQ ID NOs: 361 and 387. In various configurations, the gRNAs used to create the edit can be SEQ ID NOs: 362 and 390. In various configurations, the gRNAs used to create the edit can be SEQ ID NOs: 362 and 388. In various configurations, the gRNAs used to create the edit can be SEQ ID NOs: 362 and 395. In various configurations, the gRNAs used to create the edit can be SEQ ID NOs: 364 and 365. In various configurations, the gRNAs used to create the edit can be SEQ ID NOs: 364 and 387. In various configurations, the gRNAs used to create the edit can be SEQ ID NOs: 364 and 399. In various configurations, the gRNAs used to create the edit can be SEQ ID NOs: 365 and 368. In various configurations, the gRNAs used to create the edit can be SEQ ID NOs: 365 and 384. In various configurations, the gRNAs used to create the edit can be SEQ ID NOs: 365 and 389. In various configurations, the gRNAs used to create the edit can be SEQ ID NOs: 365 and 394. In various configurations, the gRNAs used to create the edit can be SEQ ID NOs: 365 and 397. In various configurations, the gRNAs used to create the edit can be SEQ ID NOs: 366 and 368. In various configurations, the gRNAs used to create the edit can be SEQ ID NOs: 366 and 384. In various configurations, the gRNAs used to create the edit can be SEQ ID NOs: 366 and 389. In various configurations, the gRNAs used to create the edit can be SEQ ID NOs: 366 and 394. In various configurations, the gRNAs used to create the edit can be SEQ ID NOs: 366 and 397.

In various configurations, the edited CD163 gene can have a nucleic acid sequence selected from the group consisting of SEQ ID NO: 459-504. In various configurations, the repaired gene can have a nucleic acid sequence set forth in SEQ ID NO: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, or 504. In various configurations, the repaired gene can have a nucleic acid sequence as set forth in SEQ ID NO: 489. In various configurations the predicted amino acid sequence of exon 7 can be as set forth in SEQ ID NO: 513. In various configurations, the predicted amino acid sequence of the gene can be SEQ ID NO: 513, the repaired gene can have a nucleic acid sequence set forth in SEQ ID NO: 489, and the edit can be created using sequences set forth in SEQ ID NOs: 362 and 390.

The present disclosure provides for and includes a *Sus scrofa* cell that can comprise the CD163 gene edited to comprise an exogenous stop codon as described supra. The present disclosure also provides for a cell line that can comprise a plurality of the cell comprising the CD163 gene edited to comprise an exogenous stop codon. In some configurations, the cell line can be a fibroblast cell line. In various configurations, the cell can be derived from PIC line 2, PIC line 3, PIC line 15, PIC line 19, PIC line 27, PIC line 62, or PIC line 65. The present disclosure also provides for and includes an embryo, piglet, or mature adult comprising a plurality of the cell that can comprise the CD163 gene edited to comprise an exogenous stop codon.

In various embodiments, the present teachings provide for and include a pair of gRNAs for editing a *Sus scrofa* CD163 gene having a sequence as set forth in SEQ ID NOs: 229 and 256, SEQ ID NOs: 230 and 256, SEQ ID NOs: 231 and 256, SEQ ID NOs: 237 and 256, SEQ ID NOs: 241 and 256, SEQ ID NOs: 229 and 258, SEQ ID NOs: 230 and 258, SEQ ID NOs: 231 and 258, SEQ ID NOs: 237 and 258, SEQ ID NOs: 241 and 258, SEQ ID NOs: 229 and 261, SEQ ID NOs: 230 and 261, SEQ ID NOs: 231 and 261, SEQ ID NOs: 237 and 261, SEQ ID NOs: 241 and 261, SEQ ID NOs: 219 and 256, SEQ ID NOs: 221 and 256, SEQ ID NOs: 224 and 256, SEQ ID NOs: 227 and 256, SEQ ID NOs: 219 and 258, SEQ ID NOs: 221 and 258, SEQ ID NOs: 224 and 258, SEQ ID NOs: 227 and 258, SEQ ID NOs: 219 and 261, SEQ ID NOs: 221 and 261, SEQ ID NOs: 224 and 261, SEQ ID NOs: 227 and 261, SEQ ID NOs: 249 and 256, SEQ ID NOs: 250 and 256, SEQ ID NOs: 249 and 258, SEQ ID NOs: 250 and 258, SEQ ID NOs: 249 and 261, SEQ ID NOs: 250 and 261, SEQ ID NOs: 351 and 365, SEQ ID NOs: 351 and 387, SEQ NOs: 348 and 390, SEQ ID NOs: 348 and 388, SEQ ID NOs: 348 and 395, SEQ ID NOs: 352 and 365, SEQ ID NOs: 352 and 387, SEQ ID NOs: 352 and 399, SEQ ID NOs: 353 and 365, SEQ ID NOs: 353 and 387, SEQ ID NOs: 353 and 399, SEQ ID NOs: 354 and 390, SEQ ID NOs: 354 and 388, SEQ ID NOs: 354 and 395, SEQ ID NOs: 358 and 361, SEQ ID NOs: 358 and 362, SEQ ID NOs: 358 and 368, SEQ ID NOs: 358 and 384, SEQ ID NOs: 358 and 394, SEQ ID NOs: 358 and 399, SEQ ID NOs: 359 and 390, SEQ ID NOs: 359 and 388, SEQ ID NOs: 359 and 395, SEQ ID NOs: 360 and 368, SEQ ID NOs: 360 and 384, SEQ ID NOs: 360 and 389, SEQ ID NOs: 360 and 394, SEQ ID NOs: 360 and 397, SEQ ID NOs: 361 and 365, SEQ ID NOs: 361 and 387, SEQ ID NOs: 362 and 390, SEQ ID NOs: 362 and 388, SEQ ID NOs: 362 and 395, SEQ ID NOs: 364 and 365, SEQ ID NOs: 364 and 387, SEQ ID NOs: 364 and 399, SEQ ID NOs: 365 and 368, SEQ ID NOs: 365 and 384, SEQ ID NOs: 365 and 389, SEQ ID NOs: 365 and 394, SEQ ID NOs: 365 and 397, SEQ ID NOs: 366 and 368, SEQ ID NOs: 366 and 384, SEQ ID NOs: 366 and 389, SEQ ID NOs: 366 and 394, or SEQ ID NOs: 366 and 397. In some configurations, the pair of gRNAs can have a sequence as set forth in SEQ ID NOs: 229 and 256, SEQ ID NOs: 230 and 256, SEQ ID NOs: 231 and 256, SEQ ID NOs: 241 and 256, SEQ ID NOs: 229 and 258, SEQ ID NOs: 231 and 258, SEQ ID NOs: 241 and 258, SEQ ID NOs: 219 and 256, SEQ ID NOs: 221 and 256, SEQ ID NOs: 224 and 256, SEQ ID NOs: 227 and 256, SEQ ID NOs: 227 and 258, SEQ ID NOs: 221 and 261, SEQ ID NOs: 249 and 256, SEQ ID NOs: 250 and 256, SEQ ID NOs: 249 and 258, SEQ ID NOs: 249 and 261, SEQ ID NOs: 351 and 365, SEQ ID NOs: 348 and 390, SEQ ID NOs: 348 and 388, SEQ ID NOs: 354 and 390, SEQ ID NOs: 358 and 394, SEQ ID NOs: 362 and 390, or SEQ ID NOs: 366 and 394. In various configurations, the pair of gRNAs can have a sequence as set forth in SEQ ID NOs: 249 and 256. In various configurations, the pair of gRNAs can have a sequence as set forth in SEQ ID NOs: 362 and 390.

The present disclosure provides for and includes a CRISPR complex for editing a CD163 gene of *Sus scrofa* comprising a pair of gRNAs of the present teachings.

The present disclosure provides for and includes a method for editing a CD163 gene of *Sus scrofa* comprising using a CRISPR-CAS complex comprising a pair of gRNAs of the present teachings.

The present disclosure provides for and includes a method for preparing a PRSSV resistant *Sus scrofa* cell by using a CRISPR-CAS complex comprising the pair of gRNAs of the present teachings.

The present disclosure provides for and includes a method of producing PRRSv resistant *Sus scrofa* animals, comprising: a) editing a CD163 gene of a *Sus scrofa* cell or a plurality of *Sus scrofa* cells using a CRISPR complex comprising a pair of gRNAs of the present teachings; and b) producing an animal from the cell or plurality of cells.

The present disclosure provides for and includes the use of a cell line according to the present teachings in producing PRRSv resistant animals.

The present disclosure also provides for and includes an embryo, piglet, or mature adult comprising a plurality of the cell according to the present teachings.

In various embodiments the present disclosure provides for and includes a method of determining the presence or absence of an edited sequence having 90% or 95% identity with a sequence set forth in SEQ ID NO: 453 comprising performing real time PCR with a) differentially labeled probes of sequences set forth in SEQ ID NO: 564 and SEQ ID NO: 558 or 561; b) a primer pair set forth in SEQ ID NOs: 562 and 563; and c) a primer pair set forth in SEQ ID NOs: 556 and 557 or SEQ ID NOs: 559 and 560. In some configurations, the edited sequence can have 100% identity with the sequence set forth in SEQ ID NO: 453. In some configurations, the edited sequence can have 90% identity with the sequence set forth in SEQ ID NO: 453. In some configurations, the edited sequence can have 95% identity with the sequence set forth in SEQ ID NO: 453.

In various embodiments, the present teachings provide for and include a PCR primer selected from the group consisting of SEQ ID NO: 556, SEQ ID NO: 557, SEQ ID NO: 559, SEQ ID NO: 560, SEQ ID NO: 562, and SEQ ID NO: 563. In some configurations, the PCR primer can have a sequence as set forth in SEQ ID NO: 556. In various configurations, the PCR primer can have a sequence as set forth in SEQ ID NO: 557. In various configurations, the PCR primer can have a sequence as set forth in SEQ ID NO: 559. In various configurations, the PCR primer can have a sequence as set forth in SEQ ID NO: 560. In various configurations, the PCR primer can have a sequence as set forth in SEQ ID NO: 562. In various configurations, the PCR primer can have a sequence as set forth in SEQ ID NO: 563.

In some embodiments, the present disclosure provides for and includes a real time PCR probe selected from the group consisting of SEQ ID NO: 558, SEQ ID NO: 561, and SEQ ID NO: 564. In some configurations, the probe has a sequence as set forth in SEQ ID NO: 558. In various configurations, the probe has a sequence as set forth in SEQ ID NO: 561. In various configurations, the probe has a sequence as set forth in SEQ ID NO: 564.

In various embodiments, the present teachings provide for and include the use of PCR primers set forth in a) SEQ ID NO: 556 and 557 and SEQ ID NO: 562 and 563 or b) SEQ ID NO: 559 and 560 and SEQ ID NO: 562 and 563 to determine the presence or absence of an edited genome sequence set forth in SEQ ID NO: 453.

In various embodiments, the present teachings provide for and include the use of PCR probes set forth in a) SEQ ID NOs: 558 and 564 or b) SEQ ID NOs: 561 and 564 to determine the presence or absence of an edited genome sequence set forth in SEQ ID NO: 453.

In various embodiments, the present teachings provide for and include a method of creating a PRRSv resistant pig comprising editing the pig's genome to comprise a genomic sequence as set forth in SEQ ID NO: 453. In some configurations, the editing the pig's genome can comprise administering gRNAs having sequences set forth in SEQ ID NOs: 249 and 256. In various configurations, the administering comprises injecting pre-formed RNP complexes comprising the gRNAs and a CAS protein into a zygote, embryo, or MII oocyte. In various configurations, the pig is a PIC™ line 2 (Pig Improvement Company, Ltd, Basingstoke, UK), PIC™ line 3, PIC™ line 15, PIC™ line 19, PIC™ line 27, PIC™ line 62, or PIC™ line 65 pig.

In various embodiments, the present disclosure provides for and includes, a Sus scrofa animal comprising an edited gene that confers PRRSv resistance in Sus scrofa wherein the edit excises exon 7 and the edited gene comprises a repaired genomic sequence set forth in SEQ ID NO: 453. In some configurations, the edit can be made with guide RNAs (gRNAs) having sequences set forth in SEQ ID NOs: 249 and 256. In various configurations, the animal can be an edited animal of PIC™ line 2, PIC™ line 3, PIC™ line 15, PIC™ line 19, PIC™ line 27, PIC™ line 62, or PIC™ line 65. In various configurations, the present disclosure provides for and includes a cell prepared from the animal of the present teachings. In various configurations, the present disclosure provides for and includes a cell line prepared from the cell according to the present teachings. In some configurations, the cell line can be a fibroblast cell line.

In some embodiments, the present teachings provide for and include a CD163 gene edited to confer PRRSv resistance in Sus scrofa wherein the edit excises exon 7 and the edited gene comprises a repaired genomic sequence set forth in SEQ ID NO: 453. In some configurations, the edit is created using sequences set forth in SEQ ID NOs: 249 and 256. In various configurations, the present disclosure provides for a Sus scrofa cell comprising the CD163 gene according to the present teachings. In some configurations, the present disclosure provides for a cell line comprising a plurality of the cell according to the present teachings. In some configurations, the cell line can be a fibroblast cell line. In various configurations, the cell can be isolated from PIC line 2, PIC line 3, PIC line 15, PIC line 19, PIC line 27, PIC line 62, or PIC line 65.

In various embodiments, the present disclosure provides for and includes a pair of gRNAs for editing a Sus scrofa CD163 gene comprising the guide sequences set forth in SEQ ID NOs: 249 and 256.

In various embodiments, the present teachings provide for and include a method of creating a PRRSv resistant pig comprising editing the pig's genome to comprise a genomic sequence as set forth in SEQ ID NO: 453. In some configurations, editing the pig's genome can comprise administering gRNAs having sequences set forth in SEQ ID NOs: 249 and 256. In some configurations, the administering can comprise injecting pre-formed RNP complexes comprising the gRNAs and a CAS protein into a zygote, embryo, or MII oocyte. In various configurations, the pig can be a PIC™ line 2, PIC™ line 3, PIC™ line 15, PIC™ line 19, PIC™ line 27, PIC™ line 62, or PIC™ line 65 pig.

DETAILED DESCRIPTION

The aspects of the present teachings include, but are not limited to, particular methods of improving the health of a porcine species by targeted inactivation of CD163, which can vary and are understood by skilled artisans. It is further to be understood that all terminology used herein is for the purpose of describing particular aspects only, and is not intended to be limiting in any manner or scope. For example, as used in this specification and the appended claims, the singular forms "a," "an," and "the" can include plural referents unless the content clearly indicates otherwise. Further, all units, prefixes, and symbols may be denoted in their SI accepted forms. Numeric ranges recited within the specification are inclusive of the numbers defining the range and include each integer within the defined range.

So that the present application may be more readily understood, certain terms are first defined. Unless defined otherwise, all technical and scientific terms used herein have the same meaning as commonly understood by one of ordinary skill in the art to which aspects of the present application pertain. Many methods and materials similar, modified, or equivalent to those described herein can be used in the practice of the aspects of the present application without undue experimentation, the preferred materials and methods are described herein. In describing and claiming the aspects of the present application, the following terminology will be used in accordance with the definitions set out below.

As used herein, "animal cell" means a cell, including, but not limited to, a somatic cell, culture cell, gamete cell, blood cell, zygote, and embryonic cell. These animal cells can be reproductive or non-reproductive cells. As used herein, cells may be isolated from an animal or embryo and maintained in tissue culture. Also included are mixed cultures that can comprise gene edited cells of the present specification and a non-gene edited support cell or feeder cell.

As used herein, the terms "gene edited," "genetically edited," and "genome-edited," refer to the use of homing technology with naturally occurring or artificially engineered endonucleases, often referred to as "homing endonucleases," or "targeting endonucleases." "Genome-editing" and "gene editing," refer to altering the genome by deleting, inserting, or substituting specific nucleic acid sequences. The altering can be gene or location specific, but need not be altering the sequence of a gene per se. Genome editing can use endonucleases such as the CRISPR system to cut a nucleic acid, thereby generating a site for the alteration. Other endonucleases are available and are suitable for use; however, off-site cutting and specificity can be significant problems. In systems like CRISPR and others, the nuclease can be directed to the target site by complexing with a polynucleotide, herein called a "target sequence," to introduce a site specific DSB. Not to be limited by theory, the DSB can then be repaired by endogenous non-homologous end joining (NHEJ) machinery.

A number of endonucleases are known that are suitable for, and have been adapted to, gene editing. Gene editing methods are known in the art, including Clustered Regularly Interspaced Short Palindromic Repeats (CRISPR) systems (e.g., the CRISPR/Cas9 system), Transcription Activator-Like Effector Nucleases (TALENs), and Gene editing nucleases including Zinc Finger Nucleases (ZFNs). Gene edited animals can be distinguished from transgenic animals by the incorporation of exogenous DNA sequences, particularly sequences having identity with sequences from foreign species in the latter. Here, the terms include, and provide for, small deletions and insertions that do not introduce more than 10 nucleotides. The terms also encompass progeny animals such as those created by sexual crosses or asexual propagation from the initial gene edited animal.

As used herein, the term "repair template" or "repair sequences" refers to a polynucleotide introduced into a cell undergoing DSB repair at nuclease targeted locations in the genome to guide the repair and provide accurate and selective editing. Repair templates can be used to selectively change or delete sequences at a locus having a DSB and generally comprise a 5' genome hybridizing region and a 3' genome hybridizing region. In an aspect, the 5' genome hybridizing and 3' genome hybridizing regions can share at least 80% homology. In an aspect, the 5' genome hybridizing and 3' genome hybridizing regions can share identity. Further descriptions of the repair templates of the present disclosure are provided below. For deletion templates, a contiguous region of the genome can be separated by the deletion of one or more nucleotides. Targeted editing of individual bases can be prepared using repair templates comprising a contiguous region of a genome and having one or more base changes, including addition of a stop codon. The percentage identity of a repair template to a contiguous region of the genome can be between 80% and 100% using an ungapped alignment. As provided herein, a core region of identity within a repair template is provided that may be flanked by a flanking homology region sharing between 80% and 100% homology to the targeted chromosomal region. Not to be limited by theory, the core region identity can increase the fidelity of the repair process while extended regions of homology on either side increase the efficiency and allow for genotypic variation among cells targeted for editing.

As used herein, the term "wild type" or "WT" refers to a phenotype, genotype, or gene that predominates in a natural population of pigs or line of pigs. When used to compare phenotypes and genotypes of gene edited cells and animals of specific lines, the term "wild type" refers to non-gene edited cells and animals of the same line. In an aspect, the present disclosure provides for comparison of edited pigs to non-edited pigs of a similar breed having a similar genetic background. In an aspect, the present disclosure provides for comparison of edited pigs to non-edited pigs of the same breeding line.

As used herein, the term "knock-out" refers to the disruption of gene function by reduction or elimination of its expression. Knock-outs may be generated through the creation of double-strand breaks (DSBs) in the chromosome which can then be repaired using either non-homologous end joining (NHEJ) or homologous recombination of DNA repair templates or targeting vectors by homology-directed repair (HDR). Not to be limited by theory, HDR knock-outs may also be prepared by microhomology-mediated end joining providing a repair template to insert, delete, or edit genomic sequences. Knock-outs may also be generated through replacement vectors, or hit-and-run vectors, or random insertion of a gene trap vector resulting in complete, partial, or conditional loss of gene function.

References herein to a deletion in a nucleotide sequence spanning a range are inclusive of all nucleotides in the listed range. For example, a 5 base pair deletion from nucleotide "a" to nucleotide "e" means that each of nucleotides "a," "b," "c," "d," and "e" have been deleted (where "b," "c," and "d" are between "a" and "e").

As used herein, the term "edit" includes alterations in the nucleotide sequence of a polynucleotide, such as, for example, a gene, coding DNA sequence (CDS), or non-coding DNA sequence, compared to the wild-type sequence. The term "edits" may include insertions, deletions, splice-donor site edits, point-edits, and the like.

As used herein, the term "clustered regularly interspaced short palindromic repeats" or "CRISPR" refers to a gene editing system utilizing a CRISPR segment of genetic material, and the RNA segments and enzymes it produces, to identify and modify specific DNA sequences in the genome of other organisms. CRISPR systems include Type I, Type II, and Type III CRISPR systems. As used herein, the term "CRISPR associated protein" or "Cas" refers to a protein family that can be strictly associated with CRISPR elements and always occurs near a repeat cluster of CRISPR segments. For example, Cas proteins can include, but are not limited to, Cas9 family member proteins, Cas6 family member proteins (e.g., Csy4 and Cas6), and Cas5 family member proteins. Examples of Cas protein families and methods of identifying the same have been disclosed in Haft, Daniel H., et al., *PLoS Comput. Bio.*, 2005, 1, e60.

While not being limited by any particular scientific theory, a CRISPR nuclease can form a complex with a guide RNA (gRNA), which hybridizes with a complementary target nucleic acid molecule, thereby guiding the CRISPR nuclease to the target nucleic acid molecule. The crRNA comprises a repeat sequence and a spacer sequence which can be complementary to a specific protospacer sequence in an invading pathogen. It is the spacer sequence that can be designed to be complementary to target sequences in a eukaryotic genome. CRISPR nucleases can associate with their respective crRNAs in their active forms. The present specification provides for, and includes a crRNA that can comprise an RNA spacer comprising the first 20 nucleotides of each of SEQ ID NOs: 22 to 271 and 347 to 425. As used herein, each of SEQ ID NOs: 22 to 271 and 347 to 425 provides for, and includes, the corresponding RNA sequence substituting uridine for the thymidine and ribose for deoxyribose. Also, as used herein, the SEQ ID NOs include the PAM (see below) which is present in the genome sequence targeted. Skilled artisans will recognize that the gRNA targeting this sequence would not include the PAM, and therefore would recognize that a gRNA having a sequence set forth in these SEQ ID NOs would only include the first 20 nucleotides, thus excluding the PAM.

Some CRISPR nucleases, such as CasX and Cas9, can require another non-coding RNA component, referred to as a trans-activating crRNA (tracrRNA), to have functional activity. A crRNA comprising a spacer sequence selected from the group consisting of the first 20 nucleotides of each of SEQ ID NOs: 22 to 271 and the first 20 nucleotides of each of SEQ ID NOs: 347 to 425 can be covalently linked to the 5' end of a tracrRNA into one nucleic acid molecule in what is herein referred to as a "single guide RNA" (sgRNA), as described in Jinek, et al., *Science*, 337, 2012, 816-821. As used herein, the tracrRNA is also referred to as "guide RNA backbone" or "the backbone" sequence. As used herein, gRNA includes both a single guide RNA or separate molecules comprising the spacer sequence in the crRNA for use with a separate tracrRNA. The gRNA can guide the active Cas complex to a target site complementary to the spacer sequence in the crRNA, where the Cas nuclease can cleave the target site. The crRNA can have a region of complementarity to a potential DNA target sequence and a second region that can form base-pair hydrogen bonds with the tracrRNA to form a secondary structure, typically to form at least one stem structure. The region of complementarity to the DNA target sequence can be the spacer or spacer sequence. The tracrRNA and a crRNA can interact through a number of base-pair hydrogen bonds to form secondary RNA structures. Complex formation between tracrRNA/crRNA and Cas9 protein can result in a conformational change of the Cas9 protein that facilitates binding to DNA, endonuclease activities of the Cas9 protein, and crRNA-guided site-specific DNA cleavage by the endonuclease Cas9 (Svitashev et al., Nature Communications, 2016, 7, 113274). In practice, the 20 nucleotides and the guide RNA backbone can be DNA (that can be expressed from a promoter to be transcribed in vivo (in cells) or in vitro (via T7 polymerase) to form an RNA guide or the guide RNA backbone can be chemically synthesized dual (crRNA and trRNA) guide or single guide RNA.

For a Cas9 protein/tracrRNA/crRNA complex to cleave a double-stranded DNA target sequence, the DNA target sequence can be adjacent to a cognate protospacer adjacent motif (PAM). By designing a crRNA to have an appropriate spacer sequence, the complex can be targeted to cleave at a locus of interest, e.g., a locus at which sequence modification is desired.

A variety of Type II CRISPR-Cas system crRNA and tracrRNA sequences, and associated predicted secondary structures are known in the art (see, e.g., Ran, F. A., et al., *Nature,* 2015, 520, 186-191; Fonfara et al., *Nucleic Acids Research,* 2014, 42, 2577-2590). The Type II CRISPR-Cas system of Ran et al., is provided herein in an aspect.

The spacer of Type II CRISPR-Cas systems can hybridize to a nucleic acid target sequence that is located 5' or 3' of a PAM, depending upon the Cas protein to be used. A PAM can vary depending upon the Cas polypeptide to be used. For example, if Cas9 from *S. pyogenes* is used, the PAM can be a sequence in the nucleic acid target sequence that comprises the sequence 5'-NRR-3', wherein R can be either A or G, N is any nucleotide, and N is immediately 3' of the nucleic acid target sequence targeted by the nucleic acid target binding sequence. Preferably, the PAM of *S. pyogenes* comprises 5'-NGG-3'. In another example, if Cas9 from *S. thermophilus* CRISPR3 (Sther CR3) is used, the PAM can be a sequence in the nucleic acid target sequence that comprises the sequence 5'-nGGnG-3'. (See Sapranauskas et al., *Nucleic Acids Research,* 2011, 39, 9275-9282).

Other Cas proteins recognize other PAMs, and one of skill in the art can determine the PAM for any particular Cas protein. A growing number of CAS proteins and systems are known in the art that are suitable for use with the targeting sequences of the present specification. See Shah et al., *RNA Biol.,* 2013, 10, 891-899. A representative sample of CAS systems and their PAM sequences is provided in Table 1 below.

TABLE 1

Exemplary CRISPR/Cas Systems

| Species/Variant of Cas9 | PAM Sequence | |
|---|---|---|
| *Streptococcus pyogenes* (SP); SpCas9 | 3' NGG | Wu et al., Nat Biotechnol., 2014, 32, 670-676 |
| SpCas9 D1135E variant | 3' NGG (reduced NAG binding) | Nishimasu et al., Science, 2018, 361, 1259-1262. |
| SpCas9 VRER variant | 3' NGCG | Nishimasu et al. (2018) |
| SpCas9 EQR variant | 3' NGAG | Nishimasu et al. (2018) |
| SpCas9 VQR variant | 3' NGAN or NGNG | Nishimasu et al. (2018) |
| *Staphylococcus aureus* (SA); SaCas9 | 3' NNGRRT or NNGRR(N) | Kleinstiver et al., Nature, 2015, 523, 481-485 |
| *Acidaminococcus* sp. (AsCpf1) and *Lachnospiraceae bacterium* (LbCpf1) | 5' TTTV | Fagerlund, R., et al., 2015, Genome Biology, 16, 251 |
| AsCpf1 RR variant | 5' TYCV | Nishimasu et al., Mol Cell., 2017, 67, 139-147 |
| LbCpf1 RR variant | 5' TYCV | Nishimasu et al. (2017) |
| AsCpf1 RVR variant | 5' TATV | Nishimasu et al. (2017) |

TABLE 1-continued

Exemplary CRISPR/Cas Systems

| Species/Variant of Cas9 | PAM Sequence | |
|---|---|---|
| *Neisseria meningitidis* (NM) | 3' NNNNGAT | Hou et al., 2013, Proc. Natl. Acad. Sci. USA, 110, 15644-156449 |
| *Treponema denticola* (TD) | 3' NAAAAC | Sun et al., Biotechnol J., 2018, 13, e1700588 |
| *Campylobacter jejuni* (Cj) | NNNNRYAC | Kim, et al., Nat Commun., 2017, 8, 14500. |
| *Streptococcus thermophilus* CR1 (St) | NNAGAAW | Toth et al., 2016, Biol Direct., 11, 46 |
| *Streptococcus thermophilus* CR3 | nGGnG | Müller etal., Mol Ther., 2016, 24, 636-644 |

Methods that rely on any CRISPR/CAS system can have a PAM sequence of NRR (e.g., NGG and NAA) as provided below for the *S. pyogenes* sequences or can have a PAM sequence of NGGNG as provided for the *S. thermophilus* sequences. Table 3 and the sequence listing provide the targeting sequences and chromosomal locations. It will also be appreciated by those of skill in the art that known CAS systems having different PAM requirements can be engineered to recognize and utilize the target sequences disclosed herein. Examples of modifications are presented in Table 1.

The terms "CRISPR/CasN or "CRISPR/CasN system" refer to a programmable nuclease system for genetic editing that includes a CasN (e.g., Cas2, Cas5, Cas6, Cas9, etc.) protein, or derivative thereof, and one or more non-coding RNAs that can provide the function of a CRISPR RNA (crRNA) and trans-activating RNA (tracrRNA) for the CasN. The crRNA and tracrRNA can be used individually or can be combined to produce a "guide RNA" (gRNA). The crRNA or gRNA can provide a sequence that is complementary to the genomic target.

The term "Cpf1" or "CAS12" refers to another programmable RNA-guided endonuclease of a class 2 CRISPR-Cas system, described and used for gene editing purposes (Zetsche et al., *Cell,* 163:759-771, 2015). This system can use a non-specific endonuclease unit from the Cpf1 protein family, with a specificity of cleavage conferred by a single crRNA (lacking tracrRNA). Similar to Cas9, the Cpf1 coding sequence can be fused to UTR sequences described herein to improve its stability, and thus the efficiency of the resulting gene editing method.

As used herein, the terms "transcription activator-like effector nucleases" or "TALENS" refer to nucleases engineered to enable the targeted alteration of a given DNA sequence. TALENs can comprise a non-specific DNA-cleaving nuclease fused to a TALE DNA-binding domain that can be engineered to allow targeted gene editing. A "TALE DNA-binding domain" or "TALE" can be a polypeptide comprising one or more TALE repeat domains/units. The repeat domains can be involved in binding of the TALE to its cognate target DNA sequence. A single "repeat unit" (also referred to as a "repeat") can be 33-35 amino acids in length and exhibits at least some sequence homology with other TALE repeat sequences within a naturally occurring TALE protein. A "designed" DNA binding protein can be a protein not occurring in nature whose design/composition results principally from rational criteria. TALENS are discussed and disclosed in Joung et al., *Nat. Rev. Mol. Cell. Biol.,* 2013, 14, 49-55. A "selected TALE" can be a protein not found in nature whose production results primarily from an empirical process such as phage display, interaction trap, or hybrid selection. The present specification provides for, and includes, the use of TALENS to the pigs described herein.

"Resistance" or "disease resistance" refers to the extent to which an organism can defend itself from and/or withstand the attack of a pathogen and remain unaffected. An organism may demonstrate complete resistance, meaning it remains virtually unaffected by a pathogen. Alternatively, an organism may demonstrate partial resistance, wherein the extent to which the pathogen affects the organisms can be less than a comparable organism with no resistance. Resistance may stem from a particular characteristic of the organism, allowing the organism to avoid the outcome of organism-pathogen interactions. Resistance can be demonstrated by the extent to which an organism can avoid the disease symptoms associated with, or reduce the incidence/severity of clinical signs, or reduce the clinical symptoms associated with a pathogen.

The terms "increased resistance" and "reduced susceptibility" refer to a statistically significant reduction of the incidence and/or severity of clinical signs or clinical symptoms which are associated with infection by a given pathogen. For example, "increased resistance" or "reduced susceptibility" refer to a statistically significant reduction of the incidence and/or severity of clinical signs or clinical symptoms which are associated with infection by PRRSv in an animal comprising a deleted or inactivated chromosomal sequence in a CD163 gene protein as compared to a control animal having an unmodified chromosomal sequence. The term "statistically significant reduction of clinical symptoms" means, but is not limited to, the frequency in the incidence of at least one clinical symptom in the modified group of subjects and, in some aspects, clinical symptoms may be statistically reduced by at least 80% lower than in the non-modified control group after the challenge with the infectious agent.

As used herein, the terms "reduction of the incidence and/or severity of clinical signs" or "reduction of clinical symptoms" mean reducing the number of infected subjects in a group, reducing or eliminating the number of subjects exhibiting clinical signs of infection, or reducing the severity of any clinical signs that are present in one or more subjects, in comparison to wild-type infection in an otherwise similar genetic background. For example, these terms encompass any clinical signs of infection, lung pathology, viremia, antibody production, reduction of pathogen load, pathogen shedding, reduction in pathogen transmission, or reduction of any clinical sign symptomatic of PRRS when compared to an otherwise similar background. Comparisons of clinical signs between non-edited CD163 pigs and CD163 edited pigs can be individually or between herds. In an aspect, an individual pig does not present clinical signs. In an aspect, a herd of CD163 edited pigs present reduced clinical signs. In an aspect, the size of the herd can be at least 100 animals. In an aspect, CD163 edited pigs of the present specification can have reduced clinical signs of reproductive syndrome. In an aspect, a herd of CD163 edited pigs can have a reduced number of premature farrowings, reduced numbers of stillborn or mummified piglets, reduced numbers of PRRSv-positive piglets, or reductions in delays to return to service of sow. In an aspect, CD163 edited pigs of the present specification can have reduced clinical signs in sows and gilts including, but not limited to, reduced anorexia, reduced fever, reduced lethargy, reduced pneumonia, reduced agalactica, and reduced subcutaneous and hind limb edema. In an aspect, gilts and sows that are CD163 edited pigs of the present specification can have reduced red/blue discoloration of the ears and vulva. In an aspect, CD163 edited sows can exhibit reduced delays to return to estrus after weaning. The present specification provides for, and includes, reduced deaths among a herd of CD163 edited gilts and sows. Also included and provided for by the present specification are reduced clinical signs in finishing pigs. In an aspect, a herd of CD163 edited finishing pigs can have reduced respiratory clinical signs selected from the group consisting of fever, sneezing, hyperpnoea, dyspnea, coughing, pneumonia, lethargy, periocular edema, and oculo-nasal discharge. Preferably these clinical signs can be reduced in one or more animals of the present teachings by at least 10% in comparison to subjects not having a modification in the CD163 gene and having a similar background and that become infected. In an aspect, clinical signs can be reduced in subjects of the present teachings by at least 80%. In another aspect, clinical signs can be reduced in pigs of the present teachings by at least 85%. In a further aspect, clinical signs can be reduced in pigs of the present teachings by at least 90%. In yet another aspect, clinical signs can be reduced in pigs of the present teachings by at least 95%. In aspects according to the present disclosure, clinical signs can be reduced by 80% to 100% relative to non-edited CD163 pigs.

The term "breeding" as used herein refers to a process comprising the selection of superior male and superior female animals use for creation of the next generation of offspring. This process further comprises the union of male and female gametes so that fertilization occurs. Such a union may be brought about by mating (copulation) or by in vitro or in vivo artificial methods. Such artificial methods can include, but are not limited to, artificial insemination, surgical assisted artificial insemination, in vitro fertilization, intracytoplasmic sperm injection, zona drilling, in vitro culture of fertilized oocytes, ovary transfer, and ovary splitting. The term "breeding" as used herein also can include transferring of a fertilized oocyte into the reproductive tract of a female animal in order to allow for more offspring from a particular elite female.

As used herein, "reference sequence" is a defined sequence used as a basis for sequence comparison. A reference sequence may be a subset or the entirety of a specified sequence; for example, as a segment of a full-length promoter sequence, or the complete promoter sequence. In an aspect, the reference sequence can be the Sscrofa11.1 reference genome (GenBank accession: GCA_000003025.6).

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity can be determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence can be equal to the number of identical positions between the two sequences divided by the total number of positions in the query sequence over its length (or a comparison window), which is then multiplied by 100%. When percentage of sequence identity is used in reference to proteins, it is recognized that residue positions which are not identical often can differ by conservative amino acid substitutions, where amino acid residues can be substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool (BLAST®, National Library of Medicine, Bethesda, MD), etc., that can be used to compare the sequence identity or similarity between two or more nucleotide or protein sequences. Although other alignment and comparison methods are known in the art, the alignment and percent identity between two sequences (including the percent identity ranges described above) can be as determined by the ClustalW algorithm, see, e.g., Chenna, R., et al., *Nucleic Acids Research,* 2003, 31, 3497-3500; Thompson, J. D., et al., *Nucleic Acids Research,* 1994, 22, 4673-4680; Larkin M A et al., *Bioinformatics,* 2007, 23, 2947-2948; and Altschul, S. F., et al., *J. Mol. Biol.,* 1990, 215, 403-410.

Identity to a sequence used herein can be expressed in terms of a percent identity between two sequences as determined according to alignment of the two sequences. The present specification provides for repair template sequences that can have at least 80% identity to a contiguous region of a genome. In an aspect, the repair template can have a 5' region and a 3' region sharing at least 80% identity to a contiguous region of the genome and a core region having identity to the chromosome sequences flanking the intended gene edit site.

The present specification provides for, and includes, but is not limited to, target sequences that can be 100% identical to the target sequences selected from the group consisting of SEQ ID NOs: 22 to 271 and 347 to 425. These target sequences can comprise a PAM sequence such as those listed on Table 1. Accordingly, when incorporated into a guide RNA, in an aspect the spacer region can share 100% identity to a sequence selected from the group of the first 20 nucleotides of each of SEQ ID NOs: 22 to 271 and the first 20 nucleotides of each of SEQ ID NOs: 347 to 425. Also included are spacer sequences that can have from 15 to 20 nucleotides of each of SEQ ID NOs: 22 to 271 or from 15 to 20 nucleotides of each of SEQ ID NOs: 347 to 425. (The remainder of the sequence can comprise the PAM sequence which can be present in the genome, but not the gRNA molecules.) Also included and provided for are guide RNA spacer sequences that can have one or more mismatches to the target sequence. In an aspect, the mismatch can be at the distal end of the sequence target sequence to ensure that identity at the endonuclease cleavage site is maintained. Typically, the mismatches can occur at the 5' end of the target sequence relative to the nuclease site at the 3' end. In an aspect, a target sequence, or the spacer sequences of a guide RNA prepared therefrom, may have a single mismatch. In another aspect, a target sequence, or the spacer sequences of a guide RNA prepared therefrom, may have two (2) mismatches. In another aspect, a sequence, or the spacer sequences of a guide RNA prepared therefrom, may have three (3) mismatches. In another aspect, a sequence, or the spacer sequences of a guide RNA prepared therefrom, that may have less than four (4) mismatches are included. In some aspects, the mismatch regions can be limited to terminal nucleotides distal to the PAM sequences and cleavage site.

In an aspect, the target sequences and the spacer sequence of the gRNA guide can have at least 90% identity to a sequence selected from the group consisting of the first 20 nucleotides of each of SEQ ID NOs: 22 to 271 and the first 20 nucleotides of each of SEQ ID NOs: 347 to 425. In a further aspect, the RNA guide can have at least 90% identity and 100% identity at 15 nucleotides at the 3' end of the sequence. In an aspect, the target sequences and the RNA guide can have at least 95% identity. In a further aspect, the RNA guide can have at least 95% identity or 100% identity at 15 nucleotides at the 3' end of the sequence. In an aspect, the target sequences and the RNA guide can have at least 96% identity. In a further aspect, the RNA guide can have at least 96% identity or 100% identity at 15 nucleotides at the 3' end of the sequence. In an aspect, the target sequences and the RNA guide can have at least 97% identity. In a further aspect, the RNA guide can have at least 97% identity or 100% identity at 15 nucleotides at the 3' end of the sequence. In an aspect, the target sequences and the RNA guide can have at least 98% identity. In a further aspect, the RNA guide can have at least 98% identity or 100% identity at 15 nucleotides at the 3' end of the sequence. In an aspect, the target sequences and the RNA guide can have at least 99% identity. In a further aspect, the RNA guide can have at least 99% identity or 100% identity at 15 nucleotides at the 3' end of the sequence. In an aspect, the target sequences and the RNA guide can have at least 100% identity. Also included and provided for by the present specification are spacer sequences that can comprise the first 15 nucleotides each of SEQ ID NOs: 22 to 271 or the first 15 nucleotides each of SEQ ID NOs: 347 to 425. In an aspect, the spacer sequences can comprise the first 16 nucleotides in each of SEQ ID NOs: 22 to 271 or the first 16 nucleotides in each of SEQ ID NOs: 347 to 425. In another aspect, the spacer sequences can comprise the first 17 nucleotides in each of SEQ ID NOs: 22 to 271 or the first 17 nucleotides in each of SEQ ID NOs: 347 to 425. In an aspect, the spacer sequences can comprise the first 18 nucleotides in each of SEQ ID NOs: 22 to 271 or the first 18 nucleotides in each of SEQ ID NOs: 347 to 425. In yet another aspect, the spacer sequences can comprise the first 19 nucleotides in each of SEQ ID NOs: 22 to 271 or the first 19 nucleotides in each of SEQ ID NOs: 347 to 425.

The preferred meaning of "fertilization" as used herein to refer to pig breeding encompasses any technique that produces a viable embryo. Fertilization can include both insemination of female pigs, and in vitro or ex vivo fertilization. There are three commonly available ways to inseminate a sow, namely traditional artificial insemination (AI), intrauterine insemination (IUI), and deep intrauterine insemination (DIUI). These techniques all rely on providing a dose of semen, typically fresh and unfrozen, for insemination. In vitro fertilization (IVF) can be the harvesting of unfertilized oocytes(s) and the subsequent fertilization of those oocytes with semen in vitro (i.e., in the laboratory) instead of in vivo (i.e., in the live animal; insemination discussed above) as in standard ET. The fertilized oocytes(s) or embryo(s) from the oocyte donor can then be transferred into another female (embryo recipient). Embryo transfer (ET) can be the harvesting of fertilized oocytes(s) or embryo (s) from one female (embryo donor) and transfer of those embryo(s) into another female (embryo recipient) whose reproductive status can be synchronized with that of the donor.

As described in Cameron et. al. (*Nat Methods*, 2017, 14, 600-606), the CRISPR-Cas9 system can be used for genome editing in both basic research and biotechnology. The application of CRISPR and related technologies to gene or genome editing can be accompanied by unwanted off-target cleavage activity and possible pathogenic and other negative phenotypic consequences. To minimize off-target cleavage, a variety of genome-wide experimental methods have been recently developed but some methods are potentially biased due to cellular context or inefficiencies in recovering relevant cleavage sites. On approach, the SITE-SEQ® assay (Caribou Biosciences, Inc., Berkeley CA) disclosed in Cameron et. al. enables one to comprehensively list Cas9 cleavage sites in a sample genome, then probe those sites for cellular off-target editing in follow-up experiments through (1) extraction and purification of high-molecular weight genomic DNA, (2) execution of Cas9 Ribonucleoprotein (RNP) cleavage in vitro, (3) fragmentation, adapter ligation, and affinity purification to enrich for Cas9 cleaved fragments, and (4) amplification and indexing of SITE-SEQ® libraries for ILLUMINA® (ILLUMINA®, San Diego, CA) sequencing. (See Cameron et al., *Nat Methods*, 2017, 14, 600-606.) Various other methods of discovering and reducing the number of potential off-target edits are known in the genome editing arts. While such bioinformatics tools can be invaluable for identifying suitable target sequences, the error rate is generally higher than desired and the approach can be limited when the system lacks extensive sequence data. Further, the fidelity of DSB break repair can vary, thus confounding the ability to predict and prevent unwanted off target effects. Further testing of in silico selected target sequences can identify select sequences that have higher efficiencies and fewer off target cuts. Testing in cell culture systems combined with high-throughput sequencing methods can be used to identify poor performing target constructs.

For example, the type II CRISPR system, which is derived from Streptococcus pyogenes (S. pyogenes), can be reconstituted in mammalian cells using Cas9, a specificity-determining CRISPR RNA (crRNA) comprising a backbone sequence and a sequence selected from the group consisting of the first twenty nucleotides of each of SEQ ID NOs: 22 to 271 and the first twenty nucleotides of each of SEQ ID NOs: 347 to 425, and an auxiliary trans-activating RNA (tracrRNA). The term "off target effect" broadly refers to any impact distinct from and not intended as a result of the on-target treatment or procedure. Examples of off-target edits can include double strand breaks at unintended locations that lead to DNA insertions of unintended nucleotides or repair templates, deletions, or rearrangements. For some systems, for example the S. pyogenes and S. thermophilus CRISPR system, the crRNA and tracrRNA duplexes can be fused to generate a single-guide RNA (sgRNA). The first 20 nucleotides of the sgRNA can be complementary to the target DNA sequence and can be the spacer region, and those 20 nucleotides can be followed at the 3' end by a protospacer adjacent motif (PAM) in the genome (but not the guide). In an aspect, the first 20 nucleotides of the sgRNA and PAM sequence can be a sequence selected from the group consisting of SEQ ID NOs: 22 to 271 and 347 to 425. Accordingly, as provided below at Table 2 and SEQ ID NOs: 22 to 271 and 347 to 425, specific targeting of the Cas nuclease from either S. pyogenes or S. thermophilus can be accomplished combining the crRNAs with a backbone sequence. Although the 20-nucleotide guide sequence plus PAM sequence (e.g., 23 to 25 nucleotides) of the sgRNA can provide tightly controlled targeting and cleavage, it has been discovered that off-target cleavage activity can still occur on DNA sequences with between 3-5 base pair mismatches in the PAM-distal part of the sgRNA-guiding sequence. Further, different types of guide RNA structures actually affect the cleavage precision, increasing or decreasing cleave on off-target sites. Various techniques, as well as a further description of off-target cleavage, are reviewed in Zhang et al., *Mol Ther Nucleic Acids*, 2015, 4, e264. The mechanisms and effects of off-target cleavage are still poorly understood, meaning it can be difficult to predict and to compensate for its effects. However, the consequences can be severe; off-target cleavage can ultimately lead to genomic instability and disrupt the functionality of otherwise normal genes.

The present specification provides for, and includes, pigs that can have inactivating edits in both alleles of the CD163 gene and that can be resistant to infection with PRRSv. The CD163 pigs disclosed herein further do not comprise new sequences or polypeptides, nor do they comprise non-native amino acids resulting from frameshifts or missense mutations.

The gene edits disclosed herein allow for the protection of CD163-positive fetuses (e.g., fetuses that have one or two wild-type CD163 alleles). CD163-positive fetuses can be protected from PRRSv infection while in utero so long as the dam possesses inactivating edits in both alleles of her CD163 genes (PCT/US2018/027944). For example, dams having inactivating edits in both alleles of the CD163 gene can be mated with males having two wild-type CD163 alleles, and the resulting heterozygous fetuses will be protected from PRRSv infection in utero.

In an aspect, pigs having inactivating edits in one allele of CD163 can be generated using the methods of the present specification. These pigs having heterozygous CD163 alleles (one edited, one wild-type) can be bred with other pigs also having heterozygous CD163 alleles or homozygous edited CD163 alleles, and offspring from this breeding having homozygous edited CD163 alleles can be selected for resistance to infection with PRRSv. The present disclosure also provides for, and includes, porcine animals and populations, and methods for creating or improving porcine animals and populations, in which the animals can be homozygous for one or more particular genetic markers or alleles. In various aspects, the present disclosure provides for, and includes, animals, and methods for creating or improving crossing porcine animals and populations, by generating animals that can be heterozygous for one or more particular genetic markers or alleles, and crossing said animals with other animals heterozygous for one or more of the particular genetic markers or alleles to produce animals that can be homozygous for the one or more particular genetic markers or alleles. In some aspects, multiple rounds of crossing and/or back-crossing may be required to obtain homozygosity for each of the particular genetic markers and alleles. In other aspects, a single cross may be sufficient to obtain homozygosity.

Various techniques known in the art can be used to inactivate genes to make knock-out animals and/or to introduce edited genes into animals to produce founder animals and to make animal lines, in which the knockout or nucleic acid construct can be integrated into the genome. Such techniques can include, without limitation, pronuclear microinjection (U.S. Pat. No. 4,873,191), retrovirus mediated gene transfer into germ lines (Van der Putten et al., *Proc. Natl. Acad. Sci. USA,* 1985, 82, 6148-1652), gene targeting into embryonic stem cells (Thompson et al., *Cell,* 1989, 56, 313-321), electroporation of embryos (Lo, *Mol. Cell. Biol.,* 1983, 3, 1803-1814), sperm-mediated gene transfer (Lavitrano et al., *Proc. Natl. Acad. Sci. USA,* 2002, 99, 14230-14235; Lavitrano et al., *Reprod. Fert. Develop.,* 2006, 18, 19-23), and in vitro transformation of somatic cells, such as cumulus or mammary cells, or adult, fetal, or embryonic stem cells, followed by nuclear transplantation (Wilmut et al., *Nature,* 1997, 385, 810-813 and Wakayama et al., *Nature,* 1998, 394, 369-374). Pronuclear microinjection, sperm mediated gene transfer, and somatic cell nuclear transfer can be other useful techniques. An animal can be genomically edited in that all of its cells have the edit, including its germ line cells. When methods are used that produce an animal that is mosaic in its modification, the animals may be mosaic and can be further inbred and progeny that are genomically edited can be produced and selected using standard methods. Cloning, for instance, may be used to make a mosaic animal if its cells are edited at the blastocyst stage, or genomic modification can take place when a single-cell is edited. In an aspect, an inactivated knock-out edit can be homozygous.

In an embryo/zygote microinjection aspect, a nucleic acid construct, mRNA, protein, polynucleotides, or combinations thereof, can be introduced into a fertilized egg. In an aspect, one or two cell fertilized eggs can be used. One and two cell fertilized eggs can provide a visible nuclear structure containing the genetic material from the sperm head and the egg within the protoplasm. In an aspect, pronuclear staged fertilized eggs can be obtained in vitro or in vivo (i.e., surgically recovered from the oviduct of donor animals). In another aspect, in vitro fertilized eggs can be produced, for example, from collected swine ovaries by follicles aspirated using methods known in the art. See, e.g., Agung et al., *J Reprod Dev.*, 2013, 59, 103-106 and Appeltant et al., *J Reprod Dev.*, 2016, 62, 439-449. In an aspect, mature oocytes can be provided for use in the in vitro fertilization methods. In another aspect, mature oocytes can be injected with the CRISPR/Cas gene editing system of the present specification.

The present specification further provides for in vitro fertilization of mature oocytes. In an aspect, the oocytes can be matured in vitro as provided above. In another aspect, mature oocytes can be collected from gilts. In vitro fertilization is performed according to established methods. See Appeltant et al., *J Reprod Dev.*, 2011, 57, 9-16, and Fowler et al., *Reprod Biol.*, 2018, 18, 203-211.

Zygotes or embryos can be obtained for germline editing by artificial insemination and flushing. The collected zygotes or embryos can then be edited using the methods provided herein. In an aspect, linearized nucleic acid constructs, mRNA, proteins, polynucleotides or combinations thereof can be injected or otherwise introduced, for example, by electroporation, into one of the pronuclei or into the cytoplasm of a zygote or embryo post-fertilization, or into a gamete cell pre-fertilization. In an aspect, a pre-formed RNP complex comprising the Cas nuclease protein and a guide RNA comprising a backbone of SEQ ID NO: 19 and a targeting sequence selected from any one of SEQ ID NOs: 22 to 271 and 347 to 425 can be prepared and injected into the embryo, zygote, or oocyte. In another aspect, a preformed RNP complex comprising the Cas nuclease and a guide RNA comprising a backbone of SEQ ID NO: 19 and a spacer sequence selected from an RNA sequence of a sequence selected from the group consisting of the first 20 nucleotides of each of SEQ ID NOs: 22 to 271 can be prepared and injected into the embryo, zygote, or oocyte, together with a repair template comprising SEQ ID NOs: 1 to 13 listed in Table 6. Also included, and provided for, by the present specification are the combinations of spacer sequences and repair templates that can have the sequences of SEQ ID NOs:1 to 13 as recited in Table 6. In an aspect, the injected zygotes or embryos can be transferred to a recipient female (e.g., into the oviducts of a recipient female) and allowed to develop in the recipient female to produce the transgenic or gene edited animals. In an aspect, the methods further provide for in vitro or in vivo fertilized zygotes or embryos that can be centrifuged at 15,000×g for 5 minutes to sediment lipids allowing visualization of the pronucleus. The zygotes or embryos can be injected with using an EPPENDORF® FEMTOJET® (EPPENDORF® AG, Germany) injector and can be cultured until blastocyst formation. Rates of embryo cleavage and blastocyst formation and quality can be recorded.

In an aspect, the CRISPR/Cas editing system and gRNA can be provided as a nucleic acid construct. In another aspect, the Cas nuclease may be provided as an mRNA together with a guide RNA comprising a backbone sequence and a targeting sequence selected from the group consisting of the first 20 nucleotides of each of SEQ ID NOs: 22 to 271 and the first 20 nucleotides of each of SEQ ID NOs: 347 to 425. In another aspect, the Cas nuclease may be provided as an mRNA together with a guide RNA comprising a backbone sequence and a targeting sequence selected from the group consisting of the first 20 nucleotides of each of SEQ ID NOs: 22 to 271 together with a repair template listed in Table 6 and selected from the group consisting of SEQ ID NOs: 1 to 13. In a further aspect, the gene targeting complex can be provided by microinjection of a transcribable DNA encoding a Cas nuclease and a guide RNA comprising a backbone sequence and a targeting sequence selected from the group consisting of the first 20 nucleotides of each of SEQ ID NOs: 22 to 271 and the first 20 nucleotides of each of SEQ ID NOs: 347 to 425. In aspects according the present specification, the backbone sequence can be a sequence of SEQ ID NO: 19. Also included and provided for by the present specification are the combinations of targeting sequences and repair templates that can have one of the sequences recited in SEQ ID NOs: 1 to 13. It would be understood by persons of skill in the art that various combinations of nuclease, gRNA, and optionally repair template sequences, can be introduced into oocytes, zygotes, blastula, and embryos to achieve the goals of the present methods. It will be further understood that other backbone sequences can be used in conjunction with the targeting sequences of SEQ ID NOs: 22 to 271 and SEQ ID NOs: 347 to 425 for use with other Cas nucleases. Any Cas nuclease having a PAM sequence of NGG or NGGNG can be suitable for the preparation of a backbone sequence for combination with the targeting sequences of the present specification. In various aspects, the desired edit can have a final genomic sequence of SEQ ID NOs: 426 to 505. In some configurations, the desired edit lacks exon 7 and can have a final nucleotide sequence as set forth in SEQ ID NOs: 426 to 458. In various configurations, the final genomic sequence can include an exogenous stop codon and can have a final genomic sequence as set forth in SEQ ID NOs: 459-504. In various configurations, these partial CD163 genes can have an exon 7 amino acid sequence as set forth in SEQ ID NOs: 506 to 517.

In an aspect, the injected zygotes or embryos can be transferred to a recipient female (e.g., into the oviducts of a recipient female) and allowed to develop in the recipient female to produce the transgenic or gene edited animals. In an aspect, the methods further provide for in vitro or in vivo fertilized zygotes or embryos that can be centrifuged at 15,000×g for 5 minutes to sediment lipids allowing visualization of the pronucleus. The zygotes or embryos can be injected using, for example, an EPPENDORF® FEMTO-JET® injector and can be cultured until blastocyst formation. Rates of embryo cleavage and blastocyst formation and quality can be recorded.

The present specification provides for, and includes, a recipient sow having one or more embryos that can be injected with a CRISPR/Cas/gRNA combination according to the present disclosure. In an aspect, a pre-formed RNP complex can be provided comprising the Cas nuclease and a guide RNA comprising a backbone of SEQ ID NO: 19 and a spacer sequence selected from the group consisting of the first 20 nucleotides of each of SEQ ID NOs: 22 to 271 and the first 20 nucleotides of each of SEQ ID NOs: 347 to 425. In various aspects, two pre-formed RNP complexes can be provided comprising the Cas nuclease and a guide RNA comprising a backbone of SEQ ID NO: 19 and each comprising a different spacer sequence selected from the group consisting of the first 20 nucleotides of each of SEQ ID NOs: 22 to 271 and the first 20 nucleotides of each of SEQ ID NOs: 347 to 425. Also provided for, and included, are recipient sows that can have one or more embryos injected with a pre-formed RNP complex that can comprise the Cas nuclease and a guide RNA comprising a targeting sequence selected from the group consisting of the first 20 nucleotides of each of SEQ ID NOs: 22 to 271 and the first 20 nucleotides of each of SEQ ID NOs: 347-425. In an aspect, the pre-formed RNP complex can be prepared and injected into the embryo, zygote, or oocyte, together with a repair template listed in Table 6 (SEQ ID NOs: 1 to 13). In an aspect, a recipient sow can be a sow of a different line than the donor embryos.

Embryos or zygotes can be surgically transferred into uteri of synchronous recipients. Typically, 100-200 (or 150-200) embryos or zygotes can be deposited into the ampulla-isthmus junction of the oviduct using a catheter. After surgery, real-time ultrasound examination of pregnancy can be performed. In an aspect, the present specification can include a recipient sow having 1 to 100, but more typically 30 to 60 CRISPR/Cas/gRNA combination treated embryos wherein said embryos can comprise a gene edited CD163 gene comprising a sequence of SEQ ID NOs: 1 to 18 or 426 to 505. In an aspect, the transferred embryos can comprise a mosaic of edited cells. Also included are CD163 gene edited embryos that can be non-mosaic.

Methods of improving the health of a livestock animal or herd of livestock can comprise modifying a target sequence in the genome of an animal cell to form a truncated CD163 polypeptide. Also provided for, and included, are improved animals that can have truncated CD163 polypeptides. In some aspects, the predicted truncated polypeptides do not include non-native amino acids. Without being bound by theory, the truncated gene product can be rapidly digested in vivo by cellular proteases. In an aspect of the present specification, the truncated CD163 can result in the complete elimination of the protein. In a further aspect, the truncated CD163 can be non-detectable in vivo. In an aspect, the truncated CD163 can be non-detectable by immunofluorescence labelling and FACS analysis. In yet another aspect, the truncated CD163 can be non-detectable when using any of the expression analysis methods provided in the specification, including those provided in Example 5. In yet another aspect, the truncated CD163 can be non-detectable when using any of the expression analysis methods provided in the specification, including those provided in Example 8.

In another aspect, a gene edited CD163 pig can comprise a truncated CD163 gene with no more than 25 non-native amino acids. Not to be limited by theory, truncated CD163 proteins can be destabilized and targeted for degradation within the cell. Accordingly, CD163 protein sequences and CD163 polypeptides comprising non-native amino acids can be non-detectable. In another aspect, the predicted truncated CD163 protein can comprise no more than 211 amino acids of the native protein. In an aspect, the truncated CD163 protein can be predicted to comprise no more than 144 amino acids of the native protein. In an aspect, the truncated CD163 protein can be predicted to comprise no more than 133 amino acids of the native protein. In yet another aspect, the truncated CD163 protein can be predicted to comprise no more than 129 amino acids of the native protein. In an aspect, the truncated CD163 protein can be predicted to comprise no more than 113 amino acids of the native protein. In yet another aspect, the truncated CD163 protein can be predicted to comprise no more than 108 amino acids of the native protein. In a further aspect, the truncated CD163 protein can be predicted to comprise no more than 93 amino acids of the native protein. In yet another aspect, the truncated CD163 protein can be predicted to comprise no more than 74 amino acids of the native protein. As provided herein, truncated CD163 proteins can comprise between 32 to 211 amino acids of native CD163 polypeptide sequences and no more than 25 non-native amino acids and can be undetectable in cells and cell extracts.

In other aspects, altered CD163 protein can have a truncation with a single amino acid substitution. In some aspects, the altered CD163 protein can have a predicted amino acid sequence of no more than 1,010 amino acids.

The present specification provides for, and includes, gene edited CD163 pigs that can have truncations of the CD163 protein (e.g., amino acids 1 to 40 of CD163 reference sequence NP 999141). Not to be limited by theory, it is believed that truncations within the signal peptide (also known as the signal sequence) can result in a failure of the protein to translocate to the cellular membrane and the polypeptide is subsequently degraded within the cell. Accordingly, CD163 proteins having signal peptide truncations can result in CD163 null animals that are resistant to infection by PRRSv. In an aspect, the gene edited CD163 animals having proteins truncated in the signal sequence can comprise no more than 25 amino acids of non-native amino acid sequences. In an aspect, the gene edited pigs can comprise no more than the first 39 amino acids of the native CD163 protein. In an aspect, the gene edited pigs can comprise no more than the first 39 amino acids of the native CD163 protein and no more than 15 non-native amino acids. Also included, and provided for, by the present specification are gene edited pigs that can be predicted to comprise no more than the first 38 amino acids of the native CD163 protein. In an aspect, the gene edited pigs can comprise no more than the first 38 amino acids of the native CD163 protein and no more than 15 non-native amino acids. Also included, and provided for, by the present specification are gene edited pigs that can be predicted to comprise no more than the first 36 amino acids of the native CD163 protein. In an aspect, the gene edited pigs can comprise no more than the first 36 amino acids of the native CD163 protein and no more than 15 non-native amino acids. Truncated proteins can be non-detectable using methods known to those of skill in the art.

In an aspect, the gene edited pigs can be predicted to comprise no more than the first 34 amino acids of the native CD163 protein and no more than 15 non-native amino acids. In an aspect, the gene edited pigs can be predicted to comprise no more than the first 32 amino acids of the native CD163 protein and no more than 15 non-native amino acids. Truncated proteins can be non-detectable using methods known to those of skill in the art.

Further, the present disclosure provides for and includes truncations of the CD163 protein that can include deletion of exon 7 (SEQ ID NOs: 426-458), sequences where an exogenous stop codon is introduced into exon 7 (SEQ ID NO: 459-504). These truncations can include CD163 proteins comprising no more than 1,010 amino acids.

Breeding techniques can be used to create animals that are homozygous for the inactivated gene from the initial homozygous or heterozygous founder or other heterozygous animals. Homozygous animals can be generated. Gene edited pigs described herein can be bred with other edited or wild-type pigs of interest to ultimately generate pigs that are homozygous or heterozygous for the edited gene. In an aspect, the homozygous animal can be an animal of any one of the lines generated by crosses with PIC™ elite porcine lines 2, 3, 15, 19, 27, 62, 65, and combinations thereof. In an aspect, the homozygous animal can be a hybrid animal prepared by a cross between animals of Line 2 and Line 3.

Gene editing has been used to address various diseases, including PRRS, in swine. While there have been several gene editing technologies developed over the past 15 years, generally these platforms can be designed to introduce a double-stranded break at a specific region of a genome. The introduced break can then be repaired by the cell's own machinery.

One repair pathway, non-homologous end-joining (NHEJ), is evolutionarily conserved throughout all kingdoms of life and is the predominant double-strand break repair pathway in mammalian cells. This repair process can result in the random insertion or deletion of nucleotides across the cut site. As a practical matter, this incomplete fidelity can be used to advantage by providing in trans a DNA repair template. In an aspect, a DNA repair template carrying an alternative allele of the targeted site (for example, a single base polymorphism or a single or multiple base insertion or deletion) can be co-delivered with the gene editing reagents, and through the use of the cell's homologous recombination machinery, the DNA repair template can direct the repair to generate a new allele. In aspects according to the present specification, DNA repair templates can be designed and selected based on the location of high efficiency of CRISPR/CAS cleavage (e.g., high editing frequency from Table 3) and the ability to introduce deletions that can result in truncated proteins that comprise only wild type sequences. Repair templates can increase the efficiency and accuracy of gene editing. DNA repair templates suitable for the methods of the present application can include SEQ ID NOs: 1 to 13. In an aspect, the DNA repair templates can be paired with a guide sequence as described below in Table 6. Unlike transgenesis, genome editing according to the present specification does not result in the introduction of foreign DNA sequences into the genome.

However, as these exogenously added DNA repair templates have the possibility to randomly integrate in the genome, it is also advantageous to identify and use guide pairs that result in the deletion of DNA sequences such that the joined ends can result in the generation of an in-frame translational stop codon across the joined ends; when the cut sites of two guides are repaired by NHEJ in an end-to-end manner, this new DNA sequence, when transcribed into mRNA and translated into protein could terminate the production of the CD163 protein. Although function of this terminated CD163 protein can be lost, often, but not always, premature termination of protein synthesis can result in an unstable polypeptide that can be degraded and not detectable by standard methods. Guide pairs that cut exon 7 of the CD163 gene such that the joined ends form an exogenous stop codon can include SEQ ID NOs: 351 and 365, SEQ ID NOs: 351 and 387, SEQ NOs: 348 and 390, SEQ ID NOs: 348 and 388, SEQ ID NOs: 348 and 395, SEQ ID NOs: 352 and 365, SEQ ID NOs: 352 and 387, SEQ ID NOs: 352 and 399, SEQ ID NOs: 353 and 365, SEQ ID NOs: 353 and 387, SEQ ID NOs: 353 and 399, SEQ ID NOs: 354 and 390, SEQ ID NOs: 354 and 388, SEQ ID NOs: 354 and 395, SEQ ID NOs: 358 and 361, SEQ ID NOs: 358 and 362, SEQ ID NOs: 358 and 368, SEQ ID NOs: 358 and 384, SEQ ID NOs: 358 and 394, SEQ ID NOs: 358 and 399, SEQ ID NOs: 359 and 390, SEQ ID NOs: 359 and 388, SEQ ID NOs: 359 and 395, SEQ ID NOs: 360 and 368, SEQ ID NOs: 360 and 384, SEQ ID NOs: 360 and 389, SEQ ID NOs: 360 and 394, SEQ ID NOs: 360 and 397, SEQ ID NOs: 361 and 365, SEQ ID NOs: 361 and 387, SEQ ID NOs: 362 and 390, SEQ ID NOs: 362 and 388, SEQ ID NOs: 362 and 395, SEQ ID NOs: 364 and 365, SEQ ID NOs: 364 and 387, SEQ ID NOs: 364 and 399, SEQ ID NOs: 365 and 368, SEQ ID NOs: 365 and 384, SEQ ID NOs: 365 and 389, SEQ ID NOs: 365 and 394, SEQ ID NOs: 365 and 397, SEQ ID NOs: 366 and 368, SEQ ID NOs: 366 and 384, SEQ ID NOs: 366 and 389, SEQ ID NOs: 366 and 394, and SEQ ID NOs: 366 and 397.

In one aspect, the present teachings can involve a simple, precise and reproducible single CD163 loss of function edit in elite pigs such that the edit occurs early in the CD163 gene. A single guide RNA-Cas protein combination and DNA repair template can be selected for directing a specific gene edit in elite pigs, based on several considerations and approaches: efficient cutting near the 5' end of the CD163 gene in tissue culture, bioinformatic review identifying guides with few mismatches in the pig genome, high specificity of on-target cutting as determined by biochemical prescreen, and the ability to target specific gene edits at an intended site in pig embryo-like cells. Examples of specific gene edits of CD163 are discussed in detail below. In an aspect, a specific gene edit according to the present specification can include a CD163 gene comprising a sequence selected from the group consisting of SEQ ID NOs: 1 to 18 and 426 to 505. In an aspect, cells comprising an edited CD163 gene can comprise at least one allele having a sequence selected from the group consisting of SEQ ID NOs:1 to 18 and 426 to 505. In an aspect, cells comprising two gene edited alleles of the CD163 gene can comprise, at both alleles, a sequence selected from the group consisting of SEQ ID NOs: 1 to 18 and 426 to 505. In an aspect, both gene edited CD163 genes can comprise the same sequence selected from the group consisting of SEQ ID NOs: 1 to 18 and 426-505 (e.g., two alleles of SEQ ID NO: 1 or two alleles of SEQ ID NO: 2, etc.). In an aspect, the genome of a cell can comprise gene edited CD163 genes comprising one each of a sequence selected from the group consisting of SEQ ID NOs:1 to 18 and 426-505 (e.g., an allele of SEQ ID NO: 1 with an allele of SEQ ID NO: 2, and all combinations thereof).

Also provided for, and included, are mixtures of cells that can comprise CD163 edited cells and non-gene edited cells. In an aspect, the mixture can be an embryo. In another aspect, the mixture can be a cell culture. In a further aspect, the mixture of cells does not comprise a reproductive cell. In an aspect, the present specification can provide for, and includes, a tissue culture of CD163 edited cells and methods to prepare such cultures. Cultures according to the present specification can include mixtures of CD163 edited cells (e.g., cells having an allele of SEQ ID NO: 1 with cells having an allele of SEQ ID NO: 2, cells having an allele of SEQ ID NO: 1 with cells having an allele of SEQ ID NO: 3, and all combinations thereof). In an aspect, the tissue culture of non-reproductive cells can include cells comprising a single CD163 edit. In a further aspect, cells of a single CD163 edit in culture may comprise one or both edited alleles.

Specific examples of endonuclease and guide RNA backbone sequences that can be used in the products and methods of the present teachings are listed in Table 2.

TABLE 2

| Endonuclease and Guide Backbone Sequences | |
|---|---|
| Sequence Identity | SEQ ID NO: |
| Guide RNA Backbone (DNA sequence shown) | 19 |
| *Streptococcus pyogenes* endonuclease protein sequence | 20 |
| *Streptococcus thermophilus* CR3 endonuclease protein sequence | 21 |

Elite porcine nucleus lines can be sequenced and aligned against a public reference for the CD163 gene. These data can be used for the development of gene editing reagents for the PRRS-resistance project. These sequences can be scanned for the presence of conserved RNA-guided CRISPR-Cas9 recognition sites which can consist of the 3 nucleotide or 5 nucleotide motif, nGG (AGG, CGG, TGG, GGG), nGGnG (AGGTG, CGGTG, TGGTG, GGGTG, AGGGG, CGGGG, TGGGG, GGGGG, AGGAG, CGGAG, TGGAG, GGGAG, AGGCG, CGGCG, TGGCG, GGGCG), respectively. This motif, called the PAM sequence, can be located adjacent to, and 3' of, a 20 nucleotide spacer sequence which can be used for base-pairing with the RNA. Suitable sites can be identified, and crRNA guide or single guide sequences can be prepared, and are presented below in Table 3.

While not limited to any particular theory, when complexed, the guideRNA-Cas9 protein can recognize a DNA site for cleavage, which can then be repaired by cellular components by either non-homologous end joining (random repair) or by a DNA template repair pathway (homology directed repair, HDR).

Guide RNAs (gRNA) can be generated across exons 1 to exons 7 of CD163. Edits in the virus binding domain (Domain 5) of the CD163 protein can inhibit the ability of the virus to bind to the protein, thus preventing uptake of the virus into pig lung macrophages. When the edit in CD163 is homozygous in pigs, the animals can be resistant to PRRS infection. The present specification provides for, and includes, gRNA sequences including the crRNA sequences listed in Table 3 that can be selected from the group consisting of the first 20 nucleotides of each of SEQ ID NOs: 22 to 271 and 347 to 425. SEQ ID NOs: 22 to 271 and 347 to 425 are shown as DNA sequences. The corresponding RNA counterpart, and the presence of the PAM motif which is generally not included in gRNAs, would be apparent to a person of skill in the art. Also provided herein, are RNA sequences that can comprise sequences selected from the group consisting of the first 20 nucleotides of each of SEQ ID NOs: 22 to 271 and 347 to 425. SEQ ID NOs: 22 to 271 and 347 to 425 can be combined with the gRNA backbone sequence and expressed as RNA for use in the preparation of a gRNA and then mixed with the Cas nuclease to prepare an active ribonucleotide protein complex (sgRNP). The sgRNP complex can then be injected into a mature oocyte, a zygote, or early embryo, either alone or together with a repair template selected from the group consisting of SEQ ID NOs:1 to 13. After cleavage and template directed repair, the CD163 gene can be edited to incorporate the repair template sequences, and the edited genome of a CD163 gene edited cell can comprise a sequence selected from the group consisting of SEQ ID NOs: 1 to 13.

In one aspect, the present disclosure can include a simple, precise, and reproducible single CD163 loss of function edit in elite pigs such that the edit occurs early in the CD163 gene (exons 1-7). In an aspect, a pig can have a CD163 gene comprising a sequence selected from the group consisting of SEQ ID NOs: 1 to 18 and 426 to 505. Also included and provided for is a pig that can comprise SEQ ID NOs: 1 to 18 and 425 to 505 in a genomic region comprising the markers of Table 8. Also included and provided for is a pig that can comprise SEQ ID NO: 2 in a genomic region comprising the markers of Table 8. Also included and provided for is a pig that can comprise SEQ ID NO: 426-458 in a genomic region comprising the markers of Table 8. Also included and provided for is a pig that can comprise SEQ ID NO: 459-504 in a genomic region comprising the markers of Table 8. Using porcine embryonic fibroblast cell lines derived from these elite pigs, 250 guide RNA and Cas9 protein combinations can be tested to identify gene editing pairs that efficiently cut and generate edits in the CD163 gene. Selected specific guides and endonuclease protein combinations found are listed in Table 3, along with the location of the target, their endonuclease activity (average editing frequency), and the position on CD163 of the edit. Greater average editing frequency combinations are preferred because they have more effective editing activity. Combinations having an average editing frequency greater than 1 are desired. In an aspect, combinations can have an average editing frequency greater than 5. In another aspect, combinations can have an average editing frequency greater than 10. In yet another aspect, combinations can have an average editing frequency greater than 15. The present disclosure provides for, and includes, combinations that can have an average editing frequency greater than 20. In an aspect, combinations can have an average editing frequency greater than 25. In yet another aspect, combinations can have an average editing frequency greater than 30.

As shown in Table 3, the average editing frequency varied greatly between target sequences. Moreover, sequences targeting overlapping sequences resulted in different editing frequencies depending on the Cas protein source. For example, SEQ ID NOs: 24 and 25 targeted overlapping locations and had a 10-fold difference in editing frequency. At this site, with these sequences, *S. pyogenes* provided a nearly a 20-fold higher editing frequency. In contrast, RNPs incorporating SEQ ID NOs: 33 and 34 resulted in indistinguishable average editing frequencies between the Cas proteins. While RNPs incorporating a Cas9 nuclease from *S. pyogenes* can provide superior average editing frequencies, that is not always the case. As shown for SEQ ID NOs: 60 and 61, RNPs incorporating the Cas9 protein from *S. thermophilus* resulted in superior editing frequencies (e.g., 3.9 vs. 22.0). Accordingly, the present specification provides for efficient guide RNA sequences or efficient targeting sequences for targeting CD163 using the CRISPR/Cas system. In an aspect, RNPs can comprise a sequence selected from the group consisting of the first 20 nucleotides of each of SEQ ID NOs: 22 to 271 and 347 to 425.

All position designations herein refer to the Sscrofa11.1 reference genome (GenBank accession: GCA_000003025.6).

Target site sequences SEQ ID NOs: 22 to 271 and 347 to 425 can be editing target sequences within the porcine CD163 gene. In each target site sequence, the first 20 nucleotides can correspond to the guide RNA spacer, and the remaining 3 or 5 nucleotides can be the PAM sequences for *S. pyogenes* or *S. thermophilus*, respectively. The first 20 bases of SEQ ID NOs: 22 to 271 and 347 to 425 correspond to the DNA equivalent guide RNA sequences, with the appropriate ribonuclease bases substituted for deoxyribonuclease bases, although the DNA bases can be used instead of RNA bases as guides. Guide RNA sequences can be paired with *S. pyogenes* or *S. thermophilus* endonucleases to direct DNA breaks in the porcine genome in either coding or non-coding regions of the CD163 gene, which can result in DNA deletions and/or DNA nucleotide insertions. Depending on the locations of the target sites as disclosed in Table 3, pairs of guide/endonuclease combinations can be selected to delete regions of the CD163 gene between the pairs of guide/endonuclease combinations.

Target site sequences SEQ ID NOs: 212 to 271 and 347 to 425 are targeting sequences that can be used to design guides for deletion of exon 7 of the CD163 gene. Pairing of intron 6 targeting guides SEQ ID NOs: 212 to 253, and 262 to 271 with intron 7 targeting guides SEQ ID NOs: 254 to 261 using *S. pyogenes* can cause two double strand breaks on the CD163 gene, resulting in excision of exon 7. Pairing of targeting guides SEQ ID NOs: 249 and 256 also can result in excision of Exon 7. Pairing of some guides can result in the introduction of a stop codon in Exon 7, including SEQ ID NOs: 351 and 365, SEQ ID NOs: 351 and 387, SEQ NOs.: 348 and 390, SEQ ID NOs: 348 and 388, SEQ ID NOs: 348 and 498, SEQ ID NOs: 352 and 365, SEQ ID NOs: 352 and 387, SEQ ID NOs: 352 and 399, SEQ ID NOs: 353 and 365, SEQ ID NOs: 353 and 387, SEQ ID NOs: 353 and 399, SEQ ID NOs: 354 and 390, SEQ ID NOs: 354 and 388, SEQ ID NOs: 354 and 395, SEQ ID NOs: 358 and 361, SEQ ID NOs: 358 and 362, SEQ ID NOs: 358 and 368, SEQ ID NOs: 358 and 384, SEQ ID NOs: 358 and 394, SEQ ID NOs: 358 and 399, SEQ ID NOs: 359 and 390, SEQ ID NOs: 359 and 388, SEQ ID NOs: 359 and 395, SEQ ID NOs: 360 and 368, SEQ ID NOs: 360 and 384, SEQ ID NOs: 360 and 389, SEQ ID NOs: 360 and 394, SEQ ID NOs: 360 and 397, SEQ ID NOs: 361 and 365, SEQ ID NOs: 361 and 387, SEQ ID NOs: 362 and 390, SEQ ID NOs: 362 and 388, SEQ ID NOs: 362 and 395, SEQ ID NOs. 364 and 365, SEQ ID NOs: 364 and 387, SEQ ID NOs: 364 and 399, SEQ ID NOs: 365 and 368, SEQ ID NOs: 365 and 384, SEQ ID NOs: 365 and 389, SEQ ID NOs: 365 and 394, SEQ ID NOs: 365 and 397, SEQ ID NOs: 366 and 368, SEQ ID NOs: 366 and 384, SEQ ID NOs: 366 and 389, SEQ ID NOs: 366 and 394, or SEQ ID NOs: 366 and 397.

For each targeting sequence, Table 3 lists its SEQ ID No., the species of CAS9 nuclease homing arm used, the location of the targeting sequence on the *Sus scrofa* genome including the PAM sequence, the editing efficiency as measured by the average fraction of edits for a particular guide in fetal fibroblast cell assays, and the exon on CD163 targeted.

TABLE 3

List of target sequences and editing activities in porcine fetal fibroblasts

| SEQ ID NO: | Cas9 Nuclease | Location of target | Average edited fraction | Position on CD163 |
|---|---|---|---|---|
| 22 | S. pyogenes | chr5: 63300192-63300214 | 12.9 | Exon 1/15 |
| 23 | S. pyogenes | chr5: 63300222-63300244 | 1.4 | Exon 1/15 |
| 24 | S. pyogenes | chr5: 63300236-63300258 | 5.8 | Exon 1/15 |
| 25 | S. thermophilus | chr5: 63300236-63300260 | 0.3 | Exon 1/15 |
| 26 | S. pyogenes | chr5: 63300250-63300272 | 8.6 | Exon 1/15 |
| 27 | S. pyogenes | chr5: 63300251-63300273 | 0.1 | Exon 1/15 |
| 28 | S. pyogenes | chr5: 63300275-63300297 | 25.7 | Exon 1/15 |
| 29 | S. pyogenes | chr5: 63300288-63300310 | 24.9 | Exon 1/15 |
| 30 | S. pyogenes | chr5: 63300293-63300315 | 12.8 | Exon 1/15 |
| 31 | S. pyogenes | chr5: 63300305-63300327 | 0.4 | Exon 1/15 |
| 32 | S. pyogenes | chr5: 63300308-63300330 | 3.4 | Exon 1/15 |
| 33 | S. thermophilus | chr5: 63300308-63300332 | 3.7 | Exon 1/15 |
| 34 | S. pyogenes | chr5: 63300327-63300349 | 5.3 | Exon 1/15 |
| 35 | S. pyogenes | chr5: 63300336-63300358 | 3.5 | Exon 1/15 |
| 36 | S. pyogenes | chr5: 63301950-63301972 | 14.4 | Exon 2/15 |
| 37 | S. pyogenes | chr5: 63301951-63301973 | 16.3 | Exon 2/15 |
| 38 | S. pyogenes | chr5: 63301962-63301984 | 13.6 | Exon 2/15 |
| 39 | S. pyogenes | chr5: 63301981-63302003 | 3.6 | Exon 2/15 |
| 40 | S. pyogenes | chr5: 63301995-63302017 | 21.8 | Exon 2/15 |
| 41 | S. pyogenes | chr5: 63301997-63302019 | 8.2 | Exon 2/15 |
| 42 | S. thermophilus | chr5: 63301997-63302021 | 10.1 | Exon 2/15 |
| 43 | S. pyogenes | chr5: 63303121-63303143 | 16.4 | Exon 3/15 |
| 44 | S. thermophilus | chr5: 63303121-63303145 | 16.1 | Exon 3/15 |
| 45 | S. pyogenes | chr5: 63303129-63303151 | 31.4 | Exon 3/15 |
| 46 | S. pyogenes | chr5: 63303136-63303158 | 22.8 | Exon 3/15 |
| 47 | S. pyogenes | chr5: 63303137-63303159 | 42.9 | Exon 3/15 |
| 48 | S. thermophilus | chr5: 63303137-63303161 | 10.7 | Exon 3/15 |
| 49 | S. pyogenes | chr5: 63303140-63303162 | 36.7 | Exon 3/15 |
| 50 | S. thermophilus | chr5: 63303140-63303164 | 32.6 | Exon 3/15 |
| 51 | S. pyogenes | chr5: 63303158-63303180 | 21.1 | Exon 3/15 |
| 52 | S. pyogenes | chr5: 63303166-63303188 | 23.6 | Exon 3/15 |
| 53 | S. thermophilus | chr5: 63303166-63303190 | 22.1 | Exon 3/15 |
| 54 | S. pyogenes | chr5: 63303169-63303191 | 40.0 | Exon 3/15 |
| 55 | S. thermophilus | chr5: 63303169-63303193 | 19.5 | Exon 3/15 |
| 56 | S. pyogenes | chr5: 63303181-63303203 | 9.9 | Exon 3/15 |

TABLE 3-continued

List of target sequences and editing activities in porcine fetal fibroblasts

| SEQ ID NO: | Cas9 Nuclease | Location of target | Average edited fraction | Position on CD163 |
|---|---|---|---|---|
| 57 | S. thermophilus | chr5: 63303181-63303205 | 10.4 | Exon 3/15 |
| 58 | S. pyogenes | chr5: 63303184-63303206 | 20.6 | Exon 3/15 |
| 59 | S. thermophilus | chr5: 63303184-63303208 | 2.8 | Exon 3/15 |
| 60 | S. pyogenes | chr5: 63303189-63303211 | 3.9 | Exon 3/15 |
| 61 | S. thermophilus | chr5: 63303189-63303213 | 22.0 | Exon 3/15 |
| 62 | S. pyogenes | chr5: 63303190-63303212 | 18.1 | Exon 3/15 |
| 63 | S. pyogenes | chr5: 63303191-63303213 | 23.5 | Exon 3/15 |
| 64 | S. pyogenes | chr5: 63303209-63303231 | 23.6 | Exon 3/15 |
| 65 | S. pyogenes | chr5: 63303213-63303235 | 4.1 | Exon 3/15 |
| 66 | S. pyogenes | chr5: 63303214-63303236 | 16.2 | Exon 3/15 |
| 67 | S. pyogenes | chr5: 63303220-63303242 | 14.6 | Exon 3/15 |
| 68 | S. pyogenes | chr5: 63303226-63303248 | 15.4 | Exon 3/15 |
| 69 | S. pyogenes | chr5: 63303243-63303265 | 21.6 | Exon 3/15 |
| 70 | S. pyogenes | chr5: 63303250-63303272 | 1.5 | Exon 3/15 |
| 71 | S. pyogenes | chr5: 63303251-63303273 | 30.3 | Exon 3/15 |
| 72 | S. pyogenes | chr5: 63303278-63303300 | 20.1 | Exon 3/15 |
| 73 | S. pyogenes | chr5: 63303278-63303300 | 1.5 | Exon 3/15 |
| 74 | S. pyogenes | chr5: 63303282-63303304 | 23.9 | Exon 3/15 |
| 75 | S. pyogenes | chr5: 63303283-63303305 | 20.8 | Exon 3/15 |
| 76 | S. pyogenes | chr5: 63303294-63303316 | 33.8 | Exon 3/15 |
| 77 | S. pyogenes | chr5: 63303299-63303321 | 8.2 | Exon 3/15 |
| 78 | S. pyogenes | chr5: 63303305-63303327 | 6.1 | Exon 3/15 |
| 79 | S. pyogenes | chr5: 63303315-63303337 | 25.2 | Exon 3/15 |
| 80 | S. pyogenes | chr5: 63303319-63303341 | 28.7 | Exon 3/15 |
| 81 | S. pyogenes | chr5: 63303338-63303360 | 4.5 | Exon 3/15 |
| 82 | S. pyogenes | chr5: 63303339-63303361 | 2.8 | Exon 3/15 |
| 83 | S. pyogenes | chr5: 63303357-63303379 | 18.3 | Exon 3/15 |
| 84 | S. pyogenes | chr5: 63303358-63303380 | 26.6 | Exon 3/15 |
| 85 | S. pyogenes | chr5: 63303374-63303396 | 16.1 | Exon 3/15 |
| 86 | S. pyogenes | chr5: 63303378-63303400 | 35.4 | Exon 3/15 |
| 87 | S. thermophilus | chr5: 63303378-63303402 | 40.0 | Exon 3/15 |
| 88 | S. pyogenes | chr5: 63303379-63303401 | 24.4 | Exon 3/15 |
| 89 | S. pyogenes | chr5: 63303380-63303402 | 25.6 | Exon 3/15 |
| 90 | S. pyogenes | chr5: 63303406-63303428 | 28.1 | Exon 3/15 |
| 91 | S. pyogenes | chr5: 63303413-63303435 | 13.7 | Exon 3/15 |
| 92 | S. thermophilus | chr5: 63303413-63303437 | 19.0 | Exon 3/15 |
| 93 | S. thermophilus | chr5: 63303419-63303443 | 15.2 | Exon 3/15 |
| 94 | S. pyogenes | chr5: 63303421-63303443 | 16.5 | Exon 3/15 |
| 95 | S. pyogenes | chr5: 63303428-63303450 | 35.8 | Exon 3/15 |
| 96 | S. pyogenes | chr5: 63303441-63303463 | 3.4 | Exon 3/15 |
| 97 | S. pyogenes | chr5: 63306087-63306109 | 19.8 | Exon 4/15 |
| 98 | S. pyogenes | chr5: 63306091-63306113 | 4.5 | Exon 4/15 |
| 99 | S. thermophilus | chr5: 63306091-63306115 | 3.1 | Exon 4/15 |
| 100 | S. pyogenes | chr5: 63306098-63306120 | 29.9 | Exon 4/15 |
| 101 | S. thermophilus | chr5: 63306098-63306122 | 31.5 | Exon 4/15 |
| 102 | S. pyogenes | chr5: 63306101-63306123 | 29.2 | Exon 4/15 |
| 103 | S. pyogenes | chr5: 63306108-63306130 | 6.9 | Exon 4/15 |
| 104 | S. thermophilus | chr5: 63306108-63306132 | 14.7 | Exon 4/15 |
| 105 | S. pyogenes | chr5: 63306116-63306138 | 21.6 | Exon 4/15 |
| 106 | S. pyogenes | chr5: 63306127-63306149 | 26.4 | Exon 4/15 |
| 107 | S. pyogenes | chr5: 63306140-63306162 | 6.9 | Exon 4/15 |
| 108 | S. pyogenes | chr5: 63306144-63306166 | 35.2 | Exon 4/15 |
| 109 | S. thermophilus | chr5: 63306144-63306168 | 3.3 | Exon 4/15 |
| 110 | S. pyogenes | chr5: 63306147-63306169 | 8.8 | Exon 4/15 |
| 111 | S. thermophilus | chr5: 63306147-63306171 | 3.2 | Exon 4/15 |
| 112 | S. pyogenes | chr5: 63306148-63306170 | 5.2 | Exon 4/15 |
| 113 | S. pyogenes | chr5: 63306149-63306171 | 28.0 | Exon 4/15 |
| 114 | S. pyogenes | chr5: 63306193-63306215 | 9.3 | Exon 4/15 |
| 115 | S. pyogenes | chr5: 63306236-63306258 | 14.2 | Exon 4/15 |
| 116 | S. pyogenes | chr5: 63306251-63306273 | 26.3 | Exon 4/15 |
| 117 | S. thermophilus | chr5: 63306251-63306275 | 4.4 | Exon 4/15 |
| 118 | S. pyogenes | chr5: 63306257-63306279 | 1.3 | Exon 4/15 |
| 119 | S. pyogenes | chr5: 63306263-63306285 | 7.8 | Exon 4/15 |
| 120 | S. pyogenes | chr5: 63306273-63306295 | 35.0 | Exon 4/15 |
| 121 | S. pyogenes | chr5: 63306287-63306309 | 13.4 | Exon 4/15 |
| 122 | S. pyogenes | chr5: 63306296-63306318 | 2.0 | Exon 4/15 |
| 123 | S. pyogenes | chr5: 63306315-63306337 | 31.2 | Exon 4/15 |
| 124 | S. pyogenes | chr5: 63306332-63306354 | 10.1 | Exon 4/15 |
| 125 | S. pyogenes | chr5: 63306336-63306358 | 31.1 | Exon 4/15 |
| 126 | S. thermophilus | chr5: 63306336-63306360 | 52.8 | Exon 4/15 |
| 127 | S. pyogenes | chr5: 63306337-63306359 | 30.3 | Exon 4/15 |
| 128 | S. pyogenes | chr5: 63306338-63306360 | 43.2 | Exon 4/15 |
| 129 | S. pyogenes | chr5: 63306364-63306386 | 2.5 | Exon 4/15 |
| 130 | S. pyogenes | chr5: 63306371-63306393 | 0.2 | Exon 4/15 |

TABLE 3-continued

List of target sequences and editing activities in porcine fetal fibroblasts

| SEQ ID NO: | Cas9 Nuclease | Location of target | Average edited fraction | Position on CD163 |
|---|---|---|---|---|
| 131 | S. thermophilus | chr5: 63306371-63306395 | 0.3 | Exon 4/15 |
| 132 | S. pyogenes | chr5: 63309028-63309050 | 4.5 | Exon 5/15 |
| 133 | S. pyogenes | chr5: 63309034-63309056 | 5.1 | Exon 5/15 |
| 134 | S. pyogenes | chr5: 63309035-63309057 | 41.8 | Exon 5/15 |
| 135 | S. thermophilus | chr5: 63309035-63309059 | 21.9 | Exon 5/15 |
| 136 | S. pyogenes | chr5: 63309053-63309075 | 15.1 | Exon 5/15 |
| 137 | S. pyogenes | chr5: 63309061-63309083 | 0.2 | Exon 5/15 |
| 138 | S. pyogenes | chr5: 63309077-63309099 | 15.7 | Exon 5/15 |
| 139 | S. thermophilus | chr5: 63309077-63309101 | 11.2 | Exon 5/15 |
| 140 | S. pyogenes | chr5: 63309084-63309106 | 10.1 | Exon 5/15 |
| 141 | S. thermophilus | chr5: 63309084-63309108 | 23.8 | Exon 5/15 |
| 142 | S. pyogenes | chr5: 63309085-63309107 | 11.3 | Exon 5/15 |
| 143 | S. pyogenes | chr5: 63309086-63309108 | 23.4 | Exon 5/15 |
| 144 | S. pyogenes | chr5: 63309094-63309116 | 13.8 | Exon 5/15 |
| 145 | S. pyogenes | chr5: 63309104-63309126 | 7.8 | Exon 5/15 |
| 146 | S. pyogenes | chr5: 63309108-63309130 | 1.4 | Exon 5/15 |
| 147 | S. pyogenes | chr5: 63309109-63309131 | 7.0 | Exon 5/15 |
| 148 | S. pyogenes | chr5: 63309130-63309152 | 24.8 | Exon 5/15 |
| 149 | S. pyogenes | chr5: 63309144-63309166 | 20.8 | Exon 5/15 |
| 150 | S. pyogenes | chr5: 63309145-63309167 | 0.1 | Exon 5/15 |
| 151 | S. pyogenes | chr5: 63309146-63309168 | 37.4 | Exon 5/15 |
| 152 | S. pyogenes | chr5: 63309173-63309195 | 2.5 | Exon 5/15 |
| 153 | S. pyogenes | chr5: 63309173-63309195 | 11.5 | Exon 5/15 |
| 154 | S. pyogenes | chr5: 63309189-63309211 | 11.5 | Exon 5/15 |
| 155 | S. pyogenes | chr5: 63309193-63309215 | 2.7 | Exon 5/15 |
| 156 | S. pyogenes | chr5: 63309194-63309216 | 10.4 | Exon 5/15 |
| 157 | S. pyogenes | chr5: 63309200-63309222 | 3.8 | Exon 5/15 |
| 158 | S. thermophilus | chr5: 63309205-63309229 | 19.0 | Exon 5/15 |
| 159 | S. pyogenes | chr5: 63309207-63309229 | 21.0 | Exon 5/15 |
| 160 | S. pyogenes | chr5: 63309210-63309232 | 19.0 | Exon 5/15 |
| 161 | S. pyogenes | chr5: 63309233-63309255 | 8.3 | Exon 5/15 |
| 162 | S. pyogenes | chr5: 63309250-63309272 | 13.6 | Exon 5/15 |
| 163 | S. pyogenes | chr5: 63309252-63309274 | 23.0 | Exon 5/15 |
| 164 | S. pyogenes | chr5: 63309273-63309295 | 2.3 | Exon 5/15 |
| 165 | S. thermophilus | chr5: 63309273-63309297 | 34.4 | Exon 5/15 |
| 166 | S. pyogenes | chr5: 63309274-63309296 | 15.1 | Exon 5/15 |
| 167 | S. pyogenes | chr5: 63309275-63309297 | 19.4 | Exon 5/15 |
| 168 | S. thermophilus | chr5: 63309284-63309308 | 14.4 | Exon 5/15 |
| 169 | S. pyogenes | chr5: 63309286-63309308 | 7.0 | Exon 5/15 |
| 170 | S. pyogenes | chr5: 63309308-63309330 | 0.5 | Exon 5/15 |
| 171 | S. thermophilus | chr5: 63309308-63309332 | 2.4 | Exon 5/15 |
| 172 | S. pyogenes | chr5: 63309323-63309345 | 16.0 | Exon 5/15 |
| 173 | S. pyogenes | chr5: 63309841-63309863 | 0.1 | Exon 6/15 |
| 174 | S. pyogenes | chr5: 63309857-63309879 | 8.4 | Exon 6/15 |
| 175 | S. thermophilus | chr5: 63309857-63309881 | 8.0 | Exon 6/15 |
| 176 | S. pyogenes | chr5: 63309860-63309882 | 40.3 | Exon 6/15 |
| 177 | S. thermophilus | chr5: 63309860-63309884 | 32.3 | Exon 6/15 |
| 178 | S. pyogenes | chr5: 63309863-63309885 | 37.2 | Exon 6/15 |
| 179 | S. pyogenes | chr5: 63309886-63309908 | 4.7 | Exon 6/15 |
| 180 | S. thermophilus | chr5: 63309886-63309910 | 3.5 | Exon 6/15 |
| 181 | S. pyogenes | chr5: 63309889-63309911 | 38.1 | Exon 6/15 |
| 182 | S. pyogenes | chr5: 63309889-63309911 | 34.1 | Exon 6/15 |
| 183 | S. thermophilus | chr5: 63309889-63309913 | 17.5 | Exon 6/15 |
| 184 | S. pyogenes | chr5: 63309892-63309914 | 4.9 | Exon 6/15 |
| 185 | S. pyogenes | chr5: 63309907-63309929 | 13.5 | Exon 6/15 |
| 186 | S. pyogenes | chr5: 63309911-63309933 | 5.5 | Exon 6/15 |
| 187 | S. pyogenes | chr5: 63309933-63309955 | 0.7 | Exon 6/15 |
| 188 | S. thermophilus | chr5: 63309933-63309957 | 10.0 | Exon 6/15 |
| 189 | S. pyogenes | chr5: 63309934-63309956 | 6.4 | Exon 6/15 |
| 190 | S. pyogenes | chr5: 63309935-63309957 | 18.7 | Exon 6/15 |
| 191 | S. pyogenes | chr5: 63309955-63309977 | 12.0 | Exon 6/15 |
| 192 | S. pyogenes | chr5: 63309963-63309985 | 5.6 | Exon 6/15 |
| 193 | S. pyogenes | chr5: 63309970-63309992 | 0.5 | Exon 6/15 |
| 194 | S. pyogenes | chr5: 63309971-63309993 | 12.5 | Exon 6/15 |
| 195 | S. pyogenes | chr5: 63309977-63309999 | 5.3 | Exon 6/15 |
| 196 | S. pyogenes | chr5: 63310021-63310043 | 2.2 | Exon 6/15 |
| 197 | S. pyogenes | chr5: 63310035-63310057 | 10.3 | Exon 6/15 |
| 198 | S. pyogenes | chr5: 63310038-63310060 | 0.2 | Exon 6/15 |
| 199 | S. pyogenes | chr5: 63310058-63310080 | 8.2 | Exon 6/15 |
| 200 | S. pyogenes | chr5: 63310077-63310099 | 6.2 | Exon 6/15 |
| 201 | S. pyogenes | chr5: 63310078-63310100 | 8.6 | Exon 6/15 |
| 202 | S. pyogenes | chr5: 63310092-63310114 | 2.7 | Exon 6/15 |
| 203 | S. pyogenes | chr5: 63310098-63310120 | 11.1 | Exon 6/15 |
| 204 | S. thermophilus | chr5: 63310098-63310122 | 8.0 | Exon 6/15 |
| 205 | S. pyogenes | chr5: 63310099-63310121 | 12.2 | Exon 6/15 |
| 206 | S. pyogenes | chr5: 63310100-63310122 | 21.1 | Exon 6/15 |
| 207 | S. thermophilus | chr5: 63310100-63310124 | 0.1 | Exon 6/15 |
| 208 | S. pyogenes | chr5: 63310103-63310125 | 3.3 | Exon 6/15 |
| 209 | S. pyogenes | chr5: 63310152-63310174 | 4.8 | Exon 6/15 |
| 210 | S. pyogenes | chr5: 63323061-63323083 | 32.8 | Exon 7/15 |
| 211 | S. pyogenes | chr5: 63323147-63323169 | 17.0 | Exon 7/15 |
| 212 | S. pyogenes | chr5: 63322548-63322570 | 13.6 | Intron 6 |
| 213 | S. pyogenes | chr5: 63322549-63322571 | 1.7 | Intron 6 |
| 214 | S. pyogenes | chr5: 63322566-63322588 | 15.6 | Intron 6 |
| 215 | S. pyogenes | chr5: 63322594-63322616 | 0.0 | Intron 6 |
| 216 | S. pyogenes | chr5: 63322597-63322619 | 0.0 | Intron 6 |
| 217 | S. pyogenes | chr5: 63322646-63322668 | 21.1 | Intron 6 |
| 218 | S. pyogenes | chr5: 63322647-63322669 | 12.6 | Intron 6 |
| 219 | S. pyogenes | chr5: 63322681-63322703 | 44.3 | Intron 6 |
| 220 | S. pyogenes | chr5: 63322683-63322705 | 3.9 | Intron 6 |
| 221 | S. pyogenes | chr5: 63322693-63322715 | 33.9 | Intron 6 |
| 222 | S. pyogenes | chr5: 63322694-63322716 | 26.1 | Intron 6 |
| 223 | S. pyogenes | chr5: 63322714-63322736 | 5.7 | Intron 6 |
| 224 | S. pyogenes | chr5: 63322731-63322753 | 42.8 | Intron 6 |
| 225 | S. pyogenes | chr5: 63322756-63322778 | 5.8 | Intron 6 |
| 226 | S. pyogenes | chr5: 63322757-63322779 | 21.2 | Intron 6 |
| 227 | S. pyogenes | chr5: 63322770-63322792 | 36.1 | Intron 6 |
| 228 | S. pyogenes | chr5: 63322799-63322821 | 29.9 | Intron 6 |
| 229 | S. pyogenes | chr5: 63322800-63322822 | 43.2 | Intron 6 |
| 230 | S. pyogenes | chr5: 63322809-63322831 | 33.3 | Intron 6 |
| 231 | S. pyogenes | chr5: 63322810-63322832 | 46.8 | Intron 6 |
| 232 | S. pyogenes | chr5: 63322834-63322856 | 7.8 | Intron 6 |
| 233 | S. pyogenes | chr5: 63322835-63322857 | 18.3 | Intron 6 |
| 234 | S. pyogenes | chr5: 63322839-63322861 | 18.8 | Intron 6 |
| 235 | S. pyogenes | chr5: 63322839-63322861 | 13.2 | Intron 6 |
| 236 | S. pyogenes | chr5: 63322840-63322862 | 2.8 | Intron 6 |
| 237 | S. pyogenes | chr5: 63322845-63322867 | 55.3 | Intron 6 |
| 238 | S. pyogenes | chr5: 63322848-63322870 | 27.2 | Intron 6 |
| 239 | S. pyogenes | chr5: 63322852-63322874 | 24.4 | Intron 6 |
| 240 | S. pyogenes | chr5: 63322859-63322881 | 22.2 | Intron 6 |
| 241 | S. pyogenes | chr5: 63322875-63322897 | 25.3 | Intron 6 |
| 242 | S. pyogenes | chr5: 63322887-63322909 | 4.2 | Intron 6 |
| 243 | S. pyogenes | chr5: 63322888-63322910 | 3.5 | Intron 6 |
| 244 | S. pyogenes | chr5: 63322891-63322913 | 44.3 | Intron 6 |
| 245 | S. pyogenes | chr5: 63322900-63322922 | 58.2 | Intron 6 |
| 246 | S. pyogenes | chr5: 63322906-63322928 | 3.7 | Intron 6 |
| 247 | S. pyogenes | chr5: 63322926-63322948 | 38.1 | Intron 6 |
| 248 | S. pyogenes | chr5: 63322927-63322949 | 0.5 | Intron 6 |
| 249 | S. pyogenes | chr5: 63322947-63322969 | 31.7 | Intron 6 |
| 250 | S. pyogenes | chr5: 63322957-63322979 | 50.0 | Intron 6 |
| 251 | S. pyogenes | chr5: 63322957-63322979 | 11.0 | Intron 6 |
| 252 | S. pyogenes | chr5: 63322991-63323013 | 4.5 | Intron 6 |
| 253 | S. pyogenes | chr5: 63322992-63323014 | 0.5 | Intron 6 |
| 254 | S. pyogenes | chr5: 63323338-63323360 | 19.8 | Intron 7 |
| 255 | S. pyogenes | chr5: 63323339-63323361 | 8.1 | Intron 7 |
| 256 | S. pyogenes | chr5: 63323361-63323383 | 21.1 | Intron 7 |
| 257 | S. pyogenes | chr5: 63323362-63323384 | 30.4 | Intron 7 |
| 258 | S. pyogenes | chr5: 63323362-63323384 | 5.6 | Intron 7 |
| 259 | S. pyogenes | chr5: 63323363-63323385 | 2.8 | Intron 7 |
| 260 | S. pyogenes | chr5: 63323367-63323389 | 23.2 | Intron 7 |
| 261 | S. pyogenes | chr5: 63323368-63323390 | 26.2 | Intron 7 |
| 262 | S. thermophilus | chr5: 63322644-63322668 | Activity not tested | Intron 6 |
| 263 | S. thermophilus | chr5: 63322647-63322671 | Activity not tested | Intron 6 |
| 264 | S. thermophilus | chr5: 63322678-63322702 | Activity not tested | Intron 6 |
| 265 | S. thermophilus | chr5: 63322681-63322705 | Activity not tested | Intron 6 |
| 266 | S. thermophilus | chr5: 63322755-63322779 | Activity not tested | Intron 6 |
| 267 | S. thermophilus | chr5: 63322807-63322831 | Activity not tested | Intron 6 |
| 268 | S. thermophilus | chr5: 63322845-63322869 | Activity not tested | Intron 6 |
| 269 | S. thermophilus | chr5: 63322850-63322874 | Activity not tested | Intron 6 |

TABLE 3-continued

List of target sequences and editing activities in porcine fetal fibroblasts

| SEQ ID NO: | Cas9 Nuclease | Location of target | Average edited fraction | Position on CD163 |
|---|---|---|---|---|
| 270 | S. thermophilus | chr5: 63322955-63322979 | Activity not tested | Intron 6 |
| 271 | S. thermophilus | chr5: 63322989-63323013 | Activity not tested | Intron 6 |
| 347 | S. pyogenes | chr5: 63323002-63323024 | 2.1 | Exon 7 |
| 348 | S. pyogenes | chr5: 63323011-63323033 | 31.9 | Exon 7 |
| 349 | S. pyogenes | chr5: 63323015-63323037 | 7.7 | Exon 7 |
| 350 | S. pyogenes | chr5: 63323017-63323039 | 56.5 | Exon 7 |
| 351 | S. pyogenes | chr5: 63323018-63323040 | 74.3 | Exon 7 |
| 352 | S. pyogenes | chr5: 63323019-63323041 | 52.3 | Exon 7 |
| 353 | S. pyogenes | chr5: 63323022-63323044 | 44.0 | Exon 7 |
| 354 | S. pyogenes | chr5: 63323023-63323045 | 61.6 | Exon 7 |
| 355 | S. pyogenes | chr5: 63323024-63323046 | 49.4 | Exon 7 |
| 356 | S. pyogenes | chr5: 63323028-63323050 | 3.1 | Exon 7 |
| 357 | S. pyogenes | chr5: 63323029-63323051 | 0.8 | Exon 7 |
| 358 | S. pyogenes | chr5: 63323040-63323062 | 42.4 | Exon 7 |
| 359 | S. pyogenes | chr5: 63323052-63323074 | 66.7 | Exon 7 |
| 360 | S. pyogenes | chr5: 63323053-63323075 | 13.4 | Exon 7 |
| 361 | S. pyogenes | chr5: 63323061-63323083 | 77.9 | Exon 7 |
| 362 | S. pyogenes | chr5: 63323071-63323093 | 60.8 | Exon 7 |
| 363 | S. pyogenes | chr5: 63323072-63323094 | 70.6 | Exon 7 |
| 364 | S. pyogenes | chr5: 63323073-63323095 | 75.2 | Exon 7 |
| 365 | S. pyogenes | chr5: 63323098-63323120 | 64.4 | Exon 7 |
| 366 | S. pyogenes | chr5: 63323102-63323124 | 55.0 | Exon 7 |
| 367 | S. pyogenes | chr5: 63323105-63323127 | 51.2 | Exon 7 |
| 368 | S. pyogenes | chr5: 63323108-63323130 | 58.3 | Exon 7 |
| 369 | S. pyogenes | chr5: 63323125-63323147 | 14.5 | Exon 7 |
| 370 | S. pyogenes | chr5: 63323126-63323148 | 22.6 | Exon 7 |
| 371 | S. pyogenes | chr5: 63323131-63323153 | 49.9 | Exon 7 |
| 372 | S. pyogenes | chr5: 63323139-63323161 | 68.9 | Exon 7 |
| 373 | S. pyogenes | chr5: 63323147-63323169 | 57.4 | Exon 7 |
| 374 | S. pyogenes | chr5: 63323159-63323181 | 12.9 | Exon 7 |
| 375 | S. pyogenes | chr5: 63323160-63323182 | 19.7 | Exon 7 |
| 376 | S. pyogenes | chr5: 63323161-63323183 | 33.6 | Exon 7 |
| 377 | S. pyogenes | chr5: 63323162-63323184 | 65.3 | Exon 7 |
| 378 | S. pyogenes | chr5: 63323163-63323185 | 51.4 | Exon 7 |
| 379 | S. pyogenes | chr5: 63323173-63323195 | 57.6 | Exon 7 |
| 380 | S. pyogenes | chr5: 63323174-63323196 | 52.1 | Exon 7 |
| 381 | S. pyogenes | chr5: 63323175-63323197 | 48.2 | Exon 7 |
| 382 | S. pyogenes | chr5: 63323177-63323199 | 33.7 | Exon 7 |
| 383 | S. pyogenes | chr5: 63323181-63323203 | 18.3 | Exon 7 |
| 384 | S. pyogenes | chr5: 63323187-63323209 | 57.0 | Exon 7 |
| 385 | S. pyogenes | chr5: 63323197-63323219 | 33.3 | Exon 7 |
| 386 | S. pyogenes | chr5: 63323198-63323220 | 58.3 | Exon 7 |
| 387 | S. pyogenes | chr5: 63323219-63323241 | 20.7 | Exon 7 |
| 388 | S. pyogenes | chr5: 63323220-63323242 | 42.2 | Exon 7 |
| 389 | S. pyogenes | chr5: 63323221-63323243 | 43.4 | Exon 7 |
| 390 | S. pyogenes | chr5: 63323231-63323253 | 21.8 | Exon 7 |
| 391 | S. pyogenes | chr5: 63323251-63323273 | 46.8 | Exon 7 |
| 392 | S. pyogenes | chr5: 63323252-63323274 | 42.6 | Exon 7 |
| 393 | S. pyogenes | chr5: 63323255-63323277 | 22.8 | Exon 7 |
| 394 | S. pyogenes | chr5: 63323267-63323289 | 85.4 | Exon 7 |
| 395 | S. pyogenes | chr5: 63323268-63323290 | 41.1 | Exon 7 |
| 396 | S. pyogenes | chr5: 63323268-63323290 | 53.6 | Exon 7 |
| 397 | S. pyogenes | chr5: 63323269-63323291 | 32.1 | Exon 7 |
| 398 | S. pyogenes | chr5: 63323277-63323299 | 16.6 | Exon 7 |
| 399 | S. pyogenes | chr5: 63323278-63323300 | 39.0 | Exon 7 |
| 400 | S. pyogenes | chr5: 63323279-63323301 | 11.7 | Exon 7 |
| 401 | S. pyogenes | chr5: 63323282-63323304 | 48.9 | Exon 7 |
| 402 | S. pyogenes | chr5: 63323283-63323305 | n/a | Exon 7 |
| 403 | S. pyogenes | chr5: 63323287-63323309 | 11.6 | Exon 7 |
| 404 | S. pyogenes | chr5: 63323288-63323310 | 69.3 | Exon 7 |
| 405 | S. pyogenes | chr5: 63323295-63323317 | 46.0 | Exon 7 |
| 406 | S. pyogenes | chr5: 63323300-63323322 | 54.2 | Exon 7 |
| 407 | S. thermophilus | chr5: 63323019-63323043 | 25.5 | Exon 7 |
| 408 | S. thermophilus | chr5: 63323022-63323046 | 24.7 | Exon 7 |
| 409 | S. thermophilus | chr5: 63323061-63323085 | 37.8 | Exon 7 |
| 410 | S. thermophilus | chr5: 63323071-63323095 | 30.4 | Exon 7 |
| 411 | S. thermophilus | chr5: 63323096-63323120 | 33.4 | Exon 7 |
| 412 | S. thermophilus | chr5: 63323102-63323126 | 19.8 | Exon 7 |
| 413 | S. thermophilus | chr5: 63323105-63323129 | 0.6 | Exon 7 |
| 414 | S. thermophilus | chr5: 63323159-63323183 | 14.8 | Exon 7 |
| 415 | S. thermophilus | chr5: 63323160-63323184 | 7.8 | Exon 7 |
| 416 | S. thermophilus | chr5: 63323161-63323185 | 3.6 | Exon 7 |
| 417 | S. thermophilus | chr5: 63323163-63323187 | 7.9 | Exon 7 |
| 418 | S. thermophilus | chr5: 63323175-63323199 | 33.8 | Exon 7 |
| 419 | S. thermophilus | chr5: 63323175-63323199 | 11.5 | Exon 7 |
| 420 | S. thermophilus | chr5: 63323219-63323243 | 8.1 | Exon 7 |
| 421 | S. thermophilus | chr5: 63323253-63323277 | 32.6 | Exon 7 |
| 422 | S. thermophilus | chr5: 63323275-63323299 | 0.2 | Exon 7 |
| 423 | S. thermophilus | chr5: 63323277-63323301 | 12.3 | Exon 7 |
| 424 | S. thermophilus | chr5: 63323280-63323304 | 26.0 | Exon 7 |
| 425 | S. thermophilus | chr5: 63323295-63323319 | 30.5 | Exon 7 |

Efficient guideRNA-Cas9 pairs which cut sites early in the CD163 gene (exons 1-4) were selected and further screened for potential off-target binding within the pig genome.

In some instances, the use of guide RNA and endonuclease has been observed to result in cleavage of DNA at unintended locations in the genome. Because the repair process for dsDNA breaks can be random, off-target cleavage events can result in undesirable changes to coding or regulatory regions in the genome. Therefore, in instances where a number of single or paired guides can perform an intended edit with similar editing frequencies, it is advantageous to consider off-target cleavage in choosing a guide or guide pair for editing experiments.

A number of computational and biochemical approaches for elucidating off-targets have been developed. Computational approaches can include, but are not limited to, Cas-OFFinder (Bae, S., et al., Bioinformatics, 2014, 30, 1473-1475.), CRISPR-offender (Zhao, C., et al., Int. J. Biol. Sci., 2017, 13, 1470-1478), and CRISPR-OFF (Alkan, F., et al., Genome Biol., 2018, 19, 177). Other computational approaches are readily available to those skilled in the art. Biochemical approaches can include, but are not limited to, GUIDE-Seq (Tsai, S. Q., et al., Nat Biotechnol. 2015, 33, 187-197), SITE-SEQ® (Cameron, P., et al., Nat Methods 2017, 14, 600-606), and CIRCLE-seq (Tsai, S. Q., et al., Nat. Methods, 2017, 14, 607-614). Other biochemical approaches are readily available to those skilled in the art. While computational methods are relatively fast and inexpensive compared to biochemical ones, biochemical approaches have been shown to be superior in identifying validated off-target edits.

A subset of guideRNAs that have demonstrated a high frequency of intended edits in porcine fetal fibroblasts, as described above, were assayed for specificity using SITE-SEQ®. Using naked gDNA and RNP editing reagents in vitro, SITE-SEQ® can provide a list of potential cleavage sites. Off-target cleavage in a cellular environment can be more complicated than that simulated biochemically in vitro. Factors such as effective RNP concentration and target availability due to chromatin state, among other factors, can contribute to the number of off-target edits realized in porcine cells or in edited pigs. Fortunately, biochemical methods such as SITE-SEQ® can provide researchers a list of sites to interrogate. These sites can be interrogated by methods that include, but are not limited to, TOPO cloning and sequencing of TOPO clones, ILLUMINA® amplicon sequencing, Nanopore sequencing, other NGS sequencing methods, and sequence capture (Gnirke, A., et al., Nat. Biotechnol., 2009, 27, 182-189).

Screening was performed for biochemically-identified off-target sites in edited porcine fibroblasts and subsequently in injected embryos. Guides with validated off-target edits were de-prioritized for use in generating edited pigs. Animals generated using guides with known off-targets can be interrogated for the presence of off-target edits using the strategies outlined above. Animals that do contain off-target edits can either be removed from the breeding program or the off-target edits can be removed via breeding. This screening can include bioinformatic methods, such as BLAST® searching, to identify sequences in the *Sus scrofa* genome that contain 1-5 mismatches with the guideRNA, that could therefore allow for off-target binding. The number of potential off-target binding sites in the genome when allowing these mismatches in the computer algorithm is detailed below in Table 4.

TABLE 4

Mismatch Detection

| | | SEQ ID | | MISMATCHES ≤ 5 | |
|---|---|---|---|---|---|
| SITE | LOCATION-Spy coordinates | SEQ ID Spy | SEQ ID Stherm | Spy | Stherm C3 |
| 1 | chr5: 63300236-63300258 | 19 | 20 | 920 | 142 |
| 2 | chr5: 63300308-63300330 | 32 | 33 | 625 | 51 |
| 3 | chr5: 63301997-63302019 | 41 | 42 | 506 | 37 |
| 4 | chr5: 63303121-63303143 | 43 | 44 | 1625 | 201 |
| 5 | chr5: 63303137-63303159 | 47 | 48 | 474 | 32 |
| 6 | chr5: 63303140-63303162 | 49 | 50 | 548 | 49 |
| 7 | chr5: 63303166-63303188 | 52 | 53 | 692 | 92 |
| 8 | chr5: 63303169-63303191 | 54 | 55 | 782 | 94 |
| 9 | chr5: 63303181-63303203 | 56 | 57 | 1346 | 200 |
| 10 | chr5: 63303184-63303206 | 58 | 59 | 1873 | 382 |
| 11 | chr5: 63303189-63303211 | 60 | 61 | 1642 | 240 |
| 12 | chr5: 63303378-63303400 | 86 | 87 | 588 | 53 |
| 13 | chr5: 63303413-63303435 | 91 | 92 | 545 | 50 |
| 14 | chr5: 63306108-63306130 | 103 | 104 | 480 | 49 |
| 15 | chr5: 63306144-63306166 | 108 | 109 | 344 | 21 |
| 16 | chr5: 63306147-63306169 | 110 | 111 | 451 | 44 |
| 17 | chr5: 63306251-63306273 | 116 | 117 | 1343 | 65 |
| 18 | chr5: 63306336-63306358 | 125 | 126 | 718 | 66 |
| 19 | chr5: 63306371-63306393 | 130 | 131 | 1310 | 131 |
| 20 | chr5: 63309035-63309057 | 134 | 135 | 690 | 83 |
| 21 | chr5: 63309077-63309099 | 138 | 139 | 949 | 95 |
| 22 | chr5: 63309084-63309106 | 140 | 141 | 1234 | 99 |
| 23 | chr5: 63309273-63309295 | 164 | 165 | 418 | 47 |
| 24 | chr5: 63309308-63309330 | 170 | 171 | 747 | 95 |
| 25 | chr5: 63309857-63309879 | 174 | 175 | 795 | 47 |
| 26 | chr5: 63309860-63309882 | 176 | 177 | 736 | 94 |
| 27 | chr5: 63309886-63309908 | 179 | 180 | 1829 | 124 |
| 28 | chr5: 63309889-63309911 | 182 | 183 | 1575 | 94 |
| 29 | chr5: 63309933-63309955 | 187 | 188 | 871 | 95 |
| 30 | chr5: 63310098-63310120 | 203 | 204 | 533 | 73 |
| 31 | chr5: 63310100-63310122 | 206 | 207 | 537 | 53 |

One of the factors that contributes to cutting at these off-target sites can be whether the gene editing components are delivered as a DNA vector or as an RNA-protein complex; sites that may have as few as 1 or 2 base mismatches can be faithfully discriminated from the intended target site when the Cas9 and guide RNA can be delivered as a single guide ribonucleotide protein complex (sgRNP) rather than delivered on a DNA vector.

A second consideration to maximize specificity of a Cas9 guide-RNA reagent can be to prescreen guide RNA-protein pairs using in vitro biochemical methods. Several laboratories have published methods to screen for off-target edit sites. These biochemical approaches can identify potential off-target Cas9 cleavage sites in purified genomic DNA. Using these assays, genomic DNA can be digested with a range of sgRNP concentrations, from limiting to saturating, thus permitting the recovery of both high- and low-cleavage-sensitivity off-target sites. See, e.g., Cameron et al., "SITE-SEQ®: A Genome-wide Method to Measure Cas9 Cleavage," Protocol Exchange (2017).

The off-target sites identified by off-target screening can be used to guide careful and comprehensive examination of possible off-target sites in cells, measuring both editing frequency and functional cellular consequence. Several selected guide RNA-Cas protein pairs can be screened, and the screening can demonstrate: 1) efficient cutting nearer to the 5' end of the CD163 gene, and 2) few mismatch sequences as determined by bioinformatic methods.

Using this guide selection criteria, several guide RNA-Cas protein pairs can be selected for cutting activity in porcine parthenotes. Porcine oocytes can be doubled using an electric current, injected with guide RNA-Cas protein, allowed to develop for 7 days, then harvested and DNA sequenced across the intended target site. Several guide RNA-Cas protein pairs can be identified to confer edits at a high frequency in parthenotes and are selected for further development.

The present specification provides for, and includes, methods for identifying and selecting optimal target sites for CRISPR/Cas mediated cleavage and gene editing. In an aspect, the method can comprise identifying a target region of a genome for editing; identifying all 20 nucleotide sequences in the target region; performing a bioinformatic screen to identify and remove sequences that match non-target sites in the pig genome that contain 1 to 4 mismatches and have a suitable PAM sequence based on the Cas protein; preparing CRISPR/Cas RNP complexes comprising a guide RNA backbone and target sequences, introducing the CRISPR/Cas RNP complexes into a porcine cell in culture, and determining the average editing frequency of the guide RNA/Cas combination. In an aspect, determining the average editing frequency of the guide RNA/Cas combination can comprise amplifying, by PCR, a region surrounding the target site, performing amplicon deep sequencing, and comparing it to untreated cells. In an aspect, the method provides for selecting preferred target sequences that can have an average editing frequency of at least 15. Also provided for are methods for identifying and selecting optimal target sites for CRISPR/Cas mediated cleavage and gene editing wherein the guide RNA and Cas proteins can be provided as part of an expression vector or vectors. Suitable cells are known to persons of skill in the art and can include, but are not limited to, primary fetal fibroblasts of an intended porcine breeding line.

Multiple repair templates can be designed to generate in-frame stop codons. The repair templates listed, when used with appropriate guide RNAs in an endonuclease system, can generate an in-frame termination codon (TAA, TGA, TAG) after repair. Different lengths of repair templates can be used, having sequence identity on either side of the edit site. In an aspect, a repair template can share at least 15 nucleotides on either side of the CRISPR/Cas endonuclease cleavage site (e.g., 15-15 nucleotides). In other aspects, repair templates can share more than 100 nucleotides on either side of the edit site (e.g., >100->100). Repair templates can be single, double, or staggered strands of complementary DNA using overhangs on the ends. In addition, these templates are not limited to DNA but also could be RNA or modified nucleotides (inosine, for example) or a mixture of these bases and have 5' and or 3' ends protected from degradation. Because there are exonucleases that cleave nucleotides from the ends, protecting the ends with modified bases can prevent exonuclease digestion in the cell of both DNA and RNA. Not to be limited by theory, increasing the length of the region of identity on both sides of the edit site can increase the efficiency and specificity of the repair process (e.g., homology arms). Included and provided for by the present specification are repair templates that can have 100% identity over at least 25 nucleotides on both sides of the edit site. This core identity region ensures that the desired edit (for example, deletions for SEQ ID NOs: 1 to 13) is accurate and efficient. In an aspect, the core identity region can be at least 40 nucleotides flanking the edit site. In yet another aspect, the core identity region can be at least 50 nucleotides on both sides of the edit site. In an aspect, the flanking core region can comprise 60 nucleotides of 100% identity. Also included in an aspect are repair templates that can have 70 identical nucleotides to the chromosomal region flanking the edit site. In an aspect, the core identity region can comprise 75 nucleotides of identity to the chromosomal region flanking the edit site. In an aspect, the core identity region can comprise 25 to 40 flanking nucleotides. In a further aspect, the core identity region can comprise 40 to 75 flanking nucleotides.

In some aspects, the core identity region can be further flanked by additional regions of homology to the target site (the "flanking homology regions"). As provided herein, in an aspect, the flanking homology regions can comprise 100% identity to the target site. As examples, SEQ ID NOs: 1 to 13 shared 100% homology to the CD163 region on either side of the targeted edit site as found in lines 2, 3, 15, 19, 27, 62, or 65 (e.g., 100% homology in the core region and the flanking homology regions). Also included are repair templates that can comprise SEQ ID NOs: 1 to 13, wherein the core identity region can comprise 100% identity to 25 nucleotides of the genome on either side of the desired edit (e.g., bases 50 to 100) and can be flanked by at least 80% identity to the genome on either side of the core region (e.g., nucleotides 1 to 49 and 101 to 150 of SEQ ID NOs: 1 to 18). In another aspect, the core region can have 100% homology and the flanking homology regions can share 85% homology. In a further aspect, the core region can have 100% homology and the flanking homology regions can share 90% homology. In yet another aspect, the core region can have 100% homology and the flanking homology regions can share 95% homology. Also included in an aspect are repair templates that can have a core region that has 100% homology and the flanking homology regions share 97% homology. In some aspects, the flanking homology regions can share 99% homology. Not to be limited by theory, it is thought that increasing the length of the flanking homology regions can introduce the desired CD163 edits into related animals without further modifying the genome. That is, specific repair sequences incorporating polymorphisms or changes in the CD163 genome of other pigs are specifically included and provided for.

The present specification includes, and provides for, flanking homology regions that can have greater than 50 nucleotides on each side of the edit site. In an aspect, the flanking homology regions can have greater than 75 nucleotides on each side of the edit site. In an aspect, the flanking homology regions can have greater than 100 nucleotides on each side of the edit site. Also included are flanking homology regions that can have greater than 200 nucleotides on each side of the edit site. In aspects, the flanking homology regions can have between 30 and 1000 nucleotides on each side of the edit site.

The present specification includes, and provides for, additional modifications at the 5' and 3' ends of repair template. Repair templates are not limited to DNA but also could be RNA or modified nucleotides (inosine, for example) or a mixture of these bases and can have 5' and or 3' ends protected from degradation. Because there are exonucleases that cleave nucleotides from the ends, protecting the ends with modified bases can prevent exonuclease digestion in the cell of both DNA and RNA. Accordingly, as provided herein, the 5' and 3' ends of a repair template comprising a flanking homology region can be modified to prevent degradation.

The present specification provides for, and includes, ribonucleoprotein (RNP) complexes that can comprise a guide polynucleotide and a Cas protein. In an aspect, the Cas protein can be a *S. thermophilus* Cas9. In another aspect, the Cas protein can be Cas9 from *S. pyogenes*. Other suitable Cas proteins are known in the art and exemplary Cas systems are described above in Table 1. The selection of suitable Cas proteins depends on the required PAM sequence combination, and methods of identifying Cas proteins and modifying Pam sequences are known. Similarly, Cas systems differ in their requirements for guide RNA backbone sequences (e.g., tracrRNA sequences). In an aspect, the RNP complex can comprise a Cas protein and a guide nucleotide having at least 98% sequence identity to an RNA sequence selected from the group consisting of the first 20 nucleotides of each of SEQ ID NOs: 22 to 271 and 347 to 425. In another aspect, the RNP complex can comprise a guide RNA comprising a sequence selected from the group consisting of the first 20 nucleotides of each of SEQ ID NOs: 22 to 271 and 347 to 425. In an aspect, the RNP complex can comprise a guide polynucleotide having 99% identity to a sequence selected from the group consisting of the first 20 nucleotides of each of SEQ ID NOs: 22 to 271 and 347 to 425. In an aspect, the guide polynucleotide of the RNP complex can comprise a sequence selected from the group consisting of the first 20 nucleotides of each of SEQ ID NOs: 22 to 271 and 347 to 425. As provided herein, the RNP complex can comprise the sequences of any one of SEQ ID NOs: 22 to 271 and 347 to 425 combined with an RNA backbone as part of an sgRNA. In an aspect, the RNP complex can be pre-formed prior to injection into a target cell or can be injected or introduced separately.

Also provided for, and included, in the present specification are isolated guide RNAs that can comprise a spacer selected from the group consisting of the first 20 nucleotides of each of SEQ ID NOs: 22 to 271 and the first 20 nucleotides of each of SEQ ID NOs: 347 to 425. In an aspect, the Cas protein can be a protein comprising SEQ ID NOs: 20 or 21.

The present specification also includes, and provides for, DNA vectors that can encode guide RNAs for the preparation of CRISPR/Cas RNPs. In general, a vector encoding a guide RNA can comprise a sequence selected from the group consisting of the first 20 nucleotides of each of SEQ ID NOs: 22 to 271 or SEQ ID NOs: 347 to 425 and a guide RNA backbone arranged in cis and as part of a single transcription unit. Upon expression in a suitable cell, the DNA vector can produce an sgRNA of the present specification. Suitable expression vector backbones, including promoters, selectable markers and replication origins, are well known to persons of skill in the art. In practice, the 20 nucleotides and the guide RNA backbone can be DNA (when expressed from a promoter to be transcribed in vivo (in cells) or in vitro (via T7 polymerase) to form an RNA guide or the backbone can be chemically synthesized dual (crRNA and trRNA) guide or single guide RNA.

Specific guideRNAs can be paired to excise parts of the CD163 gene by using paired guideRNAs to delete sections of the gene located between those guides. Exemplary pairs of guideRNAs (listed as DNA sequences) are provided in Table 5. Guide pairs without an exon 7 amino acid sequence listed remove the entire exon. The complete amino acid sequence for these deletions is set forth in SEQ ID NO: 553. All guides in Table 5 can create the desired sequence by excising the DNA in between the two guides and NHEJ repair between the cut sites without the use of a DNA repair template. The guide pairs that result in the amino acid sequences set forth in SEQ ID NOs. 506-517 can introduce an exogenous stop codon across the cut ends of the DNA introduced by the guide.

TABLE 5

Exemplary Guide RNA Pairs

| SEQ ID NO: (5') | Cut site (5') | SEQ ID NO: (3') | Cut site (3') | Deletion size (bp) | Repaired Sequence SEQ ID | Exon 7AA SEQ ID |
|---|---|---|---|---|---|---|
| 229 | 63322816 | 256 | 63323377 | 561 | 426 | N/A |
| 230 | 63322814 | 256 | 63323377 | 562 | 427 | N/A |
| 231 | 63322826 | 256 | 63323377 | 551 | 428 | N/A |
| 237 | 63322861 | 256 | 63323377 | 516 | 429 | N/A |
| 241 | 63322891 | 256 | 63323377 | 486 | 430 | N/A |
| 229 | 63322816 | 258 | 63323378 | 562 | 431 | N/A |
| 230 | 63322814 | 258 | 63323378 | 563 | 432 | N/A |
| 231 | 63322826 | 258 | 63323378 | 552 | 433 | N/A |
| 237 | 63322861 | 258 | 63323378 | 517 | 434 | N/A |
| 241 | 63322891 | 258 | 63323378 | 487 | 435 | N/A |
| 229 | 63322816 | 261 | 63323373 | 558 | 436 | N/A |
| 230 | 63322814 | 261 | 63323373 | 559 | 437 | N/A |
| 231 | 63322826 | 261 | 63323373 | 548 | 438 | N/A |
| 237 | 63322861 | 261 | 63323373 | 513 | 439 | N/A |
| 241 | 63322891 | 261 | 63323373 | 483 | 440 | N/A |
| 219 | 63322697 | 256 | 63323377 | 680 | 441 | N/A |
| 221 | 63322709 | 256 | 63323377 | 668 | 442 | N/A |
| 224 | 63322747 | 256 | 63323377 | 630 | 443 | N/A |
| 227 | 63322786 | 256 | 63323377 | 591 | 444 | N/A |
| 219 | 63322697 | 258 | 63323378 | 681 | 445 | N/A |
| 221 | 63322709 | 258 | 63323378 | 669 | 446 | N/A |
| 224 | 63322747 | 258 | 63323378 | 631 | 447 | N/A |
| 227 | 63322786 | 258 | 63323378 | 592 | 448 | N/A |
| 219 | 63322697 | 261 | 63323373 | 677 | 449 | N/A |
| 221 | 63322709 | 261 | 63323373 | 665 | 450 | N/A |
| 224 | 63322747 | 261 | 63323373 | 627 | 451 | N/A |
| 227 | 63322786 | 261 | 63323373 | 588 | 452 | N/A |
| 249 | 63322963 | 256 | 63323377 | 414 | 453 | N/A |
| 250 | 63322973 | 256 | 63323377 | 404 | 454 | N/A |
| 249 | 63322963 | 258 | 63323378 | 415 | 455 | N/A |
| 250 | 63322973 | 258 | 63323378 | 405 | 456 | N/A |
| 249 | 63322963 | 261 | 63323373 | 411 | 457 | N/A |
| 250 | 63322973 | 261 | 63323373 | 401 | 458 | N/A |
| 351 | 63323023 | 365 | 63323103 | 80 | 459 | 506 |
| 351 | 63323023 | 387 | 63323235 | 212 | 460 | 506 |
| 348 | 63323027 | 390 | 63323236 | 209 | 461 | 507 |
| 348 | 63323027 | 388 | 63323236 | 209 | 462 | 507 |
| 348 | 63323027 | 395 | 63323284 | 257 | 463 | 507 |
| 352 | 63323035 | 365 | 63323103 | 68 | 464 | 508 |
| 352 | 63323035 | 387 | 63323235 | 200 | 465 | 508 |
| 352 | 63323035 | 399 | 63323283 | 248 | 466 | 508 |
| 353 | 63323038 | 365 | 63323103 | 65 | 467 | 509 |
| 353 | 63323038 | 387 | 63323235 | 197 | 468 | 509 |
| 353 | 63323038 | 399 | 63323283 | 245 | 469 | 509 |
| 354 | 63323039 | 390 | 63323236 | 197 | 470 | 509 |
| 354 | 63323039 | 388 | 63323236 | 197 | 471 | 509 |
| 354 | 63323039 | 395 | 63323284 | 245 | 472 | 509 |
| 358 | 63323056 | 361 | 63323077 | 21 | 473 | 510 |
| 358 | 63323056 | 362 | 63323087 | 31 | 474 | 510 |
| 358 | 63323056 | 368 | 63323124 | 68 | 475 | 510 |
| 358 | 63323056 | 384 | 63323203 | 147 | 476 | 510 |
| 358 | 63323056 | 394 | 63323272 | 216 | 477 | 510 |
| 358 | 63323056 | 399 | 63323283 | 227 | 478 | 511 |
| 359 | 63323057 | 390 | 63323236 | 179 | 479 | 511 |
| 359 | 63323057 | 388 | 63323236 | 179 | 480 | 511 |
| 359 | 63323057 | 395 | 63323284 | 227 | 481 | 511 |
| 360 | 63323058 | 368 | 63323124 | 66 | 482 | 511 |
| 360 | 63323058 | 384 | 63323203 | 145 | 483 | 511 |
| 360 | 63323058 | 389 | 63323237 | 179 | 484 | 511 |
| 360 | 63323058 | 394 | 63323272 | 214 | 485 | 511 |
| 360 | 63323058 | 397 | 63323285 | 227 | 486 | 511 |
| 361 | 63323077 | 365 | 63323103 | 26 | 487 | 512 |
| 361 | 63323077 | 387 | 63323235 | 158 | 488 | 512 |
| 362 | 63323087 | 390 | 63323236 | 149 | 489 | 513 |
| 362 | 63323087 | 388 | 63323236 | 149 | 490 | 512 |
| 362 | 63323087 | 395 | 63323284 | 197 | 491 | 513 |
| 364 | 63323089 | 365 | 63323103 | 14 | 492 | 514 |
| 364 | 63323089 | 387 | 63323235 | 146 | 493 | 514 |
| 364 | 63323089 | 399 | 63323283 | 194 | 494 | 514 |
| 365 | 63323103 | 368 | 63323124 | 21 | 495 | 515 |
| 365 | 63323103 | 384 | 63323203 | 100 | 496 | 516 |
| 365 | 63323103 | 389 | 63323237 | 134 | 497 | 516 |
| 365 | 63323103 | 394 | 63323272 | 169 | 498 | 516 |
| 365 | 63323103 | 397 | 63323285 | 182 | 499 | 516 |
| 366 | 63323118 | 368 | 63323124 | 6 | 500 | 517 |
| 366 | 63323118 | 384 | 63323203 | 85 | 501 | 517 |
| 366 | 63323118 | 389 | 63323237 | 119 | 502 | 517 |
| 366 | 63323118 | 394 | 63323272 | 154 | 503 | 517 |
| 366 | 63323118 | 397 | 63323285 | 167 | 504 | 517 |
| 354 | 63323039 | 211 | 63323163 | 123 | 505 | 518 |

In aspects, the guide RNA-Cas protein pairs can further comprise a DNA repair template. Exemplary guides and repair templates creating stop codons are listed in Table 6. These and other guides can be paired with other repair templates to generate in-frame stop codons or perturb, interfere, or eliminate splicing of exons, as examples of disrupting CD163 mRNA translation or processing. Other examples can include, but are not limited to, the elimination of the start ATG codon, or programming repair outcomes when using paired guide RNAs where a repair template could promote a single repair outcome over random non-homologous end joining when paired nucleases remove an exon (e.g., deletion of exon 7 corresponding to domain 5) in CD163. Without being limited by theory, analysis reveals consistent reduction of bioinformatic mismatches with inclusion of the extra nG in the PAM (nGGnG) as well as reduced off-target cutting in vitro and in vivo. Reduction of mismatches can include those from an alignment perspective (whether the DNA sequence has mismatches with the RNA guide sequence). See Table 4. A mismatch may not be an off-target edit (cutting or presence of indel, in vitro or in vivo, respectively), but an off-target edit is likely due to a mismatch. In the most preferred aspects, the methods disclosed herein produce no off-target edits in pigs, and the pigs disclosed herein have no off-target edits in their genomes.

TABLE 6

Guide RNAs and repair templates for editing Exon 2 of CD163

| Region Chr5 Location of guideRNAs binding site | 63301998-02017 | 63301997-02016 | 63303213-03232 | 63303283-03302 | 63303315-03334 | 63303315-03334 | 63303338-03357 |
|---|---|---|---|---|---|---|---|
| Repair template SEQ ID NO | 1 | 2 | 3 | 4 | 5 | 6 | 7 |
| Guide RNA spacer (DNA) SEQ ID NO | 274 | 275 | 276 | 277 | 278 | 279 | 280 |
| Guide RNA spacer (RNA) SEQ ID NO | 287 | 288 | 289 | 290 | 291 | 292 | 293 |
| WT Region SEQ ID NO. | 300 | 301 | 302 | 303 | 304 | 305 | 306 |
| Trans-lation of WT region | 313 | 314 | 315 | 316 | 317 | 318 | 319 |
| Translation of Deletion | 326 | 327 | 328 | 329 | 330 | 331 | 332 |
| Base deletion coordinates | chr5: 63301999-63302005 | chr5: 63301999-63302005 | chr5: 63303234-63303235 | chr5: 63303304-63303307 | chr5: 63303336-63303336 | chr5: 63303337-63303337 | chr5: 63303351-63303356 |
| Deleted bases (#) | CTTGGTC (7) | CTTGGTC (7) | GG (2) | GGCT (4) | G (1) | G (1) | CTTGTC (6) |

| Region Chr5 Location of guideRNAs binding site | 63303379-03398 | 63303379-03398 | 63306148-06167 | 63306263-06282 | 63306364-06383 | 63323147-23166 |
|---|---|---|---|---|---|---|
| Repair template SEQ ID NO | 8 | 9 | 10 | 11 | 12 | 13 |
| Guide RNA spacer (DNA) SEQ ID NO | 281 | 282 | 283 | 284 | 285 | 286 |
| Guide RNA spacer (RNA) SEQ ID NO | 294 | 295 | 296 | 297 | 298 | 299 |
| WT Region SEQ ID NO. | 307 | 308 | 309 | 310 | 311 | 312 |
| Trans-lation of WT region | 320 | 321 | 322 | 323 | 324 | 325 |
| Translation of Deletion | 333 | 334 | 335 | 336 | 337 | 338 |
| Base deletion coordinates | chr5: 63303399-63303401 | chr5: 63303400-63303402 | chr5: 63306156-63306158 | chr5: 63306282-63306284 | chr5: 63306373-63306377 | chr5: 63323159-63323162 |
| Deleted bases (#) | GGG (3) | GGG (3) | TTC (3) | CTC (3) | CGATC (5) | CGGC (4) |

The stochastic natural cellular repair process of non-homologous end joining (NHEJ) repair sometimes involves inserting or deleting single or multiple nucleotides at the double-strand break. As a consequence of this repair process, if a double-strand break occurs in the coding region of a gene, a shift in the translational reading frame of the encoded mRNA can result until an in-frame stop codon, terminating protein translation. Although the translation of this naturally, accidentally mutated gene can produce a shortened protein relative to the protein product of an unmodified version, the amino acid sequence of this newly encoded polypeptide would be unique, possibly reducing or even improving the fitness of cells within the target organism. In an aspect, to preclude the creation of frame shifting mutations and the translation of this set of undesirable polypeptides, edited pigs can be screened for formation of an in-frame translational stop codon at or near the endonuclease cut site that is a consequence of a separate, naturally occurring NHEJ repair.

The excision of genomic DNA sequence using two intronic guideRNAs in conjunction with an endonuclease can be accomplished by NHEJ repairs that include, but are not limited to, the end-to-end joining of nuclease cut sites. Because introns are non-coding, NHEJ repair outcomes that include indels around the nuclease cut sites can accomplish the excision of the intended region of DNA which can include intron and/or exon sequences. Because some NHEJ repair outcomes occur more frequently than others, it is advantageous to consider repair outcome frequency when choosing a guideRNA pair for use in gene editing experiments. SEQ ID NO: 520-555 illustrate repair outcomes of exon 7 excisions observed in blastocysts from guide pairs as set forth in Table 7. The designed repair outcome for these guide pairs is listed in Table 5.

TABLE 7

Observed Repair Outcomes in Blastocysts

| SEQ ID NO: (5') | SEQ ID NO: (3') | Repair outcome SEQ ID |
|---|---|---|
| 249 | 261 | 520 |
| 249 | 261 | 521 |
| 249 | 261 | 522 |

TABLE 7-continued

Observed Repair Outcomes in Blastocysts

| SEQ ID NO: (5') | SEQ ID NO: (3') | Repair outcome SEQ ID |
|---|---|---|
| 249 | 261 | 523 |
| 249 | 261 | 524 |
| 249 | 261 | 525 |
| 249 | 261 | 526 |
| 249 | 261 | 527 |
| 249 | 256 | 528 |
| 249 | 256 | 529 |
| 249 | 256 | 530 |
| 249 | 256 | 531 |
| 249 | 256 | 532 |
| 249 | 256 | 533 |
| 249 | 256 | 534 |
| 249 | 256 | 535 |
| 241 | 258 | 536 |
| 241 | 258 | 537 |
| 241 | 258 | 538 |
| 241 | 258 | 539 |
| 241 | 258 | 540 |
| 241 | 258 | 541 |
| 241 | 258 | 542 |
| 241 | 258 | 543 |
| 241 | 258 | 544 |
| 221 | 261 | 545 |
| 221 | 261 | 546 |
| 221 | 261 | 547 |
| 221 | 261 | 548 |
| 221 | 261 | 549 |
| 229 | 256 | 550 |
| 229 | 256 | 551 |
| 229 | 256 | 552 |
| 229 | 256 | 553 |
| 229 | 256 | 554 |
| 229 | 256 | 555 |

In another aspect, during gene editing, in-frame stop codons that do not result in the addition of new amino acids can be created by including a DNA repair template together with the guide RNA-Cas protein pair. In an aspect, a DNA repair template can be a dsDNA. In another aspect, the DNA repair template can be a ssDNA. Co-introduction of a double- or single-stranded DNA repair template can be used to either delete or insert DNA nucleotides to form an in-frame translational stop codon (TAA, TGA, TAG) at or near the double-strand break site initiated by the endonuclease. DNA repair templates can further comprise polynucleotide modification templates containing several nucleotide changes in comparison to the native sequence, which can directly edit the target DNA sequence and can be co-transfected with the endonuclease editing reagents to generate edited CD163 genes with in-frame stop codons. In an aspect, the encoded proteins from these gene edited CD163 genes, when transcribed into mRNA and then translated into protein, can only synthesize a shortened and non-functional form of the CD163 polypeptide. Not to be limited by theory, DNA repair templates having longer regions of sequence homology can be more efficient. In certain embodiments, DNA repair templates can contain regions of sequence identity (homology arms) within the DNA repair template which can flank the sequence change and can range from fewer than 50 nucleotides to greater than 1000 nucleotides.

Several aspects of Cas9-protein/guide RNA combinations together with DNA repair templates are shown in Table 6. As provided in Table 6, several Cas9-protein/guide RNA combinations can be paired with DNA repair templates having, but not being limited to, 75 bases of sequence homology on each side of the targeted deletion (50 core homology bases and flanking homology regions of 50 on either side). In an aspect, the protein-guide RNA complexes and template combinations can be transfected into cells. Without being limited by theory, repair of the double-strand break using the DNA repair template can direct the formation of an in-frame translational stop codon as the result of deletion of single or multiple nucleotides at or adjacent to the break site. Animals and cells obtained from this method demonstrate that endonuclease-directed double-strand breaks at the porcine CD163 gene can be repaired using a co-introduced DNA repair template. As provided herein, repair templates having a sequence of SEQ ID NOs: 1 to 13 can introduce an in-frame translational stop codon in Exon 2, thereby producing a shortened and non-functional CD163 protein.

Use of a DNA repair template according to the present specification is not limited to abolishing the function of CD163. The present specification further includes, and provides for, a repair template that can direct the removal or addition of nucleotides to the gene. In an aspect, the stability or half-life modulation of the encoded CD163 mRNA can be modulated by editing according to the present methods. In yet another aspect, DNA sequences which encode amino acids of the mature protein responsible for binding PRRS virus can be removed or replaced. In an aspect, CD163 expression and or activity can be reduced by at least 90% but not abolished. In an aspect of the present teachings, using the spacer sequences described with other repair templates would be contemplated by those skilled in the art to allow for the formation of an in frame stop codon by the removal of bases and the introduction of bases or a combination thereof.

Included, and provided for, by the present specification are pigs derived from elite porcine lines comprising edited CD163 genes. In aspects, the elite porcine lines can be PIC™ Line 15, PIC™ Line 17, PIC™ Line 27, PIC™ Line 65, PIC™ Line 14, PIC™ Line 62, PIC337, PIC800, PIC280, PIC327, PIC408, PIC™ 399, PIC410, PIC415, PIC359, PIC380, PIC837, PIC260, PIC265, PIC210, PIC™ Line 2, PIC™ Line 3, PIC™ Line 4, PIC™ Line 5, PIC™ Line 18, PIC™ Line 19, PIC™ Line 92, PIC95, PIC™ CAMBOROUGH® (Pig Improvement Company, Limited, Basingstoke, UK), PIC1070, PIC™ CAMBOROUGH® 40, PIC™ CAMBOROUGH® 22, PIC1050, PIC™ CAMBOROUGH® 29, PIC™ CAMBOROUGH® 48, or PIC™ CAMBOROUGH® ×54. In various aspects, the elite porcine lines can be PIC™ elite porcine lines 2, 3, 15, 19, 27, 62, or 65. In another aspect, the pigs can comprise edited CD163 genes derived from elite porcine lines. In aspects, the pigs can comprise an edited CD163 in a CD163 genomic region having the genotypes shown in Table 8 to Table 14. Table 8 to Table 14 present each position on chromosome 5 in the vicinity of the CD163 gene in which a single nucleotide polymorphism exists.

Each table presents alleles that are homozygous in that line and provides a distinguishing genetic signature of the line, as well as its unique genome edited region. All the genetic signatures are based on the Sscrofa11.1 reference genome (GenBank accession: GCA_000003025.6). Accordingly, the transmission of the edited CD163 line can be followed, and animals comprising an edited CD163 gene obtained from the line can be identified. Pigs of other lines are heterozygous or opposite genotype at multiple alleles when compared to the lines of Table 8 to Table 14. In this way, the combination of genetic signatures in each line can be used to distinguish between pigs belonging to a particular line and pigs not belonging to a particular line. In an aspect, the genetic signatures provide for methods to breed and track the CD163 edited genomes from generation to generation. In an aspect, progeny generations that comprise the CD163 edited genomes having a genetic signature according to Table 8 to Table 14 can be prepared.

TABLE 8

Line 2 Genetic Signatures

| Position | Genotype |
| --- | --- |
| 60306428 | C/C |
| 60306527 | C/C |
| 60308030 | C/C |
| 60320580 | C/C |
| 60322529 | A/A |
| 60324162 | T/T |
| 60327987 | C/C |
| 60328009 | T/T |
| 60335421 | T/T |
| 60338654 | G/G |
| 60344946 | A/A |
| 60345163 | C/C |
| 60345689 | G/G |
| 60345715 | G/G |
| 60345722 | A/A |
| 60345749 | G/G |
| 60345775 | A/A |
| 60345825 | A/A |
| 60346409 | G/G |
| 60346607 | A/A |
| 60346641 | G/G |
| 60346691 | T/T |
| 60346734 | A/A |
| 60347297 | G/G |
| 60350295 | C/C |
| 60350343 | G/G |
| 60350448 | C/C |
| 60350470 | T/T |
| 60350475 | C/C |
| 60350564 | A/A |
| 60350571 | A/A |
| 60350572 | A/A |
| 60350911 | C/C |
| 60351055 | G/G |
| 60351604 | C/C |
| 60351855 | T/T |
| 60351857 | C/C |
| 60351972 | G/G |
| 60352165 | C/C |
| 60352923 | C/C |
| 60353408 | A/A |
| 60353562 | T/T |
| 60353576 | C/C |
| 60353659 | T/T |
| 60353721 | G/G |
| 60354428 | G/G |
| 60354925 | C/C |
| 60355415 | G/G |
| 60355420 | T/T |
| 60355448 | G/G |
| 60355529 | A/A |
| 60355530 | A/A |
| 60355774 | C/C |
| 60356277 | C/C |
| 60356351 | C/C |
| 60356575 | C/C |
| 60356578 | T/T |
| 60356861 | G/G |
| 60356885 | T/T |
| 60356898 | T/T |
| 60356914 | C/C |
| 60357001 | T/T |
| 60357014 | T/T |
| 60358409 | C/C |
| 60358449 | G/G |
| 60358469 | T/T |
| 60358475 | T/T |
| 60358551 | A/A |
| 60358568 | G/G |
| 60358641 | T/T |

TABLE 8-continued

Line 2 Genetic Signatures

| Position | Genotype |
| --- | --- |
| 60358704 | T/T |
| 60358774 | T/T |
| 60368913 | C/C |
| 60368916 | A/A |
| 60368921 | T/T |
| 60368940 | G/G |
| 60368963 | C/C |
| 60416097 | G/G |
| 60543479 | C/C |
| 60614797 | G/G |
| 60614964 | G/G |
| 60920926 | G/G |
| 61479206 | C/C |
| 61479353 | T/T |
| 61653091 | C/C |
| 61783688 | A/A |
| 62091204 | A/A |
| 62416522 | A/A |
| 62476273 | C/C |
| 62687883 | C/C |
| 63044336 | A/A |
| 63546615 | C/C |
| 63553656 | G/G |
| 63558087 | G/G |
| 63640722 | G/G |
| 63792071 | T/T |
| 64009226 | C/C |
| 64459105 | T/T |
| 64460101 | A/A |
| 64527707 | A/A |
| 64577968 | C/C |
| 64943306 | T/T |
| 65242696 | T/T |
| 65242725 | A/A |
| 65242729 | A/A |
| 65242736 | G/G |
| 65249484 | T/T |
| 65260283 | T/T |
| 65269510 | C/C |
| 65273886 | T/T |
| 65276133 | C/C |
| 65277053 | T/T |
| 65277156 | C/C |
| 65277320 | G/G |
| 65280282 | A/A |
| 65282683 | C/C |
| 65283434 | C/C |
| 65283970 | C/C |
| 65284829 | C/C |
| 65285100 | C/C |
| 65285902 | G/G |
| 65285914 | T/T |
| 65286400 | C/C |
| 65294497 | T/T |
| 65383805 | C/C |
| 65405986 | C/C |
| 65410118 | C/C |
| 65410147 | G/G |
| 65410198 | C/C |
| 65410435 | C/C |
| 65410440 | T/T |
| 65410441 | C/C |
| 65410443 | C/C |
| 65410447 | C/C |
| 65411265 | C/C |
| 65411431 | G/G |
| 65411524 | C/C |
| 65411698 | G/G |
| 65411831 | C/C |
| 65411848 | G/G |
| 65411854 | T/T |
| 65411966 | C/C |
| 65412729 | G/G |
| 65413215 | G/G |
| 65413759 | C/C |
| 65417199 | A/A |

TABLE 8-continued

Line 2 Genetic Signatures

| Position | Genotype |
|---|---|
| 65417256 | G/G |
| 65417261 | A/A |
| 65417273 | C/C |
| 65417287 | G/G |
| 65417716 | G/G |
| 65417797 | C/C |
| 65417800 | C/C |
| 65419169 | G/G |
| 65419410 | G/G |
| 65420017 | T/T |
| 65420184 | G/G |
| 65420415 | A/A |
| 65420591 | G/G |
| 65420680 | C/C |
| 65420681 | A/A |
| 65420693 | G/G |
| 65420947 | G/G |
| 65420949 | T/T |
| 65421133 | G/G |
| 65421195 | G/G |
| 65421255 | G/G |
| 65421365 | G/G |
| 65421421 | C/C |
| 65422005 | G/G |
| 65422008 | G/G |
| 65422057 | T/T |
| 65422141 | C/C |
| 65422701 | C/C |
| 65422725 | C/C |
| 65425730 | G/G |
| 65601310 | C/C |
| 65602328 | C/C |
| 65711602 | C/C |
| 65761990 | C/C |
| 66293766 | G/G |
| 66296268 | A/A |

TABLE 9

Line 3 Genetic Signatures

| Position | Genotype |
|---|---|
| 60414864 | T/T |
| 60415813 | C/C |
| 60415854 | G/G |
| 60572371 | A/A |
| 60663464 | C/C |
| 60663499 | A/A |
| 61016527 | G/G |
| 61442674 | T/T |
| 61870484 | C/C |
| 61989476 | G/G |
| 62510031 | G/G |
| 62602514 | T/T |
| 63044336 | A/A |
| 63345577 | G/G |
| 63452493 | A/A |
| 63669675 | G/G |
| 63754659 | T/T |
| 63810627 | C/C |
| 63810632 | G/G |
| 63810707 | T/T |
| 63810733 | G/G |
| 63810819 | C/C |
| 63810857 | C/C |
| 63810861 | G/G |
| 64010555 | T/T |
| 64010599 | A/A |
| 64452338 | T/T |
| 64455982 | C/C |
| 64457532 | T/T |
| 64458163 | T/T |

TABLE 9-continued

Line 3 Genetic Signatures

| Position | Genotype |
|---|---|
| 64458711 | G/G |
| 64555715 | G/G |
| 64561148 | G/G |
| 64561209 | G/G |
| 64561659 | G/G |
| 64561828 | T/T |
| 64561873 | G/G |
| 64561935 | C/C |
| 64562021 | C/C |
| 64562771 | C/C |
| 64563462 | G/G |
| 64682243 | C/C |
| 64682929 | G/G |
| 64685072 | T/T |
| 64692673 | G/G |
| 64692905 | T/T |
| 64693058 | T/T |
| 64705228 | G/G |
| 64720067 | A/A |
| 64722426 | T/T |
| 64722539 | C/C |
| 64726936 | G/G |
| 64729340 | C/C |
| 64730596 | G/G |
| 64736752 | G/G |
| 64761650 | G/G |
| 64767369 | G/G |
| 64768411 | G/G |
| 64769978 | T/T |
| 64769989 | C/C |
| 64770307 | G/G |
| 64773053 | A/A |
| 64774093 | G/G |
| 64775512 | G/G |
| 64775565 | C/C |
| 64780089 | C/C |
| 64780152 | C/C |
| 64780196 | C/C |
| 64783169 | G/G |
| 64783774 | C/C |
| 64783896 | G/G |
| 64784000 | T/T |
| 64784139 | C/C |
| 64784235 | T/T |
| 64784410 | A/A |
| 64784653 | A/A |
| 64784725 | C/C |
| 64784844 | A/A |
| 64784875 | T/T |
| 64785001 | A/A |
| 64785078 | C/C |
| 64813032 | G/G |
| 64819974 | C/C |
| 64893099 | G/G |
| 64899922 | A/A |
| 64934758 | C/C |
| 65348500 | G/G |
| 65546268 | A/A |
| 65546327 | G/G |
| 65841270 | T/T |
| 65858531 | G/G |
| 65979134 | G/G |
| 65985520 | C/C |
| 66035868 | A/A |
| 66042409 | C/C |
| 66042542 | C/C |
| 66042551 | C/C |
| 66042557 | A/A |
| 66042563 | G/G |
| 66155827 | A/A |
| 66155859 | A/A |
| 66155863 | T/T |
| 66156160 | A/A |
| 66156183 | G/G |
| 66156533 | G/G |
| 66167582 | C/C |

TABLE 9-continued

Line 3 Genetic Signatures

| Position | Genotype |
|---|---|
| 66167809 | C/C |
| 66167823 | T/T |
| 66167877 | A/A |
| 66167888 | C/C |
| 66167905 | A/A |
| 66168135 | C/C |
| 66168261 | C/C |
| 66168311 | G/G |
| 66168615 | G/G |
| 66168688 | G/G |
| 66168742 | G/G |
| 66168880 | G/G |
| 66168947 | T/T |
| 66168952 | A/A |
| 66168993 | A/A |

TABLE 10

Line 15 Genetic Signatures

| Position | Genotype |
|---|---|
| 60391943 | G/G |
| 60392234 | T/T |
| 60394009 | A/A |
| 60414796 | T/T |
| 60601475 | A/A |
| 60630898 | A/A |
| 60630910 | A/A |
| 60786421 | G/G |
| 60787517 | G/G |
| 60792231 | G/G |
| 60795724 | C/C |
| 60915104 | C/C |
| 61016227 | A/A |
| 61086145 | T/T |
| 61275101 | C/C |
| 61396087 | A/A |
| 61434042 | G/G |
| 61515967 | T/T |
| 61759785 | C/C |
| 61759821 | C/C |
| 61865586 | A/A |
| 61867498 | C/C |
| 62192420 | G/G |
| 62195570 | A/A |
| 62196101 | C/C |
| 62442547 | G/G |
| 62509196 | T/T |
| 62675268 | G/G |
| 62843969 | G/G |
| 62852334 | A/A |
| 63025151 | A/A |
| 63025152 | C/C |
| 63168616 | A/A |
| 63266682 | T/T |
| 63367266 | G/G |
| 63424311 | T/T |
| 63535058 | T/T |
| 63653754 | G/G |
| 63655538 | T/T |
| 63669242 | A/A |
| 63669944 | C/C |
| 63669946 | G/G |
| 63900332 | A/A |
| 64138082 | C/C |
| 64171653 | C/C |
| 64471845 | G/G |
| 64472363 | A/A |
| 64472504 | T/T |
| 64472616 | T/T |
| 64523343 | A/A |
| 64536599 | G/G |

TABLE 10-continued

Line 15 Genetic Signatures

| Position | Genotype |
|---|---|
| 64537982 | T/T |
| 64893205 | A/A |
| 64916422 | G/G |
| 65039734 | C/C |
| 65175496 | C/C |
| 65177506 | G/G |
| 65294016 | C/C |
| 65571397 | A/A |
| 65573608 | T/T |
| 65576707 | C/C |
| 65984917 | G/G |
| 65984984 | T/T |
| 65985058 | T/T |
| 65985392 | C/C |
| 66042472 | C/C |
| 66099282 | A/A |
| 66119075 | T/T |

TABLE 11

Line 19 Genetic Signatures

| Position | Genotype |
|---|---|
| 60320100 | A/A |
| 60320144 | G/G |
| 60320580 | C/C |
| 60507836 | C/C |
| 60512716 | G/G |
| 60564418 | A/A |
| 60666662 | T/T |
| 60683738 | T/T |
| 60782197 | T/T |
| 60782278 | T/T |
| 60782642 | A/A |
| 60782683 | G/G |
| 60782756 | G/G |
| 60782997 | G/G |
| 60783031 | C/C |
| 60783198 | G/G |
| 61131519 | G/G |
| 61131736 | C/C |
| 61189029 | C/C |
| 61359517 | A/A |
| 61390748 | C/C |
| 61465215 | T/T |
| 61567329 | C/C |
| 61567357 | A/A |
| 61567365 | A/A |
| 61567410 | C/C |
| 61567494 | C/C |
| 61567594 | G/G |
| 61975156 | G/G |
| 61975367 | G/G |
| 61975382 | A/A |
| 61975388 | C/C |
| 62363513 | T/T |
| 62367647 | G/G |
| 62378299 | G/G |
| 62610431 | T/T |
| 62952267 | T/T |
| 62965473 | T/T |
| 63108711 | G/G |
| 63109224 | T/T |
| 63174233 | T/T |
| 63174257 | A/A |
| 63393845 | G/G |
| 63393849 | T/T |
| 63393851 | T/T |
| 63860532 | A/A |
| 63861247 | A/A |
| 63862368 | T/T |
| 64138082 | C/C |

TABLE 11-continued

Line 19 Genetic Signatures

| Position | Genotype |
|---|---|
| 64171653 | C/C |
| 64181448 | G/G |
| 64402245 | T/T |
| 64455172 | G/G |
| 64514012 | C/C |
| 64514013 | A/A |
| 64522169 | G/G |
| 64522173 | T/T |
| 64522177 | T/T |
| 64522178 | C/C |
| 64794635 | G/G |
| 65031621 | C/C |
| 65031630 | C/C |
| 65031684 | T/T |
| 65222383 | T/T |
| 65222385 | A/A |
| 65242693 | C/C |
| 65497229 | G/G |
| 65499233 | C/C |
| 65502398 | G/G |
| 65562917 | C/C |
| 65566225 | T/T |
| 65567066 | T/T |
| 65894449 | C/C |
| 65904537 | T/T |
| 65959573 | A/A |
| 65998062 | C/C |
| 66158553 | A/A |
| 66158950 | C/C |
| 66159103 | A/A |
| 66159212 | G/G |

TABLE 12

Line 27 Genetic Signatures

| Position | Genotype |
|---|---|
| 60347934 | A/A |
| 60356984 | C/C |
| 60692943 | C/C |
| 60693260 | G/G |
| 60693769 | G/G |
| 60938885 | T/T |
| 60960728 | A/A |
| 61436306 | G/G |
| 61464114 | C/C |
| 61468375 | G/G |
| 61736415 | A/A |
| 61736429 | G/G |
| 61757961 | G/G |
| 61820110 | A/A |
| 61822513 | T/T |
| 61858837 | G/G |
| 62159353 | T/T |
| 62313847 | C/C |
| 62315464 | A/A |
| 62570257 | C/C |
| 62570793 | A/A |
| 62571313 | T/T |
| 62917536 | G/G |
| 62917597 | T/T |
| 62917618 | C/C |
| 62917629 | T/T |
| 62917780 | G/G |
| 62917866 | T/T |
| 62917889 | T/T |
| 62918448 | G/G |
| 62918456 | A/A |
| 62918465 | A/A |
| 62918655 | T/T |
| 63042154 | C/C |
| 63043261 | G/G |

TABLE 12-continued

Line 27 Genetic Signatures

| Position | Genotype |
|---|---|
| 63046692 | G/G |
| 63433705 | G/G |
| 63490990 | A/A |
| 63626018 | A/A |
| 63626423 | T/T |
| 63626826 | C/C |
| 63630149 | A/A |
| 63631098 | C/C |
| 63977777 | A/A |
| 63977821 | G/G |
| 64460204 | C/C |
| 64582243 | C/C |
| 64582246 | G/G |
| 64582272 | A/A |
| 64600735 | G/G |
| 65056396 | A/A |
| 65056671 | T/T |
| 65332987 | A/A |
| 65335837 | C/C |
| 65390844 | A/A |
| 65404042 | A/A |
| 65404045 | A/A |
| 65404063 | C/C |
| 65705261 | G/G |
| 65740018 | T/T |
| 65740030 | A/A |
| 66235840 | G/G |

TABLE 13

Line 62 Genetic Signatures

| Position | Genotype |
|---|---|
| 60336383 | A/A |
| 60343172 | A/A |
| 60345254 | G/G |
| 60447765 | G/G |
| 60452143 | C/C |
| 60452167 | T/T |
| 60462769 | T/T |
| 60653700 | T/T |
| 60654939 | A/A |
| 60654943 | A/A |
| 61085770 | A/A |
| 61108831 | G/G |
| 61117357 | A/A |
| 61234908 | C/C |
| 61331270 | A/A |
| 61388824 | G/G |
| 61755575 | C/C |
| 61759095 | C/C |
| 61760230 | C/C |
| 61927492 | T/T |
| 61927506 | A/A |
| 62006220 | T/T |
| 62115641 | T/T |
| 62169134 | T/T |
| 62368918 | C/C |
| 62471593 | C/C |
| 62474001 | A/A |
| 62474006 | C/C |
| 62474365 | A/A |
| 62480042 | A/A |
| 62480261 | G/G |
| 62480699 | A/A |
| 62480892 | A/A |
| 62481902 | G/G |
| 62482914 | T/T |
| 62483893 | C/C |
| 62483897 | T/T |
| 62847072 | G/G |
| 62874766 | G/G |

TABLE 13-continued

Line 62 Genetic Signatures

| Position | Genotype |
|---|---|
| 62897778 | A/A |
| 63100290 | C/C |
| 63219344 | G/G |
| 63361759 | G/G |
| 63388357 | C/C |
| 63442314 | G/G |
| 63590333 | T/T |
| 63670724 | G/G |
| 63714834 | A/A |
| 63792005 | T/T |
| 63985848 | A/A |
| 63985923 | G/G |
| 64131088 | C/C |
| 64471400 | C/C |
| 64483848 | G/G |
| 64484177 | T/T |
| 64689271 | A/A |
| 64758235 | C/C |
| 64790188 | C/C |
| 64895383 | C/C |
| 64991645 | A/A |
| 65045805 | T/T |
| 65146186 | C/C |
| 65368620 | C/C |
| 65432698 | C/C |
| 65542716 | A/A |
| 65637507 | G/G |
| 65771614 | C/C |
| 65771615 | G/G |
| 65772162 | T/T |
| 66033248 | T/T |
| 66033476 | C/C |
| 66033484 | C/C |

TABLE 14

Line 65 Genetic Signatures

| Position | Genotype |
|---|---|
| 60322300 | C/C |
| 60411747 | A/A |
| 60412758 | G/G |
| 60412775 | A/A |
| 60412826 | C/C |
| 60413294 | G/G |
| 60459719 | A/A |
| 60462179 | C/C |
| 60492928 | A/A |
| 60492938 | T/T |
| 60666662 | T/T |
| 60722708 | C/C |
| 60770183 | G/G |
| 60770197 | C/C |
| 60777431 | C/C |
| 60781592 | T/T |
| 60782197 | T/T |
| 60782278 | T/T |
| 60782642 | A/A |
| 60782683 | G/G |
| 60782756 | G/G |
| 60782997 | G/G |
| 60783006 | G/G |
| 60783031 | C/C |
| 60783198 | G/G |
| 60791719 | T/T |
| 60900261 | G/G |
| 60911551 | A/A |
| 60912669 | A/A |
| 61223574 | A/A |
| 61486607 | C/C |
| 61756324 | G/G |
| 61832527 | C/C |

TABLE 14-continued

Line 65 Genetic Signatures

| Position | Genotype |
|---|---|
| 61895566 | C/C |
| 61895833 | A/A |
| 62354225 | C/C |
| 62364072 | G/G |
| 62383525 | G/G |
| 62399452 | T/T |
| 62404734 | A/A |
| 62432982 | C/C |
| 62841388 | G/G |
| 62931496 | T/T |
| 63156406 | C/C |
| 63156417 | T/T |
| 63266198 | A/A |
| 63383925 | A/A |
| 63392495 | T/T |
| 63549670 | C/C |
| 63593491 | G/G |
| 63609938 | A/A |
| 63641998 | C/C |
| 63678793 | G/G |
| 63784770 | G/G |
| 63810897 | C/C |
| 63810903 | C/C |
| 63810920 | G/G |
| 63810922 | T/T |
| 63810928 | G/G |
| 63872757 | C/C |
| 63944636 | G/G |
| 63944765 | C/C |
| 64138639 | C/C |
| 64194054 | G/G |
| 64242768 | T/T |
| 64270989 | G/G |
| 64753488 | G/G |
| 64758888 | A/A |
| 64758900 | C/C |
| 64759492 | T/T |
| 64795760 | T/T |
| 64797970 | A/A |
| 64798690 | G/G |
| 64860395 | G/G |
| 64860396 | C/C |
| 64862131 | C/C |
| 65371202 | T/T |
| 65371472 | G/G |
| 65371901 | G/G |
| 65371970 | C/C |
| 65372072 | A/A |
| 65409493 | A/A |
| 65437347 | G/G |
| 65573362 | T/T |
| 65601655 | G/G |
| 65747069 | T/T |
| 65843843 | A/A |
| 65849424 | T/T |
| 66248756 | A/A |

Elite PIC™ lines 2, 3, 15, 19, 27, 62 and 65 are lines selected for superior commercial phenotypes. In an aspect, the CD163 gene edited cells and animals can be free of deleterious alleles that are present in wild populations and in many commercial herds. In aspects, CD163 gene edited cells and animals can be free of one of more of the deleterious alleles selected from the group consisting of epetheliogenesis imperfecta, melanotic skin tumors, dermatosis vegetans, abnormal mamae, shortened vertebral column, kinky tail, rudimentary tail, Hairlessness, Hairlessness (2), Woolly hair, Hydrocephalus, Tassels, Legless, Three-legged, Syndactyly, Polydactyly, Pulawska factor, Heterochromia iridis, Congenital tremor A III, Congenital tremor A IV, Congenital ataxia, Hind leg paralysis, Bentleg, Thickleg, Malignant hyperthermia, Hemophilia (von Willebrand's disease), Leukemia, Hemolytic disease, edema, Acute respiratory distress ("barker"), Rickets, 25 Renal hypoplasia, Renal cysts, Uterus aplasia, Porcine Stress Syndrome (PSS), halothane (HAL), Dipped Shoulder (Humpy Back, Kinky Back, Kyphosis), Hyperostosis, Mammary Hypoplasia, and Undeveloped Udder. As provided herein, the improved methods of preparing CD163 gene edited animals can avoid introducing new mutations at the deleterious loci or generating new amorphic, hypomorphic, hypermorphic, neomorphic, antimorphic mutations at non-target sites. These latter changes can be particularly undesirable in elite lines as they can interfere with genes involved in desirable traits that can be controlled by multiple loci in a continuous, quantitative way in a population. Many such Quantitative Trait Loci (QTL) are known and can be typically characterized by a bell-shaped curve the trait value can be plotted against the number of observed animals. Such polygenic inheritance of traits can be common among traits recognized as commercially important such as, but not limited to, backfat, average daily feed intake, lifetime daily gain, and loin depth.

Similarly, traits associated with productivity can be multigenic and controlled by multiple QTLs. These traits were typically measured by visual inspection but methods now can include ultrasound to measure backfat thickness (bfp), loin depth (ldp) and intramuscular fat (uip). As provided in Table 15, elite lines can have desirable phenotypic traits including high backfat and loin depth while having high lifetime daily gain. Similarly, the sows of the elite lines can be fecund and have large litters, few still-born, and sufficient teats to ween and nurse the piglets.

TABLE 15

Desirable Phenotypic Traits

| LINE | TRT | average | standard deviation |
|---|---|---|---|
| 2 | Backfat, mm | 7.8 | 1.81 |
| 3 | Backfat, mm | 9.44 | 2.77 |
| 15 | Backfat, mm | 8.16 | 2.03 |
| 65 | Backfat, mm | 7.45 | 1.88 |
| 2 | Average Daily Feed Intake, kg | 1.99 | 0.24 |
| 3 | Average Daily Feed Intake, kg | 2.13 | 0.25 |
| 15 | Average Daily Feed Intake, kg | 2.22 | 0.24 |
| 65 | Average Daily Feed Intake, kg | 2.2 | 0.27 |
| 2 | Lifetime Daily Gain, grams/day | 683.83 | 73.53 |
| 3 | Lifetime Daily Gain, grams/day | 704.23 | 80.15 |
| 15 | Lifetime Daily Gain, grams/day | 755.61 | 69.32 |
| 65 | Lifetime Daily Gain, grams/day | 800.6 | 84.48 |
| 2 | Loin depth, mm | 65.31 | 7.09 |
| 3 | Loin depth, mm | 62.61 | 7.14 |
| 15 | Loin depth, mm | 67.17 | 7.15 |
| 65 | Loin depth, mm | 81.2 | 8 |
| 2 | Total Born per litter | 13.71 | 3.19 |
| 3 | Total Born per litter | 15.06 | 3.41 |
| 15 | Total Born per litter | 10.39 | 2.71 |
| 65 | Total Born per litter | 10.31 | 2.52 |
| 2 | Still born per litter | 1.19 | 1.43 |
| 3 | Still born per litter | 1.25 | 1.50 |
| 15 | Still born per litter | 1.22 | 1.37 |
| 65 | Still born per litter | 0.77 | 1.16 |
| 2 | Teat number | 15.43 | 1.27 |
| 3 | Teat number | 15.44 | 1.29 |

The present specification provides for, and includes, gene edited pigs of selected elite lines that can be homozygous for CD163 knockout edits (CD163$^{-/-}$). In an aspect, the line can be selected from the group consisting of PIC™ Line 2, Line 3, Line 15, Line 19, Line 27, Line 62, Line 65, and progeny thereof comprising the edited CD163 genes described herein. Gene edited lines 2, 3, 15, 19, 27, 62 and 65 can comprise CD163 genomic regions as provided at Table 8 to Table 14, and can be readily distinguished from each other, from unimproved lines, and from other elite lines. In aspects according to the present specification, the heterozygous and homozygous pigs of the present specification can be free of off-site mutations. The present specification provides for, and includes, pigs and cells that can have edited CD163 genes comprising SEQ ID NOs: 1 to 18 and 426 to 505 and that can share a genetic signature comprising at least 90% of the genotypic markers of Table 8 to Table 14. The present specification provides for, and includes, pigs and cells that can have edited CD163 genes comprising SEQ ID NO: 2 and sharing a genetic signature comprising at least 90% of the genotypic markers of Table 8 to Table 14. In an aspect, the genetic signature of a CD163 edited pig or cell can share a genetic signature comprising at least 95% of the genotypic markers of Table 8 to Table 14. Also included are CD163 edited pigs or cells that can share a genetic signature comprising at least 97% of the genotypic markers of Table 8 to Table 14. In an aspect, the CD163 edited pigs or cells can share a genetic signature comprising at least 98% of the genotypic markers of Table 8 to Table 14. Another aspect provides for CD163 edited pigs or cells that can share a genetic signature comprising at least 99% of the genotypic markers of Table 8 to Table 14.

As provided herein, the gene-edited CD163$^{-/-}$ animals and cells of Lines 2, 3, 15, 19, 27, 62, and 65, can retain desirable commercial traits and can be free of deleterious off-target mutations and can comprise an edited CD163 gene comprising any of SEQ ID NOs: 1 to 18 and 426-505. In aspects of the present disclosure, the gene-edited CD163$^{-/-}$ animals and cells of Lines 2, 3, 15, 19, 27, 62, and 65, can comprise at least 90% of the loin depth of the non-edited pig line and can comprise an edited CD163 gene comprising any of SEQ ID NOs: 1 to 18 and 426-505. In aspects of the present disclosure, the gene-edited CD163$^{-/-}$ animals and cells of Lines 2, 3, 15, 19, 27, 62, and 65, can comprise at least 90% of the lifetime daily gain of the non-edited pig line. In aspects of the present disclosure, the gene-edited CD163$^{-/-}$ animals and cells of Lines 2, 3, 15, 19, 27, 62, and 65, can comprise at least 90% of the average daily feed intake of the non-edited pig line. The present specification provides for, and includes, pigs and cells that can have edited CD163 genes comprising SEQ ID NOs: 1 to 18 and 426 to 505 and can share a genetic signature comprising at least 90% of the genotypic markers of Table 8 to Table 14.

As provided herein, the gene-edited CD163$^{-/-}$ animals and cells of Lines 2, 3, 15, 19, 27, 62, and 65, can retain desirable reproductive traits. In aspects of the present disclosure, the gene-edited CD163$^{-/-}$ animals and cells of Lines 2, 3, 15, 19, 27, 62, and 65, comprising a gene-edited CD163$^{-/-}$ of SEQ ID NOs:1 to 18 or 426 to 505 can comprise at least 90% of the total born per litter of the non-edited pig line. In aspects of the present disclosure, the gene-edited CD163$^{-/-}$ animals and cells of Lines 2, 3, 15, 19, 27, 62, and 65, comprising a gene-edited CD163$^{-/-}$ of SEQ ID NOs:1 to 18 or 426 to 505 can comprise no more than 110% of the number of still born piglets compared to the non-edited pig line. In aspects of the present disclosure, the gene-edited CD163$^{-/-}$ animals and cells of Lines 2, 3, 15, 19, 27, 62, and 65, comprising a gene-edited CD163$^{-/-}$ of SEQ ID NOs:1 to 18 or 426 to 505 can comprise at least 90% of the average number of teats compared to the non-edited pig line.

In an aspect, the gene edited CD163$^{-/-}$ animals and cells of Line 2 having a gene-edited CD163$^{-/-}$ of SEQ ID NOs:1 to 18 or 426 to 505 can have backfat that is at least 90% of the amount found in unedited Line 2 animals. In an aspect, gene edited CD163$^{-/-}$ animals and cells of Line 2 can have backfat that is at least 97% of the unedited Line 2 animal.

In an aspect, the gene edited CD163$^{-/-}$ animals and cells of Line 3 having a gene-edited CD163$^{-/-}$ of SEQ ID NOs:1 to 18 or 426 to 505 can have backfat that is at least 90% of the amount found in unedited Line 3 animals. In an aspect, gene edited CD163$^{-/-}$ animals and cells of Line 3 can have backfat that is at least 95% of the unedited Line 3 animal. In an aspect, gene edited CD163$^{-/-}$ animals and cells of Line 3 can have backfat that is at least 97% of the unedited Line 2 animal.

In an aspect, the gene edited CD163$^{-/-}$ animals and cells of Line 15 having a gene-edited CD163$^{-/-}$ of SEQ ID NOs:1 to 18 or 426 to 505 can have backfat that is at least 90% of the amount found in unedited Line 15 animals. In an aspect, gene edited CD163$^{-/-}$ animals and cells of Line 15 can have backfat that is at least 95% of the unedited Line 15 animal. In an aspect, gene edited CD163$^{-/-}$ animals and cells of Line 15 can have backfat that is at least 97% of the unedited Line 2 animal.

In an aspect, the gene edited CD163$^{-/-}$ animals and cells of Line 19 having a gene-edited CD163$^{-/-}$ of SEQ ID NOs:1 to 18 or 426 to 505 can have backfat that is at least 90% of the amount found in unedited Line 19 animals. In an aspect, gene edited CD163$^{-/-}$ animals and cells of Line 19 can have backfat that is at least 95% of the unedited Line 19 animal. In an aspect, gene edited CD163$^{-/-}$ animals and cells of Line 19 have can backfat that is at least 97% of the unedited Line 2 animal.

In an aspect, the gene edited CD163$^{-/-}$ animals and cells of Line 27 having a gene-edited CD163$^{-/-}$ of SEQ ID NOs: 1 to 18 or 426 to 505 can have backfat that is at least 90% of the amount found in unedited Line 27 animals. In an aspect, gene edited CD163$^{-/-}$ animals and cells of Line 27 can have backfat that is at least 95% of the unedited Line 27 animal. In an aspect, gene edited CD163$^{-/-}$ animals and cells of Line 27 can have backfat that is at least 97% of the unedited Line 2 animal.

In an aspect, the gene edited CD163$^{-/-}$ animals and cells of Line 62 having a gene-edited CD163$^{-/-}$ of SEQ ID NOs:1 to 18 or 426 to 505 can have backfat that is at least 90% of the amount found in unedited Line 62 animals. In an aspect, gene edited CD163$^{-/-}$ animals and cells of Line 62 can have backfat that is at least 95% of the unedited Line 62 animal. In an aspect, the gene edited CD163$^{-/-}$ animals and cells of Line 62 having a gene-edited CD163$^{-/-}$ of SEQ ID NO: 2 can have backfat that is at least 95% of the amount found in unedited Line 62 animals. In an aspect, gene edited CD163$^{-/-}$ animals and cells of Line 62 can have backfat that is at least 97% of the unedited Line 2 animal.

In an aspect, the gene edited CD163$^{-/-}$ animals and cells of Line 65 having a gene-edited CD163$^{-/-}$ of SEQ ID NOs:1 to 18 or 426 to 505 can have backfat that is at least 90% of the amount found in unedited Line 65 animals. In an aspect, gene edited CD163$^{-/-}$ animals and cells of Line 65 can have backfat that is at least 95% of the unedited Line 65 animal. In an aspect, gene edited CD163$^{-/-}$ animals and cells of Line 65 can have backfat that is at least 97% of the unedited Line 2 animal.

In an aspect, the gene edited CD163$^{-/-}$ animals and cells of Line 2 having a gene-edited CD163$^{-/-}$ of SEQ ID NOs:1 to 18 or 426 to 505 can have a number of total born per litter that is at least 90% of the amount found in unedited Line 2 animals. In an aspect, gene edited CD163$^{-/-}$ animals and cells of Line 2 can have a number of total born per litter that is at least 95% of the unedited Line 2 animal. In an aspect, gene edited CD163$^{-/-}$ animals and cells of Line 2 can have a number of total born per litter that is at least 97% of the unedited Line 2 animal.

In an aspect, the gene edited CD163$^{-/-}$ animals and cells of Line 3 having a gene-edited CD163$^{-/-}$ of SEQ ID NOs: 1 to 18 or 426 to 505 can have a number of total born per litter that is at least 90% of the amount found in unedited Line 3 animals. In an aspect, gene edited CD163$^{-/-}$ animals and cells of Line 3 can have a number of total born per litter that is at least 95% of the unedited Line 3 animal. In an aspect, gene edited CD163$^{-/-}$ animals and cells of Line 3 can have a number of total born per litter that is at least 97% of the unedited Line 3 animal.

In an aspect, the gene edited CD163$^{-/-}$ animals and cells of Line 15 having a gene-edited CD163$^{-/-}$ of SEQ ID NOs: 1 to 18 or 426 to 505 can have a number of total born per litter that is at least 90% of the amount found in unedited Line 15 animals. In an aspect, gene edited CD163$^{-/-}$ animals and cells of Line 15 can have a number of total born per litter that is at least 95% of the unedited Line 15 animal. In an aspect, gene edited CD163$^{-/-}$ animals and cells of Line 15 can have a number of total born per litter that is at least 97% of the unedited Line 15 animal.

In an aspect, the gene edited CD163$^{-/-}$ animals and cells of Line 19 having a gene-edited CD163$^{-/-}$ of SEQ ID NOs:1 to 18 or 426 to 505 can have a number of total born per litter that is at least 90% of the amount found in unedited Line 19 animals. In an aspect, gene edited CD163$^{-/-}$ animals and cells of Line 19 can have a number of total born per litter that is at least 95% of the unedited Line 19 animal. In an aspect, gene edited CD163$^{-/-}$ animals and cells of Line 19 can have a number of total born per litter that is at least 97% of the unedited Line 19 animal.

In an aspect, the gene edited CD163$^{-/-}$ animals and cells of Line 27 having a gene-edited CD163$^{-/-}$ of SEQ ID NOs:1 to 18 or 426 to 505 can have a number of total born per litter that is at least 90% of the amount found in unedited Line 27 animals. In an aspect, gene edited CD163$^{-/-}$ animals and cells of Line 27 can have a number of total born per litter that is at least 95% of the unedited Line 27 animal. In an aspect, gene edited CD163$^{-/-}$ animals and cells of Line 27 can have a number of total born per litter that is at least 97% of the unedited Line 27 animal.

In an aspect, the gene edited CD163$^{-/-}$ animals and cells of Line 62 having a gene-edited CD163$^{-/-}$ of SEQ ID NOs:1 to 18 or 426 to 505 can have a number of total born per litter that is at least 90% of the amount found in unedited Line 62 animals. In an aspect, gene edited CD163$^{-/-}$ animals and cells of Line 62 can have a number of total born per litter that is at least 95% of the unedited Line 62 animal. In an aspect, gene edited CD163$^{-/-}$ animals and cells of Line 62 can have a number of total born per litter that is at least 97% of the unedited Line 62 animal.

In an aspect, the gene edited CD163$^{-/-}$ animals and cells of Line 65 having a gene-edited CD163$^{-/-}$ of SEQ ID NOs:1 to 18 or 426 to 505 can have a number of total born per litter that is at least 90% of the amount found in unedited Line 65 animals. In an aspect, gene edited CD163$^{-/-}$ animals and cells of Line 65 can have a number of total born per litter that is at least 95% of the unedited Line 65 animal. In an aspect, gene edited CD163$^{-/-}$ animals and cells of Line 65 can have a number of total born per litter that is at least 97% of the unedited Line 65 animal.

The present specification provides for and includes CD163 edited animals comprising the germplasm of PIC™ Line 15, PIC™ Line 17, PIC™ Line 27, PIC™ Line 65, PIC™ Line 14, PIC™ Line 62, PIC337, PIC800, PIC280, PIC327, PIC408, PIC™ 399, PIC410, PIC415, PIC359, PIC380, PIC837, PIC260, PIC265, PIC210, PIC™ Line 2, PIC™ Line 3, PIC™ Line 4, PIC™ Line 5, PIC™ Line 18, PIC™ Line 19, PIC™ Line 92, PIC95, PIC™ CAMBOROUGH®, PIC1070, PIC™ CAMBOROUGH® 40, PIC™ CAMBOROUGH® 22, PIC1050, PIC™ CAMBOROUGH® 29, PIC™ CAMBOROUGH® 48, or PIC™ CAMBOROUGH® x54. As used herein, the term germplasm includes an intact genome present in cells or nuclei and comprising chromosomes. The term germplasm may include any gamete, germ cell, or any somatic cell from which an animal can be cloned. The edited germplasm can comprise an edit having an edited genomic sequence of any one of SEQ ID NOs: 426 to 505. The edited germplasm can comprise an edit having an edited genomic sequence of any one of SEQ ID NOs: 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, or 505. The edited germplasm can comprise a genome that is 80%, 85%, 90%, 95% similar or identical to PIC™ Line 15. The edited germplasm can comprise a genome that is 80%, 85%, 90%, 95% similar or identical to PIC™ Line 17. The edited germplasm can comprise a genome that is 80%, 85%, 90%, 95% similar or identical to PIC™ Line 27. The edited germplasm can comprise a genome that is 80%, 85%, 90%, 95% similar or identical to PIC™ Line 65. The edited germplasm can comprise a genome that is 80%, 85%, 90%, 95% similar or identical to PIC™ Line 14. The edited germplasm can comprise a genome that is 80%, 85%, 90%, 95% similar or identical to PIC™ Line 62. The edited germplasm can comprise a genome that is 80%, 85%, 90%, 95% similar or identical to PIC337. The edited germplasm can comprise a genome that is 80%, 85%, 90%, 95% similar or identical to PIC800. The edited germplasm can comprise a genome that is 80%, 85%, 90%, 95% similar or identical to PIC280. The edited germplasm can comprise a genome that is 80%, 85%, 90%, 95% similar or identical to PIC327. The edited germplasm can comprise a genome that is 80%, 85%, 90%, 95% similar or identical to PIC408. The edited germplasm can comprise a genome that is 80%, 85%, 90%, 95% similar or identical to PIC™ 399. The edited germplasm can comprise a genome that is 80%, 85%, 90%, 95% similar or identical to PIC410. The edited germplasm can comprise a genome that is 80%, 85%, 90%, 95% similar or identical to PIC415. The edited germplasm can comprise a genome that is 80%, 85%, 90%, 95% similar or identical to PIC359. The edited germplasm can comprise a genome that is 80%, 85%, 90%, 95% similar or identical to PIC380. The edited germplasm can comprise a genome that is 80%, 85%, 90%, 95% similar or identical to PIC837. The edited germplasm can comprise a genome that is 80%, 85%, 90%, 95% similar or identical to PIC260. The edited germplasm can comprise a genome that is 80%, 85%, 90%, 95% similar or identical to PIC265. The edited germplasm can comprise a genome that is 80%, 85%, 90%, 95% similar or identical to PIC210. The edited germplasm can comprise a genome that is 80%, 85%, 90%, 95% similar or identical to PIC™ Line 2. The edited germplasm can comprise a genome that is 80%, 85%, 90%, 95% similar or identical to PIC™ Line 3. The edited germplasm can comprise a genome that is 80%, 85%, 90%, 95% similar or identical to PIC™ Line 4. The edited germplasm can comprise a genome that is 80%, 85%, 90%, 95% similar or identical to PIC™ Line 5. The edited germplasm can comprise a genome that is 80%, 85%, 90%, 95% similar or identical to PIC™ Line 18. The edited germplasm can comprise a genome that is 80%, 85%, 90%, 95% similar or identical to PIC™ Line 19. The edited germplasm can comprise a genome that is 80%, 85%, 90%, 95% similar or identical to PIC™ Line 92. The edited germplasm can comprise a genome that is 80%, 85%, 90%, 95% similar or identical to PIC95. The edited germplasm can comprise a genome that is 80%, 85%, 90%, 95% similar or identical to PIC™ CAMBOROUGH®. The edited germplasm can comprise a genome that is 80%, 85%, 90%, 95% similar or identical to PIC1070. The edited germplasm can comprise a genome that is 80%, 85%, 90%, 95% similar or identical to PIC™ CAMBOROUGH® 40. The edited germplasm can comprise a genome that is 80%, 85%, 90%, 95% similar or identical to PIC™ CAMBOROUGH® 22. The edited germplasm can comprise a genome that is 80%, 85%, 90%, 95% similar or identical to PIC1050. The edited germplasm can comprise a genome that is 80%, 85%, 90%, 95% similar or identical to PIC™ CAMBOROUGH® 29. The edited germplasm can comprise a genome that is 80%, 85%, 90%, 95% similar or identical to PIC™ CAMBOROUGH® 48. The edited germplasm can comprise a genome that is 80%, 85%, 90%, 95% similar or identical to PIC™ CAMBOROUGH® x54.

The present specification provides for and includes CD163 edited animals comprising the germplasm of PIC™ Line 2, Line 3, Line 15, Line 19, Line 27, Line 62, or Line 65. The edited germplasm can comprise an edit having an edited genomic sequence of any one of SEQ ID NOs: 426 to 505. The edited germplasm can comprise an edit having an edited genomic sequence of any one of SEQ ID NOs: 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, or 505. The edited germplasm can comprise an edit having an edited genomic sequence as set forth in SEQ ID NO: 453. The edited germplasm can comprise a genome that is 80%, 85%, 90%, 95% similar or identical to PIC™ Line 2 with a CD163 edited sequence comprising SEQ ID NO: 453. The edited germplasm can comprise a genome that is 80%, 85%, 90%, 95% similar or identical to PIC™ Line 3 with a CD163 edited sequence comprising SEQ ID NO: 453. The edited germplasm can comprise a genome that is 80%, 85%, 90%, 95% similar or identical to PIC™ Line 15 with a CD163 edited sequence comprising SEQ ID NO: 453. The edited germplasm can comprise a genome that is 80%, 85%, 90%, 95% similar or identical to PIC™ Line 19 with a CD163 edited sequence comprising SEQ ID NO: 453. The edited germplasm can comprise a genome that is 80%, 85%, 90%, 95% similar or identical to 80%, 85%, 90%, 95% similar or identical to PIC™ Line 27 with a CD163 edited sequence comprising SEQ ID NO: 453. The edited germplasm can comprise a genome that is 80%, 85%, 90%, 95% similar or identical to PIC™ Line 62 with a CD163 edited sequence comprising SEQ ID NO: 453. The edited germplasm can comprise a genome that is 80%, 85%, 90%, 95% similar or identical to PIC™ Line 65 with a CD163 edited sequence comprising SEQ ID NO: 453.

The edited germplasm can comprise an edit having an edited genomic sequence as set forth in SEQ ID NO: 489. The edited germplasm can comprise a genome that is 80%, 85%, 90%, 95% similar or identical to PIC™ Line 2 with a CD163 edited sequence comprising SEQ ID NO: 489. The edited germplasm can comprise a genome that is 80%, 85%, 90%, 95% similar or identical to PIC™ Line 3 with a CD163 edited sequence comprising SEQ ID NO: 489. The edited germplasm can comprise a genome that is 80%, 85%, 90%, 95% similar or identical to PIC™ Line 15 with a CD163 edited sequence comprising SEQ ID NO: 489. The edited germplasm can comprise a genome that is 80%, 85%, 90%, 95% similar or identical to PIC™ Line 19 with a CD163 edited sequence comprising SEQ ID NO: 489. The edited germplasm can comprise a genome that is 80%, 85%, 90%, 95% similar or identical to 80%, 85%, 90%, 95% similar or identical to PIC™ Line 27 with a CD163 edited sequence comprising SEQ ID NO: 489. The edited germplasm can comprise a genome that is 80%, 85%, 90%, 95% similar or identical to PIC™ Line 62 with a CD163 edited sequence comprising SEQ ID NO: 489. The edited germplasm can comprise a genome that is 80%, 85%, 90%, 95% similar or identical to PIC™ Line 65 with a CD163 edited sequence comprising SEQ ID NO: 489. The edited germplasm can have a predicted exon 7 amino acid sequence from any one of SEQ ID NOs: 506-517. The edited germplasm can have a predicted exon 7 amino acid sequence as set forth in SEQ ID NO: 513.

The edited germplasm can comprise an edit having an edited genomic sequence as set forth in SEQ ID NO: 505. The edited germplasm can comprise a genome that is 80%, 85%, 90%, 95% similar or identical to PIC™ Line 2 with a CD163 edited sequence comprising SEQ ID NO: 505. The edited germplasm can comprise a genome that is 80%, 85%, 90%, 95% similar or identical to PIC™ Line 3 with a CD163 edited sequence comprising SEQ ID NO: 505. The edited germplasm can comprise a genome that is 80%, 85%, 90%, 95% similar or identical to PIC™ Line 15 with a CD163 edited sequence comprising SEQ ID NO: 505. The edited germplasm can comprise a genome that is 80%, 85%, 90%, 95% similar or identical to PIC™ Line 19 with a CD163 edited sequence comprising SEQ ID NO: 505. The edited germplasm can comprise a genome that is 80%, 85%, 90%, 95% similar or identical to 80%, 85%, 90%, 95% similar or identical to PIC™ Line 27 with a CD163 edited sequence comprising SEQ ID NO: 505. The edited germplasm can comprise a genome that is 80%, 85%, 90%, 95% similar or identical to PIC™ Line 62 with a CD163 edited sequence comprising SEQ ID NO: 505. The edited germplasm can comprise a genome that is 80%, 85%, 90%, 95% similar or identical to PIC™ Line 65 with a CD163 edited sequence comprising SEQ ID NO: 505. The edited germplasm can have a predicted exon 7 amino acid sequence as set forth in SEQ ID NO: 518.

The present specification also provides for and includes cells of PIC™ Line 2, Line 3, Line 15, Line 19, Line 27, Line 62, or Line 65. In some embodiments, a cell of PIC™ Line 2 can comprise an edited genomic sequence of any one of SEQ ID NOs: 426 to 505. The cell of PIC™ Line 2 can comprise an editing genomic sequence as set forth in SEQ ID NO: 453. In some embodiments, a cell of PIC™ Line 3 can comprise an edited genomic sequence of any one of SEQ ID NOs: 426 to 505. The cell of PIC™ Line 3 can comprise an editing genomic sequence as set forth in SEQ ID NO: 453. In some embodiments, a cell of PIC™ Line 15 can comprise an edited genomic sequence of any one of SEQ ID NOs: 426 to 505. The cell of PIC™ Line 15 can comprise an editing genomic sequence as set forth in SEQ Id NO: 453. In some embodiments, a cell of PIC™ Line 19 can comprise an edited genomic sequence of any one of SEQ ID NOs: 426 to 505. The cell of PIC™ Line 19 can comprise an editing genomic sequence as set forth in SEQ Id NO: 453. In some embodiments, a cell of PIC™ Line 27 can comprise an edited genomic sequence of any one of SEQ ID NOs: 426 to 505. The cell of PIC™ Line 27 can comprise an editing genomic sequence as set forth in SEQ ID NO: 453. In some embodiments, a cell of PIC™ Line 62 can comprise an edited genomic sequence of any one of SEQ ID NOs: 426 to 505. The cell of PIC™ Line 62 can comprise an editing genomic sequence as set forth in SEQ Id NO: 453. In some embodiments, a cell of PIC™ Line 65 can comprise an edited genomic sequence of any one of SEQ ID NOs: 426 to 505. The cell of PIC™ Line 65 can comprise an editing genomic sequence as set forth in SEQ Id NO: 453. The edited germplasm can have a predicted exon 7 amino acid sequence as set forth in SEQ ID NO: 513.

The present specification provides for, and includes, hybrid animals that can comprise the CD163 gene edits characterized by SEQ ID NOs: 1 to 18 and 426 to 505. In some configurations, gene edit can comprise SEQ ID NO: 453. In an aspect, the hybrid animal can be a CD163$^{-/-}$ hybrid animal of the CAMBOROUGH® (PIC™ UK Limited, Basingstoke, UK) line. CAMBOROUGH® pigs are hybrids that can be prepared by a cross between Line 2 and Line 3. In an aspect, the hybrid animal can be a CD163$^{-/-}$ hybrid animal of the CAMBOROUGH® line having an edited CD163 gene of SEQ ID NO: 2. In an aspect, the hybrid animal can be a CD163$^{-/-}$ hybrid animal of the CAMBOROUGH® line having an edited CD163 gene of SEQ ID NO: 426-458. In various aspects, the hybrid animal can be a CD163$^{-/-}$ hybrid animal of the CAMBOROUGH® line having an edited CD163 gene of SEQ ID NO: 453. In an aspect, the hybrid animal can be a CD163$^{-/-}$ hybrid animal of the CAMBOROUGH® line having an edited CD163 gene of SEQ ID NO: 459-504. In various aspects, the hybrid animal can be a CD163$^{-/-}$ hybrid animal of the CAMBOROUGH® line having an edited CD163 gene sequence of SEQ ID NO: 489. CAMBOROUGH® hybrid pigs are pigs that have large litters with uniform and vigorous piglets. CAMBOROUGH® hybrid pigs have a long productive life and have a low mortality. CAMBOROUGH® CD163$^{-/-}$ hybrid pigs retain these desirable commercial traits. In an aspect, CAMBOROUGH® CD163$^{-/-}$ hybrid pigs have litter sizes that are indistinguishable from non-gene edited CAMBOROUGH® hybrid pigs. In aspects according to the present specification, the heterozygous and homozygous pigs of the present specification are free of off-site mutations.

The present specification further provides, and includes, methods for preparing CD163 gene edited hybrid animals. In an aspect, a first parent can comprise a CD163 gene edited boar, gilt, or sow of one of PIC™ Line 2, Line 3, Line 15, Line 19, Line 27, Line 62, or Line 65 for crossing to a second parent. In an aspect, the genome of a gene edited first parent can comprise a sequence selected from the group consisting of SEQ ID NOs: 1 to 18 or 426 to 505. In some aspects, the genome can comprise SEQ ID NO: 453. In various aspects, the genome can comprise SEQ ID NO: 489. In various aspects, the genome can comprise SEQ ID NO: 505. In an aspect, the method can comprise a second parent selected from the group consisting of a CD163 gene edited boar, gilt, or sow of one of PIC™ Line 2, Line 3, Line 15, Line 19, Line 27, Line 62, or Line 65. Also provided for, and included, by the present specification are methods of preparing CD163 edited animals that can comprise crossing a progeny of any one of PIC™ Line 2, Line 3, Line 15, Line 19, Line 27, Line 62, or Line 65.

In an aspect, the present specification provides for heterozygous pigs from lines 2, 3, 15, and 65 (Table 8, Table 9, Table 10, and Table 14, respectively) that can have at least one copy of the CD163 gene successfully edited in a knock-out edit. These edited pigs can exhibit a healthy phenotype with no noticeable deleterious effects from the edit. In another aspect, the specification provides for pigs from lines 19, 27, and 62 (Table 11, Table 12, and Table 13, respectively) that can be edited using the methods disclosed herein to generate edited pigs with healthy phenotypes. The heterozygous pigs can be crossed with non-edited animals of the corresponding line to produce F1 heterozygous pigs. In an embodiment, heterozygous pigs of lines 2, 3, 15, and 65 can be crossed to a second heterozygous pig of lines 2, 3, 15, and 65, and homozygous CD163 edited pigs can be produced in Mendelian proportions. Notably, the gene edits can be unique and identifiable using SEQ ID NOs: 1 to 18 and 426 to 505 and share genetic signatures comprising at least 90% of the genotypic markers of Table 8 to Table 14, thereby enabling the detection and breeding of the CD163 gene edited genomes in any progeny generation. In an aspect, the genetic signatures can share 95% or more of the genotypic markers of Table 8 to Table 14. In another aspect, the genetic signatures share 97% or more of the genotypic markers of Table 8 to Table 14. Also included are genetic signatures that can share 98% or more of the genotypic markers of Table 8 to Table 14. Importantly, the linkage of the CD163 edits to the genomic regions identifiable using the genotypic markers of Table 8 to Table 14 can enable the preparation of any progeny animal having the desired edits and the tracking of the edited regions in any number of progeny generations. In aspects according to the present specification, the heterozygous and homozygous pigs of the present specification can be free of off-site mutations.

The present specification provides for, and includes, an embryo or zygote that can be obtained from an elite line of pigs. In an aspect, the embryo or zygote can be obtained from an elite porcine line selected from the group consisting of PIC™ Line 2, Line 3, Line 15, Line 19, Line 27, Line 62, or Line 65. In an aspect, the embryo or zygote can be a frozen embryo or zygote. In another aspect, the embryo or zygote can be a frozen blastocyst. As provided herein, the embryos can be prepared from in vitro matured oocytes collected from estrus synchronized gilts. The surrounding cumulus cells can be removed from the in vitro matured oocytes and incubated with washed boar spermatozoa and incubated. After incubation, presumptive zygotes can be microinjected with an RNP mixture comprising the CRISPR-Cas endonuclease and guide RNA combinations comprising the first 20 nucleotides of SEQ ID NOs: 22 to 271 or 347 to 425 listed in Table 3. Injected embryos can be transferred to a surrogate female at the 1 to 4 cell stage. In an aspect, the RNP mixture can further include repair templates listed in Table 6 (SEQ ID NOs: 1 to 13). In an aspect, injected zygotes can be surgically implanted into the oviducts of estrus synchronized, un-mated surrogate females by a mid-line laparotomy under general anesthesia (each surrogate receives 40-60 injected embryos).

The present specification provides for, and includes, gene edited pigs of selected elite lines that can be CD163$^{-/-}$. In an aspect, the line can be PIC™ Line 15, PIC™ Line 17, PIC™ Line 27, PIC™ Line 65, PIC™ Line 14, PIC™ Line 62, PIC337, PIC800, PIC280, PIC327, PIC408, PIC™ 399, PIC410, PIC415, PIC359, PIC380, PIC837, PIC260, PIC265, PIC210, PIC™ Line 2, PIC™ Line 3, PIC™ Line 4, PIC™ Line 5, PIC™ Line 18, PIC™ Line 19, PIC™ Line 92, PIC95, PIC™ CAMBOROUGH®, PIC1070, PIC™ CAMBOROUGH® 40, PIC™ CAMBOROUGH® 22, PIC1050, PIC™ CAMBOROUGH® 29, PIC™ CAMBOROUGH® 48, or PIC™ CAMBOROUGH® x54. In an aspect, the line can be selected from the group consisting of PIC™ Line 2, Line 3, Line 15, Line 19, Line 27, Line 62, Line 65, and progeny thereof comprising the edited CD163 genes described herein. Gene edited lines 2, 3, 15, 19, 27, 62, and 65 comprise CD163 genomic regions as provided above at Table 8 to Table 14, and can be readily distinguished from each other, from unimproved lines, and from other elite lines. Similarly, progeny of lines 2, 3, 15, 19, 27, 62, and 65 comprising the CD163$^{-/-}$ genomic regions as provided in Table 8 to Table 14 can be identified. Accordingly, the present specification provides for progeny pigs that can have a CD163$^{-/-}$ genomic region.

The present specification provides for and includes hybrid porcine lines comprising an edited CD163 gene of the present teachings. In some aspects, the hybrid porcine line can be produced by crossing an edited PIC™ line with at least one other edited PIC™ line. In some aspects, the porcine line can be produced by serial crosses to introduce germplasm from three or more porcine lines. In an aspect, the line can be PIC™ Line 15, PIC™ Line 17, PIC™ Line 27, PIC™ Line 65, PIC™ Line 14, PIC™ Line 62, PIC337, PIC800, PIC280, PIC327, PIC408, PIC™ 399, PIC410, PIC415, PIC359, PIC380, PIC837, PIC260, PIC265, PIC210, PIC™ Line 2, PIC™ Line 3, PIC™ Line 4, PIC™ Line 5, PIC™ Line 18, PIC™ Line 19, PIC™ Line 92, PIC95, PIC™ CAMBOROUGH®, PIC1070, PIC™ CAMBOROUGH® 40, PIC™ CAMBOROUGH® 22, PIC1050, PIC™ CAMBOROUGH® 29, PIC™ CAMBOROUGH® 48, or PIC™ CAMBOROUGH® x54.

In various aspects, PIC™ Line 65 is sold under the trade name PIC337. In various aspects, PIC™ line 62 is sold under the tradename PIC408. In various aspects, hybrid pigs made by crossing PIC™ lines 15 and 17 are sold under the tradenames PIC800 or PIC280. In various aspects, PIC™ Line 27 is sold under the tradename PIC327. In various aspects, hybrids created from crossing PIC™ Line 65 and PIC™ Line 62 is sold under the tradenames PIC399, PIC410 or PIC415. In various aspects, hybrids created from crossing PIC™ Line 65 and Pic Line 27 are sold under the tradename PIC359. In various aspects, hybrids prepared from crossing PIC™ Line 800 pigs (which is a hybrid of PIC™ Line 15 and PIC™ Line 17) to PIC™ Line 65 pigs are sold under the tradenames PIC380 or PIC837. In various aspects, PIC™ Line 14 is sold under the trade name PIC260. In various aspects, hybrids created from crossing PIC™ Line 14 and PIC™ Line 65 are sold under the tradename PIC265. In various aspects, hybrids created by crossing PIC™ Line 2 and PIC™ Line 3 are sold under the tradenames PIC210, PIC™ CAMBOROUGH®, and PIC1050. In various aspects, hybrids of PIC™ Line 3 and PIC™ Line 92 are sold under the tradename PIC95. In various configurations, hybrids made from crossing PIC™ Line 19 and PIC™ Line 3 are sold under the tradename PIC1070. In various aspects, hybrids created by crossing PIC™ Line 18 and PIC™ Line 3 are sold under the tradename PIC™ CAMBOROUGH® 40. In various aspects, hybrids created from crossing PIC™ Line 19 and PIC1050 (which is itself a hybrid of PIC™ lines 2 and 3) are sold under the tradename PIC™ CAMBOROUGH® 22. In various aspects, hybrids created from crossing PIC™ Line 2 and PIC1070 (which is itself a hybrid of PIC™ lines 19 and 3) are sold under the tradename PIC™ CAMBOROUGH® 29. In various aspects, hybrids created from crossing PIC™ Line 18 and PIC1050 (which is itself a hybrid of PIC™ lines 2 and 3) are sold under the tradename PIC™ CAMBOROUGH® 48. In various aspects, hybrids created from crossing PIC™ Line 4 and PIC™ Line 5 are sold under the tradename PIC™ CAMBOROUGH® ×54. The present teachings provide for and include pigs of any of the forgoing lines or hybrids comprising a CD163 edit of the present teachings.

In various aspects, the present teachings provide for an include pigs comprising an edited CD163 gene comprising an edited sequence set forth in SEQ ID NOs: 453, 489, or 505 wherein the pig can be a pig of PIC™ Line 15, PIC™ Line 17, PIC™ Line 27, PIC™ Line 65, PIC™ Line 14, PIC™ Line 62, PIC™ Line 2, PIC™ Line 3, PIC™ Line 4, PIC™ Line 5, PIC™ Line 18, PIC™ Line 19, PIC™ Line 92, or a hybrid of two or more of these lines. In various aspects, the hybrid pig can be a cross of PIC™ Line 15 and PIC™ Line 17, PIC™ Line 65 and PIC™ Line 62, PIC™ Line 65 and PIC™ Line 27, a serial hybrid of PIC™ Line 15 and PIC™ Line 17, wherein the hybrid offspring is then crossed to PIC™ Line 65, PIC™ Line 14 and PIC™ Line 65, PIC™ Line 2 and PIC™ Line 3, PIC™ Line 3 and PIC™ Line 92, PIC™ Line 19 and PIC™ Line 3, PIC™ Line 18 and PIC™ Line 3, a serial hybrid between a hybrid pig of PIC™ Line 2 and PIC™ Line 3 and a pig of PIC™ Line 19, a serial hybrid between a hybrid pig of PIC™ Line 19 and PIC™ Line 3 and a pig of PIC™ Line 2, a serial hybrid between a hybrid of PIC™ Line 2 and PIC™ Line 3 crossed to a pig of PIC™ Line 18, or a hybrid of PIC™ Line 4 and PIC™ Line 5.

In various aspects, the hybrid line comprising an edited CD163 gene can be produced by crossing two or more of lines 2, 3, 15, 19, 27, 62, or 65. In some aspects, the hybrid line comprising an edited CD163 gene can be a CAMBOROUGH® line. CAMBOROUGH® pigs are hybrids that can be prepared by a cross between Line 2 and Line 3. In various aspects, the hybrid line can comprise a PIC™ 837 hybrid line comprising an edited CD163 gene. PIC™ 837 pigs are hybrids that can be prepared by crossing PIC™ Line 800 pigs to PIC™ Line 65 pigs.

The present specification provides for, and includes, hybrid CD163$^{-/-}$ progeny lines comprising one CD163$^{-/-}$ genomic region that can be obtained from lines 2, 3, 15, 19, 27, 62, or 65, and a second CD163$^{-/-}$ genomic region that can be obtained from a different line selected from lines 2, 3, 15, 19, 27, 62, or 65. In an aspect, a hybrid CD163$^{-/-}$ progeny line can comprise a CD163$^{-/-}$ allele in a genomic region according to Table 8 and a CD163$^{-/-}$ allele in a genomic region according to Table 10. In an aspect, a hybrid CD163$^{-/-}$ progeny line can comprise a CD163$^{-/-}$ allele in a genomic region according to Table 8 and a CD163$^{-/-}$ allele in a genomic region according to Table 14. In an aspect, a hybrid CD163$^{-/-}$ progeny line can comprise a CD163$^{-/-}$ allele in a genomic region according to Table 9 and a CD163$^{-/-}$ allele in a genomic region according to Table 10. In an aspect, a hybrid CD163$^{-/-}$ progeny line can comprise a CD163$^{-/-}$ allele in a genomic region according to Table 9 and a CD163$^{-/-}$ allele in a genomic region according to Table 14.

The present specification provides for, and includes, hybrid animals that can comprise the CD163 gene edits characterized by SEQ ID NOs: 1 to 18 and 426 to 505. In an aspect, the hybrid animals comprising the CD163 gene edits can be characterized by SEQ ID NO: 2. In an aspect, the hybrid animals comprising the CD163 gene edits can be characterized by SEQ ID NO: 426-458. In an aspect, the hybrid animals comprising the CD163 gene edits can be characterized by SEQ ID NO: 453. In an aspect, the hybrid animals comprising the CD163 gene edits can be characterized by SEQ ID NO: 459-504. In an aspect, the hybrid animals comprising the CD163 gene edits can be characterized by SEQ ID NO: 489. In an aspect, the hybrid animal can be a CD163$^{-/-}$ hybrid animals of the CAMBOROUGH® line. CAMBOROUGH® pigs are hybrids that can be prepared by a cross between Line 2 and Line 3.

In various aspects, the hybrid pig can comprise SEQ ID NO: 2 in a genomic region according to Table 8 and SEQ ID NO: 2 in a genomic region according to Table 10. In an aspect, the hybrid pig can comprise SEQ ID NO: 453 in a genomic region according to Table 8 and SEQ ID NO: 453 in a genomic region according to Table 10. In an aspect, the hybrid pig can comprise SEQ ID NO: 489 in a genomic region according to Table 8 and SEQ ID NO: 489 in a genomic region according to Table 10. In an aspect, a hybrid CD163$^{-/-}$ progeny line can comprise SEQ ID NO: 2 in a genomic region according to Table 8 and SEQ ID NO: 2 in a genomic region according to Table 14. In an aspect, a hybrid CD163$^{-/-}$ progeny line can comprise SEQ ID NO: 453 in a genomic region according to Table 8 and SEQ ID NO: 453 in a genomic region according to Table 14. In an aspect, a hybrid CD163$^{-/-}$ progeny line can comprise SEQ ID NO: 489 in a genomic region according to Table 8 and SEQ ID NO: 489 in a genomic region according to Table 14. In an aspect, a hybrid CD163$^{-/-}$ progeny line can comprise SEQ ID NO: 2 in a genomic region according to Table 9 and SEQ ID NO: 2 in a genomic region according to Table 10. In an aspect, a hybrid CD163$^{-/-}$ progeny line can comprise SEQ ID NO: 453 in a genomic region according to Table 9 and SEQ ID NO: 453 in a genomic region according to Table 10. In an aspect, a hybrid CD163$^{-/-}$ progeny line can comprise SEQ ID NO: 489 in a genomic region according to Table 9 and SEQ ID NO: 489 in a genomic region according to Table 10. In an aspect, the hybrid pig can comprise SEQ ID NO: 2 in a genomic region according to Table 8 and SEQ ID NO: 2 in a genomic region according to Table 10. In an aspect, the hybrid pig can comprise SEQ ID NO: 453 in a genomic region according to Table 8 and SEQ ID NO: 453 in a genomic region according to Table 10. In an aspect, the hybrid pig can comprise SEQ ID NO: 489 in a genomic region according to Table 8 and SEQ ID NO: 489 in a genomic region according to Table 10. In an aspect, a hybrid CD163$^{-/-}$ progeny line can comprise SEQ ID NO: 2 in a genomic region according to Table 8 and SEQ ID NO: 2 in a genomic region according to Table 14. In an aspect, a hybrid CD163$^{-/-}$ progeny line can comprise SEQ ID NO: 453 in a genomic region according to Table 8 and SEQ ID NO: 453 in a genomic region according to Table 14. In an aspect, a hybrid CD163$^{-/-}$ progeny line can comprise SEQ ID NO: 489 in a genomic region according to Table 8 and SEQ ID NO: 489 in a genomic region according to Table 14. In an aspect, a hybrid CD163$^{-/-}$ progeny line can comprise SEQ ID NO: 2 in a genomic region according to Table 9 and SEQ ID NO: 2 in a genomic region according to Table 10. In an aspect, a hybrid CD163$^{-/-}$ progeny line can comprise SEQ ID NO: 453 in a genomic region according to Table 9 and SEQ ID NO: 453 in a genomic region according to Table 10. In an aspect, a hybrid CD163$^{-/-}$ progeny line can comprise SEQ ID NO: 489 in a genomic region according to Table 9 and SEQ ID NO: 489 in a genomic region according to Table 10. In aspects according to the present specification, the heterozygous and homozygous pigs of the present specification can be free of off-site mutations.

In an aspect, the hybrid animal can be a CD163$^{-/-}$ hybrid animals of the CAMBOROUGH® line. CAMBOROUGH® pigs are hybrids that can be prepared by a cross between Line 2 and Line 3. In an aspect, the hybrid pig can comprise SEQ ID NO: 426 to 505 in a genomic region according to Table 8 and SEQ ID NO: 426-505 in a genomic region according to Table 10. In an aspect, the hybrid pig can comprise SEQ ID NO: 453 in a genomic region according to Table 8 and SEQ ID NO: 453 in a genomic region according to Table 10. In an aspect, the hybrid pig can comprise SEQ ID NO: 489 in a genomic region according to Table 8 and SEQ ID NO: 489 in a genomic region according to Table 10. In an aspect, a hybrid CD163$^{-/-}$ progeny line can comprise SEQ ID NO: 426 to 505 in a genomic region according to Table 8 and SEQ ID NO: 426 to 505 in a genomic region according to Table 14. In an aspect, a hybrid CD163$^{-/-}$ progeny line can comprise SEQ ID NO: 453 in a genomic region according to Table 8 and SEQ ID NO: 489 in a genomic region according to Table 14. In an aspect, a hybrid CD163$^{-/-}$ progeny line can comprise SEQ ID NO: 489 in a genomic region according to Table 8 and SEQ ID NO: 453 in a genomic region according to Table 14. In an aspect, a hybrid CD163$^{-/-}$ progeny line can comprise SEQ ID NO: 426 to 505 in a genomic region according to Table 9 and SEQ ID NO: 426 to 505 in a genomic region according to Table 10. In an aspect, a hybrid CD163$^{-/-}$ progeny line can comprise SEQ ID NO: 453 in a genomic region according to Table 9 and SEQ ID NO: 453 in a genomic region according to Table 10. In an aspect, a hybrid CD163$^{-/-}$ progeny line can comprise SEQ ID NO: 489 in a genomic region according to Table 9 and SEQ ID NO: 489 in a genomic region according to Table 10.

In various aspects, an edited pig of PIC™ line 2, PIC™ line 3, PIC™ line 15, PIC™ line 19, PIC™ line 27, PIC™ line 62, or PIC™ line 65 can have a CD163 gene comprising a predicted amino acid sequence as set forth in SEQ ID NO: 518. In various aspects, the edited CD163 gene can have a 123 bp deletion as set forth in SEQ ID NO: 505. In various configurations, this deletion can have an Exon 7 Amino Acid sequence of AHRKPRLV - - - TVVSLLGGAHFGEGSGQI-WAEEFQCEGHESHLSLCPVAPRPDGTCSHSRDVGVV CS (SEQ ID NO: 518). In various aspects, a pig having an edited CD163 gene comprising an amino acid sequence set forth in SEQ ID NO: 518 can be a hybrid offspring between two PIC™ lines. In various aspects, the pig can have an edited CD163 Exon 7 sequence comprising a nucleotide sequence set forth in SEQ ID NO: 505. In various aspects, the pig can be an offspring of a cross between PIC™ line 2 and PIC™ line 3. In aspects according to the present specification, the heterozygous and homozygous pigs of the present specification can be free of off-site mutations.

Importantly, the CD163 edited pigs and cells of the present specification retain their desirable commercial phenotypes. The edited pigs can exhibit a healthy phenotype with no noticeable acute deleterious effects from the edit. In an aspect, the pigs of lines 2, 3, 15, 19, 27, 62, and 65, can retain the commercially desirable phenotypes as provided in Table 15.

Methods for improving the health of existing herds of livestock can comprise modifying the CD163 gene locus using the methods described above. In an aspect, the method can comprise introducing into a pig cell an endonuclease or a polynucleotide encoding said endonuclease, and a guide polynucleotide comprising a sequence selected from the group consisting of the first 20 nucleotides of each of SEQ ID NOs: 22 to 271 or the first 20 nucleotides of each of 347 to 425, incubating the cell under conditions that permit the endonuclease to act upon the DNA at, or near, the target sequence and thereby induce recombination, homology-directed repair, or non-homologous end joining at or near the target site, identifying at least one cell having a modification at said target sequence, and producing an animal from an animal cell. In aspects of the present specification, the endonuclease can be an RNP complex of a guide RNA and a Cas protein from *S. thermophilus*. In another aspect, the endonuclease can be an RNP complex of a guide RNA and a Cas protein from *S. pyogenes*.

In an aspect, the method can further comprise providing to the cell a repair guide comprising a sequence selected from the group consisting of nucleotides 50 to 100 of SEQ ID NOs: 1 to 13. In another aspect, a repair guide can comprise a sequence selected from the group consisting of nucleotides 50 to 100 of SEQ ID NOs: 1 to 13 and can further comprise 85% homology to nucleotides 1 to 49 and 101 to 150 of SEQ ID NOs: 1 to 13. In an aspect, the repair guide can comprise a sequence selected from the group consisting of SEQ ID NOs: 1 to 13. As provided herein, the method for improving the health of existing herds provides for the maintenance of desirable commercial phenotypes as discussed above. In an aspect, the desirable commercial phenotypes can be at least 90% of the phenotypes observed in herds of non-edited pigs having a similar genetic background.

The CD163 gene edited locus can be introduced into the herd by conventional breeding or by methods incorporating artificial insemination. To prepare homozygous animals, crosses between parents having at least one gene edited CD163 locus comprising a sequence of SEQ ID NOs: 1 to 18 or 426 to 505 can be performed and homozygous progeny (present at a 1:4 Mendelian ratio) can be selected. As provided herein, a combination of parents and one gene edited CD163 locus can be suitable for improving the herd. Further breeding of animals having the CD163 gene edited loci can improve the health of the herd until all the animals of the herd comprise a CD163 gene edited locus as described. Notably, the health of the herd can improve significantly well before the herd has been bred fully to a CD163 gene edited herd. Specifically, and as discussed above, pig fetuses in a PRRSv resistant gene edited CD163 sow are themselves protected from PRRSv. Further, one of ordinary skill in the art would know that, as the numbers of homozygous CD163 edited animals increase, suitable pig vectors for PRRSv transmission decrease (e.g., herd immunity develops). Accordingly, the present methods can provide for improving a herd by introducing herd immunity.

One useful method of detecting the desired edit is to use real-time PCR. PCR primers flanking the region of interest and a probe that specifically anneals to the region of interest. The probe is labelled with both a fluorophore and a quencher. In the PCR reaction, the primers and probe hybridize in a sequence-dependent manner to the complementary DNA strand of the region of interest. Because the probe is intact, the fluorophore and quencher are in close proximity and the quencher absorbs fluorescence emitted by the fluorophore. The polymerase extends from the primers and begins DNA synthesis. When the polymerase reaches the probe, the exonuclease activity of the polymerase cleaves the hybridized probe. As a result of cleavage, the fluorophore is separated from the quencher and fluoresces. This fluorescence is detected by the real time instrument. These steps are repeated for each PCR cycle and allow detection of specific products.

In the instant application, three separate sets of primers and probes were designed. The first set of primers (SEQ ID NO: 556 and 557) flanked the unedited genomic sequence comprising SEQ ID NO: 249 and a probe (SEQ ID NO: 558) which binds to the unedited genomic DNA in between the primers. The second set of primers (SEQ ID NO: 559 and 560) flanked the unedited genomic sequence comprising SEQ ID NO: 256, and a probe (SEQ ID NO: 561) binds the unedited between the primers. The final set of primers (SEQ ID NO: 562 and 563) flanked the desired Exon 7 deletion edit created by excision of the sequence between the cut sites of SEQ ID NO: 249 and SEQ ID NO: 256. A probe (SEQ ID NO: 564) was designed to bind the desired edit in between these primers. A commercial real-time PCR kit was then used to probe various animals for the desired edit. A variety of commercial real-time PCR kits exist including, such as, but without limitation, PRIMETIME® from IDT, TAQMAN® (Roche Molecular Systems, Inc, Pleasonton, CA) from Applied Biosystems, and various kits from Qiagen and Bio-Rad. Skilled persons will recognize that any such kit can be used with the primers and methods of the present teachings to achieve like results.

EXAMPLES

Example 1

This Example illustrates target site selection of a porcine CD163 gene knockout in pig cells.

A *Streptococcus* Cas9/gRNA RNA-directed DNA endonuclease was used to generate DNA sequence insertions, deletions, and combinations thereof, in the porcine CD163 gene (Sscrofa11.1, GenBank accession: GCA 000003025.6), whereby guide RNAs and protein combinations were delivered singly or as pairs, such that sequence changes in the CD163 gene reduce or abolish the function, stability, or expression of the CD163 messenger RNA or protein. The sequence of the CD163 gene from 120 nucleotides upstream (chr5:63300192) of the translational start site to 59 nucleotides downstream of CD163 exon 7 (chr5:63323390), was screened for the guide RNA binding sites having either an adjacent nGG or nGGnG PAM sequence required for cutting by the Cas9 proteins derived from *Streptococcus pyogenes* or *Streptococcus thermophilus* CRISPR3 (*S. thermophilus* CR3), respectively, the sequences of which are in the sequence listing filed herewith, as listed in Table 2. The DNA sequences for the target sites for editing, the locations of the target sites on the CD163 gene, and the editing activity (measured as described in Example 3) are provided in Table 3. Guide RNA molecules had the same sequence as the target, with corresponding RNA nucleotides, without the PAM sequence (nGG for *S. pyogenes* and nGGnG for *S. thermophilus*). Guide polynucleotide molecules could also consist of DNA bases or mixtures of DNA and RNA bases. The target site sequences are listed in the sequence listing filed herewith as SEQ ID NOs: 22 to 271 and 347 to 425. The target site sequences shown are conserved across pig germplasm and screened by DNA sequencing.

Example 2

This example illustrates nucleofection for the delivery of guide RNA/Cas9 endonuclease to porcine fetal fibroblasts.

To test the DNA cutting activity in living cells to produce an edited porcine CD163 allele, the CRISPR-Cas endonuclease and guide RNA targeting the sequences listed in Table 3 were nucleofected into porcine fetal fibroblast cells. Porcine fetal fibroblast (PFF) cells lines were prepared from 28-35 day-old fetuses and 3.2 µg of Cas9 protein (*S. pyogenes* or *S. thermophilus*) and 2.2 µg of in vitro transcribed single guide RNA were combined in water to a total volume of 2.23 µl, then were nucleofected into PFF cells using a Lonza electroporator. In preparation for nucleofection, PFF cells were harvested using TrypLE express (recombinant Trypsin), upon which the culture medium was removed from cells, washed 1× with HBSS or DPBS, and incubated for 3-5 minutes at 38.5° C. in the presence of TrypLE. Cells were then harvested with complete medium. Cells were pelleted via centrifugation (300×g for 5 minutes at room temperature), supernatant was discarded, then the cells were resuspended in 10 mL PBS to obtain single cell suspension counting cells using trypan blue staining.

The appropriate amount of cells was pelleted by centrifugation (300×g for 5 minutes at room temperature), the supernatant was discarded, and the cells were resuspended in nucleofection buffer P3 at a final concentration of $7.5 \times 10^6$ cells/ml. 20 µl of the cell suspension were added to each well of a nucleofection plate containing the RNP mixture using a multichannel pipette, then mixed gently to resuspend the cells. The RNP/cell mixture was transferred in the nucleofection plate, nucleofected with program CM138 (supplied by the manufacturer). 80 µl of warm Embryonic Fibroblast Medium, EFM, (Dulbecco's Modified Eagle's Medium (DMEM) containing 2.77 mM glucose, 1.99 mM L-glutamine, and 0.5 mM sodium pyruvate, supplemented with 100 µM 2-Mercaptoethanol, 1× Eagle's minimum essential medium non-essential amino acids (MEM NEAA), 100 µg/mL Penicillin-Streptomycin, and 12% Fetal Bovine Serum were added to each well after nucleofection. The suspensions were mixed gently by pipetting, then 100 µl were transferred to a 12 well plate containing 900 µl of EFM pre-incubated at 38.5° C. The plate was then incubated at 38.5° C., 5% $CO_2$ for 48 hours. Forty-eight hours post nucleofection, genomic DNA was prepared from transfected and control PFF cells, 15 µl of QUICKEXTRACT™ DNA Extraction Solution (Lucigen, Madison, WI) were added to pelleted cells then lysed by incubating for 10 mins at 37° C., for 8 mins at 65° C., for 5 mins at 95° C., then lysate was held at 4° C. until used for DNA sequencing.

Example 3

This example illustrates the editing frequency of guide RNA/Cas9 combinations directed against porcine CD163.

Nucleotide sequence changes were introduced into the porcine CD163 gene by delivering Cas9 protein complexed with guide RNAs to fetal fibroblast cells as described in Example 2.

To evaluate DNA double strand cleavage at a porcine CD163 genomic target site mediated by the guide RNA/Cas endonuclease system, a region of approximately 250 bp genomic DNA surrounding the target site was amplified by PCR and the PCR product was then examined by amplicon deep sequencing for the presence of edits. After transfection in triplicate, PFF genomic DNA was extracted as described in Example 2. The region surrounding the intended target site was PCR amplified with NEB Q5 Polymerase, adding sequences necessary for amplicon-specific barcodes and ILLUMINA® (ILLUMINA®, San Diego, CA) sequencing using tailed primers through two rounds of PCR. The resulting PCR amplifications were deep sequenced on an ILLUMINA® MISEQ® Personal Sequencer (ILLUMINA®, San Diego, CA). The resulting reads were examined for the presence of edits at the expected site of cleavage by comparison to control experiments where the Cas9 protein and guide RNA were omitted from the transfection or by comparison to the reference genome. To calculate the frequency of NHEJ edits for a target site, Cas9 protein, guide RNA combination, the total number of edited reads (amplicon sequences containing insertions or deletions when compared to the DNA sequences from control treatments or reference genome) were divided by total read number (wild-type plus edited reads) of an appropriate length containing a perfect match to the barcode and forward primer. Total read counts averaged approximately 7000 per sample and NHEJ activity is expressed as the average (n=3) edited fraction in Table 3. As shown in Table 3, from 0 to 58.2% of the reads contained edits and the average editing frequency across all combinations was approximately 16%. This example demonstrates that, in fetal fibroblast cells, the porcine CD163 gene nucleotide sequence was edited through the stimulation of double-strand breaks mediated by transfecting Cas9 protein from either *S. pyogenes* or *S. thermophilus* complexed with various guide RNAs.

Example 4

This example illustrates generation of an in-frame stop codon using DNA repair template.

DNA repair templates were used to introduce stop codons in the porcine CD163 gene when co-delivered with Cas9 protein and guide RNA. The endonuclease-guide complexes and repair templates disclosed in Table 5 were generated and used to edit CD163 genes in blastocysts. The base deletions were verified by the methods of Example 5.

Example 5

This example illustrates the molecular characterization of edited animal genomes.

A tissue sample was taken from an animal whose genome was been edited according to the examples herein. Tail, ear notch, or blood samples were suitable tissue types. The tissue sample was frozen at −20° C. within 1 hour of sampling to preserve integrity of the DNA in the tissue sample.

DNA was extracted from tissue samples after proteinase K digestion in lysis buffer. Characterization was performed on two different sequence platforms, short sequence reads using the ILLUMINA® platform and long sequence reads on an Oxford NANOPORE™ platform (Oxford NANOPORE™ Technologies, Oxford, UK).

For short sequence reads, two-step PCR was used to amplify and sequence the region of interest. The first step was a locus-specific PCR which amplified the locus of interest from the DNA sample using a combined locus-specific primer with a vendor-specific primer. The second step attached the sequencing index and adaptor sequences to the amplicon from the first step so that sequencing could occur.

The locus-specific primers for the first step PCR were chosen so that they amplified a region <300 bp such that ILLUMINA® paired-end sequencing reads could span the amplified fragment. Multiple amplicons were preferred to provide redundancy should deletions or naturally occurring point mutations prevent primers from correctly binding. Sequence data for the amplicon was generated using an ILLUMINA® sequencing platform (MISEQ®, ILLUMINA®, San Diego, CA). Sequence reads are analyzed to characterize the outcome of the editing process.

For long sequence reads, two-step PCR was used to amplify and sequence the region of interest. The first step is a locus-specific PCR which amplified the locus of interest from the DNA sample using a combined locus-specific primer with a vendor-specific adapter. The second step PCR attached the sequencing index to the amplicon from the first-step PCR so that the DNA was ready for preparing a sequencing library. The step 2 PCR products underwent a set of chemical reactions from a vendor kit to polish the ends of the DNA and ligate on the adapter containing the motor protein to allow access to the pores for DNA strand-based sequencing.

The locus specific primers for the first step PCR range were designed to amplify different regions of the CD163 gene and amplified regions differed in length. Normalized DNA is then mixed with vendor supplied loading buffer and is loaded onto the NANOPORE™ flowcell.

Long sequence reads, while having lower per base accuracy than short reads, are very useful for observing the long range context of the sequence around the target site.

Example 6

This example illustrates methods of making pigs having edited CD163 genes conferring PRRSv resistance.

Porcine oocytes were isolated, fertilized, and then the resulting zygotes are edited to generate gene edited pigs.

CD163 RNP complexes were microinjected into the cytoplasm of in vivo or in vitro fertilized porcine one-cell zygotes. These zygotes were then incubated to generate edited multicellular embryos and transferred to surrogate gilts via standard methods to birth gene edited pigs. To prepare embryo donors and surrogates, pubertal gilts from PIC™ Line 2, Line 3, Line 15, and Line 65 were subjected to estrus synchronization by treatment with 0.22% altrenogest solution (20-36 mg/animal) for 14 days. Follicular growth was induced by the administration of PMSG 36 hours following the last dose of Matrix, and ovulation was induced by the administration of hCG 82 hours after PMSG administration. To generate in vivo fertilized zygotes, females in standing heat were then artificially inseminated (AI) with boar semen from the corresponding PIC™ line. In vivo derived zygotes were recovered surgically 12-24 hours after AI by retrograde flushing the oviduct with sterile TL-HEPES medium supplemented with 0.3% BSA (w/v). Fertilized zygotes were subjected to a single 2-50 picoliter (pl) cytoplasmic injection of Cas9 protein and guide RNA complex (25-50 ng/µl and 12.5-35 ng/µl) targeting CD163 and cultured in PZM5 medium (Yoshioka, K., et al., Biol. Reprod., 2002, 60: 112-119; Suzuki, C., et al., Reprod. Fertil. Dev., 2006 18, 789-795; Yoshioka, K., J. Reprod. Dev. 2008, 54, 208-213). Injected zygotes were surgically implanted into the oviducts of estrus synchronized, un-mated surrogate females by a mid-line laparotomy under general anesthesia (each surrogate received 20-60 injected embryos).

In vitro fertilized embryos for gene editing were derived from non-fertilized PIC™ oocytes. Immature oocytes from estrus synchronized PIC™ gilts were collected from medium size (3-6 mm) follicles. Oocytes with evenly dark cytoplasm and intact surrounding cumulus cells were then selected for maturation. Cumulus oocyte complexes were placed in a well containing 500 µl of maturation medium, TCM-199 (Invitrogen) with 3.05 mM glucose, 0.91 mM sodium pyruvate, 0.57 mM cysteine, 10 ng/ml EGF, 0.5 µg/ml luteinizing hormone (LH), 0.5 µg/ml FSH, 10 ng/ml gentamicin (Sigma), and 10% follicular fluid for 42-44 h at 38.5° C. and 5% $CO_2$, in humidified air. At the end of the maturation, the surrounding cumulus cells were removed from the oocytes by vortexing for 3 min in the presence of 0.1% hyaluronidase. Then, in vitro matured oocytes were placed in 100 µl droplets of IVF medium (modified Tris-buffered medium containing 113.1 mM NaCl, 3 mM KCl, 7.5 mM $CaCl_2$), 11 mM glucose, 20 mM Tris, 2 mM caffeine, 5 mM sodium pyruvate, and 2 mg/ml bovine serum albumin (BSA)) in groups of 25-30 oocytes and were fertilized according to established protocol (Abeydeera, *Biol. Reprod.*, 57:729-734, 1997) using fresh extended boar semen. One ml of extended semen was mixed with Dulbecco's Phosphate Buffered Saline (DPBS) containing 1 mg/ml BSA to a final volume of 10 ml and centrifuged at 1000×g, 25° C. for 4 minutes, and spermatozoa were washed in DPBS three times. After the final wash, spermatozoa were re-suspended in mTBM medium and added to oocytes at a final concentration of $1 \times 10^5$ spermatozoa/ml, and co-incubated for 4-5 h at 38.5° C. and 5% $CO_2$. Presumptive zygotes were microinjected 5 hours post IVF and transferred to a surrogate female after 18-42 hours (1-4 cell stage). Each surrogate receives 20-60 injected embryos. Pregnancies were confirmed by lack of return to estrus (21 days) and ultrasound at 28 days post embryo transfer.

To establish the frequency of Cas9-guide RNA targeted gene editing in porcine embryos, uninjected control zygotes and injected surplus zygotes generated by in vitro fertilization were cultivated in PZM3 or PZM5 medium at 38.5° C. for 5-7 days. Blastocysts were harvested at day 7 post cultivation and the genomic DNA isolated for next generation sequencing.

Example 7

This example illustrates the generation and characterization of gene edited pigs.

Animals from PIC™ lines 2, 3, 15, and 65 were edited by the methods described in Example 6. Successful edits were confirmed using the methods of Example 5. Fibroblast cell lines were grown from collagenase treated ear notch samples extracted from the edited animals and deposited with the American Type Culture Collection (ATCC®). The ATCC® has an address of 10801 University Boulevard, Manassas, VA 20110-2209. A representative sample of CD163 edited PIC™ Line 2 was deposited with the ATCC on Apr. 3, 2019 and assigned ATTC® Patent Deposit Number PTA-125814. A representative sample of CD163 edited PIC™ Line 3 was deposited with the ATCC on Apr. 3, 2019 and assigned ATTC® Patent Deposit Number PTA-125815. A representative sample of CD163 edited PIC™ Line 15 was deposited with the ATCC on Apr. 3, 2019 and assigned ATTC® Patent Deposit Number PTA-125816. A representative sample of CD163 edited PIC™ Line 65 was deposited with the ATCC® on Apr. 3, 2019 and assigned ATTC® Patent Deposit Number PTA-125813. Each deposit was made according to the Budapest Treaty. Representative animals from each line were confirmed to have heterozygous edits as specified in Table 16.

TABLE 16

Verified Gene Edited Animals

| Line number | CD163 Allele 1 | CD163 Allele 2 | ATCC Deposit No. |
|---|---|---|---|
| 2 | Wild type sequence | Deleted nucleotides chr5: 63301999-63302005 | PTA-125814 |
| 3 | Wild type sequence | Deleted nucleotides chr5: 63301999-63302005 | PTA-125815 |
| 15 | Wild type sequence | Deleted nucleotides chr5: 63301999-63302005 | PTA-125816 |
| 65 | Wild type sequence | Deleted nucleotides chr5: 63301999-63302005 | PTA-125813 |

Each of the animals in Table 16 presented a healthy phenotype with deleted nucleotides 63301999-63302005 (in exon 2) from chromosome 5.

Additional cell lines were grown from collagenase treated ear notch samples from unedited animals from PIC™ lines 19, 27, and 62, were deposited with the ATCC. A representative sample of PIC™ Line 19 was deposited with the ATCC® on Apr. 3, 2019 and assigned ATTC® Patent Deposit Number PTA-125811. A representative sample of PIC™ Line 27 was deposited with the ATCC on Apr. 3, 2019 and assigned ATTC® Patent Deposit Number PTA-125907. A representative sample of PIC™ Line 62 was deposited with the ATCC on Apr. 3, 2019 and assigned ATTC® Patent Deposit Number PTA-125812. Each deposit was made according to the Budapest Treaty. Using conventional cloning methods, animals are generated from the cell lines deposited as PTA-125811, PTA-125812, and PTA-125907 and edited using the methods of Example 6 in order to generate edited lines.

Single nucleotide polymorphisms (SNPs) in the vicinity of the CD163 gene were analyzed for each of the deposited PIC™ lines (2, 3, 15, 19, 27, 62, and 65) and SNP profiles of each of the lines that are capable of distinguishing each line are selected. The starting dataset for defining the line signatures was a collection of 330 whole genome sequenced animals from the 7 deposited PIC™ lines. A 6 Mb region of Chromosome 5 centered on the CD163 gene was extracted for the signatures, and variation within and between the lines was examined for each nucleotide in this region in order to identify a relatively small number of SNPs that together formed a signature for the line.

To be a candidate for inclusion in the signature of a given line, the following criteria were imposed on each chromosomal position: sequence coverage had to exist for 90% of animals in the line; the above had to be true for at least 5 of the 7 lines; and all animals with data in the target line must have had the same homozygous genotype. For each of the other lines, a genotype frequency for this genotype was calculated across all the sequenced animals for that line. A cutoff was imposed of at least 30% of the difference between the highest and lowest per-line genotype frequency of the other 6 lines (i.e., there must be a spread of genotype frequencies within the 6 lines).

A combination of metrics for discriminating power and even distribution were used to select a subset of genotypes that could define each line. Table 8 to Table 14 provide the positions on chromosome 5 for the SNPs for which the homozygous allele was fixed in each porcine line. These sets of homozygous alleles distinguish each porcine line from the other lines. The genotype listed indicates which allele is homozygous at each position, as indicated in Table 8 to Table 14.

Example 8

This example compares differing levels of PRRSv resistance of immune cells isolated from wild type and gene edited pigs.

CD163 surface expression analysis was conducted on Monocyte Derived Macrophages (MoMØs) recovered from edited and wild type animals, each with and without edits to the CD163 gene according to the methods described in the previous examples. The edits tested are presented in Table 17. Four edits comprise deletions of various sizes as shown, and the fifth comprises a 2 base pair insertion; all edits in Table 15 are in exon 2. All deletions or insertions result in a truncated CD163 polypeptide. CD163 expression was assessed by immunofluorescence labelling and FACS analysis using clone 2A10/11, a mouse anti-pig CD163 monoclonal antibody. CD163 edited cells, MoMØs, lacked a functional epitope on the surface of the cell as evident from cell surface expression analysis.

to transfection. Editing frequency for guide pairs was determined as described in Example 3. The frequencies of NHEJ-mediated repairs whereby the endonuclease cut sites are brought together resulting in the deletion of CD163 exon 7 are shown in Table 18.

TABLE 17

CD163 gene edits tested for protein expression

| Region Chr5 Location of guideRNAs binding site | 63301997-02016 | 63301997-02016 | 63301997-02016 | 63301997-02016 | 63301997-02016 |
|---|---|---|---|---|---|
| SEQ ID NO Guide RNA spacer (DNA) | 14 | 15 | 16 | 17 | 18 |
| SEQ ID NO Guide RNA spacer (RNA) | 42 | 42 | 42 | 42 | 42 |
| SEQ ID NO Translation of Deletion | 288 | 288 | 288 | 288 | 288 |
|  | 339 | 340 | 341 | 342 | 343 |
| Base deletion or insertion coordinates | chr5: 63302012-63302013 | chr5: 63302009-63302041 | chr5: 63302012-63302013 | chr5: 63302015-63302020 | chr5: 63302011-63302020 |
| Deleted or inserted bases (#) | TC (2 bp deletion) | SEQ ID NO: 344; (33 bp deletion) | TC (2 bp insertion) | SEQ ID NO: 345; (16 bp deletion) | SEQ ID NO: 346; (10 bp deletion) |

To test the two base pair deletion edit to CD163 in homozygous edited cells for PRRSv viral infection, MoMØs were infected with PRRSv type 1 and type 2. Twenty-four (24) hours post infectivity, in a microscope field of view, cells were counted to determine the number of cells which contain replicating PRRSv. CD163 homozygous edited MoMØcells were found to be not permissive to both PRRSv types 1 and 2.

Example 9

This example demonstrates the use of two guides for removal of exon 7 from *S. scrofa* CD163 in porcine fibroblasts.

In order to remove CD163 exon 7 DNA sequences which encode SRCR5 of the mature CD163 polypeptide, DNA sequences located in the intronic regions 450 bp upstream and 59 bp downstream of CD163 exon 7 were examined for *Streptococcus pyogenes* (NGG) and *Streptococcus thermophilus* (NGGNG) Cas9 protein and guideRNA recognition sites. 48 sites were identified within the 450 bp of intron 6 and 10 sites were identified within a 59 bp region of intron 7. The ability of these 58 sites to bind to Cas9 and guideRNAs to direct gene editing was first tested using single guides in porcine fetal fibroblasts. A subset of these single guideRNA-Cas9 proteins—the guideRNAs which generated a high frequency of edits across the spacer recognition site—were further tested as guide pairs for their ability to remove CD163 exon 7. Guides were introduced to porcine fetal fibroblasts by nucleofection as described in Example 2: each guide was prepared as an RNP and then the two sets of complexes were combined in a total volume of 2.23 µl prior

TABLE 18

End-to-end repair frequencies using paired guideRNAs for CD163 exon 7 deletion in porcine fetal fibroblasts

| SEQ ID NO: (5') | Cut site (5') | SEQ ID NO: (3') | Cut site (3') | Deletion size (bp) | Desired repair outcome (%) |
|---|---|---|---|---|---|
| 229 | 63322816 | 256 | 63323377 | 561 | 23.3 |
| 230 | 63322814 | 256 | 63323377 | 562 | 24.7 |
| 231 | 63322826 | 256 | 63323377 | 551 | 15.3 |
| 237 | 63322861 | 256 | 63323377 | 516 | 20.7 |
| 241 | 63322891 | 256 | 63323377 | 486 | 20.0 |
| 229 | 63322816 | 258 | 63323378 | 562 | 5.3 |
| 230 | 63322814 | 258 | 63323378 | 563 | 7.0 |
| 231 | 63322826 | 258 | 63323378 | 552 | 4.3 |
| 237 | 63322861 | 258 | 63323378 | 517 | 15.7 |
| 241 | 63322891 | 258 | 63323378 | 487 | 5.7 |
| 229 | 63322816 | 261 | 63323373 | 558 | 15.0 |
| 230 | 63322814 | 261 | 63323373 | 559 | 18.0 |
| 231 | 63322826 | 261 | 63323373 | 548 | 0.0 |
| 237 | 63322861 | 261 | 63323373 | 513 | 12.0 |
| 241 | 63322891 | 261 | 63323373 | 483 | 14.0 |
| 219 | 63322697 | 256 | 63323377 | 680 | 28.0 |
| 221 | 63322709 | 256 | 63323377 | 668 | 33.7 |
| 224 | 63322747 | 256 | 63323377 | 630 | 27.0 |
| 227 | 63322786 | 256 | 63323377 | 591 | 22.7 |
| 219 | 63322697 | 258 | 63323378 | 681 | 7.7 |
| 221 | 63322709 | 258 | 63323378 | 669 | 13.0 |
| 224 | 63322747 | 258 | 63323378 | 631 | 7.3 |
| 227 | 63322786 | 258 | 63323378 | 592 | 6.3 |
| 219 | 63322697 | 261 | 63323373 | 677 | 14.5 |
| 221 | 63322709 | 261 | 63323373 | 665 | 20.7 |
| 224 | 63322747 | 261 | 63323373 | 627 | 14.7 |
| 227 | 63322786 | 261 | 63323373 | 588 | 11.3 |
| 249 | 63322963 | 256 | 63323377 | 414 | 38.0 |
| 250 | 63322973 | 256 | 63323377 | 404 | 36.7 |
| 249 | 63322963 | 258 | 63323378 | 415 | 20.3 |
| 250 | 63322973 | 258 | 63323378 | 405 | 14.7 |
| 249 | 63322963 | 261 | 63323373 | 411 | 17.7 |
| 250 | 63322973 | 261 | 63323373 | 401 | 11.7 |

The excision guides had a wide range of editing frequencies for the desired edit.

Example 10

This example illustrates the excision of Exon 7 in porcine blastocysts using dual guide RNAs.

A subset of guides screened in porcine fetal fibroblasts were additionally tested for their ability to remove CD163 exon 7 in porcine blastocysts. The subset of guides to be tested in porcine embryos was chosen based on a combination of their efficacy in generating exon 7 deletions in porcine fibroblasts and low number of off-target edits for each guide in the pair (see Detailed Description). Edited porcine embryos were generated as described above. Briefly, oocytes recovered from slaughterhouse ovaries were in vitro fertilized as described in Example 6. The sgRNP solution was injected into the cytoplasm of presumptive zygotes at 4-5 hours post-fertilization by using a single pulse from a FEMTOJET® 4i microinjector (Eppendorf; Hamburg, Germany) with settings at pi=200 hPa, ti=0.25 s, pc=15 hPa. Glass capillary pipettes (Sutter Instrument, Navato, CA, USA) with an outer diameter of 1.2 mm and an inner diameter of 0.94 mm were pulled to a very fine point of <0.5 Microinjection was performed in TL-Hepes (ABT360, LLC) supplemented with 3 mg/ml BSA (Proliant) on the heated stage of an inverted microscope equipped with Narishige (Narishige International USA, Amityville, NY) micromanipulators. Following injections, presumptive zygotes were cultured for 7 days in PZM5 (Cosmo Bio, Co LTD, Tokyo, Japan) in an incubator environment of 5% $CO_2$, 5% $O_2$, 90% $N_2$. Editing frequency of blastocysts was determined as described in Example 3. The frequencies of end-to-end NHEJ repairs resulting in the deletion of CD163 exon 7 are shown in Table 19.

TABLE 19

End-to-end repair frequencies using paired guideRNAs for in CD163 exon 7 deletion in porcine embryos

| SEQ ID NO: (5') | Cut site (5') | SEQ ID NO: (3') | Cut site (3') | Deletion size (bp) | Desired repair outcome (%) |
|---|---|---|---|---|---|
| 229 | 63322816 | 256 | 63323377 | 561 | 38.0 |
| 230 | 63322814 | 256 | 63323377 | 562 | 21.0 |
| 231 | 63322826 | 256 | 63323377 | 551 | 24.0 |
| 241 | 63322891 | 256 | 63323377 | 486 | 29.0 |
| 229 | 63322816 | 258 | 63323378 | 562 | 7.0 |
| 231 | 63322826 | 258 | 63323378 | 552 | 12.0 |
| 241 | 63322891 | 258 | 63323378 | 487 | 20.0 |
| 219 | 63322697 | 256 | 63323377 | 680 | 35.0 |
| 221 | 63322709 | 256 | 63323377 | 668 | 36.0 |
| 224 | 63322747 | 256 | 63323377 | 630 | 24.0 |
| 227 | 63322786 | 256 | 63323377 | 591 | 0.0 |
| 227 | 63322786 | 258 | 63323378 | 592 | 0.0 |
| 221 | 63322709 | 261 | 63323373 | 665 | 15.0 |
| 249 | 63322963 | 256 | 63323377 | 414 | 44.0 |
| 250 | 63322973 | 256 | 63323377 | 404 | 14.0 |
| 249 | 63322963 | 258 | 63323378 | 415 | 7.0 |
| 249 | 63322963 | 261 | 63323373 | 411 | 53.0 |

This example demonstrates that a number of guide pairs can be used to delete CD163 exon 7, but the efficiency can vary greatly between guide pairs and cell types.

Example 11

This example demonstrates the use of two guides to introduce a premature stop codon into exon 7 of *S. scrofa* CD163.

Guides within exon 7 of CD163 were screened by bioinformatic methods for their ability to generate an in-frame stop codon when the cuts generated by those guides are ligated together during NHEJ. Bioinformatic predictions were tested in porcine fetal fibroblasts as described in Example 2: guides were complexed separately before being combined in a total volume of 2.23 μl prior to transfection. Editing frequency was determined as described in Example 3. The frequencies of end-to-end NHEJ repairs resulting in the introduction of a premature stop codon in exon 7 of CD163 are shown in Table 20.

TABLE 20

End-to-end repair frequencies for introduction of a stop codon in CD163 exon 7 deletion in porcine fetal fibroblasts

| SEQ ID NO: (5') | Cut site (5') | SEQ ID NO: (3') | Cut site (3') | Deletion size (bp) | Desired repair outcome (%) |
|---|---|---|---|---|---|
| 351 | 63323023 | 365 | 63323103 | 80 | 50.5 |
| 351 | 63323023 | 387 | 63323235 | 212 | 1.0 |
| 348 | 63323027 | 390 | 63323236 | 209 | 53.5 |
| 348 | 63323027 | 388 | 63323236 | 209 | 50.0 |
| 348 | 63323027 | 395 | 63323284 | 257 | 31.0 |
| 352 | 63323035 | 365 | 63323103 | 68 | 29.0 |
| 352 | 63323035 | 387 | 63323235 | 200 | 12.5 |
| 352 | 63323035 | 399 | 63323283 | 248 | 21.0 |
| 353 | 63323038 | 365 | 63323103 | 65 | 21.0 |
| 353 | 63323038 | 387 | 63323235 | 197 | 6.0 |
| 353 | 63323038 | 399 | 63323283 | 245 | 11.0 |
| 354 | 63323039 | 390 | 63323236 | 197 | 55.5 |
| 354 | 63323039 | 388 | 63323236 | 197 | 18.0 |
| 354 | 63323039 | 395 | 63323284 | 245 | 17.0 |
| 358 | 63323056 | 361 | 63323077 | 21 | 0.0 |
| 358 | 63323056 | 362 | 63323087 | 31 | 4.0 |
| 358 | 63323056 | 368 | 63323124 | 68 | 37.0 |
| 358 | 63323056 | 384 | 63323203 | 147 | 34.0 |
| 358 | 63323056 | 394 | 63323272 | 216 | 56.0 |
| 358 | 63323056 | 399 | 63323283 | 227 | 34.0 |
| 359 | 63323057 | 390 | 63323236 | 179 | 13.0 |
| 359 | 63323057 | 388 | 63323236 | 179 | 3.0 |
| 359 | 63323057 | 395 | 63323284 | 227 | 4.0 |
| 360 | 63323058 | 368 | 63323124 | 66 | 7.5 |
| 360 | 63323058 | 384 | 63323203 | 145 | 6.0 |
| 360 | 63323058 | 389 | 63323237 | 179 | 0.0 |
| 360 | 63323058 | 394 | 63323272 | 214 | 16.5 |
| 360 | 63323058 | 397 | 63323285 | 227 | 0.0 |
| 361 | 63323077 | 365 | 63323103 | 26 | 42.0 |
| 361 | 63323077 | 387 | 63323235 | 158 | 0.0 |
| 362 | 63323087 | 390 | 63323236 | 149 | 45.0 |
| 362 | 63323087 | 388 | 63323236 | 149 | 17.5 |
| 362 | 63323087 | 395 | 63323284 | 197 | 22.5 |
| 364 | 63323089 | 365 | 63323103 | 14 | 0.0 |
| 364 | 63323089 | 387 | 63323235 | 146 | 14.5 |
| 364 | 63323089 | 399 | 63323283 | 194 | 35.5 |
| 365 | 63323103 | 368 | 63323124 | 21 | 0.0 |
| 365 | 63323103 | 384 | 63323203 | 100 | 17.0 |
| 365 | 63323103 | 389 | 63323237 | 134 | 0.0 |
| 365 | 63323103 | 394 | 63323272 | 169 | 32.5 |
| 365 | 63323103 | 397 | 63323285 | 182 | 1.0 |
| 366 | 63323118 | 368 | 63323124 | 6 | 0.0 |
| 366 | 63323118 | 384 | 63323203 | 85 | 29.0 |
| 366 | 63323118 | 389 | 63323237 | 119 | 14.0 |
| 366 | 63323118 | 394 | 63323272 | 154 | 48.5 |
| 366 | 63323118 | 397 | 63323285 | 167 | 10.0 |
| 354 | 63323039 | 211 | 63323163 | 123 | 29.0 |

This example illustrates that guide pairs designed to introduce a stop codon have a wide variety of editing efficiencies in porcine fibroblasts.

Example 12

This example illustrates the editing efficiency of guides introducing stop codons in porcine blastocysts.

A subset of guides screened in porcine fetal fibroblasts were additionally tested for their ability to introduce a premature stop codon in exon 7 of CD163 in porcine embryos. The subset of guides to be tested in porcine embryos was chosen based on a combination of their efficacy in introducing a premature stop codon in exon 7 of CD163 in porcine fibroblasts and the lack of observed off-targets for each guide in the pair as described supra. Editing frequency was determined as described in Example 3. The frequencies of end-to-end NHEJ repairs resulting in the introduction of a premature stop codon in exon 7 of CD163 are shown in Table 21.

TABLE 21

End-to-end repair frequencies for introduction of a stop codon in CD163 exon 7 deletion in porcine blastocysts

| SEQ ID NO: (5') | Cut site (5') | SEQ ID NO: (3') | Cut site (3') | Deletion size (bp) | Desired repair outcome (%) |
|---|---|---|---|---|---|
| 351 | 63323023 | 365 | 63323103 | 80 | 39.6 |
| 348 | 63323027 | 390 | 63323236 | 209 | 31 |
| 348 | 63323027 | 388 | 63323236 | 209 | 35.4 |
| 354 | 63323039 | 390 | 63323236 | 197 | 30.4 |
| 358 | 63323056 | 394 | 63323272 | 216 | 29.2 |
| 362 | 63323087 | 390 | 63323236 | 149 | 31 |
| 366 | 63323118 | 394 | 63323272 | 154 | 33 |
| 354 | 63323039 | 211 | 63323163 | 123 | 27.4 |

This example demonstrates that guide pairs that can be used to introduce a premature stop codon into exon 7 of CD163 have a wide variety of editing efficiencies.

Example 13

This example illustrates variable repair outcomes for NHEJ repair.

A subset of guideRNAs designed to delete CD163 exon 7 were tested for their ability to delete the exon 7 coding and flanking regions in porcine blastocysts, as described in Example 9. Editing frequency of blastocysts was determined as described in Example 3. In this example, a subset of the DNA sequences observed in porcine blastocysts in vivo as the result of NHEJ-mediated repair are shown for five guideRNA pairs in Table 7. It is known that simple nucleotide deletions also occur, as well as more complex NHEJ-mediated repair DNA sequences which contain deletions, insertions, rearrangements, inversions, and any combination thereof. Without being limited by theory, these varied repair outcomes also occur as a result of endonuclease cutting of DNA using single and paired guides in porcine blastocysts. Table 7 also shows that the frequencies of the observed DNA sequence associated with each repair outcome vary between guideRNA pairs. In some, but not all, instances the frequency of DNA sequence associated with the end-to-end joining of cut sites of the paired guideRNA was the most highly represented repair outcome. For some guideRNA pairs there was a single predominant DNA repair outcome, while for other guideRNA pairs there were DNA repair outcomes that occurred with equal frequency. Most of the DNA repair outcomes shown for these five guideRNA pairs resulted in the deletion of CD163 exon 7 DNA sequences corresponding to the SRCR 5 domain. Therefore, the decision for which guideRNA pair to use for generation of edited pigs depends largely on the tolerance for multiple alleles in a population.

This example demonstrates that the NHEJ-mediated repair outcomes that result when two intronic guideRNAs are used to delete genomic DNA vary between guideRNA pairs, not only in the manner in which DNA breaks are resolved but in the frequency of these resolutions. It is advantageous to screen guideRNA pairs in fibroblasts or embryos to observe DNA repair outcomes of single or dual guideRNAs for the generation of edited animals.

Example 14

This example illustrates a real time PCR assay for identifying the presence of the spacer sequence set forth in SEQ ID NO: 249 and/or the desired Exon 7 excision edit in cells.

Two sets of primers and two probes were designed for this assay. One set of primers were designed to flank the spacer sequence set forth in SEQ ID NO: 249 in the unedited genome. The sequences of these primers are set forth in SEQ ID NOs: 556 and 557. A probe of sequence SEQ ID NO: 558 and labeled with the HEX fluorescent moiety was designed to anneal to the unedited genome between the PCR primers. The other set of primers, having sequences set forth in SEQ ID NOs: 562 and 563, were designed to flank the desired edit sequence. A probe, having a sequence set forth in SEQ ID NO: 564 and labeled with the FAM fluorescent moiety, was designed to anneal to nucleotides spanning the joining region of the edit. Real time PCR was performed using both primer sets and with genomic DNA extracted from tail and/or ear samples of pigs that had known allelic status (wild type, homozygous, or heterozygous). 5 µl of 2× PRIME-TIME® Master Mix (Integrated DNA Technologies, Coralville, IA) was mixed with 0.5 µl of each primer (10 µM), 0.5 µl of each probe (2.5 µM), and 2 µl of genomic DNA. PCR was performed with 3 minutes initial denaturing at 95° C., then 35 cycles of: 95° C. for 15 seconds, 64° C. for 30 seconds, and 72° C. for 30 seconds. A final elongation was performed at 72° C. for 2 minutes, and then the reaction was held in the cycler at 4° C. Fluorescence was measured and charted and, as expected, the homozygotes were close to the y axis (representing the FAM moiety wavelength), the heterozygotes grouped near the center of the chart, and the wild type pigs grouped close to the X axis (representing the HEX moiety wavelength). The assay was therefore successful in detecting the edit based on the spacer sequence set forth in SEQ ID NO: 249.

Example 15

This example illustrates a real time PCR assay for identifying the presence of the spacer sequence set forth in SEQ ID NO: 256 and/or the desired Exon 7 excision edit in cells.

Two sets of primers and two probes were designed for this assay. One set of primers flanked the spacer sequence set forth in SEQ ID NO: 256. The sequence of these primers is set forth in SEQ ID NOs: 559 and 560. A probe, having a sequence set forth in SEQ ID NO: 561 and labeled with the HEX fluorescent moiety, was designed to anneal to the unedited version of the spacer sequence. The other set of primers and probe are designed to target the desired edit and are described in Example 14 (SEQ ID NOs: 562-564.) Real time PCR was performed as described in Example 14, but with the instant primers and probes. Fluorescence was charted and, as expected, the homozygotes were close to the y axis (representing the FAM moiety), the heterozygotes grouped near the center of the chart, and the wild type pigs grouped close to the X axis (representing the HEX moiety). The assay was therefore successful in detecting the edit based on the spacer sequence set forth in SEQ ID NO: 256.

Example 16

This example illustrates a comparison of CD163 CRISPR-CAS gRNA activity in cells between previously published guide pairs and guide pairs of the present teachings.

Each pair of guides was tested in porcine fibroblasts as described in Example 2. Each pair was further tested in porcine blastocysts as described in Example 10. The results are shown below in Table 22.

TABLE 22

Comparative Activity in Porcine Cells

| guide pair SEQ ID NOs: | Source | % desired repair fibroblasts | % desired repair blastocysts |
|---|---|---|---|
| 272 and 273 | Burkard 2017 | 6 | 20 |
| 249 and 256 | Present Disclosure | 38 | 44 |
| 354 and 211 | Whitworth 2014 | 17 | n.d. |
| 362 and 390 | Present Disclosure | 45 | 31 |

These data illustrate that the guides of the present disclosure provide at least a two-fold improvement in the percentage of cells that have the desired edit relative to the guides that were previously disclosed in the literature. Therefore, the guides of the present disclosure are more efficient than the guides previously disclosed in the literature.

Example 17

This example illustrates CD163 edited pigs challenged with PRRSv Type I.

Pigs from PIC™ Line 2 were edited with guides as set forth in SEQ ID NOs: 249 and 256 as described in Example 6. Edits were confirmed as described in Example 5. Edited pigs were then crossbred to create pigs that were homozygous for the edit. These homozygous edited pigs were inoculated with 3 ml of PRSSv Type I (SD13-15) having $10^4$ to $10^5$ virions (4-5 log $TCID_{50}$). 1.5 ml was administered intramuscularly with a 21 gauge needle. The remaining 1.5 ml was administered intranasally. Serum samples were obtained on Day 0 (prior to inoculation on that day), Day 3, Day 5, Day 10, Day 14, and Day 21. Realtime PCR to determine the presence of virus in the serum samples using TETRACORE® EZ-PRRSV MPX 4.0 Master Mix and Enzyme with ROX (TETRACORE®, Rockville, MD) according to manufacturer directions. The real time PCR EU adjusted counts are shown in Table 23. The counts have been inverted using standard methods known in the art to make the data more intuitive—higher numbers indicate more virus detected.

TABLE 23

Realtime PCR EU Adjusted Counts for Type I PRRSv Challenge

| Animal | CD163 | Day 0 | Day 3 | Day 5 | Day 10 | Day 14 | Day 21 |
|---|---|---|---|---|---|---|---|
| 2 | WT | 0 | 19.8 | 22.6 | 20 | 19.6 | 18.3 |
| 4 | WT | 0 | 17 | 17.7 | 18.6 | 16.8 | 17.5 |
| 5 | WT | 0 | 18.9 | 21.5 | 17.3 | 14.2 | 13.6 |
| 6 | WT | 0 | 15.8 | 19.7 | 15.6 | 14.5 | 13.4 |
| 17 | WT | 0 | 17.1 | 17.8 | 18.5 | 18 | 15.8 |
| 18 | WT | 0 | 15.8 | 17.9 | 17 | 16.8 | 15 |
| 20 | WT | 0 | 17.2 | 20.3 | 18.8 | 17 | 12.8 |
| 3 | Edit | 0 | 0 | 0 | 0 | 0 | 0 |
| 7 | Edit | 0 | 0 | 0 | 0 | 0 | 0 |
| 14 | Edit | 0 | 0 | 0 | 0 | 0 | 0 |
| 19 | Edit | 0 | 0 | 0 | 0 | 0 | 0 |

No PRRSv was detected in the serum of the edited animals throughout the experiment.

The serum samples were also subjected to ELISA using the IDEXX PRRS X3 antibody test kit; the test was performed by an accredited Veterinary Diagnostic Laboratory. The results are shown as a Sample:Positive ratio. Ratios greater than or equal to 0.40 are considered positive. The ratios for each sample are shown in Table 24.

TABLE 24

ELISA S/P Results for Type I PRRSv Challenge

| Animal | CD163 | Day 0 | Day 3 | Day 5 | Day 10 | Day 14 | Day 21 |
|---|---|---|---|---|---|---|---|
| 2 | WT | 0.0 | 0.0 | 0.0 | 0.5 | 0.6 | 1.4 |
| 4 | WT | 0.0 | 0.0 | 0.0 | 0.1 | 0.2 | 0.8 |
| 5 | WT | 0.0 | 0.0 | 0.0 | 0.9 | 1.3 | 1.8 |
| 6 | WT | 0.0 | 0.0 | 0.0 | 1.3 | 1.3 | 1.9 |
| 17 | WT | 0.0 | 0.0 | 0.0 | 0.2 | 0.2 | 1.1 |
| 18 | WT | 0.0 | 0.0 | 0.0 | 0.3 | 0.3 | 1.4 |
| 20 | WT | 0.0 | 0.0 | 0.0 | 0.3 | 0.4 | 1.2 |
| 3 | Edit | 0.0 | 0.0 | 0.0 | 0.0 | 0.0 | 0.0 |
| 7 | Edit | 0.0 | 0.0 | 0.0 | 0.0 | 0.0 | 0.0 |
| 14 | Edit | 0.0 | 0.0 | 0.0 | 0.0 | 0.0 | 0.0 |
| 19 | Edit | 0.0 | 0.0 | 0.0 | 0.0 | 0.0 | 0.0 |

The edited pigs do not have any positive ratios. In contrast, by day 21, all of the wild type pigs have positive ratios. This further illustrates that there is no PRRSv circulating in the edited pigs' serum.

This example illustrates that pigs edited with guides of SEQ ID NOs: 249 and 256 are resistant to PRRSv Type I virus infection.

Example 18

This example illustrates CD163 edited pigs challenged with PRRSv Type II.

Pigs from PIC™ Lines 2 and 3 were edited with guides as set forth in SEQ ID NOs: 249 and 256 as described in Example 6. Edits were confirmed as described in Example 5. Edited pigs were then crossbred to create pigs that were homozygous for the edit. These homozygous edited pigs were then inoculated with 3 ml of PRRSv Type II (NVSL 97-7895) having $10^4$ to $10^5$ virions (4-5 log $TCID_{50}$). 1.5 ml was administered intramuscularly with a 21 gauge needle. The remaining 1.5 ml was administered intranasally. Serum samples were obtained on Day 0 (prior to inoculation on that day), Day 3, Day 5, Day 10, Day 14, and Day 21. Realtime PCR to determine the presence of virus in the serum samples using TETRACORE® EZ-PRRSV MPX 4.0 Master Mix and Enzyme with ROX according to manufacturer directions. The NA adjusted counts for real time PCR are shown in Table 25. The numbers were inverted to make them more intuitive—the higher the count, the more virus is present.

TABLE 25

Realtime PCR NA Adjusted Counts for Type II PRRSv Challenge

| Animal | CD163 | Day 0 | Day 3 | Day 5 | Day 10 | Day 14 | Day 21 |
|---|---|---|---|---|---|---|---|
| 21 | WT | 0.0 | 18.4 | 22.0 | 21.9 | 18.0 | 16.1 |
| 23 | WT | 0.0 | 16.4 | 22.0 | 21.8 | 20.0 | 19.7 |
| 25 | WT | N/A | 17.2 | 21.2 | 21.9 | 19.2 | 19.8 |
| 30 | WT | 0.0 | 16.2 | 17.8 | 21.4 | 21.1 | 17.6 |
| 33 | WT | 0.0 | 18.5 | N/A | 21.8 | 18.5 | 15.3 |
| 35 | WT | N/A | 17.0 | 22.9 | 21.8 | 20.5 | 20.9 |
| 36 | WT | 0.0 | 16.7 | 21.4 | 21.9 | 19.9 | 17.4 |
| 38 | WT | 0.0 | 16.0 | 18.1 | 20.2 | 20.9 | 9.4 |
| 24 | Edit | N/A | 1.9 | 0.0 | 0.0 | 0.0 | 0.0 |
| 37 | Edit | 0.0 | 0.0 | 0.0 | 0.0 | 0.0 | 0.0 |

The edited pigs have very little to no virus counts relative to the wild type pigs.

The serum samples were also subjected to ELISA using the IDEXX PRRS X3 antibody test kit; the test was performed by an accredited Veterinary Diagnostic Laboratory. The results are shown as a Sample:Positive ratio. Ratios greater than or equal to 0.40 are considered positive. The ratios for each sample are shown in Table 26.

TABLE 26

ELISA S/P Ratios for Type II PRRSv Challenge

| Animal | Edit | Day 0 | Day 3 | Day 5 | Day 10 | Day 14 | Day 21 |
|---|---|---|---|---|---|---|---|
| 21 | WT | 0.0 | 0.0 | 0.0 | 1.7 | 2.0 | 1.9 |
| 23 | WT | 0.0 | 0.0 | 0.0 | 1.2 | 1.7 | 1.9 |
| 25 | WT | N/A | 0.0 | 0.0 | 1.2 | 1.6 | 1.7 |
| 30 | WT | 0.0 | 0.0 | 0.0 | 0.4 | 0.6 | 0.6 |
| 33 | WT | 0.0 | 0.0 | N/A | 0.7 | 0.6 | 0.7 |
| 35 | WT | N/A | 0.0 | 0.0 | 1.3 | 1.3 | 1.4 |
| 36 | WT | 0.0 | 0.0 | 0.0 | 1.2 | 1.5 | 1.8 |
| 38 | WT | 0.0 | 0.0 | 0.0 | 0.5 | 0.9 | 1.0 |
| 24 | Edit | N/A | 0.2 | 0.1 | 0.2 | 0.1 | 0.1 |
| 37 | Edit | 0.0 | 0.0 | 0.0 | 0.0 | 0.0 | 0.0 |

The edited pigs do not have any positive ratios; in contrast, by day 10, all of the wild type pigs have positive ratios. Taken together, these data illustrate that there is no virus circulating in the edited pigs' blood.

This example illustrates that the pigs with a CD163 gene edited with SEQ ID NOs: 249 and 256 are resistant to PRRSv Type II infection.

The contents of each of the foregoing references and applications are incorporated herein by reference in their entireties. Having described the present disclosure in detail, it will be apparent that modifications and variations are possible without departing from the scope of the teachings defined in the appended claims.

What is claimed is:

1. A method of screening comprising:
   i) breeding a genetically edited pig whose genome comprises a CD163 gene that has a homozygous deletion of exon 7 and comprises the nucleic acid sequence of SEQ ID NO: 453, wherein the pig exhibits resistance to porcine reproductive and respiratory syndrome virus (PRRSV) such that offspring are obtained;
   ii) screening the genomes of the offspring for the presence of a CD163 gene that has a homozygous deletion of exon 7 and comprises the nucleic acid sequence of SEQ ID NO: 453; and
   iii) screening the offspring for resistance to PRRSV.

2. The method of claim 1, wherein the screening is performed using polymerase chain reaction (PCR) and primers comprising the nucleic acid sequences of SEQ ID NO: 556 and 557.

3. The method of claim 1, wherein the screening is performed using polymerase chain reaction (PCR) and primers comprising the nucleic acid sequences of SEQ ID NO: 562 and 563.

* * * * *

SEQUENCE LISTING

```
<160> NUMBER OF SEQ ID NOS: 564

<210> SEQ ID NO 1
<211> LENGTH: 150
<212> TYPE: DNA
<213> ORGANISM: Sus scrofa

<400> SEQUENCE: 1
tttcgcagac tttagaagat gttctgccca tttaagttcc ttcactttttg ctgtagtcgc      60 tgttctcagt gcctgactag ttctcttggt gagtactttg acaaatttac ttgtaaccta     120
gcccactgtg acaagaaaca ctgaaaagca                                       150

<210> SEQ ID NO 2
<211> LENGTH: 150
<212> TYPE: DNA
<213> ORGANISM: Sus scrofa

<400> SEQUENCE: 2
tttcgcagac tttagaagat gttctgccca tttaagttcc ttcactttttg ctgtagtcgc      60 tgttctcagt gcctgactag ttctcttggt gagtactttg acaaatttac ttgtaaccta     120
gcccactgtg acaagaaaca ctgaaaagca                                       150

<210> SEQ ID NO 3
<211> LENGTH: 150
<212> TYPE: DNA
<213> ORGANISM: Sus scrofa

<400> SEQUENCE: 3
gtggtgaaaa caagtgctct ggaagagtgg aggtgaaagt gcaggaggag tggggaactg      60
tgtgtaataa tggctgacat ggatgtggtc tctgttgttt gtaggcagct gggatgtcca     120
actgctatca aagccactgg atgggctaat                                       150
```

<210> SEQ ID NO 4
<211> LENGTH: 150
<212> TYPE: DNA
<213> ORGANISM: Sus scrofa

<400> SEQUENCE: 4
tggctgggac atggatgtgg tctctgttgt ttgtaggcag ctgggatgtc caactgctat    60
caaagccact ggatgaattt tagtgcaggt tctggacgca tttggatgga tcatgtttct   120
tgtcgaggga atgagtcagc tctctgggac                                    150

<210> SEQ ID NO 5
<211> LENGTH: 150
<212> TYPE: DNA
<213> ORGANISM: Sus scrofa

<400> SEQUENCE: 5
gtaggcagct gggatgtcca actgctatca aagccactgg atgggctaat tttagtgcag    60
gttctggacg catttgatgg atcatgtttc ttgtcgaggg aatgagtcag ctctctggga   120
ctgcaaacat gatggatggg gaaagcataa                                    150

<210> SEQ ID NO 6
<211> LENGTH: 150
<212> TYPE: DNA
<213> ORGANISM: Sus scrofa

<400> SEQUENCE: 6
taggcagctg ggatgtccaa ctgctatcaa agccactgga tgggctaatt ttagtgcagg    60
ttctggacgc atttgatgga tcatgtttct tgtcgaggga atgagtcagc tctctgggac   120
tgcaaacatg atggatgggg aaagcataac                                    150

<210> SEQ ID NO 7
<211> LENGTH: 150
<212> TYPE: DNA
<213> ORGANISM: Sus scrofa

<400> SEQUENCE: 7
gtccaactgc tatcaaagcc actggatggg ctaattttag tgcaggttct ggacgcattt    60
ggatggatca tgtttgaggg aatgagtcag ctctctggga ctgcaaacat gatggatggg   120
gaaagcataa ctgtactcac caacaggatg                                    150

<210> SEQ ID NO 8
<211> LENGTH: 150
<212> TYPE: DNA
<213> ORGANISM: Sus scrofa

<400> SEQUENCE: 8
ctggacgcat ttggatggat catgtttctt gtcgagggaa tgagtcagct ctctgggact    60
gcaaacatga tggatgaaag cataactgta ctcaccaaca ggatgctgga gtaacctgct   120
caggtaagac atacacaaat aagtcaagcc                                    150

<210> SEQ ID NO 9
<211> LENGTH: 150
<212> TYPE: DNA
<213> ORGANISM: Sus scrofa

<400> SEQUENCE: 9
tggacgcatt tggatggatc atgtttcttg tcgagggaat gagtcagctc tctgggactg    60

-continued

```
caaacatgat ggatgaaagc ataactgtac tcaccaacag gatgctggag taacctgctc    120
aggtaagaca tacacaaata agtcaagcct                                     150

<210> SEQ ID NO 10
<211> LENGTH: 150
<212> TYPE: DNA
<213> ORGANISM: Sus scrofa

<400> SEQUENCE: 10
ctctagatgg atctgattta gagatgaggc tggtgaatgg aggaaaccgg tgcttaggaa    60
gaatagaagt caaataagga cggtggggaa cagtgtgtga tgataacttc aacataaatc    120
atgcttctgt ggtttgtaaa caacttgaat                                     150

<210> SEQ ID NO 11
<211> LENGTH: 150
<212> TYPE: DNA
<213> ORGANISM: Sus scrofa

<400> SEQUENCE: 11
cttctgtggt ttgtaaacaa cttgaatgtg gaagtgctgt cagtttctct ggttcagcta    60
attttggaga aggttgacca atctggtttg atgatcttgt atgcaatgga aatgagtcag    120
ctctctggaa ctgcaaacat gaaggatggg                                     150

<210> SEQ ID NO 12
<211> LENGTH: 150
<212> TYPE: DNA
<213> ORGANISM: Sus scrofa

<400> SEQUENCE: 12
tgatgatctt gtatgcaatg gaaatgagtc agctctctgg aactgcaaac atgaaggatg    60
gggaaagcac aattgatgct gaggatgctg gagtgatttg cttaagtaag gactgacctg    120
ggtttgttct gttctccatg agagggcaaa                                     150

<210> SEQ ID NO 13
<211> LENGTH: 150
<212> TYPE: DNA
<213> ORGANISM: Sus scrofa

<400> SEQUENCE: 13
agacacgtgg ggcaccgtct gtgattctga cttctctctg gaggcggcca gcgtgctgtg    60
cagggaacta cagtgactgt ggtttccctc ctggggggag ctcactttgg agaaggaagt    120
ggacagatct gggctgaaga attccagtgt                                     150

<210> SEQ ID NO 14
<211> LENGTH: 150
<212> TYPE: DNA
<213> ORGANISM: Sus scrofa

<400> SEQUENCE: 14
agaagatgtt ctgcccattt aagttccttc actttttgctg tagtcgctgt tctcagtgcc    60
tgcttggtca ctagttcttg gtgagtactt tgacaaattt acttgtaacc tagcccactg    120
tgacaagaaa cactgaaaag caaataattc                                     150

<210> SEQ ID NO 15
<211> LENGTH: 150
<212> TYPE: DNA
```

<213> ORGANISM: Sus scrofa

<400> SEQUENCE: 15

```
gactttagaa gatgttctgc ccatttaagt tccttcactt ttgctgtagt cgctgttctc    60
agtgcctgct tggtcacttg taacctagcc cactgtgaca agaaacactg aaaagcaaat   120
aattctcctg aagtctagat agcatctaaa                                    150
```

<210> SEQ ID NO 16
<211> LENGTH: 150
<212> TYPE: DNA
<213> ORGANISM: Sus scrofa

<400> SEQUENCE: 16

```
gaagatgttc tgcccattta agttccttca cttttgctgt agtcgctgtt ctcagtgcct    60
gcttggtcac tagttctctc ttggtgagta ctttgacaaa tttacttgta acctagccca   120
ctgtgacaag aaacactgaa agcaaataa                                     150
```

<210> SEQ ID NO 17
<211> LENGTH: 150
<212> TYPE: DNA
<213> ORGANISM: Sus scrofa

<400> SEQUENCE: 17

```
tttcgcagac tttagaagat gttctgccca tttaagttcc ttcacttttg ctgtagtcgc    60
tgttctcagt gcctgcttgg tgagtacttt gacaaattta cttgtaacct agcccactgt   120
gacaagaaac actgaaaagc aaataattct                                    150
```

<210> SEQ ID NO 18
<211> LENGTH: 150
<212> TYPE: DNA
<213> ORGANISM: Sus scrofa

<400> SEQUENCE: 18

```
tagaagatgt tctgcccatt taagttcctt cacttttgct gtagtcgctg ttctcagtgc    60
ctgcttggtc actaggagta ctttgacaaa tttacttgta acctagccca ctgtgacaag   120
aaacactgaa aagcaaataa ttctcctgaa                                    150
```

<210> SEQ ID NO 19
<211> LENGTH: 82
<212> TYPE: DNA
<213> ORGANISM: Sus scrofa

<400> SEQUENCE: 19

```
gttttagagc tagaaatagc aagttaaaat aaggctagtc cgttatcaac ttgaaaaagt    60
ggcaccgagt cggtgctttt tt                                             82
```

<210> SEQ ID NO 20
<211> LENGTH: 1380
<212> TYPE: PRT
<213> ORGANISM: Streptococcus pyogenes

<400> SEQUENCE: 20

Gly Met Asp Lys Lys Tyr Ser Ile Gly Leu Asp Ile Gly Thr Asn Ser
1               5                   10                  15

Val Gly Trp Ala Val Ile Thr Asp Glu Tyr Lys Val Pro Ser Lys Lys
            20                  25                  30

Phe Lys Val Leu Gly Asn Thr Asp Arg His Ser Ile Lys Lys Asn Leu

```
                35                  40                  45
Ile Gly Ala Leu Leu Phe Asp Ser Gly Glu Thr Ala Glu Ala Thr Arg
 50                  55                  60
Leu Lys Arg Thr Ala Arg Arg Tyr Thr Arg Arg Lys Asn Arg Ile
 65                  70                  75                  80
Cys Tyr Leu Gln Glu Ile Phe Ser Asn Glu Met Ala Lys Val Asp Asp
                     85                  90                  95
Ser Phe Phe His Arg Leu Glu Glu Ser Phe Leu Val Glu Glu Asp Lys
                    100                 105                 110
Lys His Glu Arg His Pro Ile Phe Gly Asn Ile Val Asp Glu Val Ala
                    115                 120                 125
Tyr His Glu Lys Tyr Pro Thr Ile Tyr His Leu Arg Lys Lys Leu Val
                    130                 135                 140
Asp Ser Thr Asp Lys Ala Asp Leu Arg Leu Ile Tyr Leu Ala Leu Ala
145                 150                 155                 160
His Met Ile Lys Phe Arg Gly His Phe Leu Ile Glu Gly Asp Leu Asn
                    165                 170                 175
Pro Asp Asn Ser Asp Val Asp Lys Leu Phe Ile Gln Leu Val Gln Thr
                    180                 185                 190
Tyr Asn Gln Leu Phe Glu Glu Asn Pro Ile Asn Ala Ser Gly Val Asp
                    195                 200                 205
Ala Lys Ala Ile Leu Ser Ala Arg Leu Ser Lys Ser Arg Arg Leu Glu
210                 215                 220
Asn Leu Ile Ala Gln Leu Pro Gly Glu Lys Lys Asn Gly Leu Phe Gly
225                 230                 235                 240
Asn Leu Ile Ala Leu Ser Leu Gly Leu Thr Pro Asn Phe Lys Ser Asn
                    245                 250                 255
Phe Asp Leu Ala Glu Asp Ala Lys Leu Gln Leu Ser Lys Asp Thr Tyr
                    260                 265                 270
Asp Asp Asp Leu Asp Asn Leu Leu Ala Gln Ile Gly Asp Gln Tyr Ala
                    275                 280                 285
Asp Leu Phe Leu Ala Ala Lys Asn Leu Ser Asp Ala Ile Leu Leu Ser
    290                 295                 300
Asp Ile Leu Arg Val Asn Thr Glu Ile Thr Lys Ala Pro Leu Ser Ala
305                 310                 315                 320
Ser Met Ile Lys Arg Tyr Asp Glu His His Gln Asp Leu Thr Leu Leu
                    325                 330                 335
Lys Ala Leu Val Arg Gln Gln Leu Pro Glu Lys Tyr Lys Glu Ile Phe
                    340                 345                 350
Phe Asp Gln Ser Lys Asn Gly Tyr Ala Gly Tyr Ile Asp Gly Gly Ala
                    355                 360                 365
Ser Gln Glu Glu Phe Tyr Lys Phe Ile Lys Pro Ile Leu Glu Lys Met
                    370                 375                 380
Asp Gly Thr Glu Glu Leu Leu Val Lys Leu Asn Arg Glu Asp Leu Leu
385                 390                 395                 400
Arg Lys Gln Arg Thr Phe Asp Asn Gly Ser Ile Pro His Gln Ile His
                    405                 410                 415
Leu Gly Glu Leu His Ala Ile Leu Arg Arg Gln Glu Asp Phe Tyr Pro
                    420                 425                 430
Phe Leu Lys Asp Asn Arg Glu Lys Ile Glu Lys Ile Leu Thr Phe Arg
                    435                 440                 445
Ile Pro Tyr Tyr Val Gly Pro Leu Ala Arg Gly Asn Ser Arg Phe Ala
450                 455                 460
```

```
Trp Met Thr Arg Lys Ser Glu Glu Thr Ile Thr Pro Trp Asn Phe Glu
465                 470                 475                 480

Glu Val Val Asp Lys Gly Ala Ser Ala Gln Ser Phe Ile Glu Arg Met
            485                 490                 495

Thr Asn Phe Asp Lys Asn Leu Pro Asn Glu Lys Val Leu Pro Lys His
        500                 505                 510

Ser Leu Leu Tyr Glu Tyr Phe Thr Val Tyr Asn Glu Leu Thr Lys Val
            515                 520                 525

Lys Tyr Val Thr Glu Gly Met Arg Lys Pro Ala Phe Leu Ser Gly Glu
530                 535                 540

Gln Lys Lys Ala Ile Val Asp Leu Leu Phe Lys Thr Asn Arg Lys Val
545                 550                 555                 560

Thr Val Lys Gln Leu Lys Glu Asp Tyr Phe Lys Lys Ile Glu Cys Phe
                565                 570                 575

Asp Ser Val Glu Ile Ser Gly Val Glu Asp Arg Phe Asn Ala Ser Leu
            580                 585                 590

Gly Thr Tyr His Asp Leu Leu Lys Ile Ile Lys Asp Lys Asp Phe Leu
            595                 600                 605

Asp Asn Glu Glu Asn Glu Asp Ile Leu Glu Asp Ile Val Leu Thr Leu
610                 615                 620

Thr Leu Phe Glu Asp Arg Glu Met Ile Glu Glu Arg Leu Lys Thr Tyr
625                 630                 635                 640

Ala His Leu Phe Asp Asp Lys Val Met Lys Gln Leu Lys Arg Arg Arg
                645                 650                 655

Tyr Thr Gly Trp Gly Arg Leu Ser Arg Lys Leu Ile Asn Gly Ile Arg
                660                 665                 670

Asp Lys Gln Ser Gly Lys Thr Ile Leu Asp Phe Leu Lys Ser Asp Gly
            675                 680                 685

Phe Ala Asn Arg Asn Phe Met Gln Leu Ile His Asp Asp Ser Leu Thr
690                 695                 700

Phe Lys Glu Asp Ile Gln Lys Ala Gln Val Ser Gly Gln Gly Asp Ser
705                 710                 715                 720

Leu His Glu His Ile Ala Asn Leu Ala Gly Ser Pro Ala Ile Lys Lys
                725                 730                 735

Gly Ile Leu Gln Thr Val Lys Val Val Asp Glu Leu Val Lys Val Met
                740                 745                 750

Gly Arg His Lys Pro Glu Asn Ile Val Ile Glu Met Ala Arg Glu Asn
                755                 760                 765

Gln Thr Thr Gln Lys Gly Gln Lys Asn Ser Arg Glu Arg Met Lys Arg
            770                 775                 780

Ile Glu Glu Gly Ile Lys Glu Leu Gly Ser Gln Ile Leu Lys Glu His
785                 790                 795                 800

Pro Val Glu Asn Thr Gln Leu Gln Asn Glu Lys Leu Tyr Leu Tyr Tyr
                805                 810                 815

Leu Gln Asn Gly Arg Asp Met Tyr Val Asp Gln Glu Leu Asp Ile Asn
            820                 825                 830

Arg Leu Ser Asp Tyr Asp Val Asp His Ile Val Pro Gln Ser Phe Leu
            835                 840                 845

Lys Asp Asp Ser Ile Asp Asn Lys Val Leu Thr Arg Ser Asp Lys Asn
            850                 855                 860

Arg Gly Lys Ser Asp Asn Val Pro Ser Glu Glu Val Val Lys Lys Met
865                 870                 875                 880
```

```
Lys Asn Tyr Trp Arg Gln Leu Leu Asn Ala Lys Leu Ile Thr Gln Arg
            885                 890                 895

Lys Phe Asp Asn Leu Thr Lys Ala Glu Arg Gly Gly Leu Ser Glu Leu
            900                 905                 910

Asp Lys Ala Gly Phe Ile Lys Arg Gln Leu Val Glu Thr Arg Gln Ile
            915                 920                 925

Thr Lys His Val Ala Gln Ile Leu Asp Ser Arg Met Asn Thr Lys Tyr
            930                 935                 940

Asp Glu Asn Asp Lys Leu Ile Arg Glu Val Lys Val Ile Thr Leu Lys
945                 950                 955                 960

Ser Lys Leu Val Ser Asp Phe Arg Lys Asp Phe Gln Phe Tyr Lys Val
            965                 970                 975

Arg Glu Ile Asn Asn Tyr His His Ala His Asp Ala Tyr Leu Asn Ala
            980                 985                 990

Val Val Gly Thr Ala Leu Ile Lys Lys Tyr Pro Lys Leu Glu Ser Glu
            995                 1000                1005

Phe Val Tyr Gly Asp Tyr Lys Val Tyr Asp Val Arg Lys Met Ile
            1010                1015                1020

Ala Lys Ser Glu Gln Glu Ile Gly Lys Ala Thr Ala Lys Tyr Phe
            1025                1030                1035

Phe Tyr Ser Asn Ile Met Asn Phe Phe Lys Thr Glu Ile Thr Leu
            1040                1045                1050

Ala Asn Gly Glu Ile Arg Lys Arg Pro Leu Ile Glu Thr Asn Gly
            1055                1060                1065

Glu Thr Gly Glu Ile Val Trp Asp Lys Gly Arg Asp Phe Ala Thr
            1070                1075                1080

Val Arg Lys Val Leu Ser Met Pro Gln Val Asn Ile Val Lys Lys
            1085                1090                1095

Thr Glu Val Gln Thr Gly Gly Phe Ser Lys Glu Ser Ile Leu Pro
            1100                1105                1110

Lys Arg Asn Ser Asp Lys Leu Ile Ala Arg Lys Lys Asp Trp Asp
            1115                1120                1125

Pro Lys Lys Tyr Gly Gly Phe Asp Ser Pro Thr Val Ala Tyr Ser
            1130                1135                1140

Val Leu Val Val Ala Lys Val Glu Lys Gly Lys Ser Lys Lys Leu
            1145                1150                1155

Lys Ser Val Lys Glu Leu Leu Gly Ile Thr Ile Met Glu Arg Ser
            1160                1165                1170

Ser Phe Glu Lys Asn Pro Ile Asp Phe Leu Glu Ala Lys Gly Tyr
            1175                1180                1185

Lys Glu Val Lys Lys Asp Leu Ile Ile Lys Leu Pro Lys Tyr Ser
            1190                1195                1200

Leu Phe Glu Leu Glu Asn Gly Arg Lys Arg Met Leu Ala Ser Ala
            1205                1210                1215

Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly
            1235                1240                1245

Ser Pro Glu Asp Asn Glu Gln Lys Gln Leu Phe Val Glu Gln His
            1250                1255                1260

Lys His Tyr Leu Asp Glu Ile Ile Glu Gln Ile Ser Glu Phe Ser
            1265                1270                1275

Lys Arg Val Ile Leu Ala Asp Ala Asn Leu Asp Lys Val Leu Ser
```

```
           1280            1285            1290
Ala Tyr Asn Lys His Arg Asp Lys Pro Ile Arg Glu Gln Ala Glu
           1295            1300            1305

Asn Ile Ile His Leu Phe Thr Leu Thr Asn Leu Gly Ala Pro Ala
           1310            1315            1320

Ala Phe Lys Tyr Phe Asp Thr Thr Ile Asp Arg Lys Arg Tyr Thr
           1325            1330            1335

Ser Thr Lys Glu Val Leu Asp Ala Thr Leu Ile His Gln Ser Ile
           1340            1345            1350

Thr Gly Leu Tyr Glu Thr Arg Ile Asp Leu Ser Gln Leu Gly Gly
           1355            1360            1365

Asp Gly Ser Gly Ser Pro Lys Lys Lys Arg Lys Val
           1370            1375            1380

<210> SEQ ID NO 21
<211> LENGTH: 1400
<212> TYPE: PRT
<213> ORGANISM: Streptococcus thermophilus

<400> SEQUENCE: 21

Ser Asn Ala Met Thr Lys Pro Tyr Ser Ile Gly Leu Asp Ile Gly
1               5                   10                  15

Thr Asn Ser Val Gly Trp Ala Val Ile Thr Asp Asn Tyr Lys Val
                20                  25                  30

Pro Ser Lys Lys Met Lys Val Leu Gly Asn Thr Ser Lys Lys Tyr
                35                  40                  45

Ile Lys Lys Asn Leu Leu Gly Val Leu Leu Phe Asp Ser Gly Ile
                50                  55                  60

Thr Ala Glu Gly Arg Arg Leu Lys Arg Thr Ala Arg Arg Arg Tyr
65                  70                  75                  80

Thr Arg Arg Arg Asn Arg Ile Leu Tyr Leu Gln Glu Ile Phe Ser
                85                  90                  95

Thr Glu Met Ala Thr Leu Asp Asp Ala Phe Phe Gln Arg Leu Asp
                100                 105                 110

Asp Ser Phe Leu Val Pro Asp Asp Lys Arg Asp Ser Lys Tyr Pro
                115                 120                 125

Ile Phe Gly Asn Leu Val Glu Glu Lys Val Tyr His Asp Glu Phe
                130                 135                 140

Pro Thr Ile Tyr His Leu Arg Lys Tyr Leu Ala Asp Ser Thr Lys
145                 150                 155                 160

Lys Ala Asp Leu Arg Leu Val Tyr Leu Ala Leu Ala His Met Ile
                165                 170                 175

Lys Tyr Arg Gly His Phe Leu Ile Glu Gly Glu Phe Asn Ser Lys
                180                 185                 190

Asn Asn Asp Ile Gln Lys Asn Phe Gln Asp Phe Leu Asp Thr Tyr
                195                 200                 205

Asn Ala Ile Phe Glu Ser Asp Leu Ser Leu Glu Asn Ser Lys Gln
                210                 215                 220

Leu Glu Glu Ile Val Lys Asp Lys Ile Ser Lys Leu Glu Lys Lys
225                 230                 235                 240

Asp Arg Ile Leu Lys Leu Phe Pro Gly Glu Lys Asn Ser Gly Ile
                245                 250                 255

Phe Ser Glu Phe Leu Lys Leu Ile Val Gly Asn Gln Ala Asp Phe
                260                 265                 270

Arg Lys Cys Phe Asn Leu Asp Glu Lys Ala Ser Leu His Phe Ser Lys Glu
```

```
Ser Tyr Asp Glu Asp Leu Glu Thr Leu Leu Gly Tyr Ile Gly Asp Asp
            275                 280                 285

Tyr Ser Asp Val Phe Leu Lys Ala Lys Lys Leu Tyr Asp Ala Ile Leu
        290                 295                 300

Leu Ser Gly Phe Leu Thr Val Thr Asp Asn Glu Thr Glu Ala Pro Leu
305                 310                 315                 320

Ser Ser Ala Met Ile Lys Arg Tyr Asn Glu His Lys Glu Asp Leu Ala
                325                 330                 335

Leu Leu Lys Glu Tyr Ile Arg Asn Ile Ser Leu Lys Thr Tyr Asn Glu
            340                 345                 350

Val Phe Lys Asp Asp Thr Lys Asn Gly Tyr Ala Gly Tyr Ile Asp Gly
        355                 360                 365

Lys Thr Asn Gln Glu Asp Phe Tyr Val Tyr Leu Lys Asn Leu Leu Ala
370                 375                 380

Glu Phe Glu Gly Ala Asp Tyr Phe Leu Glu Lys Ile Asp Arg Glu Asp
385                 390                 395                 400

Phe Leu Arg Lys Gln Arg Thr Phe Asp Asn Gly Ser Ile Pro Tyr Gln
                405                 410                 415

Ile His Leu Gln Glu Met Arg Ala Ile Leu Asp Lys Gln Ala Lys Phe
            420                 425                 430

Tyr Pro Phe Leu Ala Lys Asn Lys Glu Arg Ile Glu Lys Ile Leu Thr
        435                 440                 445

Phe Arg Ile Pro Tyr Tyr Val Gly Pro Leu Ala Arg Gly Asn Ser Asp
450                 455                 460

Phe Ala Trp Ser Ile Arg Lys Arg Asn Glu Lys Ile Thr Pro Trp Asn
465                 470                 475                 480

Phe Glu Asp Val Ile Asp Lys Glu Ser Ala Glu Ala Phe Ile Asn
                485                 490                 495

Arg Met Thr Ser Phe Asp Leu Tyr Leu Pro Glu Glu Lys Val Leu Pro
            500                 505                 510

Lys His Ser Leu Leu Tyr Glu Thr Phe Asn Val Tyr Asn Glu Leu Thr
        515                 520                 525

Lys Val Arg Phe Ile Ala Glu Ser Met Arg Asp Tyr Gln Phe Leu Asp
530                 535                 540

Ser Lys Gln Lys Lys Asp Ile Val Arg Leu Tyr Phe Lys Asp Lys Arg
545                 550                 555                 560

Lys Val Thr Asp Lys Asp Ile Ile Glu Tyr Leu His Ala Ile Tyr Gly
                565                 570                 575

Tyr Asp Gly Ile Glu Leu Lys Gly Ile Glu Lys Gln Phe Asn Ser Ser
            580                 585                 590

Leu Ser Thr Tyr His Asp Leu Leu Asn Ile Ile Asn Asp Lys Glu Phe
        595                 600                 605

Leu Asp Asp Ser Ser Asn Glu Ala Ile Ile Glu Glu Ile Ile His Thr
610                 615                 620

Leu Thr Ile Phe Glu Asp Arg Glu Met Ile Lys Gln Arg Leu Ser Lys
625                 630                 635                 640

Phe Glu Asn Ile Phe Asp Lys Ser Val Leu Lys Lys Leu Ser Arg Arg
                645                 650                 655

His Tyr Thr Gly Trp Gly Lys Leu Ser Ala Lys Leu Ile Asn Gly Ile
            660                 665                 670

Arg Asp Glu Lys Ser Gly Asn Thr Ile Leu Asp Tyr Leu Ile Asp Asp
        675                 680                 685

Gly Ile Ser Asn Arg Asn Phe Met Gln Leu Ile His Asp Asp Ala Leu
```

-continued

```
            690                 695                 700

Ser Phe Lys Lys Lys Ile Gln Lys Ala Gln Ile Ile Gly Asp Glu Asp
705                 710                 715                 720

Lys Gly Asn Ile Lys Glu Val Val Lys Ser Leu Pro Gly Ser Pro Ala
                725                 730                 735

Ile Lys Lys Gly Ile Leu Gln Ser Ile Lys Ile Val Asp Glu Leu Val
                740                 745                 750

Lys Val Met Gly Gly Arg Lys Pro Glu Ser Ile Val Val Glu Met Ala
                755                 760                 765

Arg Glu Asn Gln Tyr Thr Asn Gln Gly Lys Ser Asn Ser Gln Gln Arg
770                 775                 780

Leu Lys Arg Leu Glu Lys Ser Leu Lys Glu Leu Gly Ser Lys Ile Leu
785                 790                 795                 800

Lys Glu Asn Ile Pro Ala Lys Leu Ser Lys Ile Asp Asn Asn Ala Leu
                805                 810                 815

Gln Asn Asp Arg Leu Tyr Leu Tyr Tyr Leu Gln Asn Gly Lys Asp Met
                820                 825                 830

Tyr Thr Gly Asp Asp Leu Asp Ile Asp Arg Leu Ser Asn Tyr Asp Ile
                835                 840                 845

Asp His Ile Ile Pro Gln Ala Phe Leu Lys Asp Asn Ser Ile Asp Asn
                850                 855                 860

Lys Val Leu Val Ser Ser Ala Ser Asn Arg Gly Lys Ser Asp Asp Phe
865                 870                 875                 880

Pro Ser Leu Glu Val Val Lys Lys Arg Lys Thr Phe Trp Tyr Gln Leu
                885                 890                 895

Leu Lys Ser Lys Leu Ile Ser Gln Arg Lys Phe Asp Asn Leu Thr Lys
                900                 905                 910

Ala Glu Arg Gly Gly Leu Leu Pro Glu Asp Lys Ala Gly Phe Ile Gln
                915                 920                 925

Arg Gln Leu Val Glu Thr Arg Gln Ile Thr Lys His Val Ala Arg Leu
                930                 935                 940

Leu Asp Glu Lys Phe Asn Asn Lys Lys Asp Glu Asn Asn Arg Ala Val
945                 950                 955                 960

Arg Thr Val Lys Ile Ile Thr Leu Lys Ser Thr Leu Val Ser Gln Phe
                965                 970                 975

Arg Lys Asp Phe Glu Leu Tyr Lys Val Arg Glu Ile Asn Asp Phe His
                980                 985                 990

His Ala His Asp Ala Tyr Leu Asn Ala Val Ile Ala Ser Ala Leu Leu
                995                 1000                1005

Lys Lys Tyr Pro Lys Leu Glu Pro Glu Phe Val Tyr Gly Asp Tyr
       1010                1015                1020

Pro Lys Tyr Asn Ser Phe Arg Glu Arg Lys Ser Ala Thr Glu Lys
       1025                1030                1035

Val Tyr Phe Tyr Ser Asn Ile Met Asn Ile Phe Lys Lys Ser Ile
       1040                1045                1050

Ser Leu Ala Asp Gly Arg Val Ile Glu Arg Pro Leu Ile Glu Val
       1055                1060                1065

Asn Glu Glu Thr Gly Glu Ser Val Trp Asn Lys Glu Ser Asp Leu
       1070                1075                1080

Ala Thr Val Arg Arg Val Leu Ser Tyr Pro Gln Val Asn Val Val
       1085                1090                1095

Lys Lys Val Glu Glu Gln Asn His Gly Leu Asp Arg Gly Lys Pro
       1100                1105                1110
```

```
Lys Gly Leu Phe Asn Ala Asn Leu Ser Ser Lys Pro Lys Pro Asn
    1115                1120                1125

Ser Asn Glu Asn Leu Val Gly Ala Lys Glu Tyr Leu Asp Pro Lys
    1130                1135                1140

Lys Tyr Gly Gly Tyr Ala Gly Ile Ser Asn Ser Phe Ala Val Leu
    1145                1150                1155

Val Lys Gly Thr Ile Glu Lys Gly Ala Lys Lys Ile Thr Asn
    1160                1165                1170

Val Leu Glu Phe Gln Gly Ile Ser Ile Leu Asp Arg Ile Asn Tyr
    1175                1180                1185

Arg Lys Asp Lys Leu Asn Phe Leu Leu Glu Lys Gly Tyr Lys Asp
    1190                1195                1200

Ile Glu Leu Ile Ile Glu Leu Pro Lys Tyr Ser Leu Phe Glu Leu
    1205                1210                1215

Ser Asp Gly Ser Arg Arg Met Leu Ala Ser Ile Leu Ser Thr Asn
    1220                1225                1230

Asn Lys Arg Gly Glu Ile His Lys Gly Asn Gln Ile Phe Leu Ser
    1235                1240                1245

Gln Lys Phe Val Lys Leu Leu Tyr His Ala Lys Arg Ile Ser Asn
    1250                1255                1260

Thr Ile Asn Glu Asn His Arg Lys Tyr Val Glu Asn His Lys Lys
    1265                1270                1275

Glu Phe Glu Glu Leu Phe Tyr Tyr Ile Leu Glu Phe Asn Glu Asn
    1280                1285                1290

Tyr Val Gly Ala Lys Lys Asn Gly Lys Leu Leu Asn Ser Ala Phe
    1295                1300                1305

Gln Ser Trp Gln Asn His Ser Ile Asp Glu Leu Cys Ser Ser Phe
    1310                1315                1320

Ile Gly Pro Thr Gly Ser Glu Arg Lys Gly Leu Phe Glu Leu Thr
    1325                1330                1335

Ser Arg Gly Ser Ala Ala Asp Phe Glu Phe Leu Gly Val Lys Ile
    1340                1345                1350

Pro Arg Tyr Arg Asp Tyr Thr Pro Ser Ser Leu Leu Lys Asp Ala
    1355                1360                1365

Thr Leu Ile His Gln Ser Val Thr Gly Leu Tyr Glu Thr Arg Ile
    1370                1375                1380

Asp Leu Ala Lys Leu Gly Glu Gly Gly Ser Pro Lys Lys Lys Arg
    1385                1390                1395

Lys Val
    1400

<210> SEQ ID NO 22
<211> LENGTH: 23
<212> TYPE: DNA
<213> ORGANISM: Sus scrofa

<400> SEQUENCE: 22
gaagcctttc tgtatttttg tgg                                          23

<210> SEQ ID NO 23
<211> LENGTH: 23
<212> TYPE: DNA
<213> ORGANISM: Sus scrofa

<400> SEQUENCE: 23
```

```
atgatttttta gaattcttag tgg                                              23

<210> SEQ ID NO 24
<211> LENGTH: 23
<212> TYPE: DNA
<213> ORGANISM: Sus scrofa

<400> SEQUENCE: 24
tcttagtggt tctcttcttc agg                                               23

<210> SEQ ID NO 25
<211> LENGTH: 25
<212> TYPE: DNA
<213> ORGANISM: Sus scrofa

<400> SEQUENCE: 25
tcttagtggt tctcttcttc aggag                                             25

<210> SEQ ID NO 26
<211> LENGTH: 23
<212> TYPE: DNA
<213> ORGANISM: Sus scrofa

<400> SEQUENCE: 26
ttcttcagga gaacatttct agg                                               23

<210> SEQ ID NO 27
<211> LENGTH: 23
<212> TYPE: DNA
<213> ORGANISM: Sus scrofa

<400> SEQUENCE: 27
tcttcaggag aacatttcta ggg                                               23

<210> SEQ ID NO 28
<211> LENGTH: 23
<212> TYPE: DNA
<213> ORGANISM: Sus scrofa

<400> SEQUENCE: 28
ataatacaag aagatttaaa tgg                                               23

<210> SEQ ID NO 29
<211> LENGTH: 23
<212> TYPE: DNA
<213> ORGANISM: Sus scrofa

<400> SEQUENCE: 29
atttaaatgg cataaaacct tgg                                               23

<210> SEQ ID NO 30
<211> LENGTH: 23
<212> TYPE: DNA
<213> ORGANISM: Sus scrofa

<400> SEQUENCE: 30
aatggcataa aaccttggaa tgg                                               23

<210> SEQ ID NO 31
<211> LENGTH: 23
<212> TYPE: DNA
<213> ORGANISM: Sus scrofa

<400> SEQUENCE: 31
```
ttctgagttt gtccattcca agg                                           23

<210> SEQ ID NO 32
<211> LENGTH: 23
<212> TYPE: DNA
<213> ORGANISM: Sus scrofa

<400> SEQUENCE: 32
tggaatggac aaactcagaa tgg                                           23

<210> SEQ ID NO 33
<211> LENGTH: 25
<212> TYPE: DNA
<213> ORGANISM: Sus scrofa

<400> SEQUENCE: 33
tggaatggac aaactcagaa tggtg                                         25

<210> SEQ ID NO 34
<211> LENGTH: 23
<212> TYPE: DNA
<213> ORGANISM: Sus scrofa

<400> SEQUENCE: 34
atggtgctac atgaaaactc tgg                                           23

<210> SEQ ID NO 35
<211> LENGTH: 23
<212> TYPE: DNA
<213> ORGANISM: Sus scrofa

<400> SEQUENCE: 35
catgaaaact ctggatctgc agg                                           23

<210> SEQ ID NO 36
<211> LENGTH: 23
<212> TYPE: DNA
<213> ORGANISM: Sus scrofa

<400> SEQUENCE: 36
aaaagtgaag gaacttaaat ggg                                           23

<210> SEQ ID NO 37
<211> LENGTH: 23
<212> TYPE: DNA
<213> ORGANISM: Sus scrofa

<400> SEQUENCE: 37
caaaagtgaa ggaacttaaa tgg                                           23

<210> SEQ ID NO 38
<211> LENGTH: 23
<212> TYPE: DNA
<213> ORGANISM: Sus scrofa

<400> SEQUENCE: 38
agcgactaca gcaaaagtga agg                                           23

<210> SEQ ID NO 39
<211> LENGTH: 23
<212> TYPE: DNA
<213> ORGANISM: Sus scrofa

```
<400> SEQUENCE: 39
cgctgttctc agtgcctgct tgg                                          23

<210> SEQ ID NO 40
<211> LENGTH: 23
<212> TYPE: DNA
<213> ORGANISM: Sus scrofa

<400> SEQUENCE: 40
aagagaacta gtgaccaagc agg                                          23

<210> SEQ ID NO 41
<211> LENGTH: 23
<212> TYPE: DNA
<213> ORGANISM: Sus scrofa

<400> SEQUENCE: 41
tgcttggtca ctagttctct tgg                                          23

<210> SEQ ID NO 42
<211> LENGTH: 25
<212> TYPE: DNA
<213> ORGANISM: Sus scrofa

<400> SEQUENCE: 42
tgcttggtca ctagttctct tggtg                                        25

<210> SEQ ID NO 43
<211> LENGTH: 23
<212> TYPE: DNA
<213> ORGANISM: Sus scrofa

<400> SEQUENCE: 43
tgttacagga ggaaaagaca agg                                          23

<210> SEQ ID NO 44
<211> LENGTH: 25
<212> TYPE: DNA
<213> ORGANISM: Sus scrofa

<400> SEQUENCE: 44
tgttacagga ggaaaagaca aggag                                        25

<210> SEQ ID NO 45
<211> LENGTH: 23
<212> TYPE: DNA
<213> ORGANISM: Sus scrofa

<400> SEQUENCE: 45
gaggaaaaga caaggagctg agg                                          23

<210> SEQ ID NO 46
<211> LENGTH: 23
<212> TYPE: DNA
<213> ORGANISM: Sus scrofa

<400> SEQUENCE: 46
agacaaggag ctgaggctaa cgg                                          23

<210> SEQ ID NO 47
<211> LENGTH: 23
<212> TYPE: DNA
<213> ORGANISM: Sus scrofa
```

```
<400> SEQUENCE: 47
gacaaggagc tgaggctaac ggg                                          23

<210> SEQ ID NO 48
<211> LENGTH: 25
<212> TYPE: DNA
<213> ORGANISM: Sus scrofa

<400> SEQUENCE: 48
gacaaggagc tgaggctaac gggtg                                        25

<210> SEQ ID NO 49
<211> LENGTH: 23
<212> TYPE: DNA
<213> ORGANISM: Sus scrofa

<400> SEQUENCE: 49
aaggagctga ggctaacggg tgg                                          23

<210> SEQ ID NO 50
<211> LENGTH: 25
<212> TYPE: DNA
<213> ORGANISM: Sus scrofa

<400> SEQUENCE: 50
aaggagctga ggctaacggg tggtg                                        25

<210> SEQ ID NO 51
<211> LENGTH: 23
<212> TYPE: DNA
<213> ORGANISM: Sus scrofa

<400> SEQUENCE: 51
ggtggtgaaa acaagtgctc tgg                                          23

<210> SEQ ID NO 52
<211> LENGTH: 23
<212> TYPE: DNA
<213> ORGANISM: Sus scrofa

<400> SEQUENCE: 52
aaacaagtgc tctggaagag tgg                                          23

<210> SEQ ID NO 53
<211> LENGTH: 25
<212> TYPE: DNA
<213> ORGANISM: Sus scrofa

<400> SEQUENCE: 53
aaacaagtgc tctggaagag tggag                                        25

<210> SEQ ID NO 54
<211> LENGTH: 23
<212> TYPE: DNA
<213> ORGANISM: Sus scrofa

<400> SEQUENCE: 54
caagtgctct ggaagagtgg agg                                          23

<210> SEQ ID NO 55
<211> LENGTH: 25
<212> TYPE: DNA
```

<213> ORGANISM: Sus scrofa

<400> SEQUENCE: 55
caagtgctct ggaagagtgg aggtg                                              25

<210> SEQ ID NO 56
<211> LENGTH: 23
<212> TYPE: DNA
<213> ORGANISM: Sus scrofa

<400> SEQUENCE: 56
aagagtggag gtgaaagtgc agg                                                23

<210> SEQ ID NO 57
<211> LENGTH: 25
<212> TYPE: DNA
<213> ORGANISM: Sus scrofa

<400> SEQUENCE: 57
aagagtggag gtgaaagtgc aggag                                              25

<210> SEQ ID NO 58
<211> LENGTH: 23
<212> TYPE: DNA
<213> ORGANISM: Sus scrofa

<400> SEQUENCE: 58
agtggaggtg aaagtgcagg agg                                                23

<210> SEQ ID NO 59
<211> LENGTH: 25
<212> TYPE: DNA
<213> ORGANISM: Sus scrofa

<400> SEQUENCE: 59
agtggaggtg aaagtgcagg aggag                                              25

<210> SEQ ID NO 60
<211> LENGTH: 23
<212> TYPE: DNA
<213> ORGANISM: Sus scrofa

<400> SEQUENCE: 60
aggtgaaagt gcaggaggag tgg                                                23

<210> SEQ ID NO 61
<211> LENGTH: 25
<212> TYPE: DNA
<213> ORGANISM: Sus scrofa

<400> SEQUENCE: 61
aggtgaaagt gcaggaggag tgggg                                              25

<210> SEQ ID NO 62
<211> LENGTH: 23
<212> TYPE: DNA
<213> ORGANISM: Sus scrofa

<400> SEQUENCE: 62
ggtgaaagtg caggaggagt ggg                                                23

<210> SEQ ID NO 63
<211> LENGTH: 23

```
<212> TYPE: DNA
<213> ORGANISM: Sus scrofa

<400> SEQUENCE: 63
gtgaaagtgc aggaggagtg ggg                                      23

<210> SEQ ID NO 64
<211> LENGTH: 23
<212> TYPE: DNA
<213> ORGANISM: Sus scrofa

<400> SEQUENCE: 64
tggggaactg tgtgtaataa tgg                                      23

<210> SEQ ID NO 65
<211> LENGTH: 23
<212> TYPE: DNA
<213> ORGANISM: Sus scrofa

<400> SEQUENCE: 65
gaactgtgtg taataatggc tgg                                      23

<210> SEQ ID NO 66
<211> LENGTH: 23
<212> TYPE: DNA
<213> ORGANISM: Sus scrofa

<400> SEQUENCE: 66
aactgtgtgt aataatggct ggg                                      23

<210> SEQ ID NO 67
<211> LENGTH: 23
<212> TYPE: DNA
<213> ORGANISM: Sus scrofa

<400> SEQUENCE: 67
gtgtaataat ggctgggaca tgg                                      23

<210> SEQ ID NO 68
<211> LENGTH: 23
<212> TYPE: DNA
<213> ORGANISM: Sus scrofa

<400> SEQUENCE: 68
taatggctgg gacatggatg tgg                                      23

<210> SEQ ID NO 69
<211> LENGTH: 23
<212> TYPE: DNA
<213> ORGANISM: Sus scrofa

<400> SEQUENCE: 69
atgtggtctc tgttgtttgt agg                                      23

<210> SEQ ID NO 70
<211> LENGTH: 23
<212> TYPE: DNA
<213> ORGANISM: Sus scrofa

<400> SEQUENCE: 70
ctctgttgtt tgtaggcagc tgg                                      23

<210> SEQ ID NO 71
```

```
<210> SEQ ID NO 71
<211> LENGTH: 23
<212> TYPE: DNA
<213> ORGANISM: Sus scrofa

<400> SEQUENCE: 71
tctgttgttt gtaggcagct ggg                                         23

<210> SEQ ID NO 72
<211> LENGTH: 23
<212> TYPE: DNA
<213> ORGANISM: Sus scrofa

<400> SEQUENCE: 72
ccagtggctt tgatagcagt tgg                                         23

<210> SEQ ID NO 73
<211> LENGTH: 23
<212> TYPE: DNA
<213> ORGANISM: Sus scrofa

<400> SEQUENCE: 73
ccaactgcta tcaaagccac tgg                                         23

<210> SEQ ID NO 74
<211> LENGTH: 23
<212> TYPE: DNA
<213> ORGANISM: Sus scrofa

<400> SEQUENCE: 74
ctgctatcaa agccactgga tgg                                         23

<210> SEQ ID NO 75
<211> LENGTH: 23
<212> TYPE: DNA
<213> ORGANISM: Sus scrofa

<400> SEQUENCE: 75
tgctatcaaa gccactggat ggg                                         23

<210> SEQ ID NO 76
<211> LENGTH: 23
<212> TYPE: DNA
<213> ORGANISM: Sus scrofa

<400> SEQUENCE: 76
actaaaatta gcccatccag tgg                                         23

<210> SEQ ID NO 77
<211> LENGTH: 23
<212> TYPE: DNA
<213> ORGANISM: Sus scrofa

<400> SEQUENCE: 77
ggatgggcta attttagtgc agg                                         23

<210> SEQ ID NO 78
<211> LENGTH: 23
<212> TYPE: DNA
<213> ORGANISM: Sus scrofa

<400> SEQUENCE: 78
gctaatttta gtgcaggttc tgg                                         23
```

```
<210> SEQ ID NO 79
<211> LENGTH: 23
<212> TYPE: DNA
<213> ORGANISM: Sus scrofa

<400> SEQUENCE: 79
gtgcaggttc tggacgcatt tgg                                              23

<210> SEQ ID NO 80
<211> LENGTH: 23
<212> TYPE: DNA
<213> ORGANISM: Sus scrofa

<400> SEQUENCE: 80
aggttctgga cgcatttgga tgg                                              23

<210> SEQ ID NO 81
<211> LENGTH: 23
<212> TYPE: DNA
<213> ORGANISM: Sus scrofa

<400> SEQUENCE: 81
atggatcatg tttcttgtcg agg                                              23

<210> SEQ ID NO 82
<211> LENGTH: 23
<212> TYPE: DNA
<213> ORGANISM: Sus scrofa

<400> SEQUENCE: 82
tggatcatgt ttcttgtcga ggg                                              23

<210> SEQ ID NO 83
<211> LENGTH: 23
<212> TYPE: DNA
<213> ORGANISM: Sus scrofa

<400> SEQUENCE: 83
gagggaatga gtcagctctc tgg                                              23

<210> SEQ ID NO 84
<211> LENGTH: 23
<212> TYPE: DNA
<213> ORGANISM: Sus scrofa

<400> SEQUENCE: 84
agggaatgag tcagctctct ggg                                              23

<210> SEQ ID NO 85
<211> LENGTH: 23
<212> TYPE: DNA
<213> ORGANISM: Sus scrofa

<400> SEQUENCE: 85
ctctgggact gcaaacatga tgg                                              23

<210> SEQ ID NO 86
<211> LENGTH: 23
<212> TYPE: DNA
<213> ORGANISM: Sus scrofa

<400> SEQUENCE: 86
gggactgcaa acatgatgga tgg                                              23
```

```
<210> SEQ ID NO 87
<211> LENGTH: 25
<212> TYPE: DNA
<213> ORGANISM: Sus scrofa

<400> SEQUENCE: 87
gggactgcaa acatgatgga tgggg                                       25

<210> SEQ ID NO 88
<211> LENGTH: 23
<212> TYPE: DNA
<213> ORGANISM: Sus scrofa

<400> SEQUENCE: 88
ggactgcaaa catgatggat ggg                                         23

<210> SEQ ID NO 89
<211> LENGTH: 23
<212> TYPE: DNA
<213> ORGANISM: Sus scrofa

<400> SEQUENCE: 89
gactgcaaac atgatggatg ggg                                         23

<210> SEQ ID NO 90
<211> LENGTH: 23
<212> TYPE: DNA
<213> ORGANISM: Sus scrofa

<400> SEQUENCE: 90
gcataactgt actcaccaac agg                                         23

<210> SEQ ID NO 91
<211> LENGTH: 23
<212> TYPE: DNA
<213> ORGANISM: Sus scrofa

<400> SEQUENCE: 91
tgtactcacc aacaggatgc tgg                                         23

<210> SEQ ID NO 92
<211> LENGTH: 25
<212> TYPE: DNA
<213> ORGANISM: Sus scrofa

<400> SEQUENCE: 92
tgtactcacc aacaggatgc tggag                                       25

<210> SEQ ID NO 93
<211> LENGTH: 25
<212> TYPE: DNA
<213> ORGANISM: Sus scrofa

<400> SEQUENCE: 93
aggttactcc agcatcctgt tggtg                                       25

<210> SEQ ID NO 94
<211> LENGTH: 23
<212> TYPE: DNA
<213> ORGANISM: Sus scrofa

<400> SEQUENCE: 94
aggttactcc agcatcctgt tgg                                         23
```

```
<210> SEQ ID NO 95
<211> LENGTH: 23
<212> TYPE: DNA
<213> ORGANISM: Sus scrofa

<400> SEQUENCE: 95
gatgctggag taacctgctc agg                                              23

<210> SEQ ID NO 96
<211> LENGTH: 23
<212> TYPE: DNA
<213> ORGANISM: Sus scrofa

<400> SEQUENCE: 96
tgtgtatgtc ttacctgagc agg                                              23

<210> SEQ ID NO 97
<211> LENGTH: 23
<212> TYPE: DNA
<213> ORGANISM: Sus scrofa

<400> SEQUENCE: 97
atggatctga tttagagatg agg                                              23

<210> SEQ ID NO 98
<211> LENGTH: 23
<212> TYPE: DNA
<213> ORGANISM: Sus scrofa

<400> SEQUENCE: 98
atctgattta gagatgaggc tgg                                              23

<210> SEQ ID NO 99
<211> LENGTH: 25
<212> TYPE: DNA
<213> ORGANISM: Sus scrofa

<400> SEQUENCE: 99
atctgattta gagatgaggc tggtg                                            25

<210> SEQ ID NO 100
<211> LENGTH: 23
<212> TYPE: DNA
<213> ORGANISM: Sus scrofa

<400> SEQUENCE: 100
ttagagatga ggctggtgaa tgg                                              23

<210> SEQ ID NO 101
<211> LENGTH: 25
<212> TYPE: DNA
<213> ORGANISM: Sus scrofa

<400> SEQUENCE: 101
ttagagatga ggctggtgaa tggag                                            25

<210> SEQ ID NO 102
<211> LENGTH: 23
<212> TYPE: DNA
<213> ORGANISM: Sus scrofa

<400> SEQUENCE: 102
```

```
gagatgaggc tggtgaatgg agg                                          23

<210> SEQ ID NO 103
<211> LENGTH: 23
<212> TYPE: DNA
<213> ORGANISM: Sus scrofa

<400> SEQUENCE: 103
ggctggtgaa tggaggaaac cgg                                          23

<210> SEQ ID NO 104
<211> LENGTH: 25
<212> TYPE: DNA
<213> ORGANISM: Sus scrofa

<400> SEQUENCE: 104
ggctggtgaa tggaggaaac cggtg                                        25

<210> SEQ ID NO 105
<211> LENGTH: 23
<212> TYPE: DNA
<213> ORGANISM: Sus scrofa

<400> SEQUENCE: 105
aatggaggaa accggtgctt agg                                          23

<210> SEQ ID NO 106
<211> LENGTH: 23
<212> TYPE: DNA
<213> ORGANISM: Sus scrofa

<400> SEQUENCE: 106
cttctattct tcctaagcac cgg                                          23

<210> SEQ ID NO 107
<211> LENGTH: 23
<212> TYPE: DNA
<213> ORGANISM: Sus scrofa

<400> SEQUENCE: 107
agaatagaag tcaaatttca agg                                          23

<210> SEQ ID NO 108
<211> LENGTH: 23
<212> TYPE: DNA
<213> ORGANISM: Sus scrofa

<400> SEQUENCE: 108
tagaagtcaa atttcaagga cgg                                          23

<210> SEQ ID NO 109
<211> LENGTH: 25
<212> TYPE: DNA
<213> ORGANISM: Sus scrofa

<400> SEQUENCE: 109
tagaagtcaa atttcaagga cggtg                                        25

<210> SEQ ID NO 110
<211> LENGTH: 23
<212> TYPE: DNA
<213> ORGANISM: Sus scrofa

<400> SEQUENCE: 110
```

```
aagtcaaatt tcaaggacgg tgg                                            23

<210> SEQ ID NO 111
<211> LENGTH: 25
<212> TYPE: DNA
<213> ORGANISM: Sus scrofa

<400> SEQUENCE: 111
aagtcaaatt tcaaggacgg tgggg                                          25

<210> SEQ ID NO 112
<211> LENGTH: 23
<212> TYPE: DNA
<213> ORGANISM: Sus scrofa

<400> SEQUENCE: 112
agtcaaattt caaggacggt ggg                                            23

<210> SEQ ID NO 113
<211> LENGTH: 23
<212> TYPE: DNA
<213> ORGANISM: Sus scrofa

<400> SEQUENCE: 113
gtcaaatttc aaggacggtg ggg                                            23

<210> SEQ ID NO 114
<211> LENGTH: 23
<212> TYPE: DNA
<213> ORGANISM: Sus scrofa

<400> SEQUENCE: 114
caacataaat catgcttctg tgg                                            23

<210> SEQ ID NO 115
<211> LENGTH: 23
<212> TYPE: DNA
<213> ORGANISM: Sus scrofa

<400> SEQUENCE: 115
ggaagtgctg tcagtttctc tgg                                            23

<210> SEQ ID NO 116
<211> LENGTH: 23
<212> TYPE: DNA
<213> ORGANISM: Sus scrofa

<400> SEQUENCE: 116
ttctctggtt cagctaattt tgg                                            23

<210> SEQ ID NO 117
<211> LENGTH: 25
<212> TYPE: DNA
<213> ORGANISM: Sus scrofa

<400> SEQUENCE: 117
ttctctggtt cagctaattt tggag                                          25

<210> SEQ ID NO 118
<211> LENGTH: 23
<212> TYPE: DNA
<213> ORGANISM: Sus scrofa
```

```
<400> SEQUENCE: 118
ggttcagcta attttggaga agg                                          23

<210> SEQ ID NO 119
<211> LENGTH: 23
<212> TYPE: DNA
<213> ORGANISM: Sus scrofa

<400> SEQUENCE: 119
gctaattttg gagaaggttc tgg                                          23

<210> SEQ ID NO 120
<211> LENGTH: 23
<212> TYPE: DNA
<213> ORGANISM: Sus scrofa

<400> SEQUENCE: 120
gagaaggttc tggaccaatc tgg                                          23

<210> SEQ ID NO 121
<211> LENGTH: 23
<212> TYPE: DNA
<213> ORGANISM: Sus scrofa

<400> SEQUENCE: 121
acaagatcat caaaccagat tgg                                          23

<210> SEQ ID NO 122
<211> LENGTH: 23
<212> TYPE: DNA
<213> ORGANISM: Sus scrofa

<400> SEQUENCE: 122
tttgatgatc ttgtatgcaa tgg                                          23

<210> SEQ ID NO 123
<211> LENGTH: 23
<212> TYPE: DNA
<213> ORGANISM: Sus scrofa

<400> SEQUENCE: 123
atggaaatga gtcagctctc tgg                                          23

<210> SEQ ID NO 124
<211> LENGTH: 23
<212> TYPE: DNA
<213> ORGANISM: Sus scrofa

<400> SEQUENCE: 124
ctctggaact gcaaacatga agg                                          23

<210> SEQ ID NO 125
<211> LENGTH: 23
<212> TYPE: DNA
<213> ORGANISM: Sus scrofa

<400> SEQUENCE: 125
ggaactgcaa acatgaagga tgg                                          23

<210> SEQ ID NO 126
<211> LENGTH: 25
<212> TYPE: DNA
<213> ORGANISM: Sus scrofa
```

```
<400> SEQUENCE: 126
ggaactgcaa acatgaagga tgggg                                     25

<210> SEQ ID NO 127
<211> LENGTH: 23
<212> TYPE: DNA
<213> ORGANISM: Sus scrofa

<400> SEQUENCE: 127
gaactgcaaa catgaaggat ggg                                       23

<210> SEQ ID NO 128
<211> LENGTH: 23
<212> TYPE: DNA
<213> ORGANISM: Sus scrofa

<400> SEQUENCE: 128
aactgcaaac atgaaggatg ggg                                       23

<210> SEQ ID NO 129
<211> LENGTH: 23
<212> TYPE: DNA
<213> ORGANISM: Sus scrofa

<400> SEQUENCE: 129
gcacaattgt gatcatgctg agg                                       23

<210> SEQ ID NO 130
<211> LENGTH: 23
<212> TYPE: DNA
<213> ORGANISM: Sus scrofa

<400> SEQUENCE: 130
tgtgatcatg ctgaggatgc tgg                                       23

<210> SEQ ID NO 131
<211> LENGTH: 25
<212> TYPE: DNA
<213> ORGANISM: Sus scrofa

<400> SEQUENCE: 131
tgtgatcatg ctgaggatgc tggag                                     25

<210> SEQ ID NO 132
<211> LENGTH: 23
<212> TYPE: DNA
<213> ORGANISM: Sus scrofa

<400> SEQUENCE: 132
agcagacctg aaactgagag tgg                                       23

<210> SEQ ID NO 133
<211> LENGTH: 23
<212> TYPE: DNA
<213> ORGANISM: Sus scrofa

<400> SEQUENCE: 133
catctaccac tctcagtttc agg                                       23

<210> SEQ ID NO 134
<211> LENGTH: 23
<212> TYPE: DNA
```

```
<213> ORGANISM: Sus scrofa

<400> SEQUENCE: 134
ctgaaactga gagtggtaga tgg                                               23

<210> SEQ ID NO 135
<211> LENGTH: 25
<212> TYPE: DNA
<213> ORGANISM: Sus scrofa

<400> SEQUENCE: 135
ctgaaactga gagtggtaga tggag                                             25

<210> SEQ ID NO 136
<211> LENGTH: 23
<212> TYPE: DNA
<213> ORGANISM: Sus scrofa

<400> SEQUENCE: 136
gatggagtca ctgaatgttc agg                                               23

<210> SEQ ID NO 137
<211> LENGTH: 23
<212> TYPE: DNA
<213> ORGANISM: Sus scrofa

<400> SEQUENCE: 137
cactgaatgt tcaggaagat tgg                                               23

<210> SEQ ID NO 138
<211> LENGTH: 23
<212> TYPE: DNA
<213> ORGANISM: Sus scrofa

<400> SEQUENCE: 138
agattggaag tgaaattcca agg                                               23

<210> SEQ ID NO 139
<211> LENGTH: 25
<212> TYPE: DNA
<213> ORGANISM: Sus scrofa

<400> SEQUENCE: 139
agattggaag tgaaattcca aggag                                             25

<210> SEQ ID NO 140
<211> LENGTH: 23
<212> TYPE: DNA
<213> ORGANISM: Sus scrofa

<400> SEQUENCE: 140
aagtgaaatt ccaaggagaa tgg                                               23

<210> SEQ ID NO 141
<211> LENGTH: 25
<212> TYPE: DNA
<213> ORGANISM: Sus scrofa

<400> SEQUENCE: 141
aagtgaaatt ccaaggagaa tgggg                                             25

<210> SEQ ID NO 142
<211> LENGTH: 23
```

```
<212> TYPE: DNA
<213> ORGANISM: Sus scrofa

<400> SEQUENCE: 142
agtgaaattc aaggagaat ggg                                              23

<210> SEQ ID NO 143
<211> LENGTH: 23
<212> TYPE: DNA
<213> ORGANISM: Sus scrofa

<400> SEQUENCE: 143
gtgaaattcc aaggagaatg ggg                                             23

<210> SEQ ID NO 144
<211> LENGTH: 23
<212> TYPE: DNA
<213> ORGANISM: Sus scrofa

<400> SEQUENCE: 144
agattgttcc ccattctcct tgg                                             23

<210> SEQ ID NO 145
<211> LENGTH: 23
<212> TYPE: DNA
<213> ORGANISM: Sus scrofa

<400> SEQUENCE: 145
tggggaacaa tctgtgatga tgg                                             23

<210> SEQ ID NO 146
<211> LENGTH: 23
<212> TYPE: DNA
<213> ORGANISM: Sus scrofa

<400> SEQUENCE: 146
gaacaatctg tgatgatggc tgg                                             23

<210> SEQ ID NO 147
<211> LENGTH: 23
<212> TYPE: DNA
<213> ORGANISM: Sus scrofa

<400> SEQUENCE: 147
aacaatctgt gatgatggct ggg                                             23

<210> SEQ ID NO 148
<211> LENGTH: 23
<212> TYPE: DNA
<213> ORGANISM: Sus scrofa

<400> SEQUENCE: 148
ggatagtgat gatgccgctg tgg                                             23

<210> SEQ ID NO 149
<211> LENGTH: 23
<212> TYPE: DNA
<213> ORGANISM: Sus scrofa

<400> SEQUENCE: 149
cagttgctta catgccacag cgg                                             23

<210> SEQ ID NO 150
```

```
<211> LENGTH: 23
<212> TYPE: DNA
<213> ORGANISM: Sus scrofa

<400> SEQUENCE: 150
cgctgtggca tgtaagcaac tgg                                              23

<210> SEQ ID NO 151
<211> LENGTH: 23
<212> TYPE: DNA
<213> ORGANISM: Sus scrofa

<400> SEQUENCE: 151
gctgtggcat gtaagcaact ggg                                              23

<210> SEQ ID NO 152
<211> LENGTH: 23
<212> TYPE: DNA
<213> ORGANISM: Sus scrofa

<400> SEQUENCE: 152
ccaatggcag tgacagcagt tgg                                              23

<210> SEQ ID NO 153
<211> LENGTH: 23
<212> TYPE: DNA
<213> ORGANISM: Sus scrofa

<400> SEQUENCE: 153
ccaactgctg tcactgccat tgg                                              23

<210> SEQ ID NO 154
<211> LENGTH: 23
<212> TYPE: DNA
<213> ORGANISM: Sus scrofa

<400> SEQUENCE: 154
actggcgtta actcgaccaa tgg                                              23

<210> SEQ ID NO 155
<211> LENGTH: 23
<212> TYPE: DNA
<213> ORGANISM: Sus scrofa

<400> SEQUENCE: 155
tggtcgagtt aacgccagtg agg                                              23

<210> SEQ ID NO 156
<211> LENGTH: 23
<212> TYPE: DNA
<213> ORGANISM: Sus scrofa

<400> SEQUENCE: 156
ggtcgagtta acgccagtga ggg                                              23

<210> SEQ ID NO 157
<211> LENGTH: 23
<212> TYPE: DNA
<213> ORGANISM: Sus scrofa

<400> SEQUENCE: 157
gttaacgcca gtgagggaac tgg                                              23
```

```
<210> SEQ ID NO 158
<211> LENGTH: 25
<212> TYPE: DNA
<213> ORGANISM: Sus scrofa

<400> SEQUENCE: 158
aatgtgtcca gttccctcac tggcg                                          25

<210> SEQ ID NO 159
<211> LENGTH: 23
<212> TYPE: DNA
<213> ORGANISM: Sus scrofa

<400> SEQUENCE: 159
aatgtgtcca gttccctcac tgg                                            23

<210> SEQ ID NO 160
<211> LENGTH: 23
<212> TYPE: DNA
<213> ORGANISM: Sus scrofa

<400> SEQUENCE: 160
gtgagggaac tggacacatt tgg                                            23

<210> SEQ ID NO 161
<211> LENGTH: 23
<212> TYPE: DNA
<213> ORGANISM: Sus scrofa

<400> SEQUENCE: 161
cttgacagtg tttcttgcca tgg                                            23

<210> SEQ ID NO 162
<211> LENGTH: 23
<212> TYPE: DNA
<213> ORGANISM: Sus scrofa

<400> SEQUENCE: 162
agagagcaga ctcgtgtcca tgg                                            23

<210> SEQ ID NO 163
<211> LENGTH: 23
<212> TYPE: DNA
<213> ORGANISM: Sus scrofa

<400> SEQUENCE: 163
atggacacga gtctgctctc tgg                                            23

<210> SEQ ID NO 164
<211> LENGTH: 23
<212> TYPE: DNA
<213> ORGANISM: Sus scrofa

<400> SEQUENCE: 164
ggcagtgtag acaccatgaa tgg                                            23

<210> SEQ ID NO 165
<211> LENGTH: 25
<212> TYPE: DNA
<213> ORGANISM: Sus scrofa

<400> SEQUENCE: 165
ggcagtgtag acaccatgaa tgggg                                          25
```

```
<210> SEQ ID NO 166
<211> LENGTH: 23
<212> TYPE: DNA
<213> ORGANISM: Sus scrofa

<400> SEQUENCE: 166
gcagtgtaga caccatgaat ggg                                        23

<210> SEQ ID NO 167
<211> LENGTH: 23
<212> TYPE: DNA
<213> ORGANISM: Sus scrofa

<400> SEQUENCE: 167
cagtgtagac accatgaatg ggg                                        23

<210> SEQ ID NO 168
<211> LENGTH: 25
<212> TYPE: DNA
<213> ORGANISM: Sus scrofa

<400> SEQUENCE: 168
aataatgctt tccccattca tggtg                                      25

<210> SEQ ID NO 169
<211> LENGTH: 23
<212> TYPE: DNA
<213> ORGANISM: Sus scrofa

<400> SEQUENCE: 169
aataatgctt tccccattca tgg                                        23

<210> SEQ ID NO 170
<211> LENGTH: 23
<212> TYPE: DNA
<213> ORGANISM: Sus scrofa

<400> SEQUENCE: 170
tgcaatcata atgaagatgc tgg                                        23

<210> SEQ ID NO 171
<211> LENGTH: 25
<212> TYPE: DNA
<213> ORGANISM: Sus scrofa

<400> SEQUENCE: 171
tgcaatcata atgaagatgc tggtg                                      25

<210> SEQ ID NO 172
<211> LENGTH: 23
<212> TYPE: DNA
<213> ORGANISM: Sus scrofa

<400> SEQUENCE: 172
gatgctggtg tgacatgttc tgg                                        23

<210> SEQ ID NO 173
<211> LENGTH: 23
<212> TYPE: DNA
<213> ORGANISM: Sus scrofa

<400> SEQUENCE: 173
ttttgcagat ggatcagatc tgg                                        23
```

<210> SEQ ID NO 174
<211> LENGTH: 23
<212> TYPE: DNA
<213> ORGANISM: Sus scrofa

<400> SEQUENCE: 174
gatctggaac tgagacttaa agg                                              23

<210> SEQ ID NO 175
<211> LENGTH: 25
<212> TYPE: DNA
<213> ORGANISM: Sus scrofa

<400> SEQUENCE: 175
gatctggaac tgagacttaa aggtg                                            25

<210> SEQ ID NO 176
<211> LENGTH: 23
<212> TYPE: DNA
<213> ORGANISM: Sus scrofa

<400> SEQUENCE: 176
ctggaactga gacttaaagg tgg                                              23

<210> SEQ ID NO 177
<211> LENGTH: 25
<212> TYPE: DNA
<213> ORGANISM: Sus scrofa

<400> SEQUENCE: 177
ctggaactga gacttaaagg tggag                                            25

<210> SEQ ID NO 178
<211> LENGTH: 23
<212> TYPE: DNA
<213> ORGANISM: Sus scrofa

<400> SEQUENCE: 178
gaactgagac ttaaaggtgg agg                                              23

<210> SEQ ID NO 179
<211> LENGTH: 23
<212> TYPE: DNA
<213> ORGANISM: Sus scrofa

<400> SEQUENCE: 179
cagccactgt gctgggacag tgg                                              23

<210> SEQ ID NO 180
<211> LENGTH: 25
<212> TYPE: DNA
<213> ORGANISM: Sus scrofa

<400> SEQUENCE: 180
cagccactgt gctgggacag tggag                                            25

<210> SEQ ID NO 181
<211> LENGTH: 23
<212> TYPE: DNA
<213> ORGANISM: Sus scrofa

<400> SEQUENCE: 181
cctccactgt cccagcacag tgg                                              23

<210> SEQ ID NO 182
<211> LENGTH: 23
<212> TYPE: DNA
<213> ORGANISM: Sus scrofa

<400> SEQUENCE: 182
ccactgtgct gggacagtgg agg                                              23

<210> SEQ ID NO 183
<211> LENGTH: 25
<212> TYPE: DNA
<213> ORGANISM: Sus scrofa

<400> SEQUENCE: 183
ccactgtgct gggacagtgg aggtg                                            25

<210> SEQ ID NO 184
<211> LENGTH: 23
<212> TYPE: DNA
<213> ORGANISM: Sus scrofa

<400> SEQUENCE: 184
ctgtgctggg acagtggagg tgg                                              23

<210> SEQ ID NO 185
<211> LENGTH: 23
<212> TYPE: DNA
<213> ORGANISM: Sus scrofa

<400> SEQUENCE: 185
ggaggtggaa attcagaaac tgg                                              23

<210> SEQ ID NO 186
<211> LENGTH: 23
<212> TYPE: DNA
<213> ORGANISM: Sus scrofa

<400> SEQUENCE: 186
gtggaaattc agaaactggt agg                                              23

<210> SEQ ID NO 187
<211> LENGTH: 23
<212> TYPE: DNA
<213> ORGANISM: Sus scrofa

<400> SEQUENCE: 187
gaaaagtgtg tgatagaagc tgg                                              23

<210> SEQ ID NO 188
<211> LENGTH: 25
<212> TYPE: DNA
<213> ORGANISM: Sus scrofa

<400> SEQUENCE: 188
gaaaagtgtg tgatagaagc tgggg                                            25

<210> SEQ ID NO 189
<211> LENGTH: 23
<212> TYPE: DNA
<213> ORGANISM: Sus scrofa

<400> SEQUENCE: 189

```
aaaagtgtgt gatagaagct ggg                                          23

<210> SEQ ID NO 190
<211> LENGTH: 23
<212> TYPE: DNA
<213> ORGANISM: Sus scrofa

<400> SEQUENCE: 190
aaagtgtgtg atagaagctg ggg                                          23

<210> SEQ ID NO 191
<211> LENGTH: 23
<212> TYPE: DNA
<213> ORGANISM: Sus scrofa

<400> SEQUENCE: 191
gggactgaaa gaagctgatg tgg                                          23

<210> SEQ ID NO 192
<211> LENGTH: 23
<212> TYPE: DNA
<213> ORGANISM: Sus scrofa

<400> SEQUENCE: 192
aagaagctga tgtggtttgc agg                                          23

<210> SEQ ID NO 193
<211> LENGTH: 23
<212> TYPE: DNA
<213> ORGANISM: Sus scrofa

<400> SEQUENCE: 193
tgatgtggtt tgcaggcagc tgg                                          23

<210> SEQ ID NO 194
<211> LENGTH: 23
<212> TYPE: DNA
<213> ORGANISM: Sus scrofa

<400> SEQUENCE: 194
gatgtggttt gcaggcagct ggg                                          23

<210> SEQ ID NO 195
<211> LENGTH: 23
<212> TYPE: DNA
<213> ORGANISM: Sus scrofa

<400> SEQUENCE: 195
gtttgcaggc agctgggatg tgg                                          23

<210> SEQ ID NO 196
<211> LENGTH: 23
<212> TYPE: DNA
<213> ORGANISM: Sus scrofa

<400> SEQUENCE: 196
tcaagtttat tccaaaacca agg                                          23

<210> SEQ ID NO 197
<211> LENGTH: 23
<212> TYPE: DNA
<213> ORGANISM: Sus scrofa
```

```
<400> SEQUENCE: 197
aaaccaaggc aacaaacaca tgg                                              23

<210> SEQ ID NO 198
<211> LENGTH: 23
<212> TYPE: DNA
<213> ORGANISM: Sus scrofa

<400> SEQUENCE: 198
cagccatgtg tttgttgcct tgg                                              23

<210> SEQ ID NO 199
<211> LENGTH: 23
<212> TYPE: DNA
<213> ORGANISM: Sus scrofa

<400> SEQUENCE: 199
ctgtttgtaa gcagctgtaa tgg                                              23

<210> SEQ ID NO 200
<211> LENGTH: 23
<212> TYPE: DNA
<213> ORGANISM: Sus scrofa

<400> SEQUENCE: 200
atggaaatga aacttctctt tgg                                              23

<210> SEQ ID NO 201
<211> LENGTH: 23
<212> TYPE: DNA
<213> ORGANISM: Sus scrofa

<400> SEQUENCE: 201
tggaaatgaa acttctcttt ggg                                              23

<210> SEQ ID NO 202
<211> LENGTH: 23
<212> TYPE: DNA
<213> ORGANISM: Sus scrofa

<400> SEQUENCE: 202
ctctttggga ctgcaagaat tgg                                              23

<210> SEQ ID NO 203
<211> LENGTH: 23
<212> TYPE: DNA
<213> ORGANISM: Sus scrofa

<400> SEQUENCE: 203
gggactgcaa gaattggcag tgg                                              23

<210> SEQ ID NO 204
<211> LENGTH: 25
<212> TYPE: DNA
<213> ORGANISM: Sus scrofa

<400> SEQUENCE: 204
gggactgcaa gaattggcag tgggg                                            25

<210> SEQ ID NO 205
<211> LENGTH: 23
<212> TYPE: DNA
<213> ORGANISM: Sus scrofa
```

<400> SEQUENCE: 205
ggactgcaag aattggcagt ggg                                        23

<210> SEQ ID NO 206
<211> LENGTH: 23
<212> TYPE: DNA
<213> ORGANISM: Sus scrofa

<400> SEQUENCE: 206
gactgcaaga attggcagtg ggg                                        23

<210> SEQ ID NO 207
<211> LENGTH: 25
<212> TYPE: DNA
<213> ORGANISM: Sus scrofa

<400> SEQUENCE: 207
gactgcaaga attggcagtg gggtg                                      25

<210> SEQ ID NO 208
<211> LENGTH: 23
<212> TYPE: DNA
<213> ORGANISM: Sus scrofa

<400> SEQUENCE: 208
tgcaagaatt ggcagtgggg tgg                                        23

<210> SEQ ID NO 209
<211> LENGTH: 23
<212> TYPE: DNA
<213> ORGANISM: Sus scrofa

<400> SEQUENCE: 209
cttacctgag caggtaattt tgg                                        23

<210> SEQ ID NO 210
<211> LENGTH: 23
<212> TYPE: DNA
<213> ORGANISM: Sus scrofa

<400> SEQUENCE: 210
ggtcgtgttg aagtacaaca tgg                                        23

<210> SEQ ID NO 211
<211> LENGTH: 23
<212> TYPE: DNA
<213> ORGANISM: Sus scrofa

<400> SEQUENCE: 211
ggaactacag tgcggcactg tgg                                        23

<210> SEQ ID NO 212
<211> LENGTH: 23
<212> TYPE: DNA
<213> ORGANISM: Sus scrofa

<400> SEQUENCE: 212
agaggcaatt caatttactt ggg                                        23

<210> SEQ ID NO 213
<211> LENGTH: 23
<212> TYPE: DNA

<213> ORGANISM: Sus scrofa

<400> SEQUENCE: 213
gagaggcaat tcaatttact tgg  23

<210> SEQ ID NO 214
<211> LENGTH: 23
<212> TYPE: DNA
<213> ORGANISM: Sus scrofa

<400> SEQUENCE: 214
gtttctttta acagactgag agg  23

<210> SEQ ID NO 215
<211> LENGTH: 23
<212> TYPE: DNA
<213> ORGANISM: Sus scrofa

<400> SEQUENCE: 215
ggttaagagt acaatcatca agg  23

<210> SEQ ID NO 216
<211> LENGTH: 23
<212> TYPE: DNA
<213> ORGANISM: Sus scrofa

<400> SEQUENCE: 216
tgatgattgt actcttaacc tgg  23

<210> SEQ ID NO 217
<211> LENGTH: 23
<212> TYPE: DNA
<213> ORGANISM: Sus scrofa

<400> SEQUENCE: 217
cagaaataaa gcagaagaca tgg  23

<210> SEQ ID NO 218
<211> LENGTH: 23
<212> TYPE: DNA
<213> ORGANISM: Sus scrofa

<400> SEQUENCE: 218
catgtcttct gctttatttc tgg  23

<210> SEQ ID NO 219
<211> LENGTH: 23
<212> TYPE: DNA
<213> ORGANISM: Sus scrofa

<400> SEQUENCE: 219
ctccagatta cagtaaatgg agg  23

<210> SEQ ID NO 220
<211> LENGTH: 23
<212> TYPE: DNA
<213> ORGANISM: Sus scrofa

<400> SEQUENCE: 220
gtcctccatt tactgtaatc tgg  23

<210> SEQ ID NO 221
<211> LENGTH: 23

```
<212> TYPE: DNA
<213> ORGANISM: Sus scrofa

<400> SEQUENCE: 221
gtaaatggag gactgagtat agg                                              23

<210> SEQ ID NO 222
<211> LENGTH: 23
<212> TYPE: DNA
<213> ORGANISM: Sus scrofa

<400> SEQUENCE: 222
taaatggagg actgagtata ggg                                              23

<210> SEQ ID NO 223
<211> LENGTH: 23
<212> TYPE: DNA
<213> ORGANISM: Sus scrofa

<400> SEQUENCE: 223
gggctaaaaa gtagagagaa tgg                                              23

<210> SEQ ID NO 224
<211> LENGTH: 23
<212> TYPE: DNA
<213> ORGANISM: Sus scrofa

<400> SEQUENCE: 224
gaatggatgc atattatctg tgg                                              23

<210> SEQ ID NO 225
<211> LENGTH: 23
<212> TYPE: DNA
<213> ORGANISM: Sus scrofa

<400> SEQUENCE: 225
tccaatgtga tgaatgaagt agg                                              23

<210> SEQ ID NO 226
<211> LENGTH: 23
<212> TYPE: DNA
<213> ORGANISM: Sus scrofa

<400> SEQUENCE: 226
gcctacttca ttcatcacat tgg                                              23

<210> SEQ ID NO 227
<211> LENGTH: 23
<212> TYPE: DNA
<213> ORGANISM: Sus scrofa

<400> SEQUENCE: 227
tgaagtaggc aaatactcaa agg                                              23

<210> SEQ ID NO 228
<211> LENGTH: 23
<212> TYPE: DNA
<213> ORGANISM: Sus scrofa

<400> SEQUENCE: 228
aaagcatgct ccaagaatta tgg                                              23

<210> SEQ ID NO 229
```

```
<211> LENGTH: 23
<212> TYPE: DNA
<213> ORGANISM: Sus scrofa

<400> SEQUENCE: 229
aagcatgctc caagaattat ggg                                              23

<210> SEQ ID NO 230
<211> LENGTH: 23
<212> TYPE: DNA
<213> ORGANISM: Sus scrofa

<400> SEQUENCE: 230
cttctggaac ccataattct tgg                                              23

<210> SEQ ID NO 231
<211> LENGTH: 23
<212> TYPE: DNA
<213> ORGANISM: Sus scrofa

<400> SEQUENCE: 231
caagaattat gggttccaga agg                                              23

<210> SEQ ID NO 232
<211> LENGTH: 23
<212> TYPE: DNA
<213> ORGANISM: Sus scrofa

<400> SEQUENCE: 232
aaagtcccag aattgtctcc agg                                              23

<210> SEQ ID NO 233
<211> LENGTH: 23
<212> TYPE: DNA
<213> ORGANISM: Sus scrofa

<400> SEQUENCE: 233
aagtcccaga attgtctcca ggg                                              23

<210> SEQ ID NO 234
<211> LENGTH: 23
<212> TYPE: DNA
<213> ORGANISM: Sus scrofa

<400> SEQUENCE: 234
ccttccctgg agacaattct ggg                                              23

<210> SEQ ID NO 235
<211> LENGTH: 23
<212> TYPE: DNA
<213> ORGANISM: Sus scrofa

<400> SEQUENCE: 235
cccagaattg tctccaggga agg                                              23

<210> SEQ ID NO 236
<211> LENGTH: 23
<212> TYPE: DNA
<213> ORGANISM: Sus scrofa

<400> SEQUENCE: 236
tccttccctg gagacaattc tgg                                              23
```

```
<210> SEQ ID NO 237
<211> LENGTH: 23
<212> TYPE: DNA
<213> ORGANISM: Sus scrofa

<400> SEQUENCE: 237
attgtctcca gggaaggaca ggg                                              23

<210> SEQ ID NO 238
<211> LENGTH: 23
<212> TYPE: DNA
<213> ORGANISM: Sus scrofa

<400> SEQUENCE: 238
gtctccaggg aaggacaggg agg                                              23

<210> SEQ ID NO 239
<211> LENGTH: 23
<212> TYPE: DNA
<213> ORGANISM: Sus scrofa

<400> SEQUENCE: 239
tagacctccc tgtccttccc tgg                                              23

<210> SEQ ID NO 240
<211> LENGTH: 23
<212> TYPE: DNA
<213> ORGANISM: Sus scrofa

<400> SEQUENCE: 240
aggacaggga ggtctagaat cgg                                              23

<210> SEQ ID NO 241
<211> LENGTH: 23
<212> TYPE: DNA
<213> ORGANISM: Sus scrofa

<400> SEQUENCE: 241
gaatcggcta agcccactgt agg                                              23

<210> SEQ ID NO 242
<211> LENGTH: 23
<212> TYPE: DNA
<213> ORGANISM: Sus scrofa

<400> SEQUENCE: 242
ttggtttttc tgcctacagt ggg                                              23

<210> SEQ ID NO 243
<211> LENGTH: 23
<212> TYPE: DNA
<213> ORGANISM: Sus scrofa

<400> SEQUENCE: 243
cttggttttt ctgcctacag tgg                                              23

<210> SEQ ID NO 244
<211> LENGTH: 23
<212> TYPE: DNA
<213> ORGANISM: Sus scrofa

<400> SEQUENCE: 244
ctgtaggcag aaaaaccaag agg                                              23
```

<210> SEQ ID NO 245
<211> LENGTH: 23
<212> TYPE: DNA
<213> ORGANISM: Sus scrofa

<400> SEQUENCE: 245
gaaaaaccaa gaggcatgaa tgg                                           23

<210> SEQ ID NO 246
<211> LENGTH: 23
<212> TYPE: DNA
<213> ORGANISM: Sus scrofa

<400> SEQUENCE: 246
gggaagccat tcatgcctct tgg                                           23

<210> SEQ ID NO 247
<211> LENGTH: 23
<212> TYPE: DNA
<213> ORGANISM: Sus scrofa

<400> SEQUENCE: 247
agagagtgaa aagtgagaaa ggg                                           23

<210> SEQ ID NO 248
<211> LENGTH: 23
<212> TYPE: DNA
<213> ORGANISM: Sus scrofa

<400> SEQUENCE: 248
cagagagtga aaagtgagaa agg                                           23

<210> SEQ ID NO 249
<211> LENGTH: 23
<212> TYPE: DNA
<213> ORGANISM: Sus scrofa

<400> SEQUENCE: 249
ctggcttact cctatcatga agg                                           23

<210> SEQ ID NO 250
<211> LENGTH: 23
<212> TYPE: DNA
<213> ORGANISM: Sus scrofa

<400> SEQUENCE: 250
cctatcatga aggaaaatat tgg                                           23

<210> SEQ ID NO 251
<211> LENGTH: 23
<212> TYPE: DNA
<213> ORGANISM: Sus scrofa

<400> SEQUENCE: 251
ccaatatttt ccttcatgat agg                                           23

<210> SEQ ID NO 252
<211> LENGTH: 23
<212> TYPE: DNA
<213> ORGANISM: Sus scrofa

<400> SEQUENCE: 252
aaaaaatagc atttcggtga ggg                                           23

```
<210> SEQ ID NO 253
<211> LENGTH: 23
<212> TYPE: DNA
<213> ORGANISM: Sus scrofa

<400> SEQUENCE: 253
gaaaaaatag catttcggtg agg                                              23

<210> SEQ ID NO 254
<211> LENGTH: 23
<212> TYPE: DNA
<213> ORGANISM: Sus scrofa

<400> SEQUENCE: 254
acaaagtgaa cacattccct ggg                                              23

<210> SEQ ID NO 255
<211> LENGTH: 23
<212> TYPE: DNA
<213> ORGANISM: Sus scrofa

<400> SEQUENCE: 255
aacaaagtga acacattccc tgg                                              23

<210> SEQ ID NO 256
<211> LENGTH: 23
<212> TYPE: DNA
<213> ORGANISM: Sus scrofa

<400> SEQUENCE: 256
tcccatgcca tgaagagggt agg                                              23

<210> SEQ ID NO 257
<211> LENGTH: 23
<212> TYPE: DNA
<213> ORGANISM: Sus scrofa

<400> SEQUENCE: 257
ccctaccctc ttcatggcat ggg                                              23

<210> SEQ ID NO 258
<211> LENGTH: 23
<212> TYPE: DNA
<213> ORGANISM: Sus scrofa

<400> SEQUENCE: 258
cccatgccat gaagagggta ggg                                              23

<210> SEQ ID NO 259
<211> LENGTH: 23
<212> TYPE: DNA
<213> ORGANISM: Sus scrofa

<400> SEQUENCE: 259
accctaccct cttcatggca tgg                                              23

<210> SEQ ID NO 260
<211> LENGTH: 23
<212> TYPE: DNA
<213> ORGANISM: Sus scrofa

<400> SEQUENCE: 260
```
gccatgaaga gggtagggtt agg                                            23

<210> SEQ ID NO 261
<211> LENGTH: 23
<212> TYPE: DNA
<213> ORGANISM: Sus scrofa

<400> SEQUENCE: 261
acctaaccct accctcttca tgg                                            23

<210> SEQ ID NO 262
<211> LENGTH: 25
<212> TYPE: DNA
<213> ORGANISM: Sus scrofa

<400> SEQUENCE: 262
cagaaataaa gcagaagaca tggag                                          25

<210> SEQ ID NO 263
<211> LENGTH: 25
<212> TYPE: DNA
<213> ORGANISM: Sus scrofa

<400> SEQUENCE: 263
catgtcttct gctttatttc tggtg                                          25

<210> SEQ ID NO 264
<211> LENGTH: 25
<212> TYPE: DNA
<213> ORGANISM: Sus scrofa

<400> SEQUENCE: 264
tgactccaga ttacagtaaa tggag                                          25

<210> SEQ ID NO 265
<211> LENGTH: 25
<212> TYPE: DNA
<213> ORGANISM: Sus scrofa

<400> SEQUENCE: 265
gtcctccatt tactgtaatc tggag                                          25

<210> SEQ ID NO 266
<211> LENGTH: 25
<212> TYPE: DNA
<213> ORGANISM: Sus scrofa

<400> SEQUENCE: 266
gcctacttca ttcatcacat tggag                                          25

<210> SEQ ID NO 267
<211> LENGTH: 25
<212> TYPE: DNA
<213> ORGANISM: Sus scrofa

<400> SEQUENCE: 267
cttctggaac ccataattct tggag                                          25

<210> SEQ ID NO 268
<211> LENGTH: 25
<212> TYPE: DNA
<213> ORGANISM: Sus scrofa

<400> SEQUENCE: 268
attgtctcca gggaaggaca gggag                                              25

<210> SEQ ID NO 269
<211> LENGTH: 25
<212> TYPE: DNA
<213> ORGANISM: Sus scrofa

<400> SEQUENCE: 269
tagacctccc tgtccttccc tggag                                              25

<210> SEQ ID NO 270
<211> LENGTH: 25
<212> TYPE: DNA
<213> ORGANISM: Sus scrofa

<400> SEQUENCE: 270
ccaatatttt ccttcatgat aggag                                              25

<210> SEQ ID NO 271
<211> LENGTH: 25
<212> TYPE: DNA
<213> ORGANISM: Sus scrofa

<400> SEQUENCE: 271
aaaaaatagc atttcggtga gggag                                              25

<210> SEQ ID NO 272
<211> LENGTH: 23
<212> TYPE: DNA
<213> ORGANISM: Sus scrofa

<400> SEQUENCE: 272
gaatcggcta agcccactgt agg                                                23

<210> SEQ ID NO 273
<211> LENGTH: 23
<212> TYPE: DNA
<213> ORGANISM: Sus scrofa

<400> SEQUENCE: 273
cccatgccat gaagagggta ggg                                                23

<210> SEQ ID NO 274
<211> LENGTH: 20
<212> TYPE: DNA
<213> ORGANISM: Sus scrofa

<400> SEQUENCE: 274
aagagaacta gtgaccaagc                                                    20

<210> SEQ ID NO 275
<211> LENGTH: 20
<212> TYPE: DNA
<213> ORGANISM: Sus scrofa

<400> SEQUENCE: 275
tgcttggtca ctagttctct                                                    20

<210> SEQ ID NO 276
<211> LENGTH: 20
<212> TYPE: DNA
<213> ORGANISM: Sus scrofa

<400> SEQUENCE: 276
gaactgtgtg taataatggc   20

<210> SEQ ID NO 277
<211> LENGTH: 20
<212> TYPE: DNA
<213> ORGANISM: Sus scrofa

<400> SEQUENCE: 277
tgctatcaaa gccactggat   20

<210> SEQ ID NO 278
<211> LENGTH: 20
<212> TYPE: DNA
<213> ORGANISM: Sus scrofa

<400> SEQUENCE: 278
gtgcaggttc tggacgcatt   20

<210> SEQ ID NO 279
<211> LENGTH: 20
<212> TYPE: DNA
<213> ORGANISM: Sus scrofa

<400> SEQUENCE: 279
gtgcaggttc tggacgcatt   20

<210> SEQ ID NO 280
<211> LENGTH: 20
<212> TYPE: DNA
<213> ORGANISM: Sus scrofa

<400> SEQUENCE: 280
atggatcatg tttcttgtcg   20

<210> SEQ ID NO 281
<211> LENGTH: 20
<212> TYPE: DNA
<213> ORGANISM: Sus scrofa

<400> SEQUENCE: 281
ggactgcaaa catgatggat   20

<210> SEQ ID NO 282
<211> LENGTH: 20
<212> TYPE: DNA
<213> ORGANISM: Sus scrofa

<400> SEQUENCE: 282
ggactgcaaa catgatggat   20

<210> SEQ ID NO 283
<211> LENGTH: 20
<212> TYPE: DNA
<213> ORGANISM: Sus scrofa

<400> SEQUENCE: 283
agtcaaattt caaggacggt   20

<210> SEQ ID NO 284
<211> LENGTH: 20
<212> TYPE: DNA
<213> ORGANISM: Sus scrofa

<400> SEQUENCE: 284
gctaattttg gagaaggttc                                               20

<210> SEQ ID NO 285
<211> LENGTH: 20
<212> TYPE: DNA
<213> ORGANISM: Sus scrofa

<400> SEQUENCE: 285
gcacaattgt gatcatgctg                                               20

<210> SEQ ID NO 286
<211> LENGTH: 20
<212> TYPE: DNA
<213> ORGANISM: Sus scrofa

<400> SEQUENCE: 286
ggaactacag tgcggcactg                                               20

<210> SEQ ID NO 287
<211> LENGTH: 20
<212> TYPE: RNA
<213> ORGANISM: Sus scrofa

<400> SEQUENCE: 287
aagagaacua gugaccaagc                                               20

<210> SEQ ID NO 288
<211> LENGTH: 20
<212> TYPE: RNA
<213> ORGANISM: Sus scrofa

<400> SEQUENCE: 288
ugcuugguca cuaguucucu                                               20

<210> SEQ ID NO 289
<211> LENGTH: 20
<212> TYPE: RNA
<213> ORGANISM: Sus scrofa

<400> SEQUENCE: 289
gaacugugug uaauaauggc                                               20

<210> SEQ ID NO 290
<211> LENGTH: 20
<212> TYPE: RNA
<213> ORGANISM: Sus scrofa

<400> SEQUENCE: 290
ugcuaucaaa gccacuggau                                               20

<210> SEQ ID NO 291
<211> LENGTH: 20
<212> TYPE: RNA
<213> ORGANISM: Sus scrofa

<400> SEQUENCE: 291
gugcagguuc uggacgcauu                                               20

<210> SEQ ID NO 292
<211> LENGTH: 20
<212> TYPE: RNA

```
<213> ORGANISM: Sus scrofa

<400> SEQUENCE: 292
gugcagguuc uggacgcauu                                               20

<210> SEQ ID NO 293
<211> LENGTH: 20
<212> TYPE: RNA
<213> ORGANISM: Sus scrofa

<400> SEQUENCE: 293
auggaucaug uuucuugucg                                               20

<210> SEQ ID NO 294
<211> LENGTH: 20
<212> TYPE: RNA
<213> ORGANISM: Sus scrofa

<400> SEQUENCE: 294
ggacugcaaa caugauggau                                               20

<210> SEQ ID NO 295
<211> LENGTH: 20
<212> TYPE: RNA
<213> ORGANISM: Sus scrofa

<400> SEQUENCE: 295
ggacugcaaa caugauggau                                               20

<210> SEQ ID NO 296
<211> LENGTH: 20
<212> TYPE: RNA
<213> ORGANISM: Sus scrofa

<400> SEQUENCE: 296
agucaaauuu caaggacggu                                               20

<210> SEQ ID NO 297
<211> LENGTH: 20
<212> TYPE: RNA
<213> ORGANISM: Sus scrofa

<400> SEQUENCE: 297
gcuaauuuug gagaagguuc                                               20

<210> SEQ ID NO 298
<211> LENGTH: 20
<212> TYPE: RNA
<213> ORGANISM: Sus scrofa

<400> SEQUENCE: 298
gcacaauugu gaucaugcug                                               20

<210> SEQ ID NO 299
<211> LENGTH: 20
<212> TYPE: RNA
<213> ORGANISM: Sus scrofa

<400> SEQUENCE: 299
ggaacuacag ugcggcacug                                               20

<210> SEQ ID NO 300
<211> LENGTH: 157
```

```
<212> TYPE: DNA
<213> ORGANISM: Sus scrofa

<400> SEQUENCE: 300
tttcgcagac tttagaagat gttctgccca tttaagttcc ttcacttttg ctgtagtcgc    60
tgttctcagt gcctgcttgg tcactagttc tcttggtgag tactttgaca aatttacttg   120
taacctagcc cactgtgaca agaaacactg aaaagca                            157

<210> SEQ ID NO 301
<211> LENGTH: 157
<212> TYPE: DNA
<213> ORGANISM: Sus scrofa

<400> SEQUENCE: 301
tttcgcagac tttagaagat gttctgccca tttaagttcc ttcacttttg ctgtagtcgc    60
tgttctcagt gcctgcttgg tcactagttc tcttggtgag tactttgaca aatttacttg   120
taacctagcc cactgtgaca agaaacactg aaaagca                            157

<210> SEQ ID NO 302
<211> LENGTH: 152
<212> TYPE: DNA
<213> ORGANISM: Sus scrofa

<400> SEQUENCE: 302
gtggtgaaaa caagtgctct ggaagagtgg aggtgaaagt gcaggaggag tggggaactg    60
tgtgtaataa tggctgggac atggatgtgg tctctgttgt ttgtaggcag ctgggatgtc   120
caactgctat caaagccact ggatgggcta at                                 152

<210> SEQ ID NO 303
<211> LENGTH: 154
<212> TYPE: DNA
<213> ORGANISM: Sus scrofa

<400> SEQUENCE: 303
tggctgggac atggatgtgg tctctgttgt ttgtaggcag ctgggatgtc caactgctat    60
caaagccact ggatgggcta attttagtgc aggttctgga cgcatttgga tggatcatgt   120
ttcttgtcga gggaatgagt cagctctctg ggac                               154

<210> SEQ ID NO 304
<211> LENGTH: 151
<212> TYPE: DNA
<213> ORGANISM: Sus scrofa

<400> SEQUENCE: 304
gtaggcagct gggatgtcca actgctatca aagccactgg atgggctaat tttagtgcag    60
gttctggacg catttggatg gatcatgttt cttgtcgagg gaatgagtca gctctctggg   120
actgcaaaca tgatggatgg ggaaagcata a                                  151

<210> SEQ ID NO 305
<211> LENGTH: 151
<212> TYPE: DNA
<213> ORGANISM: Sus scrofa

<400> SEQUENCE: 305
gtaggcagct gggatgtcca actgctatca aagccactgg atgggctaat tttagtgcag    60
gttctggacg catttggatg gatcatgttt cttgtcgagg gaatgagtca gctctctggg   120
```

```
actgcaaaca tgatggatgg ggaaagcata a                                   151

<210> SEQ ID NO 306
<211> LENGTH: 156
<212> TYPE: DNA
<213> ORGANISM: Sus scrofa

<400> SEQUENCE: 306
gtccaactgc tatcaaagcc actggatggg ctaattttag tgcaggttct ggacgcattt    60
ggatggatca tgtttcttgt cgagggaatg agtcagctct ctgggactgc aaacatgatg   120
gatggggaaa gcataactgt actcaccaac aggatg                             156

<210> SEQ ID NO 307
<211> LENGTH: 153
<212> TYPE: DNA
<213> ORGANISM: Sus scrofa

<400> SEQUENCE: 307
ctggacgcat ttggatggat catgtttctt gtcgagggaa tgagtcagct ctctgggact    60
gcaaacatga tggatgggga aagcataact gtactcacca acaggatgct ggagtaacct   120
gctcaggtaa gacatacaca aataagtcaa gcc                                153

<210> SEQ ID NO 308
<211> LENGTH: 153
<212> TYPE: DNA
<213> ORGANISM: Sus scrofa

<400> SEQUENCE: 308
ctggacgcat ttggatggat catgtttctt gtcgagggaa tgagtcagct ctctgggact    60
gcaaacatga tggatgggga aagcataact gtactcacca acaggatgct ggagtaacct   120
gctcaggtaa gacatacaca aataagtcaa gcc                                153

<210> SEQ ID NO 309
<211> LENGTH: 153
<212> TYPE: DNA
<213> ORGANISM: Sus scrofa

<400> SEQUENCE: 309
ctctagatgg atctgattta gagatgaggc tggtgaatgg aggaaaccgg tgcttaggaa    60
gaatagaagt caaatttcaa ggacggtggg gaacagtgtg tgatgataac ttcaacataa   120
atcatgcttc tgtggtttgt aaacaacttg aat                                153

<210> SEQ ID NO 310
<211> LENGTH: 153
<212> TYPE: DNA
<213> ORGANISM: Sus scrofa

<400> SEQUENCE: 310
cttctgtggt ttgtaaacaa cttgaatgtg gaagtgctgt cagtttctct ggttcagcta    60
attttggaga aggttctgga ccaatctggt ttgatgatct tgtatgcaat ggaaatgagt   120
cagctctctg gaactgcaaa catgaaggat ggg                                153

<210> SEQ ID NO 311
<211> LENGTH: 155
<212> TYPE: DNA
<213> ORGANISM: Sus scrofa

<400> SEQUENCE: 311
```

-continued tgatgatctt gtatgcaatg gaaatgagtc agctctctgg aactgcaaac atgaaggatg    60
gggaaagcac aattgcgatc atgctgagga tgctggagtg atttgcttaa gtaaggactg   120
acctgggttt gttctgttct ccatgagagg gcaaa                              155

<210> SEQ ID NO 312
<211> LENGTH: 154
<212> TYPE: DNA
<213> ORGANISM: Sus scrofa

<400> SEQUENCE: 312
agacacgtgg ggcaccgtct gtgattctga cttctctctg gaggcggcca gcgtgctgtg    60
cagggaacta cagtgcggca ctgtggtttc cctcctgggg ggagctcact ttggagaagg   120
aagtggacag atctgggctg aagaattcca gtgt                               154

<210> SEQ ID NO 313
<211> LENGTH: 28
<212> TYPE: PRT
<213> ORGANISM: Sus scrofa

<400> SEQUENCE: 313

Phe Arg Arg Cys Ser Ala His Leu Ser Ser Phe Thr Phe Ala Val Val
1               5                   10                  15

Ala Val Leu Ser Ala Cys Leu Val Thr Ser Ser Leu
            20                  25

<210> SEQ ID NO 314
<211> LENGTH: 28
<212> TYPE: PRT
<213> ORGANISM: Sus scrofa

<400> SEQUENCE: 314

Phe Arg Arg Cys Ser Ala His Leu Ser Ser Phe Thr Phe Ala Val Val
1               5                   10                  15

Ala Val Leu Ser Ala Cys Leu Val Thr Ser Ser Leu
            20                  25

<210> SEQ ID NO 315
<211> LENGTH: 50
<212> TYPE: PRT
<213> ORGANISM: Sus scrofa

<400> SEQUENCE: 315

Gly Glu Asn Lys Cys Ser Gly Arg Val Glu Val Lys Val Gln Glu Glu
1               5                   10                  15

Trp Gly Thr Val Cys Asn Asn Gly Trp Asp Met Asp Val Val Ser Val
            20                  25                  30

Val Cys Arg Gln Leu Gly Cys Pro Thr Ala Ile Lys Ala Thr Gly Trp
        35                  40                  45

Ala Asn
    50

<210> SEQ ID NO 316
<211> LENGTH: 51
<212> TYPE: PRT
<213> ORGANISM: Sus scrofa

<400> SEQUENCE: 316

Gly Trp Asp Met Asp Val Val Ser Val Val Cys Arg Gln Leu Gly Cys
1               5                   10                  15

```
Pro Thr Ala Ile Lys Ala Thr Gly Trp Ala Asn Phe Ser Ala Gly Ser
            20                  25                  30

Gly Arg Ile Trp Met Asp His Val Ser Cys Arg Gly Asn Glu Ser Ala
        35                  40                  45

Leu Trp Asp
    50

<210> SEQ ID NO 317
<211> LENGTH: 44
<212> TYPE: PRT
<213> ORGANISM: Sus scrofa

<400> SEQUENCE: 317

Pro Thr Ala Ile Lys Ala Thr Gly Trp Ala Asn Phe Ser Ala Gly Ser
1               5                   10                  15

Gly Arg Ile Trp Met Asp His Val Ser Cys Arg Gly Asn Glu Ser Ala
            20                  25                  30

Leu Trp Asp Cys Lys His Asp Gly Trp Gly Lys His
        35                  40

<210> SEQ ID NO 318
<211> LENGTH: 44
<212> TYPE: PRT
<213> ORGANISM: Sus scrofa

<400> SEQUENCE: 318

Pro Thr Ala Ile Lys Ala Thr Gly Trp Ala Asn Phe Ser Ala Gly Ser
1               5                   10                  15

Gly Arg Ile Trp Met Asp His Val Ser Cys Arg Gly Asn Glu Ser Ala
            20                  25                  30

Leu Trp Asp Cys Lys His Asp Gly Trp Gly Lys His
        35                  40

<210> SEQ ID NO 319
<211> LENGTH: 51
<212> TYPE: PRT
<213> ORGANISM: Sus scrofa

<400> SEQUENCE: 319

Pro Thr Ala Ile Lys Ala Thr Gly Trp Ala Asn Phe Ser Ala Gly Ser
1               5                   10                  15

Gly Arg Ile Trp Met Asp His Val Ser Cys Arg Gly Asn Glu Ser Ala
            20                  25                  30

Leu Trp Asp Cys Lys His Asp Gly Trp Gly Lys His Asn Cys Thr His
        35                  40                  45

Gln Gln Asp
    50

<210> SEQ ID NO 320
<211> LENGTH: 35
<212> TYPE: PRT
<213> ORGANISM: Sus scrofa

<400> SEQUENCE: 320

Gly Arg Ile Trp Met Asp His Val Ser Cys Arg Gly Asn Glu Ser Ala
1               5                   10                  15

Leu Trp Asp Cys Lys His Asp Gly Trp Gly Lys His Asn Cys Thr His
            20                  25                  30

Gln Gln Asp
```

-continued

```
<210> SEQ ID NO 321
<211> LENGTH: 35
<212> TYPE: PRT
<213> ORGANISM: Sus scrofa

<400> SEQUENCE: 321

Gly Arg Ile Trp Met Asp His Val Ser Cys Arg Gly Asn Glu Ser Ala
1               5                   10                  15

Leu Trp Asp Cys Lys His Asp Gly Trp Gly Lys His Asn Cys Thr His
            20                  25                  30

Gln Gln Asp
        35

<210> SEQ ID NO 322
<211> LENGTH: 48
<212> TYPE: PRT
<213> ORGANISM: Sus scrofa

<400> SEQUENCE: 322

Gly Ser Asp Leu Glu Met Arg Leu Val Asn Gly Gly Asn Arg Cys Leu
1               5                   10                  15

Gly Arg Ile Glu Val Lys Phe Gln Gly Arg Trp Gly Thr Val Cys Asp
            20                  25                  30

Asp Asn Phe Asn Ile Asn His Ala Ser Val Val Cys Lys Gln Leu Glu
        35                  40                  45

<210> SEQ ID NO 323
<211> LENGTH: 50
<212> TYPE: PRT
<213> ORGANISM: Sus scrofa

<400> SEQUENCE: 323

Ser Val Val Cys Lys Gln Leu Glu Cys Gly Ser Ala Val Ser Phe Ser
1               5                   10                  15

Gly Ser Ala Asn Phe Gly Glu Gly Ser Gly Pro Ile Trp Phe Asp Asp
            20                  25                  30

Leu Val Cys Asn Gly Asn Glu Ser Ala Leu Trp Asn Cys Lys His Glu
        35                  40                  45

Gly Trp
    50

<210> SEQ ID NO 324
<211> LENGTH: 36
<212> TYPE: PRT
<213> ORGANISM: Sus scrofa

<400> SEQUENCE: 324

Asp Asp Leu Val Cys Asn Gly Asn Glu Ser Ala Leu Trp Asn Cys Lys
1               5                   10                  15

His Glu Gly Trp Gly Lys His Asn Cys Asp His Ala Glu Asp Ala Gly
            20                  25                  30

Val Ile Cys Leu
        35

<210> SEQ ID NO 325
<211> LENGTH: 51
<212> TYPE: PRT
<213> ORGANISM: Sus scrofa
```

-continued

<400> SEQUENCE: 325

Asp Thr Trp Gly Thr Val Cys Asp Ser Asp Phe Ser Leu Glu Ala Ala
1               5                   10                  15

Ser Val Leu Cys Arg Glu Leu Gln Cys Gly Thr Val Val Ser Leu Leu
            20                  25                  30

Gly Gly Ala His Phe Gly Glu Gly Ser Gly Gln Ile Trp Ala Glu Glu
        35                  40                  45

Phe Gln Cys
    50

<210> SEQ ID NO 326
<211> LENGTH: 21
<212> TYPE: PRT
<213> ORGANISM: Sus scrofa

<400> SEQUENCE: 326

Phe Arg Arg Cys Ser Ala His Leu Ser Ser Phe Thr Phe Ala Val Val
1               5                   10                  15

Ala Val Leu Ser Ala
            20

<210> SEQ ID NO 327
<211> LENGTH: 21
<212> TYPE: PRT
<213> ORGANISM: Sus scrofa

<400> SEQUENCE: 327

Phe Arg Arg Cys Ser Ala His Leu Ser Ser Phe Thr Phe Ala Val Val
1               5                   10                  15

Ala Val Leu Ser Ala
            20

<210> SEQ ID NO 328
<211> LENGTH: 24
<212> TYPE: PRT
<213> ORGANISM: Sus scrofa

<400> SEQUENCE: 328

Gly Glu Asn Lys Cys Ser Gly Arg Val Glu Val Lys Val Gln Glu Glu
1               5                   10                  15

Trp Gly Thr Val Cys Asn Asn Gly
            20

<210> SEQ ID NO 329
<211> LENGTH: 24
<212> TYPE: PRT
<213> ORGANISM: Sus scrofa

<400> SEQUENCE: 329

Gly Trp Asp Met Asp Val Val Ser Val Val Cys Arg Gln Leu Gly Cys
1               5                   10                  15

Pro Thr Ala Ile Lys Ala Thr Gly
            20

<210> SEQ ID NO 330
<211> LENGTH: 19
<212> TYPE: PRT
<213> ORGANISM: Sus scrofa

<400> SEQUENCE: 330

Pro Thr Ala Ile Lys Ala Thr Gly Trp Ala Asn Phe Ser Ala Gly Ser

```
1               5                   10                  15

Gly Arg Ile

<210> SEQ ID NO 331
<211> LENGTH: 19
<212> TYPE: PRT
<213> ORGANISM: Sus scrofa

<400> SEQUENCE: 331

Pro Thr Ala Ile Lys Ala Thr Gly Trp Ala Asn Phe Ser Ala Gly Ser
1               5                   10                  15

Gly Arg Ile

<210> SEQ ID NO 332
<211> LENGTH: 24
<212> TYPE: PRT
<213> ORGANISM: Sus scrofa

<400> SEQUENCE: 332

Pro Thr Ala Ile Lys Ala Thr Gly Trp Ala Asn Phe Ser Ala Gly Ser
1               5                   10                  15

Gly Arg Ile Trp Met Asp His Val
            20

<210> SEQ ID NO 333
<211> LENGTH: 24
<212> TYPE: PRT
<213> ORGANISM: Sus scrofa

<400> SEQUENCE: 333

Gly Arg Ile Trp Met Asp His Val Ser Cys Arg Gly Asn Glu Ser Ala
1               5                   10                  15

Leu Trp Asp Cys Lys His Asp Gly
            20

<210> SEQ ID NO 334
<211> LENGTH: 24
<212> TYPE: PRT
<213> ORGANISM: Sus scrofa

<400> SEQUENCE: 334

Gly Arg Ile Trp Met Asp His Val Ser Cys Arg Gly Asn Glu Ser Ala
1               5                   10                  15

Leu Trp Asp Cys Lys His Asp Gly
            20

<210> SEQ ID NO 335
<211> LENGTH: 22
<212> TYPE: PRT
<213> ORGANISM: Sus scrofa

<400> SEQUENCE: 335

Gly Ser Asp Leu Glu Met Arg Leu Val Asn Gly Gly Asn Arg Cys Leu
1               5                   10                  15

Gly Arg Ile Glu Val Lys
            20

<210> SEQ ID NO 336
<211> LENGTH: 24
<212> TYPE: PRT
<213> ORGANISM: Sus scrofa
```

```
<400> SEQUENCE: 336

Ser Val Val Cys Lys Gln Leu Glu Cys Gly Ser Ala Val Ser Phe Ser
1               5                   10                  15

Gly Ser Ala Asn Phe Gly Glu Gly
            20

<210> SEQ ID NO 337
<211> LENGTH: 24
<212> TYPE: PRT
<213> ORGANISM: Sus scrofa

<400> SEQUENCE: 337

Asp Asp Leu Val Cys Asn Gly Asn Glu Ser Ala Leu Trp Asn Cys Lys
1               5                   10                  15

His Glu Gly Trp Gly Lys His Asn
            20

<210> SEQ ID NO 338
<211> LENGTH: 24
<212> TYPE: PRT
<213> ORGANISM: Sus scrofa

<400> SEQUENCE: 338

Asp Thr Trp Gly Thr Val Cys Asp Ser Asp Phe Ser Leu Glu Ala Ala
1               5                   10                  15

Ser Val Leu Cys Arg Glu Leu Gln
            20

<210> SEQ ID NO 339
<211> LENGTH: 24
<212> TYPE: PRT
<213> ORGANISM: Sus scrofa

<400> SEQUENCE: 339

Val Ala Val Leu Ser Ala Cys Leu Val Thr Ser Ser Trp Arg Lys Arg
1               5                   10                  15

Gln Gly Ala Glu Ala Asn Gly Trp
            20

<210> SEQ ID NO 340
<211> LENGTH: 20
<212> TYPE: PRT
<213> ORGANISM: Sus scrofa

<400> SEQUENCE: 340

Val Ala Val Leu Ser Ala Cys Leu Val Thr Cys Asn Leu Ala His Cys
1               5                   10                  15

Asp Lys Lys His
            20

<210> SEQ ID NO 341
<211> LENGTH: 20
<212> TYPE: PRT
<213> ORGANISM: Sus scrofa

<400> SEQUENCE: 341

Val Ala Val Leu Ser Ala Cys Leu Val Thr Ser Ser Leu Leu Glu Glu
1               5                   10                  15

Lys Thr Arg Ser
            20
```

```
<210> SEQ ID NO 342
<211> LENGTH: 14
<212> TYPE: PRT
<213> ORGANISM: Sus scrofa

<400> SEQUENCE: 342

Val Ala Val Leu Ser Ala Cys Leu Glu Glu Lys Thr Arg Ser
1               5                   10

<210> SEQ ID NO 343
<211> LENGTH: 20
<212> TYPE: PRT
<213> ORGANISM: Sus scrofa

<400> SEQUENCE: 343

Val Ala Val Leu Ser Ala Cys Leu Val Thr Arg Ser Thr Leu Thr Asn
1               5                   10                  15

Leu Leu Val Thr
            20

<210> SEQ ID NO 344
<211> LENGTH: 33
<212> TYPE: DNA
<213> ORGANISM: Sus scrofa

<400> SEQUENCE: 344
agttctcttg gtgagtactt tgacaaattt act                              33

<210> SEQ ID NO 345
<211> LENGTH: 16
<212> TYPE: DNA
<213> ORGANISM: Sus scrofa

<400> SEQUENCE: 345
cactagttct cttggt                                                 16

<210> SEQ ID NO 346
<211> LENGTH: 10
<212> TYPE: DNA
<213> ORGANISM: Sus scrofa

<400> SEQUENCE: 346
ttctcttggt                                                        10

<210> SEQ ID NO 347
<211> LENGTH: 23
<212> TYPE: DNA
<213> ORGANISM: Sus scrofa

<400> SEQUENCE: 347
atgctatttt ttcagcccac agg                                         23

<210> SEQ ID NO 348
<211> LENGTH: 23
<212> TYPE: DNA
<213> ORGANISM: Sus scrofa

<400> SEQUENCE: 348
tttcagccca caggaaaccc agg                                         23

<210> SEQ ID NO 349
<211> LENGTH: 23
<212> TYPE: DNA
<213> ORGANISM: Sus scrofa
```

```
<400> SEQUENCE: 349
agcccacagg aaacccaggc tgg                                              23

<210> SEQ ID NO 350
<211> LENGTH: 23
<212> TYPE: DNA
<213> ORGANISM: Sus scrofa

<400> SEQUENCE: 350
aaccagcctg ggtttcctgt ggg                                              23

<210> SEQ ID NO 351
<211> LENGTH: 23
<212> TYPE: DNA
<213> ORGANISM: Sus scrofa

<400> SEQUENCE: 351
caaccagcct gggtttcctg tgg                                              23

<210> SEQ ID NO 352
<211> LENGTH: 23
<212> TYPE: DNA
<213> ORGANISM: Sus scrofa

<400> SEQUENCE: 352
cacaggaaac ccaggctggt tgg                                              23

<210> SEQ ID NO 353
<211> LENGTH: 23
<212> TYPE: DNA
<213> ORGANISM: Sus scrofa

<400> SEQUENCE: 353
aggaaaccca ggctggttgg agg                                              23

<210> SEQ ID NO 354
<211> LENGTH: 23
<212> TYPE: DNA
<213> ORGANISM: Sus scrofa

<400> SEQUENCE: 354
ggaaacccag gctggttgga ggg                                              23

<210> SEQ ID NO 355
<211> LENGTH: 23
<212> TYPE: DNA
<213> ORGANISM: Sus scrofa

<400> SEQUENCE: 355
gaaacccagg ctggttggag ggg                                              23

<210> SEQ ID NO 356
<211> LENGTH: 23
<212> TYPE: DNA
<213> ORGANISM: Sus scrofa

<400> SEQUENCE: 356
atgtcccctc caaccagcct ggg                                              23

<210> SEQ ID NO 357
<211> LENGTH: 23
<212> TYPE: DNA
```

```
<213> ORGANISM: Sus scrofa

<400> SEQUENCE: 357
aatgtcccct ccaaccagcc tgg                                              23

<210> SEQ ID NO 358
<211> LENGTH: 23
<212> TYPE: DNA
<213> ORGANISM: Sus scrofa

<400> SEQUENCE: 358 ggagggggaca ttccctgctc tgg                                             23

<210> SEQ ID NO 359
<211> LENGTH: 23
<212> TYPE: DNA
<213> ORGANISM: Sus scrofa

<400> SEQUENCE: 359
acttcaacac gaccagagca ggg                                              23

<210> SEQ ID NO 360
<211> LENGTH: 23
<212> TYPE: DNA
<213> ORGANISM: Sus scrofa

<400> SEQUENCE: 360
tacttcaaca cgaccagagc agg                                              23

<210> SEQ ID NO 361
<211> LENGTH: 23
<212> TYPE: DNA
<213> ORGANISM: Sus scrofa

<400> SEQUENCE: 361
ggtcgtgttg aagtacaaca tgg                                              23

<210> SEQ ID NO 362
<211> LENGTH: 23
<212> TYPE: DNA
<213> ORGANISM: Sus scrofa

<400> SEQUENCE: 362
aagtacaaca tggagacacg tgg                                              23

<210> SEQ ID NO 363
<211> LENGTH: 23
<212> TYPE: DNA
<213> ORGANISM: Sus scrofa

<400> SEQUENCE: 363
agtacaacat ggagacacgt ggg                                              23

<210> SEQ ID NO 364
<211> LENGTH: 23
<212> TYPE: DNA
<213> ORGANISM: Sus scrofa

<400> SEQUENCE: 364
gtacaacatg gagacacgtg ggg                                              23

<210> SEQ ID NO 365
<211> LENGTH: 23
```

```
<212> TYPE: DNA
<213> ORGANISM: Sus scrofa

<400> SEQUENCE: 365
agagaagtca gaatcacaga cgg                                         23

<210> SEQ ID NO 366
<211> LENGTH: 23
<212> TYPE: DNA
<213> ORGANISM: Sus scrofa

<400> SEQUENCE: 366
ctgtgattct gacttctctc tgg                                         23

<210> SEQ ID NO 367
<211> LENGTH: 23
<212> TYPE: DNA
<213> ORGANISM: Sus scrofa

<400> SEQUENCE: 367
tgattctgac ttctctctgg agg                                         23

<210> SEQ ID NO 368
<211> LENGTH: 23
<212> TYPE: DNA
<213> ORGANISM: Sus scrofa

<400> SEQUENCE: 368
ttctgacttc tctctggagg cgg                                         23

<210> SEQ ID NO 369
<211> LENGTH: 23
<212> TYPE: DNA
<213> ORGANISM: Sus scrofa

<400> SEQUENCE: 369
aggcggccag cgtgctgtgc agg                                         23

<210> SEQ ID NO 370
<211> LENGTH: 23
<212> TYPE: DNA
<213> ORGANISM: Sus scrofa

<400> SEQUENCE: 370
ggcggccagc gtgctgtgca ggg                                         23

<210> SEQ ID NO 371
<211> LENGTH: 23
<212> TYPE: DNA
<213> ORGANISM: Sus scrofa

<400> SEQUENCE: 371
tagttccctg cacagcacgc tgg                                         23

<210> SEQ ID NO 372
<211> LENGTH: 23
<212> TYPE: DNA
<213> ORGANISM: Sus scrofa

<400> SEQUENCE: 372
ctgtgcaggg aactacagtg cgg                                         23

<210> SEQ ID NO 373
```

```
<211> LENGTH: 23
<212> TYPE: DNA
<213> ORGANISM: Sus scrofa

<400> SEQUENCE: 373
ggaactacag tgcggcactg tgg                                          23

<210> SEQ ID NO 374
<211> LENGTH: 23
<212> TYPE: DNA
<213> ORGANISM: Sus scrofa

<400> SEQUENCE: 374
cggcactgtg gtttccctcc tgg                                          23

<210> SEQ ID NO 375
<211> LENGTH: 23
<212> TYPE: DNA
<213> ORGANISM: Sus scrofa

<400> SEQUENCE: 375
ggcactgtgg tttccctcct ggg                                          23

<210> SEQ ID NO 376
<211> LENGTH: 23
<212> TYPE: DNA
<213> ORGANISM: Sus scrofa

<400> SEQUENCE: 376
gcactgtggt ttccctcctg ggg                                          23

<210> SEQ ID NO 377
<211> LENGTH: 23
<212> TYPE: DNA
<213> ORGANISM: Sus scrofa

<400> SEQUENCE: 377
cactgtggtt tccctcctgg ggg                                          23

<210> SEQ ID NO 378
<211> LENGTH: 23
<212> TYPE: DNA
<213> ORGANISM: Sus scrofa

<400> SEQUENCE: 378
actgtggttt ccctcctggg ggg                                          23

<210> SEQ ID NO 379
<211> LENGTH: 23
<212> TYPE: DNA
<213> ORGANISM: Sus scrofa

<400> SEQUENCE: 379
aaagtgagct cccccagga ggg                                           23

<210> SEQ ID NO 380
<211> LENGTH: 23
<212> TYPE: DNA
<213> ORGANISM: Sus scrofa

<400> SEQUENCE: 380
caaagtgagc tcccccagg agg                                           23
```

```
<210> SEQ ID NO 381
<211> LENGTH: 23
<212> TYPE: DNA
<213> ORGANISM: Sus scrofa

<400> SEQUENCE: 381
ctcctggggg gagctcactt tgg                                              23

<210> SEQ ID NO 382
<211> LENGTH: 23
<212> TYPE: DNA
<213> ORGANISM: Sus scrofa

<400> SEQUENCE: 382
ctccaaagtg agctcccccc agg                                              23

<210> SEQ ID NO 383
<211> LENGTH: 23
<212> TYPE: DNA
<213> ORGANISM: Sus scrofa

<400> SEQUENCE: 383
gggggagctc actttggaga agg                                              23

<210> SEQ ID NO 384
<211> LENGTH: 23
<212> TYPE: DNA
<213> ORGANISM: Sus scrofa

<400> SEQUENCE: 384
gctcactttg gagaaggaag tgg                                              23

<210> SEQ ID NO 385
<211> LENGTH: 23
<212> TYPE: DNA
<213> ORGANISM: Sus scrofa

<400> SEQUENCE: 385
gagaaggaag tggacagatc tgg                                              23

<210> SEQ ID NO 386
<211> LENGTH: 23
<212> TYPE: DNA
<213> ORGANISM: Sus scrofa

<400> SEQUENCE: 386
agaaggaagt ggacagatct ggg                                              23

<210> SEQ ID NO 387
<211> LENGTH: 23
<212> TYPE: DNA
<213> ORGANISM: Sus scrofa

<400> SEQUENCE: 387
ggctgaagaa ttccagtgtg agg                                              23

<210> SEQ ID NO 388
<211> LENGTH: 23
<212> TYPE: DNA
<213> ORGANISM: Sus scrofa

<400> SEQUENCE: 388
gctgaagaat tccagtgtga ggg                                              23
```

<210> SEQ ID NO 389
<211> LENGTH: 23
<212> TYPE: DNA
<213> ORGANISM: Sus scrofa

<400> SEQUENCE: 389
ctgaagaatt ccagtgtgag ggg                                              23

<210> SEQ ID NO 390
<211> LENGTH: 23
<212> TYPE: DNA
<213> ORGANISM: Sus scrofa

<400> SEQUENCE: 390
gggactcgtg cccctcacac tgg                                              23

<210> SEQ ID NO 391
<211> LENGTH: 23
<212> TYPE: DNA
<213> ORGANISM: Sus scrofa

<400> SEQUENCE: 391
tactgggcag agtgaaaggt ggg                                              23

<210> SEQ ID NO 392
<211> LENGTH: 23
<212> TYPE: DNA
<213> ORGANISM: Sus scrofa

<400> SEQUENCE: 392
ctactgggca gagtgaaagg tgg                                              23

<210> SEQ ID NO 393
<211> LENGTH: 23
<212> TYPE: DNA
<213> ORGANISM: Sus scrofa

<400> SEQUENCE: 393
gtgctactgg gcagagtgaa agg                                              23

<210> SEQ ID NO 394
<211> LENGTH: 23
<212> TYPE: DNA
<213> ORGANISM: Sus scrofa

<400> SEQUENCE: 394
cgtcagggcg gggtgctact ggg                                              23

<210> SEQ ID NO 395
<211> LENGTH: 23
<212> TYPE: DNA
<213> ORGANISM: Sus scrofa

<400> SEQUENCE: 395
ccagtagcac cccgccctga cgg                                              23

<210> SEQ ID NO 396
<211> LENGTH: 23
<212> TYPE: DNA
<213> ORGANISM: Sus scrofa

<400> SEQUENCE: 396
ccgtcagggc ggggtgctac tgg                                              23

```
<210> SEQ ID NO 397
<211> LENGTH: 23
<212> TYPE: DNA
<213> ORGANISM: Sus scrofa

<400> SEQUENCE: 397
cagtagcacc ccgccctgac ggg                                            23

<210> SEQ ID NO 398
<211> LENGTH: 23
<212> TYPE: DNA
<213> ORGANISM: Sus scrofa

<400> SEQUENCE: 398
ctacatgtcc cgtcagggcg ggg                                            23

<210> SEQ ID NO 399
<211> LENGTH: 23
<212> TYPE: DNA
<213> ORGANISM: Sus scrofa

<400> SEQUENCE: 399
gctacatgtc ccgtcagggc ggg                                            23

<210> SEQ ID NO 400
<211> LENGTH: 23
<212> TYPE: DNA
<213> ORGANISM: Sus scrofa

<400> SEQUENCE: 400
ggctacatgt cccgtcaggg cgg                                            23

<210> SEQ ID NO 401
<211> LENGTH: 23
<212> TYPE: DNA
<213> ORGANISM: Sus scrofa

<400> SEQUENCE: 401
tgtggctaca tgtcccgtca ggg                                            23

<210> SEQ ID NO 402
<211> LENGTH: 23
<212> TYPE: DNA
<213> ORGANISM: Sus scrofa

<400> SEQUENCE: 402
ctgtggctac atgtcccgtc agg                                            23

<210> SEQ ID NO 403
<211> LENGTH: 23
<212> TYPE: DNA
<213> ORGANISM: Sus scrofa

<400> SEQUENCE: 403
acgggacatg tagccacagc agg                                            23

<210> SEQ ID NO 404
<211> LENGTH: 23
<212> TYPE: DNA
<213> ORGANISM: Sus scrofa

<400> SEQUENCE: 404
```
cgggacatgt agccacagca ggg                                          23

<210> SEQ ID NO 405
<211> LENGTH: 23
<212> TYPE: DNA
<213> ORGANISM: Sus scrofa

<400> SEQUENCE: 405
tgtagccaca gcagggacgt cgg                                          23

<210> SEQ ID NO 406
<211> LENGTH: 23
<212> TYPE: DNA
<213> ORGANISM: Sus scrofa

<400> SEQUENCE: 406
ctacgccgac gtccctgctg tgg                                          23

<210> SEQ ID NO 407
<211> LENGTH: 25
<212> TYPE: DNA
<213> ORGANISM: Sus scrofa

<400> SEQUENCE: 407
cacaggaaac ccaggctggt tggag                                        25

<210> SEQ ID NO 408
<211> LENGTH: 25
<212> TYPE: DNA
<213> ORGANISM: Sus scrofa

<400> SEQUENCE: 408
aggaaaccca ggctggttgg agggg                                        25

<210> SEQ ID NO 409
<211> LENGTH: 25
<212> TYPE: DNA
<213> ORGANISM: Sus scrofa

<400> SEQUENCE: 409
ggtcgtgttg aagtacaaca tggag                                        25

<210> SEQ ID NO 410
<211> LENGTH: 25
<212> TYPE: DNA
<213> ORGANISM: Sus scrofa

<400> SEQUENCE: 410
aagtacaaca tggagacacg tgggg                                        25

<210> SEQ ID NO 411
<211> LENGTH: 25
<212> TYPE: DNA
<213> ORGANISM: Sus scrofa

<400> SEQUENCE: 411
agagaagtca gaatcacaga cggtg                                        25

<210> SEQ ID NO 412
<211> LENGTH: 25
<212> TYPE: DNA
<213> ORGANISM: Sus scrofa

<400> SEQUENCE: 412

-continued ctgtgattct gacttctctc tggag 25

<210> SEQ ID NO 413
<211> LENGTH: 25
<212> TYPE: DNA
<213> ORGANISM: Sus scrofa

<400> SEQUENCE: 413
tgattctgac ttctctctgg aggcg 25

<210> SEQ ID NO 414
<211> LENGTH: 25
<212> TYPE: DNA
<213> ORGANISM: Sus scrofa

<400> SEQUENCE: 414
cggcactgtg gtttccctcc tgggg 25

<210> SEQ ID NO 415
<211> LENGTH: 25
<212> TYPE: DNA
<213> ORGANISM: Sus scrofa

<400> SEQUENCE: 415
ggcactgtgg tttccctcct ggggg 25

<210> SEQ ID NO 416
<211> LENGTH: 25
<212> TYPE: DNA
<213> ORGANISM: Sus scrofa

<400> SEQUENCE: 416
gcactgtggt ttccctcctg ggggg 25

<210> SEQ ID NO 417
<211> LENGTH: 25
<212> TYPE: DNA
<213> ORGANISM: Sus scrofa

<400> SEQUENCE: 417
actgtggttt ccctcctggg gggag 25

<210> SEQ ID NO 418
<211> LENGTH: 25
<212> TYPE: DNA
<213> ORGANISM: Sus scrofa

<400> SEQUENCE: 418
ctcctggggg gagctcactt tggag 25

<210> SEQ ID NO 419
<211> LENGTH: 25
<212> TYPE: DNA
<213> ORGANISM: Sus scrofa

<400> SEQUENCE: 419
ctccaaagtg agctcccccc aggag 25

<210> SEQ ID NO 420
<211> LENGTH: 25
<212> TYPE: DNA
<213> ORGANISM: Sus scrofa

```
<400> SEQUENCE: 420
ggctgaagaa ttccagtgtg agggg                                          25

<210> SEQ ID NO 421
<211> LENGTH: 25
<212> TYPE: DNA
<213> ORGANISM: Sus scrofa

<400> SEQUENCE: 421
gtgctactgg gcagagtgaa aggtg                                          25

<210> SEQ ID NO 422
<211> LENGTH: 25
<212> TYPE: DNA
<213> ORGANISM: Sus scrofa

<400> SEQUENCE: 422
ctacatgtcc cgtcagggcg gggtg                                          25

<210> SEQ ID NO 423
<211> LENGTH: 25
<212> TYPE: DNA
<213> ORGANISM: Sus scrofa

<400> SEQUENCE: 423
ggctacatgt cccgtcaggg cgggg                                          25

<210> SEQ ID NO 424
<211> LENGTH: 25
<212> TYPE: DNA
<213> ORGANISM: Sus scrofa

<400> SEQUENCE: 424
tgtggctaca tgtcccgtca gggcg                                          25

<210> SEQ ID NO 425
<211> LENGTH: 25
<212> TYPE: DNA
<213> ORGANISM: Sus scrofa

<400> SEQUENCE: 425
tgtagccaca gcagggacgt cggcg                                          25

<210> SEQ ID NO 426
<211> LENGTH: 100
<212> TYPE: DNA
<213> ORGANISM: Sus scrofa

<400> SEQUENCE: 426
gaatgaagta ggcaaatact caaaggaaag agaaagcatg ctccaagaat ggtagggtta    60
ggtagtcaca gacatctttt taaagccctg tctccttcca                         100

<210> SEQ ID NO 427
<211> LENGTH: 100
<212> TYPE: DNA
<213> ORGANISM: Sus scrofa

<400> SEQUENCE: 427
atgaatgaag taggcaaata ctcaaaggaa agagaaagca tgctccaaga ggtagggtta    60
ggtagtcaca gacatctttt taaagccctg tctccttcca                         100
```

```
<210> SEQ ID NO 428
<211> LENGTH: 100
<212> TYPE: DNA
<213> ORGANISM: Sus scrofa

<400> SEQUENCE: 428
ggcaaatact caaaggaaag agaaagcatg ctccaagaat tatgggttcc ggtagggtta      60
ggtagtcaca gacatctttt taaagccctg tctccttcca                          100

<210> SEQ ID NO 429
<211> LENGTH: 100
<212> TYPE: DNA
<213> ORGANISM: Sus scrofa

<400> SEQUENCE: 429
agaattatgg gttccagaag gcaaagtccc agaattgtct ccagggaagg ggtagggtta     60
ggtagtcaca gacatctttt taaagccctg tctccttcca                          100

<210> SEQ ID NO 430
<211> LENGTH: 100
<212> TYPE: DNA
<213> ORGANISM: Sus scrofa

<400> SEQUENCE: 430
agaattgtct ccagggaagg acagggaggt ctagaatcgg ctaagcccac ggtagggtta     60
ggtagtcaca gacatctttt taaagccctg tctccttcca                          100

<210> SEQ ID NO 431
<211> LENGTH: 100
<212> TYPE: DNA
<213> ORGANISM: Sus scrofa

<400> SEQUENCE: 431
gaatgaagta ggcaaatact caaaggaaag agaaagcatg ctccaagaat gtagggttag     60
gtagtcacag acatcttttt aaagccctgt ctccttccag                          100

<210> SEQ ID NO 432
<211> LENGTH: 100
<212> TYPE: DNA
<213> ORGANISM: Sus scrofa

<400> SEQUENCE: 432
atgaatgaag taggcaaata ctcaaaggaa agagaaagca tgctccaaga gtagggttag     60
gtagtcacag acatcttttt aaagccctgt ctccttccag                          100

<210> SEQ ID NO 433
<211> LENGTH: 100
<212> TYPE: DNA
<213> ORGANISM: Sus scrofa

<400> SEQUENCE: 433
ggcaaatact caaaggaaag agaaagcatg ctccaagaat tatgggttcc gtagggttag     60
gtagtcacag acatcttttt aaagccctgt ctccttccag                          100

<210> SEQ ID NO 434
<211> LENGTH: 100
<212> TYPE: DNA
<213> ORGANISM: Sus scrofa

<400> SEQUENCE: 434
```

```
agaattatgg gttccagaag gcaaagtccc agaattgtct ccagggaagg gtagggttag      60
gtagtcacag acatctttt aaagccctgt ctccttccag                            100
```

<210> SEQ ID NO 435
<211> LENGTH: 100
<212> TYPE: DNA
<213> ORGANISM: Sus scrofa

<400> SEQUENCE: 435

```
agaattgtct ccagggaagg acagggaggt ctagaatcgg ctaagcccac gtagggttag      60
gtagtcacag acatctttt aaagccctgt ctccttccag                            100
```

<210> SEQ ID NO 436
<211> LENGTH: 100
<212> TYPE: DNA
<213> ORGANISM: Sus scrofa

<400> SEQUENCE: 436

```
gaatgaagta ggcaaatact caaaggaaag agaaagcatg ctccaagaat agagggtagg      60
gttaggtagt cacagacatc tttttaaagc cctgtctcct                           100
```

<210> SEQ ID NO 437
<211> LENGTH: 100
<212> TYPE: DNA
<213> ORGANISM: Sus scrofa

<400> SEQUENCE: 437

```
atgaatgaag taggcaaata ctcaaaggaa agagaaagca tgctccaaga agagggtagg      60
gttaggtagt cacagacatc tttttaaagc cctgtctcct                           100
```

<210> SEQ ID NO 438
<211> LENGTH: 100
<212> TYPE: DNA
<213> ORGANISM: Sus scrofa

<400> SEQUENCE: 438

```
ggcaaatact caaaggaaag agaaagcatg ctccaagaat tatgggttcc agagggtagg      60
gttaggtagt cacagacatc tttttaaagc cctgtctcct                           100
```

<210> SEQ ID NO 439
<211> LENGTH: 100
<212> TYPE: DNA
<213> ORGANISM: Sus scrofa

<400> SEQUENCE: 439

```
agaattatgg gttccagaag gcaaagtccc agaattgtct ccagggaagg agagggtagg      60
gttaggtagt cacagacatc tttttaaagc cctgtctcct                           100
```

<210> SEQ ID NO 440
<211> LENGTH: 100
<212> TYPE: DNA
<213> ORGANISM: Sus scrofa

<400> SEQUENCE: 440

```
agaattgtct ccagggaagg acagggaggt ctagaatcgg ctaagcccac agagggtagg      60
gttaggtagt cacagacatc tttttaaagc cctgtctcct                           100
```

<210> SEQ ID NO 441
<211> LENGTH: 100

```
<212> TYPE: DNA
<213> ORGANISM: Sus scrofa

<400> SEQUENCE: 441
atgtcttctg ctttatttct ggtgtgcctt tgactccaga ttacagtaaa ggtagggtta    60
ggtagtcaca gacatctttt taaagccctg tctccttcca                         100

<210> SEQ ID NO 442
<211> LENGTH: 100
<212> TYPE: DNA
<213> ORGANISM: Sus scrofa

<400> SEQUENCE: 442
ttatttctgg tgtgcctttg actccagatt acagtaaatg gaggactgag ggtagggtta    60
ggtagtcaca gacatctttt taaagccctg tctccttcca                         100

<210> SEQ ID NO 443
<211> LENGTH: 100
<212> TYPE: DNA
<213> ORGANISM: Sus scrofa

<400> SEQUENCE: 443
tggaggactg agtatagggc taaaaagtag agagaatgga tgcatattat ggtagggtta    60
ggtagtcaca gacatctttt taaagccctg tctccttcca                         100

<210> SEQ ID NO 444
<211> LENGTH: 100
<212> TYPE: DNA
<213> ORGANISM: Sus scrofa

<400> SEQUENCE: 444
atgcatatta tctgtggtct ccaatgtgat gaatgaagta ggcaaatact ggtagggtta    60
ggtagtcaca gacatctttt taaagccctg tctccttcca                         100

<210> SEQ ID NO 445
<211> LENGTH: 100
<212> TYPE: DNA
<213> ORGANISM: Sus scrofa

<400> SEQUENCE: 445
atgtcttctg ctttatttct ggtgtgcctt tgactccaga ttacagtaaa gtagggttag    60
gtagtcacag acatcttttt aaagccctgt ctccttccag                         100

<210> SEQ ID NO 446
<211> LENGTH: 100
<212> TYPE: DNA
<213> ORGANISM: Sus scrofa

<400> SEQUENCE: 446
ttatttctgg tgtgcctttg actccagatt acagtaaatg gaggactgag gtagggttag    60
gtagtcacag acatcttttt aaagccctgt ctccttccag                         100

<210> SEQ ID NO 447
<211> LENGTH: 100
<212> TYPE: DNA
<213> ORGANISM: Sus scrofa

<400> SEQUENCE: 447
tggaggactg agtatagggc taaaaagtag agagaatgga tgcatattat gtagggttag    60
```
gtagtcacag acatctttt aaagccctgt ctccttccag                                              100

<210> SEQ ID NO 448
<211> LENGTH: 100
<212> TYPE: DNA
<213> ORGANISM: Sus scrofa

<400> SEQUENCE: 448
atgcatatta tctgtggtct ccaatgtgat gaatgaagta ggcaaatact gtagggttag        60
gtagtcacag acatctttt aaagccctgt ctccttccag                              100

<210> SEQ ID NO 449
<211> LENGTH: 100
<212> TYPE: DNA
<213> ORGANISM: Sus scrofa

<400> SEQUENCE: 449
atgtcttctg ctttatttct ggtgtgcctt tgactccaga ttacagtaaa agagggtagg        60
gttaggtagt cacagacatc tttttaaagc cctgtctcct                             100

<210> SEQ ID NO 450
<211> LENGTH: 100
<212> TYPE: DNA
<213> ORGANISM: Sus scrofa

<400> SEQUENCE: 450
ttatttctgg tgtgcctttg actccagatt acagtaaatg gaggactgag agagggtagg        60
gttaggtagt cacagacatc tttttaaagc cctgtctcct                             100

<210> SEQ ID NO 451
<211> LENGTH: 100
<212> TYPE: DNA
<213> ORGANISM: Sus scrofa

<400> SEQUENCE: 451
tggaggactg agtatagggc taaaaagtag agagaatgga tgcatattat agagggtagg        60
gttaggtagt cacagacatc tttttaaagc cctgtctcct                             100

<210> SEQ ID NO 452
<211> LENGTH: 100
<212> TYPE: DNA
<213> ORGANISM: Sus scrofa

<400> SEQUENCE: 452
atgcatatta tctgtggtct ccaatgtgat gaatgaagta ggcaaatact agagggtagg        60
gttaggtagt cacagacatc tttttaaagc cctgtctcct                             100

<210> SEQ ID NO 453
<211> LENGTH: 100
<212> TYPE: DNA
<213> ORGANISM: Sus scrofa

<400> SEQUENCE: 453
catgaatggc ttccctttct cacttttcac tctctggctt actcctatca ggtagggtta        60
ggtagtcaca gacatctttt taaagccctg tctccttcca                             100

<210> SEQ ID NO 454
<211> LENGTH: 100
<212> TYPE: DNA
<213> ORGANISM: Sus scrofa

<400> SEQUENCE: 454
ttccctttct cacttttcac tctctggctt actcctatca tgaaggaaaa ggtagggtta       60
ggtagtcaca gacatctttt taaagccctg tctccttcca                            100

<210> SEQ ID NO 455
<211> LENGTH: 100
<212> TYPE: DNA
<213> ORGANISM: Sus scrofa

<400> SEQUENCE: 455
catgaatggc ttccctttct cacttttcac tctctggctt actcctatca gtagggttag       60
gtagtcacag acatctttt aaagccctgt ctccttccag                             100

<210> SEQ ID NO 456
<211> LENGTH: 100
<212> TYPE: DNA
<213> ORGANISM: Sus scrofa

<400> SEQUENCE: 456
ttccctttct cacttttcac tctctggctt actcctatca tgaaggaaaa gtagggttag       60
gtagtcacag acatctttt aaagccctgt ctccttccag                             100

<210> SEQ ID NO 457
<211> LENGTH: 100
<212> TYPE: DNA
<213> ORGANISM: Sus scrofa

<400> SEQUENCE: 457
catgaatggc ttccctttct cacttttcac tctctggctt actcctatca agagggtagg       60
gttaggtagt cacagacatc tttttaaagc cctgtctcct                            100

<210> SEQ ID NO 458
<211> LENGTH: 100
<212> TYPE: DNA
<213> ORGANISM: Sus scrofa

<400> SEQUENCE: 458
ttccctttct cacttttcac tctctggctt actcctatca tgaaggaaaa agagggtagg       60
gttaggtagt cacagacatc tttttaaagc cctgtctcct                            100

<210> SEQ ID NO 459
<211> LENGTH: 100
<212> TYPE: DNA
<213> ORGANISM: Sus scrofa

<400> SEQUENCE: 459
tattggaatc atattctccc tcaccgaaat gctatttttt cagcccacag gtgattctga       60
cttctctctg gaggcggcca gcgtgctgtg cagggaacta                            100

<210> SEQ ID NO 460
<211> LENGTH: 100
<212> TYPE: DNA
<213> ORGANISM: Sus scrofa

<400> SEQUENCE: 460
tattggaatc atattctccc tcaccgaaat gctatttttt cagcccacag gtgaggggca       60
cgagtcccac ctttcactct gcccagtagc accccgccct                            100

```
<210> SEQ ID NO 461
<211> LENGTH: 100
<212> TYPE: DNA
<213> ORGANISM: Sus scrofa

<400> SEQUENCE: 461
ggaatcatat tctccctcac cgaaatgcta ttttttcagc ccacaggaaa tgaggggcac    60
gagtcccacc tttcactctg cccagtagca ccccgccctg                         100

<210> SEQ ID NO 462
<211> LENGTH: 100
<212> TYPE: DNA
<213> ORGANISM: Sus scrofa

<400> SEQUENCE: 462
ggaatcatat tctccctcac cgaaatgcta ttttttcagc ccacaggaaa tgaggggcac    60
gagtcccacc tttcactctg cccagtagca ccccgccctg                         100

<210> SEQ ID NO 463
<211> LENGTH: 100
<212> TYPE: DNA
<213> ORGANISM: Sus scrofa

<400> SEQUENCE: 463
ggaatcatat tctccctcac cgaaatgcta ttttttcagc ccacaggaaa tgacgggaca    60
tgtagccaca gcagggacgt cggcgtagtc tgctcaagtg                         100

<210> SEQ ID NO 464
<211> LENGTH: 100
<212> TYPE: DNA
<213> ORGANISM: Sus scrofa

<400> SEQUENCE: 464
attctccctc accgaaatgc tattttttca gcccacagga aacccaggct gtgattctga    60
cttctctctg gaggcggcca gcgtgctgtg cagggaacta                         100

<210> SEQ ID NO 465
<211> LENGTH: 100
<212> TYPE: DNA
<213> ORGANISM: Sus scrofa

<400> SEQUENCE: 465
attctccctc accgaaatgc tattttttca gcccacagga aacccaggct gtgaggggca    60
cgagtcccac ctttcactct gcccagtagc accccgccct                         100

<210> SEQ ID NO 466
<211> LENGTH: 100
<212> TYPE: DNA
<213> ORGANISM: Sus scrofa

<400> SEQUENCE: 466
attctccctc accgaaatgc tattttttca gcccacagga aacccaggct ctgacgggac    60
atgtagccac agcagggacg tcggcgtagt ctgctcaagt                         100

<210> SEQ ID NO 467
<211> LENGTH: 100
<212> TYPE: DNA
<213> ORGANISM: Sus scrofa

<400> SEQUENCE: 467
```

```
ctccctcacc gaaatgctat tttttcagcc cacaggaaac ccaggctggt gtgattctga    60
cttctctctg gaggcggcca gcgtgctgtg cagggaacta                         100

<210> SEQ ID NO 468
<211> LENGTH: 100
<212> TYPE: DNA
<213> ORGANISM: Sus scrofa

<400> SEQUENCE: 468
ctccctcacc gaaatgctat tttttcagcc cacaggaaac ccaggctggt gtgaggggca    60
cgagtcccac ctttcactct gcccagtagc accccgccct                         100

<210> SEQ ID NO 469
<211> LENGTH: 100
<212> TYPE: DNA
<213> ORGANISM: Sus scrofa

<400> SEQUENCE: 469
ctccctcacc gaaatgctat tttttcagcc cacaggaaac ccaggctggt ctgacgggac    60
atgtagccac agcagggacg tcggcgtagt ctgctcaagt                         100

<210> SEQ ID NO 470
<211> LENGTH: 100
<212> TYPE: DNA
<213> ORGANISM: Sus scrofa

<400> SEQUENCE: 470
tccctcaccg aaatgctatt ttttcagccc acaggaaacc caggctggtt tgagggcac    60 gagtcccacc tttcactctg cccagtagca ccccgccctg                         100

<210> SEQ ID NO 471
<211> LENGTH: 100
<212> TYPE: DNA
<213> ORGANISM: Sus scrofa

<400> SEQUENCE: 471
tccctcaccg aaatgctatt ttttcagccc acaggaaacc caggctggtt tgagggcac    60 gagtcccacc tttcactctg cccagtagca ccccgccctg                         100

<210> SEQ ID NO 472
<211> LENGTH: 100
<212> TYPE: DNA
<213> ORGANISM: Sus scrofa

<400> SEQUENCE: 472
tccctcaccg aaatgctatt ttttcagccc acaggaaacc caggctggtt tgacgggaca    60
tgtagccaca gcagggacgt cggcgtagtc tgctcaagtg                         100

<210> SEQ ID NO 473
<211> LENGTH: 100
<212> TYPE: DNA
<213> ORGANISM: Sus scrofa

<400> SEQUENCE: 473 atttttttcag cccacaggaa acccaggctg gttggagggg acattccctg acatggagac    60
acgtggggca ccgtctgtga ttctgacttc tctctggagg                         100

<210> SEQ ID NO 474
```

```
<211> LENGTH: 100
<212> TYPE: DNA
<213> ORGANISM: Sus scrofa

<400> SEQUENCE: 474
attttttcag cccacaggaa acccaggctg gttggagggg acattccctg acgtggggca      60
ccgtctgtga ttctgacttc tctctggagg cggccagcgt                            100

<210> SEQ ID NO 475
<211> LENGTH: 100
<212> TYPE: DNA
<213> ORGANISM: Sus scrofa

<400> SEQUENCE: 475
attttttcag cccacaggaa acccaggctg gttggagggg acattccctg aggcggccag      60
cgtgctgtgc agggaactac agtgcggcac tgtggtttcc                            100

<210> SEQ ID NO 476
<211> LENGTH: 100
<212> TYPE: DNA
<213> ORGANISM: Sus scrofa

<400> SEQUENCE: 476
attttttcag cccacaggaa acccaggctg gttggagggg acattccctg aagtggacag      60
atctgggctg aagaattcca gtgtgagggg cacgagtccc                            100

<210> SEQ ID NO 477
<211> LENGTH: 100
<212> TYPE: DNA
<213> ORGANISM: Sus scrofa

<400> SEQUENCE: 477
attttttcag cccacaggaa acccaggctg gttggagggg acattccctg agcaccccgc      60
cctgacggga catgtagcca cagcagggac gtcggcgtag                            100

<210> SEQ ID NO 478
<211> LENGTH: 100
<212> TYPE: DNA
<213> ORGANISM: Sus scrofa

<400> SEQUENCE: 478
attttttcag cccacaggaa acccaggctg gttggagggg acattccctg ctgacgggac      60
atgtagccac agcagggacg tcggcgtagt ctgctcaagt                            100

<210> SEQ ID NO 479
<211> LENGTH: 100
<212> TYPE: DNA
<213> ORGANISM: Sus scrofa

<400> SEQUENCE: 479 tttttttcagc ccacaggaaa cccaggctgg ttggagggga cattccctgc tgaggggcac     60
gagtcccacc tttcactctg cccagtagca ccccgccctg                            100

<210> SEQ ID NO 480
<211> LENGTH: 100
<212> TYPE: DNA
<213> ORGANISM: Sus scrofa

<400> SEQUENCE: 480 tttttttcagc ccacaggaaa cccaggctgg ttggagggga cattccctgc tgaggggcac     60
```

```
gagtcccacc tttcactctg cccagtagca ccccgccctg                          100
```

<210> SEQ ID NO 481
<211> LENGTH: 100
<212> TYPE: DNA
<213> ORGANISM: Sus scrofa

<400> SEQUENCE: 481

```
tttttcagc ccacaggaaa cccaggctgg ttggagggga cattccctgc tgacgggaca     60
tgtagccaca gcagggacgt cggcgtagtc tgctcaagtg                         100
```

<210> SEQ ID NO 482
<211> LENGTH: 100
<212> TYPE: DNA
<213> ORGANISM: Sus scrofa

<400> SEQUENCE: 482

```
tttttcagcc cacaggaaac ccaggctggt tggaggggac attccctgct aggcggccag    60
cgtgctgtgc agggaactac agtgcggcac tgtggtttcc                         100
```

<210> SEQ ID NO 483
<211> LENGTH: 100
<212> TYPE: DNA
<213> ORGANISM: Sus scrofa

<400> SEQUENCE: 483

```
tttttcagcc cacaggaaac ccaggctggt tggaggggac attccctgct aagtggacag    60
atctgggctg aagaattcca gtgtgagggg cacgagtccc                         100
```

<210> SEQ ID NO 484
<211> LENGTH: 100
<212> TYPE: DNA
<213> ORGANISM: Sus scrofa

<400> SEQUENCE: 484

```
tttttcagcc cacaggaaac ccaggctggt tggaggggac attccctgct gaggggcacg    60
agtcccacct ttcactctgc ccagtagcac cccgccctga                         100
```

<210> SEQ ID NO 485
<211> LENGTH: 100
<212> TYPE: DNA
<213> ORGANISM: Sus scrofa

<400> SEQUENCE: 485

```
tttttcagcc cacaggaaac ccaggctggt tggaggggac attccctgct agcaccccgc    60
cctgacggga catgtagcca cagcagggac gtcggcgtag                         100
```

<210> SEQ ID NO 486
<211> LENGTH: 100
<212> TYPE: DNA
<213> ORGANISM: Sus scrofa

<400> SEQUENCE: 486

```
tttttcagcc cacaggaaac ccaggctggt tggaggggac attccctgct gacgggacat    60
gtagccacag cagggacgtc ggcgtagtct gctcaagtga                         100
```

<210> SEQ ID NO 487
<211> LENGTH: 100
<212> TYPE: DNA

<213> ORGANISM: Sus scrofa

<400> SEQUENCE: 487
cccaggctgg ttggagggga cattccctgc tctggtcgtg ttgaagtaca gtgattctga     60
cttctctctg gaggcggcca gcgtgctgtg cagggaacta                         100

<210> SEQ ID NO 488
<211> LENGTH: 100
<212> TYPE: DNA
<213> ORGANISM: Sus scrofa

<400> SEQUENCE: 488
cccaggctgg ttggagggga cattccctgc tctggtcgtg ttgaagtaca gtgaggggca     60
cgagtcccac ctttcactct gcccagtagc accccgccct                         100

<210> SEQ ID NO 489
<211> LENGTH: 100
<212> TYPE: DNA
<213> ORGANISM: Sus scrofa

<400> SEQUENCE: 489
ttggagggga cattccctgc tctggtcgtg ttgaagtaca acatggagac tgagggcac     60 gagtcccacc tttcactctg cccagtagca ccccgccctg                         100

<210> SEQ ID NO 490
<211> LENGTH: 100
<212> TYPE: DNA
<213> ORGANISM: Sus scrofa

<400> SEQUENCE: 490
ttggagggga cattccctgc tctggtcgtg ttgaagtaca acatggagac tgagggcac     60 gagtcccacc tttcactctg cccagtagca ccccgccctg                         100

<210> SEQ ID NO 491
<211> LENGTH: 100
<212> TYPE: DNA
<213> ORGANISM: Sus scrofa

<400> SEQUENCE: 491
ttggagggga cattccctgc tctggtcgtg ttgaagtaca acatggagac tgacgggaca     60
tgtagccaca gcagggacgt cggcgtagtc tgctcaagtg                         100

<210> SEQ ID NO 492
<211> LENGTH: 100
<212> TYPE: DNA
<213> ORGANISM: Sus scrofa

<400> SEQUENCE: 492 ggagggggaca ttccctgctc tggtcgtgtt gaagtacaac atggagacac gtgattctga     60
cttctctctg gaggcggcca gcgtgctgtg cagggaacta                         100

<210> SEQ ID NO 493
<211> LENGTH: 100
<212> TYPE: DNA
<213> ORGANISM: Sus scrofa

<400> SEQUENCE: 493 ggagggggaca ttccctgctc tggtcgtgtt gaagtacaac atggagacac gtgaggggca     60
cgagtcccac ctttcactct gcccagtagc accccgccct                         100

<210> SEQ ID NO 494
<211> LENGTH: 100
<212> TYPE: DNA
<213> ORGANISM: Sus scrofa

<400> SEQUENCE: 494 ggagggggaca ttccctgctc tggtcgtgtt gaagtacaac atggagacac ctgacgggac    60
atgtagccac agcagggacg tcggcgtagt ctgctcaagt                          100

<210> SEQ ID NO 495
<211> LENGTH: 100
<212> TYPE: DNA
<213> ORGANISM: Sus scrofa

<400> SEQUENCE: 495
ctgctctggt cgtgttgaag tacaacatgg agacacgtgg ggcaccgtct aggcggccag    60
cgtgctgtgc agggaactac agtgcggcac tgtggtttcc                          100

<210> SEQ ID NO 496
<211> LENGTH: 100
<212> TYPE: DNA
<213> ORGANISM: Sus scrofa

<400> SEQUENCE: 496
ctgctctggt cgtgttgaag tacaacatgg agacacgtgg ggcaccgtct aagtggacag    60
atctgggctg aagaattcca gtgtgagggg cacgagtccc                          100

<210> SEQ ID NO 497
<211> LENGTH: 100
<212> TYPE: DNA
<213> ORGANISM: Sus scrofa

<400> SEQUENCE: 497
ctgctctggt cgtgttgaag tacaacatgg agacacgtgg ggcaccgtct gaggggcacg    60
agtcccacct ttcactctgc ccagtagcac cccgccctga                          100

<210> SEQ ID NO 498
<211> LENGTH: 100
<212> TYPE: DNA
<213> ORGANISM: Sus scrofa

<400> SEQUENCE: 498
ctgctctggt cgtgttgaag tacaacatgg agacacgtgg ggcaccgtct agcaccccgc    60
cctgacggga catgtagcca cagcagggac gtcggcgtag                          100

<210> SEQ ID NO 499
<211> LENGTH: 100
<212> TYPE: DNA
<213> ORGANISM: Sus scrofa

<400> SEQUENCE: 499
ctgctctggt cgtgttgaag tacaacatgg agacacgtgg ggcaccgtct gacgggacat    60
gtagccacag cagggacgtc ggcgtagtct gctcaagtga                          100

<210> SEQ ID NO 500
<211> LENGTH: 100
<212> TYPE: DNA
<213> ORGANISM: Sus scrofa

<400> SEQUENCE: 500
tgaagtacaa catggagaca cgtggggcac cgtctgtgat tctgacttct aggcggccag    60
cgtgctgtgc agggaactac agtgcggcac tgtggtttcc                         100

<210> SEQ ID NO 501
<211> LENGTH: 100
<212> TYPE: DNA
<213> ORGANISM: Sus scrofa

<400> SEQUENCE: 501
tgaagtacaa catggagaca cgtggggcac cgtctgtgat tctgacttct aagtggacag    60
atctgggctg aagaattcca gtgtgagggg cacgagtccc                         100

<210> SEQ ID NO 502
<211> LENGTH: 100
<212> TYPE: DNA
<213> ORGANISM: Sus scrofa

<400> SEQUENCE: 502
tgaagtacaa catggagaca cgtggggcac cgtctgtgat tctgacttct gaggggcacg    60
agtcccacct ttcactctgc ccagtagcac cccgccctga                         100

<210> SEQ ID NO 503
<211> LENGTH: 100
<212> TYPE: DNA
<213> ORGANISM: Sus scrofa

<400> SEQUENCE: 503
tgaagtacaa catggagaca cgtggggcac cgtctgtgat tctgacttct agcaccccgc    60
cctgacggga catgtagcca cagcagggac gtcggcgtag                         100

<210> SEQ ID NO 504
<211> LENGTH: 100
<212> TYPE: DNA
<213> ORGANISM: Sus scrofa

<400> SEQUENCE: 504
tgaagtacaa catggagaca cgtggggcac cgtctgtgat tctgacttct gacgggacat    60
gtagccacag cagggacgtc ggcgtagtct gctcaagtga                         100

<210> SEQ ID NO 505
<211> LENGTH: 100
<212> TYPE: DNA
<213> ORGANISM: Sus scrofa

<400> SEQUENCE: 505
tccctcaccg aaatgctatt ttttcagccc acaggaaacc caggctggtt ctgtggtttc    60
cctcctgggg ggagctcact ttggagaagg aagtggacag                         100

<210> SEQ ID NO 506
<211> LENGTH: 3
<212> TYPE: PRT
<213> ORGANISM: Sus scrofa

<400> SEQUENCE: 506

Ala His Arg
1

<210> SEQ ID NO 507

```
<211> LENGTH: 4
<212> TYPE: PRT
<213> ORGANISM: Sus scrofa

<400> SEQUENCE: 507

Ala His Arg Lys
1

<210> SEQ ID NO 508
<211> LENGTH: 7
<212> TYPE: PRT
<213> ORGANISM: Sus scrofa

<400> SEQUENCE: 508

Ala His Arg Lys Pro Arg Leu
1               5

<210> SEQ ID NO 509
<211> LENGTH: 8
<212> TYPE: PRT
<213> ORGANISM: Sus scrofa

<400> SEQUENCE: 509

Ala His Arg Lys Pro Arg Leu Val
1               5

<210> SEQ ID NO 510
<211> LENGTH: 13
<212> TYPE: PRT
<213> ORGANISM: Sus scrofa

<400> SEQUENCE: 510

Ala His Arg Lys Pro Arg Leu Val Gly Gly Asp Ile Pro
1               5                   10

<210> SEQ ID NO 511
<211> LENGTH: 14
<212> TYPE: PRT
<213> ORGANISM: Sus scrofa

<400> SEQUENCE: 511

Ala His Arg Lys Pro Arg Leu Val Gly Gly Asp Ile Pro Cys
1               5                   10

<210> SEQ ID NO 512
<211> LENGTH: 21
<212> TYPE: PRT
<213> ORGANISM: Sus scrofa

<400> SEQUENCE: 512

Ala His Arg Lys Pro Arg Leu Val Gly Gly Asp Ile Pro Cys Ser Gly
1               5                   10                  15

Arg Val Glu Val Gln
            20

<210> SEQ ID NO 513
<211> LENGTH: 24
<212> TYPE: PRT
<213> ORGANISM: Sus scrofa

<400> SEQUENCE: 513

Ala His Arg Lys Pro Arg Leu Val Gly Gly Asp Ile Pro Cys Ser Gly
1               5                   10                  15

Arg Val Glu Val Gln His Gly Asp
```

```
                20

<210> SEQ ID NO 514
<211> LENGTH: 25
<212> TYPE: PRT
<213> ORGANISM: Sus scrofa

<400> SEQUENCE: 514

Ala His Arg Lys Pro Arg Leu Val Gly Gly Asp Ile Pro Cys Ser Gly
1               5                  10                  15

Arg Val Glu Val Gln His Gly Asp Thr
            20                  25

<210> SEQ ID NO 515
<211> LENGTH: 29
<212> TYPE: PRT
<213> ORGANISM: Sus scrofa

<400> SEQUENCE: 515

Ala His Arg Lys Pro Arg Leu Val Gly Gly Asp Ile Pro Cys Ser Gly
1               5                  10                  15

Arg Val Glu Val Gln His Gly Asp Thr Trp Gly Thr Val
            20                  25

<210> SEQ ID NO 516
<211> LENGTH: 29
<212> TYPE: PRT
<213> ORGANISM: Sus scrofa

<400> SEQUENCE: 516

Ala His Arg Lys Pro Arg Leu Val Gly Gly Asp Ile Pro Cys Ser Gly
1               5                  10                  15

Arg Val Glu Val Gln His Gly Asp Thr Trp Gly Thr Val
            20                  25

<210> SEQ ID NO 517
<211> LENGTH: 34
<212> TYPE: PRT
<213> ORGANISM: Sus scrofa

<400> SEQUENCE: 517

Ala His Arg Lys Pro Arg Leu Val Gly Gly Asp Ile Pro Cys Ser Gly
1               5                  10                  15

Arg Val Glu Val Gln His Gly Asp Thr Trp Gly Thr Val Cys Asp Ser
            20                  25                  30

Asp Phe

<210> SEQ ID NO 518
<211> LENGTH: 64
<212> TYPE: PRT
<213> ORGANISM: Sus scrofa

<400> SEQUENCE: 518

Ala His Arg Lys Pro Arg Leu Val Thr Val Val Ser Leu Leu Gly Gly
1               5                  10                  15

Ala His Phe Gly Glu Gly Ser Gly Gln Ile Trp Ala Glu Glu Phe Gln
            20                  25                  30

Cys Glu Gly His Glu Ser His Leu Ser Leu Cys Pro Val Ala Pro Arg
        35                  40                  45

Pro Asp Gly Thr Cys Ser His Ser Arg Asp Val Gly Val Val Cys Ser
    50                  55                  60
```

<210> SEQ ID NO 519
<211> LENGTH: 1010
<212> TYPE: PRT
<213> ORGANISM: Sus scrofa

<400> SEQUENCE: 519

```
Met Asp Lys Leu Arg Met Val Leu His Glu Asn Ser Gly Ser Ala Asp
1               5                   10                  15

Phe Arg Arg Cys Ser Ala His Leu Ser Ser Phe Thr Phe Ala Val Val
            20                  25                  30

Ala Val Leu Ser Ala Cys Leu Val Thr Ser Ser Leu Gly Gly Lys Asp
        35                  40                  45

Lys Glu Leu Arg Leu Thr Gly Gly Glu Asn Lys Cys Ser Gly Arg Val
    50                  55                  60

Glu Val Lys Val Gln Glu Trp Gly Thr Val Cys Asn Asn Gly Trp
65                  70                  75                  80

Asp Met Asp Val Val Ser Val Val Cys Arg Gln Leu Gly Cys Pro Thr
                85                  90                  95

Ala Ile Lys Ala Thr Gly Trp Ala Asn Phe Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Asn Cys Thr His Gln Gln
    130                 135                 140

Asp Ala Gly Val Thr Cys Ser Asp Gly Ser Asp Leu Glu Met Arg Leu
145                 150                 155                 160

Val Asn Gly Gly Asn Arg Cys Leu Gly Arg Ile Glu Val Lys Phe Gln
                165                 170                 175

Gly Arg Trp Gly Thr Val Cys Asp Asp Asn Phe Asn Ile Asn His Ala
            180                 185                 190

Ser Val Val Cys Lys Gln Leu Glu Cys Gly Ser Ala Val Ser Phe Ser
        195                 200                 205

Gly Ser Ala Asn Phe Gly Glu Gly Ser Gly Pro Ile Trp Phe Asp Asp
    210                 215                 220

Leu Val Cys Asn Gly Asn Glu Ser Ala Leu Trp Asn Cys Lys His Glu
225                 230                 235                 240

Gly Trp Gly Lys His Asn Cys Asp His Ala Glu Asp Ala Gly Val Ile
                245                 250                 255

Cys Leu Asn Gly Ala Asp Leu Lys Leu Arg Val Val Asp Gly Val Thr
            260                 265                 270

Glu Cys Ser Gly Arg Leu Glu Val Lys Phe Gln Gly Glu Trp Gly Thr
        275                 280                 285

Ile Cys Asp Asp Gly Trp Asp Ser Asp Ala Ala Val Ala Cys Lys
    290                 295                 300

Gln Leu Gly Cys Pro Thr Ala Val Thr Ala Ile Gly Arg Val Asn Ala
305                 310                 315                 320

Ser Glu Gly Thr Gly His Ile Trp Leu Asp Ser Val Ser Cys His Gly
                325                 330                 335

His Glu Ser Ala Leu Trp Gln Cys Arg His His Glu Trp Gly Lys His
            340                 345                 350

Tyr Cys Asn His Asn Glu Asp Ala Gly Val Thr Cys Ser Asp Gly Ser
        355                 360                 365

Asp Leu Glu Leu Arg Leu Lys Gly Gly Gly Ser His Cys Ala Gly Thr
```

```
            370                 375                 380
Val Glu Val Glu Ile Gln Lys Leu Val Gly Lys Val Cys Asp Arg Ser
385                 390                 395                 400

Trp Gly Leu Lys Glu Ala Asp Val Val Cys Arg Gln Leu Gly Cys Gly
                405                 410                 415

Ser Ala Leu Lys Thr Ser Tyr Gln Val Tyr Ser Lys Thr Lys Ala Thr
                420                 425                 430

Asn Thr Trp Leu Phe Val Ser Ser Cys Asn Gly Asn Glu Thr Ser Leu
                435                 440                 445

Trp Asp Cys Lys Asn Trp Gln Trp Gly Gly Leu Ser Cys Asp His Tyr
            450                 455                 460

Asp Glu Ala Lys Ile Thr Cys Ser Gly Tyr Thr Gln Ile Arg Leu Val
465                 470                 475                 480

Asn Gly Lys Thr Pro Cys Glu Gly Arg Val Glu Leu Asn Ile Leu Gly
                485                 490                 495

Ser Trp Gly Ser Leu Cys Asn Ser His Trp Asp Met Glu Asp Ala His
                500                 505                 510

Val Leu Cys Gln Gln Leu Lys Cys Gly Val Ala Leu Ser Ile Pro Arg
            515                 520                 525

Gly Ala Pro Phe Gly Lys Gly Ser Glu Gln Val Trp Arg His Met Phe
            530                 535                 540

His Cys Thr Gly Thr Glu Lys His Met Gly Asp Cys Ser Val Thr Ala
545                 550                 555                 560

Leu Gly Ala Ser Leu Cys Ser Ser Gly Gln Val Ala Ser Val Ile Cys
                565                 570                 575

Ser Gly Asn Gln Ser Gln Thr Leu Ser Pro Cys Asn Ser Ser Ser Ser
                580                 585                 590

Asp Pro Ser Ser Ser Ile Ile Ser Glu Glu Asn Gly Val Ala Cys Ile
            595                 600                 605

Gly Ser Gly Gln Leu Arg Leu Val Asp Gly Gly Arg Cys Ala Gly
            610                 615                 620

Arg Val Glu Val Tyr His Glu Gly Ser Trp Gly Thr Ile Cys Asp Asp
625                 630                 635                 640

Ser Trp Asp Leu Asn Asp Ala His Val Val Cys Lys Gln Leu Ser Cys
                645                 650                 655

Gly Trp Ala Ile Asn Ala Thr Gly Ser Ala His Phe Gly Glu Gly Thr
                660                 665                 670

Gly Pro Ile Trp Leu Asp Glu Ile Asn Cys Asn Gly Lys Glu Ser His
            675                 680                 685

Ile Trp Gln Cys His Ser His Gly Trp Gly Arg His Asn Cys Arg His
            690                 695                 700

Lys Glu Asp Ala Gly Val Ile Cys Ser Glu Phe Met Ser Leu Arg Leu
705                 710                 715                 720

Ile Ser Glu Asn Ser Arg Glu Thr Cys Ala Gly Arg Leu Glu Val Phe
                725                 730                 735

Tyr Asn Gly Ala Trp Gly Ser Val Gly Arg Asn Ser Met Ser Pro Ala
                740                 745                 750

Thr Val Gly Val Val Cys Arg Gln Leu Gly Cys Ala Asp Arg Gly Asp
                755                 760                 765

Ile Ser Pro Ala Ser Ser Asp Lys Thr Val Ser Arg His Met Trp Val
            770                 775                 780

Asp Asn Val Gln Cys Pro Lys Gly Pro Asp Thr Leu Trp Gln Cys Pro
785                 790                 795                 800
```

Ser Ser Pro Trp Lys Lys Arg Leu Ala Ser Pro Ser Glu Glu Thr Trp
                805                 810                 815

Ile Thr Cys Ala Asn Lys Ile Arg Leu Gln Glu Gly Asn Thr Asn Cys
            820                 825                 830

Ser Gly Arg Val Glu Ile Trp Tyr Gly Gly Ser Trp Gly Thr Val Cys
        835                 840                 845

Asp Asp Ser Trp Asp Leu Glu Asp Ala Gln Val Val Cys Arg Gln Leu
    850                 855                 860

Gly Cys Gly Ser Ala Leu Glu Ala Gly Lys Glu Ala Ala Phe Gly Gln
865                 870                 875                 880

Gly Thr Gly Pro Ile Trp Leu Asn Glu Val Lys Cys Lys Gly Asn Glu
                885                 890                 895

Thr Ser Leu Trp Asp Cys Pro Ala Arg Ser Trp Gly His Ser Asp Cys
            900                 905                 910

Gly His Lys Glu Asp Ala Ala Val Thr Cys Ser Glu Ile Ala Lys Ser
        915                 920                 925

Arg Glu Ser Leu His Ala Thr Gly Arg Ser Ser Phe Val Ala Leu Ala
    930                 935                 940

Ile Phe Gly Val Ile Leu Leu Ala Cys Leu Ile Ala Phe Leu Ile Trp
945                 950                 955                 960

Thr Gln Lys Arg Arg Gln Arg Gln Arg Leu Ser Val Phe Ser Gly Gly
                965                 970                 975

Glu Asn Ser Val His Gln Ile Gln Tyr Arg Glu Met Asn Ser Cys Leu
            980                 985                 990

Lys Ala Asp Glu Thr Asp Met Leu Asn Pro Ser Gly Asp His Ser Glu
        995                 1000                1005

Val Gln
   1010

<210> SEQ ID NO 520
<211> LENGTH: 101
<212> TYPE: DNA
<213> ORGANISM: Sus scrofa

<400> SEQUENCE: 520 ctcactttc actctctggc ttactcctat caagagggta gggttaggta gtcacagaca    60 tcttttaaa gccctgtctc cttccaggat acacacaaat c                       101

<210> SEQ ID NO 521
<211> LENGTH: 100
<212> TYPE: DNA
<213> ORGANISM: Sus scrofa

<400> SEQUENCE: 521 ctcactttc actctctggc ttactcctat cagagggtag ggttaggtag tcacagacat    60 cttttaaag ccctgtctcc ttccaggata cacacaaatc                         100

<210> SEQ ID NO 522
<211> LENGTH: 98
<212> TYPE: DNA
<213> ORGANISM: Sus scrofa

<400> SEQUENCE: 522 ctcactttc actctctggc ttactcctat cagggtaggg ttaggtagtc acagacatct    60
ttttaaagcc ctgtctcctt ccaggataca cacaaatc                           98

<210> SEQ ID NO 523
<211> LENGTH: 108
<212> TYPE: DNA
<213> ORGANISM: Sus scrofa

<400> SEQUENCE: 523 ctcactttc actctctggc ttactcctat catggcatgg gagggtaggg ttaggtagtc      60
acagacatct ttttaaagcc ctgtctcctt ccaggataca cacaaatc                 108

<210> SEQ ID NO 524
<211> LENGTH: 72
<212> TYPE: DNA
<213> ORGANISM: Sus scrofa

<400> SEQUENCE: 524 ctcactttc agggttaggt agtcacagac atcttttaa agccctgtct ccttccagga      60
tacacacaaa tc                                                         72

<210> SEQ ID NO 525
<211> LENGTH: 90
<212> TYPE: DNA
<213> ORGANISM: Sus scrofa

<400> SEQUENCE: 525 ctcactttc actctctggc ttactcctag ggttaggtag tcacagacat cttttaaag      60 ccctgtctcc ttccaggata cacacaaatc                                     90

<210> SEQ ID NO 526
<211> LENGTH: 75
<212> TYPE: DNA
<213> ORGANISM: Sus scrofa

<400> SEQUENCE: 526 ctcactttc actctctggc ttactcccca gacatctttt taaagccctg tctccttcca     60
ggatacacac aaatc                                                      75

<210> SEQ ID NO 527
<211> LENGTH: 96
<212> TYPE: DNA
<213> ORGANISM: Sus scrofa

<400> SEQUENCE: 527 ctcactttc actctctggc ttactccaga gggtagggtt aggtagtcac agacatcttt     60
ttaaagccct gtctccttcc aggatacaca caaatc                              96

<210> SEQ ID NO 528
<211> LENGTH: 97
<212> TYPE: DNA
<213> ORGANISM: Sus scrofa

<400> SEQUENCE: 528 ctcactttc actctctggc ttactcctat caggtagggt taggtagtca cagacatctt     60
tttaaagccc tgtctccttc caggatacac acaaatc                             97

<210> SEQ ID NO 529
<211> LENGTH: 90
<212> TYPE: DNA
<213> ORGANISM: Sus scrofa

<400> SEQUENCE: 529

```
ctcactttc actctctggc ttactcctag ggttaggtag tcacagacat cttttaaag      60 ccctgtctcc ttccaggata cacacaaatc                                     90
```

<210> SEQ ID NO 530
<211> LENGTH: 99
<212> TYPE: DNA
<213> ORGANISM: Sus scrofa

<400> SEQUENCE: 530

```
ctcactttc actctctggc ttactcctat caagggtagg gttaggtagt cacagacatc      60
tttttaaagc cctgtctcct tccaggatac acacaaatc                            99
```

<210> SEQ ID NO 531
<211> LENGTH: 93
<212> TYPE: DNA
<213> ORGANISM: Sus scrofa

<400> SEQUENCE: 531

```
ctcactttc actctctggc ttactcctat cagggttagg tagtcacaga catcttttta      60
aagccctgtc tccttccagg atacacacaa atc                                  93
```

<210> SEQ ID NO 532
<211> LENGTH: 92
<212> TYPE: DNA
<213> ORGANISM: Sus scrofa

<400> SEQUENCE: 532

```
ctcactttc actctctggc ttactccggt agggttaggt agtcacagac atcttttaa       60 agccctgtct ccttccagga tacacacaaa tc                                   92
```

<210> SEQ ID NO 533
<211> LENGTH: 98
<212> TYPE: DNA
<213> ORGANISM: Sus scrofa

<400> SEQUENCE: 533

```
ctcactttc actctctggc ttactcctat caaggtaggg ttaggtagtc acagacatct      60
ttttaaagcc ctgtctcctt ccaggataca cacaaatc                             98
```

<210> SEQ ID NO 534
<211> LENGTH: 99
<212> TYPE: DNA
<213> ORGANISM: Sus scrofa

<400> SEQUENCE: 534

```
ctcactttc actctctggc ttactcctat cacaggtagg gttaggtagt cacagacatc      60
tttttaaagc cctgtctcct tccaggatac acacaaatc                            99
```

<210> SEQ ID NO 535
<211> LENGTH: 95
<212> TYPE: DNA
<213> ORGANISM: Sus scrofa

<400> SEQUENCE: 535

```
ctcactttc actctctggc ttactcctat ggtagggtta ggtagtcaca gacatctttt      60
taaagccctg tctccttcca ggatacacac aaatc                                95
```

<210> SEQ ID NO 536

```
<211> LENGTH: 125
<212> TYPE: DNA
<213> ORGANISM: Sus scrofa

<400> SEQUENCE: 536
gcaaagtccc agaattgtct ccagggaagg acagggaggt ctagaatcgg ctaagcccac      60
ggtagggtta ggtagtcaca gacatctttt taaagccctg tctccttcca ggatacacac     120
aaatc                                                                 125

<210> SEQ ID NO 537
<211> LENGTH: 124
<212> TYPE: DNA
<213> ORGANISM: Sus scrofa

<400> SEQUENCE: 537
gcaaagtccc agaattgtct ccagggaagg acagggaggt ctagaatcgg ctaagcccac      60
gtagggttag gtagtcacag acatctttt aaagccctgt ctccttccag gatacacaca     120
aatc                                                                  124

<210> SEQ ID NO 538
<211> LENGTH: 123
<212> TYPE: DNA
<213> ORGANISM: Sus scrofa

<400> SEQUENCE: 538
gcaaagtccc agaattgtct ccagggaagg acagggaggt ctagaatcgg ctaagcccat      60
tagggttagg tagtcacaga catcttttta agccctgtc tccttccagg atacacacaa     120
atc                                                                   123

<210> SEQ ID NO 539
<211> LENGTH: 114
<212> TYPE: DNA
<213> ORGANISM: Sus scrofa

<400> SEQUENCE: 539
gcaaagtccc agaattgtct ccagggaagg acagggaggt ctagaatcgg ctagggttag      60
gtagtcacag acatctttt aaagccctgt ctccttccag gatacacaca aatc           114

<210> SEQ ID NO 540
<211> LENGTH: 123
<212> TYPE: DNA
<213> ORGANISM: Sus scrofa

<400> SEQUENCE: 540
gcaaagtccc agaattgtct ccagggaagg acagggaggt ctagaatcgg ctaagcccac      60
tagggttagg tagtcacaga catcttttta agccctgtc tccttccagg atacacacaa     120
atc                                                                   123

<210> SEQ ID NO 541
<211> LENGTH: 116
<212> TYPE: DNA
<213> ORGANISM: Sus scrofa

<400> SEQUENCE: 541
gcaaagtccc agaattgtct ccagggaagg acagggaggt ctagaatcgg ctaagcccac      60
aggtagtcac agacatcttt ttaaagccct gtctccttcc aggatacaca caaatc         116
```

<210> SEQ ID NO 542
<211> LENGTH: 124
<212> TYPE: DNA
<213> ORGANISM: Sus scrofa

<400> SEQUENCE: 542

```
gcaaagtccc agaattgtct ccagggaagg acagggaggt ctagaatcgg ctaagcccag    60
gtagggttag gtagtcacag acatctttt aaagccctgt ctccttccag gatacacaca   120
aatc                                                                124
```

<210> SEQ ID NO 543
<211> LENGTH: 122
<212> TYPE: DNA
<213> ORGANISM: Sus scrofa

<400> SEQUENCE: 543

```
gcaaagtccc agaattgtct ccagggaagg acagggaggt ctagaatcgg ctaagcccat    60
ggggttaggt agtcacagac atcttttaa agccctgtct ccttccagga tacacacaaa   120
tc                                                                  122
```

<210> SEQ ID NO 544
<211> LENGTH: 113
<212> TYPE: DNA
<213> ORGANISM: Sus scrofa

<400> SEQUENCE: 544

```
gcaaagtccc agaattgtct ccagggaagg acagggaggt ctagaatcgg tagggttagg    60
tagtcacaga catcttttta aagccctgtc tccttccagg atacacacaa atc          113
```

<210> SEQ ID NO 545
<211> LENGTH: 113
<212> TYPE: DNA
<213> ORGANISM: Sus scrofa

<400> SEQUENCE: 545

```
atttctggtg tgcctttgac tccagattac agtaaatgga ggactgaggg tagggttagg    60
tagtcacaga catcttttta aagccctgtc tccttccagg atacacacaa atc          113
```

<210> SEQ ID NO 546
<211> LENGTH: 117
<212> TYPE: DNA
<213> ORGANISM: Sus scrofa

<400> SEQUENCE: 546

```
atttctggtg tgcctttgac tccagattac agtaaatgga ggactgagag agggtagggt    60
taggtagtca cagacatctt tttaaagccc tgtctccttc caggatacac acaaatc     117
```

<210> SEQ ID NO 547
<211> LENGTH: 106
<212> TYPE: DNA
<213> ORGANISM: Sus scrofa

<400> SEQUENCE: 547

```
atttctggtg tgcctttgac tccagattac agtaaatgga gggtagggtt aggtagtcac    60
agacatcttt ttaaagccct gtctccttcc aggatacaca caaatc                  106
```

<210> SEQ ID NO 548
<211> LENGTH: 112
<212> TYPE: DNA

```
<213> ORGANISM: Sus scrofa

<400> SEQUENCE: 548
atttctggtg tgcctttgac tccagattac agtaaatgga ggactgaggg tgggttaggt      60
agtcacagac atctttttaa agccctgtct ccttccagga tacacacaaa tc             112

<210> SEQ ID NO 549
<211> LENGTH: 117
<212> TYPE: DNA
<213> ORGANISM: Sus scrofa

<400> SEQUENCE: 549
atttctggtg tgcctttgac tccagattac agtaaatgga ggactgagag aggatagggt      60
taggtagtca cagacatctt tttaaagccc tgtctccttc caggatacac acaaatc       117

<210> SEQ ID NO 550
<211> LENGTH: 90
<212> TYPE: DNA
<213> ORGANISM: Sus scrofa

<400> SEQUENCE: 550
gaaagagaaa gcatgctcca agaatggtag ggttaggtag tcacagacat cttttttaaag     60 ccctgtctcc ttccaggata cacacaaatc                                      90

<210> SEQ ID NO 551
<211> LENGTH: 89
<212> TYPE: DNA
<213> ORGANISM: Sus scrofa

<400> SEQUENCE: 551
gaaagagaaa gcatgctcca agaaggtagg gttaggtagt cacagacatc tttttaaagc      60
cctgtctcct tccaggatac acacaaatc                                       89

<210> SEQ ID NO 552
<211> LENGTH: 91
<212> TYPE: DNA
<213> ORGANISM: Sus scrofa

<400> SEQUENCE: 552
gaaagagaaa gcatgctcca agaatgggta gggttaggta gtcacagaca tcttttaaa       60 gccctgtctc cttccaggat acacacaaat c                                    91

<210> SEQ ID NO 553
<211> LENGTH: 87
<212> TYPE: DNA
<213> ORGANISM: Sus scrofa

<400> SEQUENCE: 553
gaaagagaaa gcatgctcca agagtagggt taggtagtca cagacatctt tttaaagccc      60
tgtctccttc caggatacac acaaatc                                         87

<210> SEQ ID NO 554
<211> LENGTH: 97
<212> TYPE: DNA
<213> ORGANISM: Sus scrofa

<400> SEQUENCE: 554
gaaagagaaa gcatgctcca agaatccaag agggtagggt taggtagtca cagacatctt      60
tttaaagccc tgtctccttc caggatacac acaaatc                              97
```

<210> SEQ ID NO 555
<211> LENGTH: 92
<212> TYPE: DNA
<213> ORGANISM: Sus scrofa

<400> SEQUENCE: 555
gaaagagaaa gcatgctcca agaatagggt agggttaggt agtcacagac atcttttaa    60 agccctgtct ccttccagga tacacacaaa tc                                 92

<210> SEQ ID NO 556
<211> LENGTH: 21
<212> TYPE: DNA
<213> ORGANISM: Sus scrofa

<400> SEQUENCE: 556
ctaagcccac tgtaggcaga a                                             21

<210> SEQ ID NO 557
<211> LENGTH: 21
<212> TYPE: DNA
<213> ORGANISM: Sus scrofa

<400> SEQUENCE: 557
ctgggtttcc tgtgggctga a                                             21

<210> SEQ ID NO 558
<211> LENGTH: 24
<212> TYPE: DNA
<213> ORGANISM: Sus scrofa

<400> SEQUENCE: 558
tggcttactc ctatcatgaa ggaa                                          24

<210> SEQ ID NO 559
<211> LENGTH: 21
<212> TYPE: DNA
<213> ORGANISM: Sus scrofa

<400> SEQUENCE: 559
atgtagccac agcagggacg t                                             21

<210> SEQ ID NO 560
<211> LENGTH: 22
<212> TYPE: DNA
<213> ORGANISM: Sus scrofa

<400> SEQUENCE: 560
ccaagcggat ttgtgtgtat cc                                            22

<210> SEQ ID NO 561
<211> LENGTH: 28
<212> TYPE: DNA
<213> ORGANISM: Sus scrofa

<400> SEQUENCE: 561
ttcccatgcc atgaagaggg tagggtta                                      28

<210> SEQ ID NO 562
<211> LENGTH: 21
<212> TYPE: DNA
<213> ORGANISM: Sus scrofa

```
<400> SEQUENCE: 562
gctaagccca ctgtaggcag a                                              21

<210> SEQ ID NO 563
<211> LENGTH: 21
<212> TYPE: DNA
<213> ORGANISM: Sus scrofa

<400> SEQUENCE: 563
gcggatttgt gtgtatcctg g                                              21

<210> SEQ ID NO 564
<211> LENGTH: 24
<212> TYPE: DNA
<213> ORGANISM: Sus scrofa

<400> SEQUENCE: 564
tggcttactc ctatcaggta gggt                                           24
```